United States Patent
Weiner et al.

(10) Patent No.: US 11,845,787 B2
(45) Date of Patent: Dec. 19, 2023

(54) DNA ANTIBODY CONSTRUCTS FOR USE AGAINST HIV

(71) Applicants: The Wistar Institute of Anatomy and Biology, Philadelphia, PA (US); INOVIO PHARMACEUTICALS, INC., Plymouth Meeting, PA (US)

(72) Inventors: David Weiner, Merion, PA (US); Megan Wise, Raleigh, NC (US)

(73) Assignees: The Wistar Institute of Anatomy and Biology, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 816 days.

(21) Appl. No.: 16/497,945

(22) PCT Filed: Mar. 27, 2018

(86) PCT No.: PCT/US2018/024520
§ 371 (c)(1),
(2) Date: Sep. 26, 2019

(87) PCT Pub. No.: WO2018/183294
PCT Pub. Date: Oct. 4, 2018

(65) Prior Publication Data
US 2021/0107970 A1    Apr. 15, 2021

Related U.S. Application Data

(60) Provisional application No. 62/477,217, filed on Mar. 27, 2017, provisional application No. 62/477,227, filed on Mar. 27, 2017.

(51) Int. Cl.
C07K 16/10    (2006.01)
A61K 39/42    (2006.01)
A61P 31/18    (2006.01)

(52) U.S. Cl.
CPC .......... *C07K 16/1045* (2013.01); *A61P 31/18* (2018.01); *C07K 2317/55* (2013.01); *C07K 2317/76* (2013.01)

(58) Field of Classification Search
None
See application file for complete search history.

(56) References Cited

U.S. PATENT DOCUMENTS 8,333,971 B2 * 12/2012 Goldenberg ....... A61K 47/6809
424/183.1
2007/0264265 A1    11/2007 Goldenberg
2012/0020988 A1    1/2012 Auer
2015/0152167 A1    6/2015 Ho

FOREIGN PATENT DOCUMENTS

WO    2016054296    4/2016
WO    2016089862    6/2016

OTHER PUBLICATIONS

Pardi et al. (Nature Communications, Mar. 2, 2017, p. 1-8).*
Muthumani et al., 2013, "Optimized and enhanced DNA plasmid vector based in vivo construction of a neutralizing antiHIV-1 envelope glycoprotein Fab," Human Vaccines & Immunotherapeutics, 9:10, 2253-2262.
Silva et al., "The S228P mutation prevents in vivo and in vitro IgG4 Fab-arm exchange as demonstrated using a combination of novel quantitative immunoassays and physiological matrix preparation", J Biol Chem., (Feb. 27, 2015), vol. 290, No. 9, pp. 5462-5469, XP055299482.

* cited by examiner

*Primary Examiner* — Agnieszka Boesen
(74) *Attorney, Agent, or Firm* — Riverside Law LLP

(57) ABSTRACT

Disclosed herein is a composition including a recombinant nucleic acid sequence that encodes an antibody to an HIV antigen. Also disclosed herein is a method of generating a synthetic antibody in a subject by administering the composition to the subject. The disclosure also provides a method of preventing and/or treating an HIV infection in a subject using said composition and method of generation.

16 Claims, 15 Drawing Sheets
Specification includes a Sequence Listing.

A

| | Tier | Clade | Chuang: VRC01 IC$_{50}$ (µg/ml) | Huang: PGT128 IC$_{50}$ (µg/ml) | Chuang: PG9 IC$_{50}$ (µg/ml) | Chuang: 3BNC117 IC$_{50}$ (µg/ml) | Chuang: NIH45-46 IC$_{50}$ (µg/ml) |
|---|---|---|---|---|---|---|---|
| CAP210.0 | 2 | C | >50 | >50 | 0.087 | 8.16 | >50 |
| DU172 | 2 | C | >50 | 0.004 | 0.262 | 0.289 | >50 |
| Q168ENV | 2 | A1 | 0.150 | >50 | 0.106 | 0.050 | 0.138 |
| Q461ENV | 2 | A1 | 0.339 | >50 | 3.010 | 0.169 | 0.212 |
| QH0692 | 2 | B | 1.840 | 0.046 | >50 | 0.275 | 0.991 |
| WITO | 2 | B | 0.110 | >50 | 0.023 | 0.056 | 0.087 |
| ZM249 | 2 | C | 0.062 | 10.7 | 0.033 | 0.059 | 0.054 |

B

| | Tier | Clade | VRC01 IgG1 | VRC01 IgG4 | PGT128 IgG1 | PGT128 IgG4 | PG9 IgG1 | PG9 IgG4 | 3BNC117 IgG1 | 3BNC117 IgG4 | NIH45-46 IgG1 | NIH45-46 IgG4 |
|---|---|---|---|---|---|---|---|---|---|---|---|---|
| CAP210.0 | 2 | C | >20 | >20 | >20 | >20 | 0.35 | 0.357 | >20 | >20 | >20 | >20 |
| DU172 | 2 | C | >20 | >20 | 0.025 | 0.004 | 0.15 | 0.192 | 0.303 | 0.435 | >20 | >20 |
| Q168ENV | 2 | A1 | 0.219 | 0.233 | >20 | >20 | 0.046 | 0.011 | 0.046 | 0.095 | 0.046 | 0.121 |
| Q461ENV | 2 | A1 | 0.439 | 0.56 | >20 | >20 | 0.301 | 0.434 | 0.062 | 0.104 | 0.121 | 0.52 |
| QH0692 | 2 | B | >20 | >20 | >20 | >20 | >20 | >20 | 0.303 | 0.435 | 0.23 | 0.69 |
| WITO | 2 | B | 0.399 | 0.451 | >20 | >20 | 0.066 | 0.066 | 0.089 | 0.111 | 0.133 | 0.255 |
| ZM249 | 2 | C | 0.121 | 0.116 | >20 | >20 | 0.131 | 0.4 | 0.126 | 0.217 | 0.055 | 0.055 |

Figure 11A - Figure 11B

DNA ANTIBODY CONSTRUCTS FOR USE AGAINST HIV

CROSS-REFERENCE TO RELATED APPLICATIONS

This application is a U.S. national phase application filed under 35 U.S.C. § 371 claiming priority to International Patent Application No. PCT/US2018/024520, filed Mar. 27, 2018, which is entitled to priority to U.S. Provisional Application No. 62/477,227, filed Mar. 27, 2017 and U.S. Provisional Application No. 62/477,217, filed Mar. 27, 2017, the contents of each of which are incorporated by reference herein in their entireties.

TECHNICAL FIELD

The present invention relates to a composition comprising a recombinant nucleic acid sequence for generating one or more synthetic antibodies, and functional fragments thereof, in vivo, and a method of preventing and/or treating viral infection in a subject by administering said composition.

BACKGROUND

The strength of broadly neutralizing antibodies (bNabs) to protect or control HIV-1 is well established in animal models. Though these antibodies are powerful and can prevent infection or control viral loads, the cost of production could severely limit the ability to use these antibodies in the field. Additionally, current vaccine approaches have failed to induce similar antibodies.

Thus there is need in the art for improved therapeutics that prevent and/or treat HIV infection. The current invention satisfies this need.

SUMMARY

The present invention is directed to a nucleic acid molecule encoding one or more synthetic antibodies, wherein the nucleic acid molecule comprises at least one selected from the group consisting of a) a nucleotide sequence encoding an anti-HIV synthetic antibody; and b) a nucleotide sequence encoding a fragment of an anti-HIV synthetic antibody.

In one embodiment, the nucleic acid molecule comprises a nucleotide sequence encoding a cleavage domain.

In one embodiment, the nucleic acid molecule comprises a nucleotide sequence encoding one or more of a variable heavy chain region and a variable light chain region of an anti-HIV antibody.

In one embodiment, the nucleic acid molecule comprises a nucleotide sequence encoding one or more amino acid sequences at least 90% identical to an amino acid sequence as set forth in SEQ ID NO:1, SEQ ID NO:3, SEQ ID NO:5, SEQ ID NO:7, SEQ ID NO:9, SEQ ID NO:11, or SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49 SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, or SEQ ID NO:133.

In one embodiment, the nucleic acid molecule comprises a nucleotide sequence at least 95% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, or SEQ ID NO:134.

In one embodiment, the nucleic acid molecule comprises a nucleotide sequence encoding a variable heavy chain region and a variable light chain region of an anti-HIV antibody.

In one embodiment, the nucleic acid molecule comprises a nucleotide sequence encoding a heavy chain comprising an amino acid sequence at least 95% identical to SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the nucleotide sequence encoding a heavy chain comprises a nucleotide sequence at least 95% identical to SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

In one embodiment, the nucleic acid molecule comprises a nucleotide sequence encoding a light chain comprising an amino acid sequence at least 95% identical to SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the nucleotide sequence encoding a light chain comprises a nucleotide sequence at least 95% identical to SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

In one embodiment, the nucleic acid molecule comprises a nucleotide sequence encoding a polypeptide comprising a variable heavy chain region; an IRES element; and a variable light chain region. In one embodiment, the IRES element is one of a viral IRES or an eukaryotic IRES.

In one embodiment, the nucleotide sequence encodes a leader sequence. In one embodiment, the nucleic acid molecule comprises an expression vector.

The invention further provides a composition comprising any of the nucleic acid molecules described herein.

In one embodiment the composition comprises a pharmaceutically acceptable excipient.

The invention further relates to a method of preventing or treating a disease in a subject, the method comprising administering to the subject a nucleic acid molecule or a composition as described herein.

In one embodiment, the disease is an HIV infection.

In one embodiment, the method further comprises administering an antibiotic agent to the subject. In one embodiment, an antibiotic is administered less than 10 days after administration of the nucleic acid molecule or composition.

In one embodiment, the method further comprises administering an antibiotic agent to the subject. In one embodiment an antibiotic is administered less than 10 days after administration of the nucleic acid molecule or composition.

The invention further relates to a method generating an immune response in a subject, the method comprising administering to the subject a nucleic acid molecule or a composition as described herein.

BRIEF DESCRIPTION OF THE DRAWINGS

FIG. 1, comprising FIG. 1A depicts a schematic of dMAb design. Antibody sequences go through multiple rounds of optimizations to increase dMAb production level including codon and RNA optimization, amino acid sequence modification, changes to the backbone and formulation. FIG. 1B depicts a diagram of dMAb in vivo production. Plasmid DNA expressing the antibody is injected into the muscle followed by electroporation. Muscle cells then product the functional antibody which is secreted into circulation.

FIG. 2, comprising FIG. 2A depicts the expression of HIV dMAB constructs in cell media. FIG. 2B depicts the expression of HIV dMAB constructs in cell lysate. FIG. 2C depicts western blot analysis of media from two constructs to ensure proper processing of the heavy and light chain.

FIG. 5, comprising FIG. 5A through FIG. 5C depicts experimental results demonstrating how different human IgG isotypes can lead to changes in in vivo expression levels of dMAbs.

FIG. 6, comprising of FIG. 6A through FIG. 6B depicts experimental results demonstrating the in vitro expression levels of multiple broadly neutralizing antibodies expressed as either human IgG1 or human IgG4 dMAbs.

FIG. 7, comprising of FIG. 7A through FIG. 7B, depicts experimental results demonstrating the increased expression levels in vivo for multiple HIV dMAbs using IgG4 isotype compared to IgG1.

FIG. 8, comprising of FIG. 8A through FIG. 8B depicts experimental results demonstrating that the S228P mutation in the IgG4 background does not disrupt expression levels.

FIG. 10, comprising FIG. 10A through FIG. 10B depicts experimental results demonstrating the long terms expression of dMAb and how modifications can increase expression levels over time.

FIG. 11, comprising FIG. 11A through FIG. 11B depicts experimental results demonstrating dMAb modifications and optimizations maintains functionality. FIG. 11A depicts reported IC50 concentrations for a panel of tier 2 viruses against numerous bNabs. FIG. 11B depicts neutralization concentration (IC50) for original and modified in vitro produced dMAb to induce functionality after modification.

DETAILED DESCRIPTION

Figures 1A, 1B:
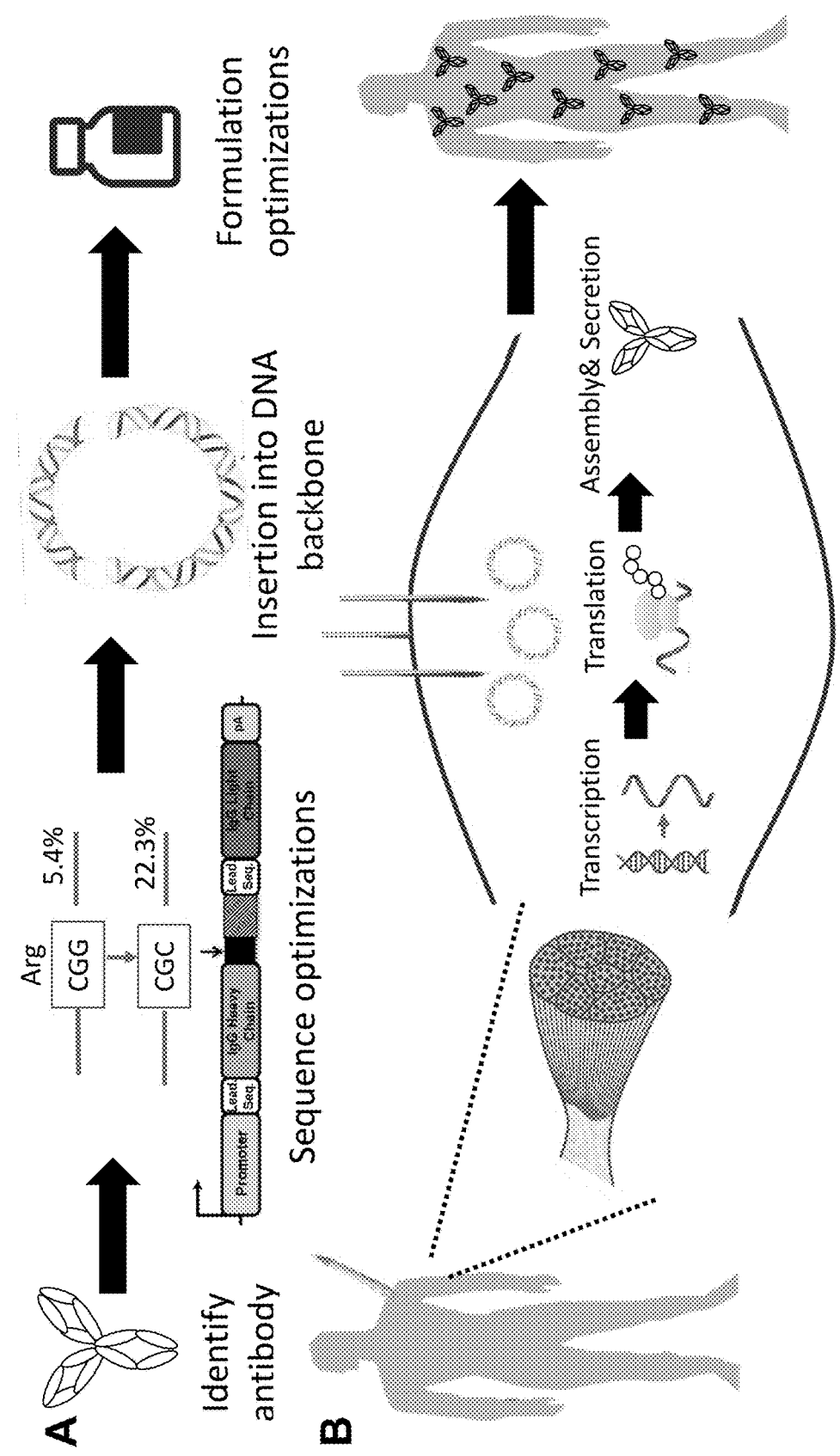
FIG. 1A through FIG. 1B, depicts dMAb concept and design.
Figures 2A, 2B, 2C:
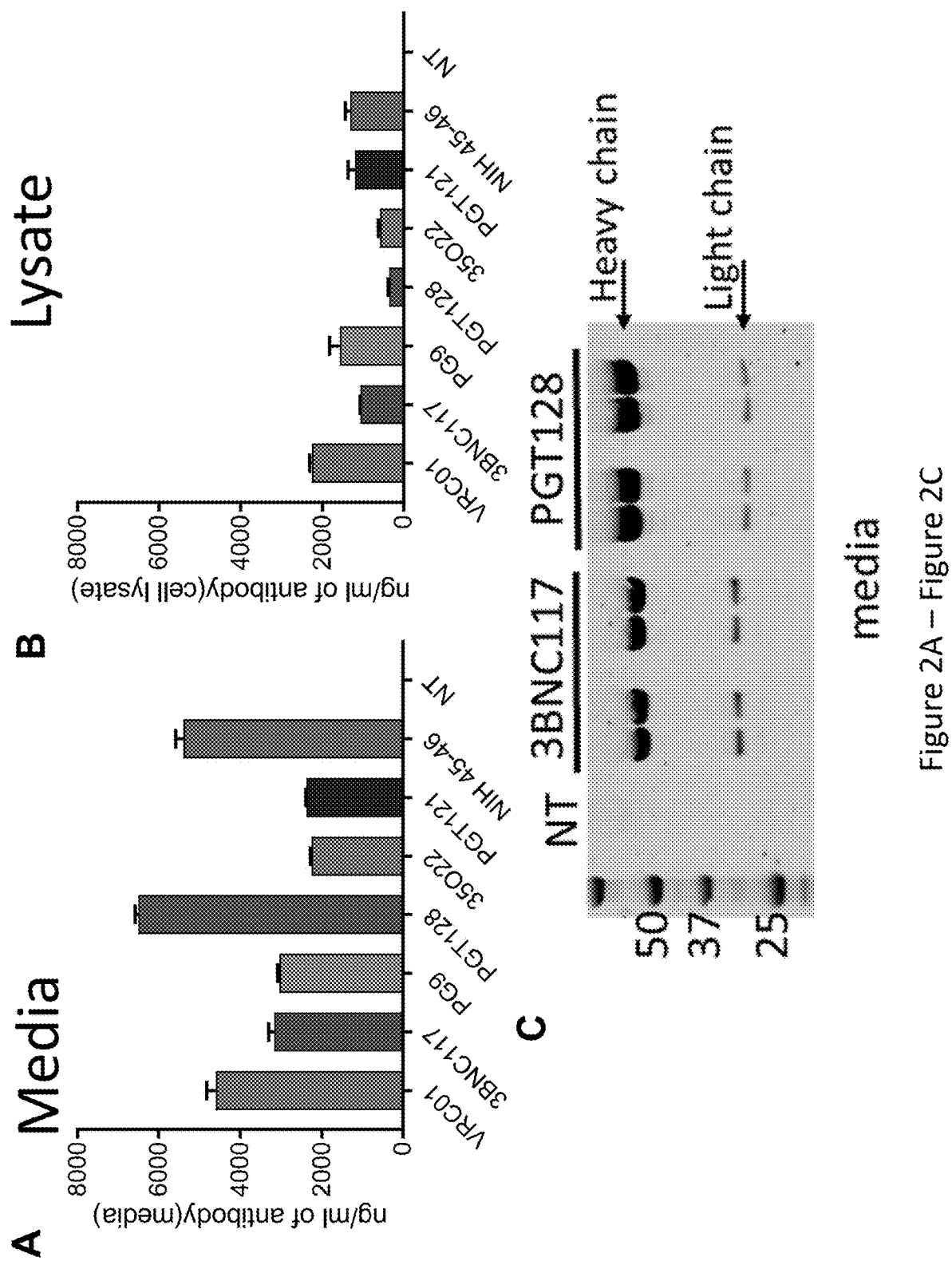
FIG. 2A through FIG. 2C, depicts experimental results demonstrating in vitro expression of HIV IgG1 dMAb constructs. 293T cells were transfected with different HIV dMAb plasmids. Forty-eight hours later cell media or lysate were harvested and quantified via ELISA.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

A sequence listing provided herewith contains a list of sequences including the following:

SEQ ID NO: 1 is the amino acid sequence of 3BNC117 human IgG1 antibody.
SEQ ID NO: 2 is the nucleotide sequence of 3BNC117 human IgG1 antibody.
SEQ ID NO: 3 is the amino acid sequence of 3BNC117 human IgG1 antibody (heavy chain).
SEQ ID NO: 4 is the nucleotide sequence of 3BNC117 human IgG1 antibody (heavy chain).
SEQ ID NO: 5 is the amino acid sequence of 3BNC117 human IgG1 antibody (light chain).
SEQ ID NO: 6 is the nucleotide sequence of 3BNC117 human IgG1 antibody (light chain).
SEQ ID NO: 7 is the amino acid sequence of 3BNC117 human IgG4.
SEQ ID NO: 8 is the nucleotide sequence of 3BNC117 human IgG4.
SEQ ID NO: 9 is the amino acid sequence of 3BNC117 human IgG4 (S228P).
SEQ ID NO: 10 is the nucleotide sequence of 3BNC117 human IgG4 (S228P).
SEQ ID NO: 11 is the amino acid sequence of 3BNC117 human IgG4 (heavy chain).
SEQ ID NO: 12 is the nucleotide sequence of 3BNC117 human IgG4 (heavy chain).
SEQ ID NO: 13 is the amino acid sequence of 3BNC117 human IgG4 (light chain).
SEQ ID NO: 14 is the nucleotide sequence of 3BNC117 human IgG4 (light chain).
SEQ ID NO: 15 is the amino acid sequence of PGT128 human IgG1.
SEQ ID NO: 16 is the nucleotide sequence of PGT128 human IgG1.
SEQ ID NO: 17 is the amino acid sequence of PGT128 human IgG1-(heavy chain).
SEQ ID NO: 18 is the nucleotide sequence of PGT128 human IgG1-(heavy chain).
SEQ ID NO: 19 is the amino acid sequence of PGT128 human IgG1-(light chain).
SEQ ID NO: 20 is the nucleotide sequence of PGT128 human IgG1-(light chain).
SEQ ID NO: 21 is the amino acid sequence of PGT128 human IgG4.
SEQ ID NO: 22 is the nucleotide sequence of PGT128 human IgG4.
SEQ ID NO: 23 is the amino acid sequence of PGT128 human IgG4mut (S228P).
SEQ ID NO: 24 is the nucleotide sequence of PGT128 human IgG4mut (S228P).
SEQ ID NO: 25 is the amino acid sequence of PGT128 human IgG4-heavy chain.
SEQ ID NO: 26 is the nucleotide sequence of PGT128 human IgG4-heavy chain.
SEQ ID NO: 27 is the amino acid sequence of PGT128 human IgG4-light chain.
SEQ ID NO: 28 is the nucleotide sequence of PGT128 human IgG4-light chain.
SEQ ID NO: 29 is the amino acid sequence of PG9 IgG1.
SEQ ID NO: 30 is the nucleotide sequence of PG9 IgG1.
SEQ ID NO: 31 is the amino acid sequence of PG9 human IgG4.
SEQ ID NO: 32 is the nucleotide sequence of PG9 human IgG4.
SEQ ID NO: 33 is the amino acid sequence of NIH45-46 human IgG1 antibody.
SEQ ID NO: 34 is the nucleotide sequence of NIH45-46 human IgG1 antibody.
SEQ ID NO: 35 is the amino acid sequence of NIH45-46 human IgG4 antibody.
SEQ ID NO: 36 is the nucleotide sequence of NIH45-46 human IgG4 antibody.
SEQ ID NO: 37 is the amino acid sequence of VRC01 human IgG1.
SEQ ID NO: 38 is the nucleotide sequence of VRC01 human IgG1.
SEQ ID NO: 39 is the amino acid sequence of VRC01 human IgG1 (heavy chain).
SEQ ID NO: 40 is the nucleotide sequence of VRC01 human IgG1 (heavy chain).
SEQ ID NO: 41 is the amino acid sequence of VRC01 human IgG1 (light chain).
SEQ ID NO: 42 is the nucleotide sequence of VRC01 human IgG1 (light chain).
SEQ ID NO: 43 is the amino acid sequence of VRC01 human IgG4.
SEQ ID NO: 44 is the nucleotide sequence of VRC01 human IgG4.
SEQ ID NO: 45 is the amino acid sequence of VRC01 human IgG4 mut (S228P).
SEQ ID NO: 46 is the nucleotide sequence of VRC01 human IgG4 mut (S228P).
SEQ ID NO: 47 is the amino acid sequence of VRC01 human IgG4 (heavy chain).
SEQ ID NO: 48 is the nucleotide sequence of VRC01 human IgG4 (heavy chain).
SEQ ID NO: 49 is the amino acid sequence of VRC01 human IgG4 (light chain).
SEQ ID NO: 50 is the nucleotide sequence of VRC01 human IgG4 (light chain).
SEQ ID NO: 51 is the amino acid sequence of VRC01 human IgG2.
SEQ ID NO: 52 is the nucleotide sequence of VRC01 human IgG2.
SEQ ID NO: 53 is the amino acid sequence of VRC01 human IgG3

SEQ ID NO: 54 is the nucleotide sequence of VRC01 human IgG3.
SEQ ID NO: 55 is the amino acid sequence of PGT145 Heavy Chain
SEQ ID NO: 56 is the nucleotide sequence of PGT145 Heavy Chain
SEQ ID NO: 57 is the amino acid sequence of PGT145 Kappa
SEQ ID NO: 58 is the nucleotide sequence of PGT145 Kappa
SEQ ID NO: 59 is the amino acid sequence of PGT151 Heavy Chain
SEQ ID NO: 60 is the nucleotide sequence of PGT151 Heavy Chain
SEQ ID NO: 61 is the amino acid sequence of PGT151 Kappa
SEQ ID NO: 62 is the nucleotide sequence of PGT151 Kappa
SEQ ID NO: 63 is the amino acid sequence of PGDM1400 Heavy Chain
SEQ ID NO: 64 is the nucleotide sequence of PGDM1400 Heavy Chain
SEQ ID NO: 65 is the amino acid sequence of PGDM1400 Kappa
SEQ ID NO: 66 is the nucleotide sequence of PGDM1400 Kappa
SEQ ID NO: 67 is the amino acid sequence of 12A21 Heavy Chain
SEQ ID NO: 68 is the nucleotide sequence of 12A21 Heavy Chain
SEQ ID NO: 69 is the amino acid sequence of 12A21 Kappa
SEQ ID NO: 70 is the nucleotide sequence of 12A21 Kappa
SEQ ID NO: 71 is the amino acid sequence of VRC3401 Heavy Chain
SEQ ID NO: 72 is the nucleotide sequence of VRC3401 Heavy Chain
SEQ ID NO: 73 is the amino acid sequence of VRC3401 Kappa
SEQ ID NO: 74 is the nucleotide sequence of VRC3401 Kappa
SEQ ID NO: 75 is the amino acid sequence of IOMA Heavy Chain
SEQ ID NO: 76 is the nucleotide sequence of IOMA Heavy Chain
SEQ ID NO: 77 is the amino acid sequence of IOMA Lambda
SEQ ID NO: 78 is the nucleotide sequence of IOMA Lambda
SEQ ID NO: 79 is the amino acid sequence of PGT130 Heavy Chain
SEQ ID NO: 80 is the nucleotide sequence of PGT130 Heavy Chain
SEQ ID NO: 81 is the amino acid sequence of PGT130 Lambda
SEQ ID NO: 82 is the nucleotide sequence of PGT130 Lambda
SEQ ID NO: 83 is the amino acid sequence of PGT121 Heavy Chain
SEQ ID NO: 84 is the nucleotide sequence of PGT121 Heavy Chain
SEQ ID NO: 85 is the amino acid sequence of PGT121 Lambda
SEQ ID NO: 86 is the nucleotide sequence of PGT121 Lambda
SEQ ID NO: 87 is the amino acid sequence of 2219 Heavy Chain
SEQ ID NO: 88 is the nucleotide sequence of 2219 Heavy Chain
SEQ ID NO: 89 is the amino acid sequence of 2219 Lambda
SEQ ID NO: 90 is the nucleotide sequence of 2219 Lambda
SEQ ID NO: 91 is the amino acid sequence of 3074 Heavy Chain
SEQ ID NO: 92 is the nucleotide sequence of 3074 Heavy Chain
SEQ ID NO: 93 is the amino acid sequence of 3074 Lambda
SEQ ID NO: 94 is the nucleotide sequence of 3074 Lambda
SEQ ID NO: 95 is the amino acid sequence of 4025 Heavy Chain
SEQ ID NO: 96 is the nucleotide sequence of 4025 Heavy Chain
SEQ ID NO: 97 is the amino acid sequence of 4025 Lambda
SEQ ID NO: 98 is the nucleotide sequence of 4025 Lambda
SEQ ID NO: 99 is the amino acid sequence of 2557 Heavy Chain
SEQ ID NO: 100 is the nucleotide sequence of 2557 Heavy Chain
SEQ ID NO: 101 is the amino acid sequence of 2557 Lambda
SEQ ID NO: 102 is the nucleotide sequence of 2557 Lambda
SEQ ID NO: 103 is the amino acid sequence of F425-B4e8 Heavy Chain
SEQ ID NO: 104 is the nucleotide sequence of F425-B4e8 Heavy Chain
SEQ ID NO: 105 is the amino acid sequence of F425-B4e8 Kappa
SEQ ID NO: 106 is the nucleotide sequence of F425-B4e8 Kappa
SEQ ID NO: 107 is the amino acid sequence of 17b Heavy Chain
SEQ ID NO: 108 is the nucleotide sequence of 17b Heavy Chain
SEQ ID NO: 109 is the amino acid sequence of 17b Kappa
SEQ ID NO: 110 is the nucleotide sequence of 17b Kappa
SEQ ID NO: 111 is the amino acid sequence of F105 Heavy Chain
SEQ ID NO: 112 is the nucleotide sequence of F105 Heavy Chain
SEQ ID NO: 113 is the amino acid sequence of F105 Kappa
SEQ ID NO: 114 is the nucleotide sequence of F105 Kappa
SEQ ID NO: 115 is the amino acid sequence of b12 Heavy Chain
SEQ ID NO: 116 is the nucleotide sequence of b12 Heavy Chain
SEQ ID NO: 117 is the amino acid sequence of b12 Kappa
SEQ ID NO: 118 is the nucleotide sequence of b12 Kappa
SEQ ID NO: 119 is the amino acid sequence of B6 Heavy Chain
SEQ ID NO: 120 is the nucleotide sequence of B6 Heavy Chain
SEQ ID NO: 121 is the amino acid sequence of B6 Kappa
SEQ ID NO: 122 is the nucleotide sequence of B6 Kappa SEQ ID NO: 123 is the amino acid sequence of 11A Heavy Chain SEQ ID NO: 124 is the nucleotide sequence of 11A Heavy Chain SEQ ID NO: 125 is the amino acid sequence of 11A Kappa SEQ ID NO: 126 is the nucleotide sequence of 11A Kappa SEQ ID NO: 127 is the amino acid sequence of 12N Heavy Chain SEQ ID NO: 128 is the nucleotide sequence of 12N Heavy Chain SEQ ID NO: 129 is the amino acid sequence of 12N Kappa SEQ ID NO: 130 is the nucleotide sequence of 12N Kappa SEQ ID NO: 131 is the amino acid sequence of 39F Heavy Chain SEQ ID NO: 132 is the nucleotide sequence of 39F Heavy Chain SEQ ID NO: 133 is the amino acid sequence of 39F Lambda pF SEQ ID NO: 134 is the nucleotide sequence of 39F Lambda pF SEQ ID NO: 135 is the nucleotide sequence of Subtype A Consensus Envelope with an IgE leader.

SEQ ID NO: 136 is the amino acid sequence of Subtype A Consensus Envelope with an IgE leader.

SEQ ID NO: 137 is the nucleotide sequence of Subtype B Consensus Envelope with an IgE leader.

SEQ ID NO: 138 is the amino acid sequence of Subtype B Consensus Envelope with an IgE leader.

SEQ ID NO: 139 is the nucleotide sequence of Subtype C Consensus Envelope with an IgE leader.

SEQ ID NO: 140 is the amino acid sequence of Subtype C Consensus Envelope with an IgE leader.

SEQ ID NO: 141 is the nucleotide sequence of Subtype D Consensus Envelope with an IgE leader.

SEQ ID NO: 142 is the amino acid sequence of Subtype D Consensus Envelope with an IgE leader.

SEQ ID NO: 143 is the nucleotide sequence of Subtype B Consensus Nef-Rev with an IgE leader.

SEQ ID NO: 144 is the amino acid sequence of Subtype B Consensus Nef-Rev with an IgE leader.

SEQ ID NO: 145 is the nucleotide sequence of Gag Consensus DNA sequence of subtype A, B, C and D with an IgE leader.

SEQ ID NO: 146 is the amino acid sequence of Gag Consensus DNA sequence of subtype A, B, C and D with an IgE leader.

SEQ ID NO: 147 is the amino acid sequence of Subtype A Consensus Envelope without an IgE leader.

SEQ ID NO: 148 is the amino acid sequence of Subtype B Consensus Envelope without an IgE leader.

SEQ ID NO: 149 is the amino acid sequence of Subtype C Consensus Envelope without an IgE leader.

SEQ ID NO: 150 is the amino acid sequence of Subtype D Consensus Envelope without an IgE leader.

SEQ ID NO: 151 is the amino acid sequence of Subtype B Consensus Nef-Rev without an IgE leader.

SEQ ID NO: 152 is the amino acid sequence of Gag Consensus DNA sequence of subtype A, B, C and D without an IgE leader.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a composition of the present invention to a subject after induction of the disease but before its clinical appearance. Repressing the disease involves administering a composition of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-HIV antibody. In one embodiment, the anti HIV-antibody is an anti-HIV broadly neutralizing antibody.

In one embodiment, the nucleotide sequence encoding an anti HIV-antibody comprises one or more codon optimized nucleic acid sequences encoding an amino acid sequence at least 95% homologous to an amino acid sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, or a fragment thereof.

In one embodiment, the nucleotide sequence encoding an anti-HIV antibody comprises one or more RNA sequence transcribed from one or more DNA sequences encoding an amino acid sequence at least 95% homologous to an amino acid sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, or a fragment thereof.

In one embodiment, the nucleotide sequence encoding an anti-HIV antibody comprises one or more codon optimized nucleic acid sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, SEQ ID NO:134, or a fragment thereof.

In one embodiment, the nucleotide sequence encoding an anti-HIV antibody comprises one or more RNA sequence transcribed from one or more DNA sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, SEQ ID NO:134, or a fragment thereof.

In one embodiment, the composition comprises a nucleotide sequence encoding a synthetic anti-HIV heavy chain. In one embodiment, the composition comprises a nucleotide sequence encoding a synthetic anti-HIV light chain. In one embodiment, the composition comprises a nucleotide sequence encoding a synthetic anti-HIV antibody. In one embodiment, the sequence encoding a synthetic anti-HIV antibody comprises a first sequence encoding a synthetic anti-HIV heavy chain and a second sequence encoding a synthetic anti-HIV light chain.

In one embodiment, the first nucleotide sequence encodes an amino acid sequence at least 90% homologous to SEQ ID NO:3 and the second nucleotide sequence encodes an amino acid sequence at least 90% homologous to SEQ ID NO:5. In one embodiment, the first nucleotide sequence encodes SEQ ID NO:3 and the second nucleotide sequence encodes SEQ ID NO:5.

In one embodiment, the first nucleotide sequence encodes an amino acid sequence at least 90% homologous to SEQ ID NO:11 and the second nucleotide sequence encodes an amino acid sequence at least 90% homologous to SEQ ID NO:13. In one embodiment, the first nucleotide sequence encodes SEQ ID NO:11 and the second nucleotide sequence encodes SEQ ID NO:13.

In one embodiment, the first nucleotide sequence encodes an amino acid sequence at least 90% homologous to SEQ ID NO:17 and the second nucleotide sequence encodes an amino acid sequence at least 90% homologous to SEQ ID NO:19. In one embodiment, the first nucleotide sequence encodes SEQ ID NO:17 and the second nucleotide sequence encodes SEQ ID NO:19.

In one embodiment, the first nucleotide sequence encodes an amino acid sequence at least 90% homologous to SEQ ID NO:25 and the second nucleotide sequence encodes an amino acid sequence at least 90% homologous to SEQ ID NO:27. In one embodiment, the first nucleotide sequence encodes SEQ ID NO:25 and the second nucleotide sequence encodes SEQ ID NO:27.

In one embodiment, the first nucleotide sequence encodes an amino acid sequence at least 90% homologous to SEQ ID NO:39 and the second nucleotide sequence encodes an amino acid sequence at least 90% homologous to SEQ ID NO:41. In one embodiment, the first nucleotide sequence encodes SEQ ID NO:39 and the second nucleotide sequence encodes SEQ ID NO:41.

In one embodiment, the first nucleotide sequence encodes an amino acid sequence at least 90% homologous to SEQ ID NO:47 and the second nucleotide sequence encodes an amino acid sequence at least 90% homologous to SEQ ID NO:49. In one embodiment, the first nucleotide sequence encodes SEQ ID NO:47 and the second nucleotide sequence encodes SEQ ID NO:49.

In one embodiment, the first nucleotide sequence encodes an amino acid sequence at least 90% homologous to SEQ ID NO:55 and the second nucleotide sequence encodes an amino acid sequence at least 90% homologous to SEQ ID NO:57. In one embodiment, the first nucleotide sequence encodes SEQ ID NO:55 and the second nucleotide sequence encodes SEQ ID NO:57.

In one embodiment, the first nucleotide sequence encodes an amino acid sequence at least 90% homologous to SEQ ID NO:59 and the second nucleotide sequence encodes an amino acid sequence at least 90% homologous to SEQ ID NO:61. In one embodiment, the first nucleotide sequence encodes SEQ ID NO:59 and the second nucleotide sequence encodes SEQ ID NO:61.

In one embodiment, the first nucleotide sequence encodes an amino acid sequence at least 90% homologous to SEQ ID NO:63 and the second nucleotide sequence encodes an amino acid sequence at least 90% homologous to SEQ ID NO:65. In one embodiment, the first nucleotide sequence encodes SEQ ID NO:63 and the second nucleotide sequence encodes SEQ ID NO:65.

In one embodiment, the first nucleotide sequence encodes an amino acid sequence at least 90% homologous to SEQ ID NO:67 and the second nucleotide sequence encodes an amino acid sequence at least 90% homologous to SEQ ID NO:69. In one embodiment, the first nucleotide sequence encodes SEQ ID NO:67 and the second nucleotide sequence encodes SEQ ID NO:69.

In one embodiment, the first nucleotide sequence encodes an amino acid sequence at least 90% homologous to SEQ ID NO:71 and the second nucleotide sequence encodes an amino acid sequence at least 90% homologous to SEQ ID NO:73. In one embodiment, the first nucleotide sequence encodes SEQ ID NO:71 and the second nucleotide sequence encodes SEQ ID NO:73.

In one embodiment, the first nucleotide sequence encodes an amino acid sequence at least 90% homologous to SEQ ID NO:75 and the second nucleotide sequence encodes an amino acid sequence at least 90% homologous to SEQ ID NO:77. In one embodiment, the first nucleotide sequence encodes SEQ ID NO:75 and the second nucleotide sequence encodes SEQ ID NO:77.

In one embodiment, the first nucleotide sequence encodes an amino acid sequence at least 90% homologous to SEQ ID NO:79 and the second nucleotide sequence encodes an amino acid sequence at least 90% homologous to SEQ ID NO:81. In one embodiment, the first nucleotide sequence encodes SEQ ID NO:79 and the second nucleotide sequence encodes SEQ ID NO:81.

In one embodiment, the first nucleotide sequence encodes an amino acid sequence at least 90% homologous to SEQ ID NO:83 and the second nucleotide sequence encodes an amino acid sequence at least 90% homologous to SEQ ID NO:85. In one embodiment, the first nucleotide sequence encodes SEQ ID NO:83 and the second nucleotide sequence encodes SEQ ID NO:85.

In one embodiment, the first nucleotide sequence encodes an amino acid sequence at least 90% homologous to SEQ ID NO:87 and the second nucleotide sequence encodes an amino acid sequence at least 90% homologous to SEQ ID NO:89. In one embodiment, the first nucleotide sequence encodes SEQ ID NO:87 and the second nucleotide sequence encodes SEQ ID NO:89.

In one embodiment, the first nucleotide sequence encodes an amino acid sequence at least 90% homologous to SEQ ID NO:91 and the second nucleotide sequence encodes an amino acid sequence at least 90% homologous to SEQ ID NO:93. In one embodiment, the first nucleotide sequence encodes SEQ ID NO:91 and the second nucleotide sequence encodes SEQ ID NO:93.

In one embodiment, the first nucleotide sequence encodes an amino acid sequence at least 90% homologous to SEQ ID NO:95 and the second nucleotide sequence encodes an amino acid sequence at least 90% homologous to SEQ ID NO:97. In one embodiment, the first nucleotide sequence encodes SEQ ID NO:95 and the second nucleotide sequence encodes SEQ ID NO:97.

In one embodiment, the first nucleotide sequence encodes an amino acid sequence at least 90% homologous to SEQ ID NO:99 and the second nucleotide sequence encodes an amino acid sequence at least 90% homologous to SEQ ID NO:101. In one embodiment, the first nucleotide sequence encodes SEQ ID NO:99 and the second nucleotide sequence encodes SEQ ID NO:101.

In one embodiment, the first nucleotide sequence encodes an amino acid sequence at least 90% homologous to SEQ ID NO:103 and the second nucleotide sequence encodes an amino acid sequence at least 90% homologous to SEQ ID NO: 105. In one embodiment, the first nucleotide sequence encodes SEQ ID NO:103 and the second nucleotide sequence encodes SEQ ID NO: 105.

In one embodiment, the first nucleotide sequence encodes an amino acid sequence at least 90% homologous to SEQ ID NO: 107 and the second nucleotide sequence encodes an amino acid sequence at least 90% homologous to SEQ ID NO: 109. In one embodiment, the first nucleotide sequence encodes SEQ ID NO: 107 and the second nucleotide sequence encodes SEQ ID NO: 109.

In one embodiment, the first nucleotide sequence encodes an amino acid sequence at least 90% homologous to SEQ ID NO:111 and the second nucleotide sequence encodes an amino acid sequence at least 90% homologous to SEQ ID NO: 113. In one embodiment, the first nucleotide sequence encodes SEQ ID NO:111 and the second nucleotide sequence encodes SEQ ID NO: 113.

In one embodiment, the first nucleotide sequence encodes an amino acid sequence at least 90% homologous to SEQ ID NO: 115 and the second nucleotide sequence encodes an amino acid sequence at least 90% homologous to SEQ ID NO: 117. In one embodiment, the first nucleotide sequence encodes SEQ ID NO: 115 and the second nucleotide sequence encodes SEQ ID NO: 117.

In one embodiment, the first nucleotide sequence encodes an amino acid sequence at least 90% homologous to SEQ ID NO: 119 and the second nucleotide sequence encodes an amino acid sequence at least 90% homologous to SEQ ID NO: 121. In one embodiment, the first nucleotide sequence encodes SEQ ID NO: 119 and the second nucleotide sequence encodes SEQ ID NO: 121.

In one embodiment, the first nucleotide sequence encodes an amino acid sequence at least 90% homologous to SEQ ID NO:123 and the second nucleotide sequence encodes an amino acid sequence at least 90% homologous to SEQ ID NO: 125. In one embodiment, the first nucleotide sequence encodes SEQ ID NO:123 and the second nucleotide sequence encodes SEQ ID NO: 125.

In one embodiment, the first nucleotide sequence encodes an amino acid sequence at least 90% homologous to SEQ ID NO: 1207 and the second nucleotide sequence encodes an amino acid sequence at least 90% homologous to SEQ ID NO: 129. In one embodiment, the first nucleotide sequence encodes SEQ ID NO: 1207 and the second nucleotide sequence encodes SEQ ID NO: 129.

In one embodiment, the first nucleotide sequence encodes an amino acid sequence at least 90% homologous to SEQ ID NO:131 and the second nucleotide sequence encodes an amino acid sequence at least 90% homologous to SEQ ID NO: 133. In one embodiment, the first nucleotide sequence encodes SEQ ID NO:131 and the second nucleotide sequence encodes SEQ ID NO: 133.

In one embodiment, the first nucleotide sequence comprises a nucleotide sequence at least 90% homologous to SEQ ID NO:4 and the second nucleotide sequence comprises a nucleotide sequence at least 90% homologous to SEQ ID NO:6. In one embodiment, the first nucleotide sequence comprises a nucleotide sequence as set forth in SEQ ID NO:4 and the second nucleotide sequence comprises a nucleotide sequence as set forth in SEQ ID NO:6.

In one embodiment, the first nucleotide sequence comprises a nucleotide sequence at least 90% homologous to SEQ ID NO:12 and the second nucleotide sequence comprises a nucleotide sequence at least 90% homologous to SEQ ID NO:14. In one embodiment, the first nucleotide sequence comprises a nucleotide sequence as set forth in SEQ ID NO:12 and the second nucleotide sequence comprises a nucleotide sequence as set forth in SEQ ID NO:14.

In one embodiment, the first nucleotide sequence comprises a nucleotide sequence at least 90% homologous to SEQ ID NO:18 and the second nucleotide sequence comprises a nucleotide sequence at least 90% homologous to SEQ ID NO:20. In one embodiment, the first nucleotide sequence comprises a nucleotide sequence as set forth in SEQ ID NO:18 and the second nucleotide sequence comprises a nucleotide sequence as set forth in SEQ ID NO:20.

In one embodiment, the first nucleotide sequence comprises a nucleotide sequence at least 90% homologous to SEQ ID NO:26 and the second nucleotide sequence comprises a nucleotide sequence at least 90% homologous to SEQ ID NO:28. In one embodiment, the first nucleotide sequence comprises a nucleotide sequence as set forth in SEQ ID NO:26 and the second nucleotide sequence comprises a nucleotide sequence as set forth in SEQ ID NO:28.

In one embodiment, the first nucleotide sequence comprises a nucleotide sequence at least 90% homologous to SEQ ID NO:40 and the second nucleotide sequence comprises a nucleotide sequence at least 90% homologous to SEQ ID NO:42. In one embodiment, the first nucleotide sequence comprises a nucleotide sequence as set forth in SEQ ID NO:40 and the second nucleotide sequence comprises a nucleotide sequence as set forth in SEQ ID NO:42.

In one embodiment, the first nucleotide sequence comprises a nucleotide sequence at least 90% homologous to SEQ ID NO:48 and the second nucleotide sequence comprises a nucleotide sequence at least 90% homologous to SEQ ID NO:50. In one embodiment, the first nucleotide sequence comprises a nucleotide sequence as set forth in SEQ ID NO:48 and the second nucleotide sequence comprises a nucleotide sequence as set forth in SEQ ID NO:50.

In one embodiment, the first nucleotide sequence comprises a nucleotide sequence at least 90% homologous to SEQ ID NO:56 and the second nucleotide sequence comprises a nucleotide sequence at least 90% homologous to SEQ ID NO:58. In one embodiment, the first nucleotide sequence comprises a nucleotide sequence as set forth in SEQ ID NO:56 and the second nucleotide sequence comprises a nucleotide sequence as set forth in SEQ ID NO:58.

In one embodiment, the first nucleotide sequence comprises a nucleotide sequence at least 90% homologous to SEQ ID NO:60 and the second nucleotide sequence comprises a nucleotide sequence at least 90% homologous to SEQ ID NO:62. In one embodiment, the first nucleotide sequence comprises a nucleotide sequence as set forth in SEQ ID NO:60 and the second nucleotide sequence comprises a nucleotide sequence as set forth in SEQ ID NO:62.

In one embodiment, the first nucleotide sequence comprises a nucleotide sequence at least 90% homologous to SEQ ID NO:64 and the second nucleotide sequence comprises a nucleotide sequence at least 90% homologous to SEQ ID NO:66. In one embodiment, the first nucleotide sequence comprises a nucleotide sequence as set forth in SEQ ID NO:64 and the second nucleotide sequence comprises a nucleotide sequence as set forth in SEQ ID NO:66.

In one embodiment, the first nucleotide sequence comprises a nucleotide sequence at least 90% homologous to SEQ ID NO:68 and the second nucleotide sequence comprises a nucleotide sequence at least 90% homologous to SEQ ID NO:70. In one embodiment, the first nucleotide sequence comprises a nucleotide sequence as set forth in SEQ ID NO:68 and the second nucleotide sequence comprises a nucleotide sequence as set forth in SEQ ID NO:70.

In one embodiment, the first nucleotide sequence comprises a nucleotide sequence at least 90% homologous to SEQ ID NO:72 and the second nucleotide sequence comprises a nucleotide sequence at least 90% homologous to SEQ ID NO:74. In one embodiment, the first nucleotide sequence comprises a nucleotide sequence as set forth in SEQ ID NO:72 and the second nucleotide sequence comprises a nucleotide sequence as set forth in SEQ ID NO:74.

In one embodiment, the first nucleotide sequence comprises a nucleotide sequence at least 90% homologous to SEQ ID NO:76 and the second nucleotide sequence comprises a nucleotide sequence at least 90% homologous to SEQ ID NO:78. In one embodiment, the first nucleotide sequence comprises a nucleotide sequence as set forth in SEQ ID NO:76 and the second nucleotide sequence comprises a nucleotide sequence as set forth in SEQ ID NO:78.

In one embodiment, the first nucleotide sequence comprises a nucleotide sequence at least 90% homologous to SEQ ID NO:80 and the second nucleotide sequence comprises a nucleotide sequence at least 90% homologous to SEQ ID NO: 82. In one embodiment, the first nucleotide sequence comprises a nucleotide sequence as set forth in SEQ ID NO:80 and the second nucleotide sequence comprises a nucleotide sequence as set forth in SEQ ID NO:82.

In one embodiment, the first nucleotide sequence comprises a nucleotide sequence at least 90% homologous to SEQ ID NO:84 and the second nucleotide sequence comprises a nucleotide sequence at least 90% homologous to SEQ ID NO: 86. In one embodiment, the first nucleotide sequence comprises a nucleotide sequence as set forth in SEQ ID NO:84 and the second nucleotide sequence comprises a nucleotide sequence as set forth in SEQ ID NO:86.

In one embodiment, the first nucleotide sequence comprises a nucleotide sequence at least 90% homologous to SEQ ID NO:88 and the second nucleotide sequence comprises a nucleotide sequence at least 90% homologous to SEQ ID NO:90. In one embodiment, the first nucleotide sequence comprises a nucleotide sequence as set forth in SEQ ID NO:88 and the second nucleotide sequence comprises a nucleotide sequence as set forth in SEQ ID NO:90.

In one embodiment, the first nucleotide sequence comprises a nucleotide sequence at least 90% homologous to SEQ ID NO:92 and the second nucleotide sequence comprises a nucleotide sequence at least 90% homologous to SEQ ID NO:94. In one embodiment, the first nucleotide sequence comprises a nucleotide sequence as set forth in SEQ ID NO:92 and the second nucleotide sequence comprises a nucleotide sequence as set forth in SEQ ID NO:94.

In one embodiment, the first nucleotide sequence comprises a nucleotide sequence at least 90% homologous to SEQ ID NO:96 and the second nucleotide sequence comprises a nucleotide sequence at least 90% homologous to SEQ ID NO:98. In one embodiment, the first nucleotide sequence comprises a nucleotide sequence as set forth in SEQ ID NO:96 and the second nucleotide sequence comprises a nucleotide sequence as set forth in SEQ ID NO:98.

In one embodiment, the first nucleotide sequence comprises a nucleotide sequence at least 90% homologous to SEQ ID NO:100 and the second nucleotide sequence comprises a nucleotide sequence at least 90% homologous to SEQ ID NO:102. In one embodiment, the first nucleotide sequence comprises a nucleotide sequence as set forth in SEQ ID NO:100 and the second nucleotide sequence comprises a nucleotide sequence as set forth in SEQ ID NO:102.

In one embodiment, the first nucleotide sequence comprises a nucleotide sequence at least 90% homologous to SEQ ID NO:104 and the second nucleotide sequence comprises a nucleotide sequence at least 90% homologous to SEQ ID NO: 106. In one embodiment, the first nucleotide sequence comprises a nucleotide sequence as set forth in SEQ ID NO:104 and the second nucleotide sequence comprises a nucleotide sequence as set forth in SEQ ID NO: 106.

In one embodiment, the first nucleotide sequence comprises a nucleotide sequence at least 90% homologous to SEQ ID NO: 108 and the second nucleotide sequence comprises a nucleotide sequence at least 90% homologous to SEQ ID NO: 110. In one embodiment, the first nucleotide sequence comprises a nucleotide sequence as set forth in SEQ ID NO: 108 and the second nucleotide sequence comprises a nucleotide sequence as set forth in SEQ ID NO: 110.

In one embodiment, the first nucleotide sequence comprises a nucleotide sequence at least 90% homologous to SEQ ID NO:112 and the second nucleotide sequence comprises a nucleotide sequence at least 90% homologous to SEQ ID NO: 114. In one embodiment, the first nucleotide sequence comprises a nucleotide sequence as set forth in SEQ ID NO:112 and the second nucleotide sequence comprises a nucleotide sequence as set forth in SEQ ID NO: 114.

In one embodiment, the first nucleotide sequence comprises a nucleotide sequence at least 90% homologous to SEQ ID NO: 116 and the second nucleotide sequence comprises a nucleotide sequence at least 90% homologous to SEQ ID NO: 118. In one embodiment, the first nucleotide sequence comprises a nucleotide sequence as set forth in SEQ ID NO: 116 and the second nucleotide sequence comprises a nucleotide sequence as set forth in SEQ ID NO: 118.

In one embodiment, the first nucleotide sequence comprises a nucleotide sequence at least 90% homologous to SEQ ID NO: 120 and the second nucleotide sequence comprises a nucleotide sequence at least 90% homologous to SEQ ID NO: 122. In one embodiment, the first nucleotide sequence comprises a nucleotide sequence as set forth in SEQ ID NO: 120 and the second nucleotide sequence comprises a nucleotide sequence as set forth in SEQ ID NO: 122.

In one embodiment, the first nucleotide sequence comprises a nucleotide sequence at least 90% homologous to SEQ ID NO:124 and the second nucleotide sequence comprises a nucleotide sequence at least 90% homologous to SEQ ID NO: 126. In one embodiment, the first nucleotide sequence comprises a nucleotide sequence as set forth in SEQ ID NO:124 and the second nucleotide sequence comprises a nucleotide sequence as set forth in SEQ ID NO: 126.

In one embodiment, the first nucleotide sequence comprises a nucleotide sequence at least 90% homologous to SEQ ID NO: 128 and the second nucleotide sequence comprises a nucleotide sequence at least 90% homologous to SEQ ID NO: 130. In one embodiment, the first nucleotide sequence comprises a nucleotide sequence as set forth in SEQ ID NO: 128 and the second nucleotide sequence comprises a nucleotide sequence as set forth in SEQ ID NO: 130.

In one embodiment, the first nucleotide sequence comprises a nucleotide sequence at least 90% homologous to SEQ ID NO:132 and the second nucleotide sequence comprises a nucleotide sequence at least 90% homologous to SEQ ID NO: 134. In one embodiment, the first nucleotide sequence comprises a nucleotide sequence as set forth in SEQ ID NO:132 and the second nucleotide sequence comprises a nucleotide sequence as set forth in SEQ ID NO: 134.

The composition of the invention can treat, prevent and/or protect against any disease, disorder, or condition associated with HIV infection. In certain embodiments, the composition can treat, prevent, and or/protect against viral infection. In certain embodiments, the composition can treat, prevent, and or/protect against condition associated with HIV infection.

In one embodiment, the present invention relates to a composition comprising a recombinant nucleic acid sequence encoding an IgG4 antibody. In one embodiment the IgG4 antibody comprises an amino acid substitution Ser288Pro. In one embodiment, IgG4 amino acid substitution Ser288Pro prevents IgG4 Fab arm switching. The IgG4 synthetic antibody can be for a foreign antigen or a self antigen. For example, IgG4 synthetic antibody can be for a viral antigen, a bacterial antigen, a parasitic antigen, a fungal antigen or a cancer antigen. Examples foreign and self antigens are described in U.S. Patent Application Publication No. US2015/0284448, the contents of which are incorporated herein in its entirety.

The composition comprising a recombinant nucleic acid sequence encoding an IgG4 antibody, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. RECOMBINANT NUCLEIC ACID SEQUENCE

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

In one embodiment, the heavy chain polypeptide comprises an amino acid sequence at least 95% identical to SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the heavy chain polypeptide comprises an amino acid sequence as set forth in SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the heavy chain polypeptide is encoded by a nucleotide sequence at least 95% identical to SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

In one embodiment, the heavy chain polypeptide is encoded by a nucleotide sequence as set forth in SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

In one embodiment, the light chain polypeptide comprises an amino acid sequence at least 95% identical to SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the light chain polypeptide comprises an amino acid sequence as set forth in SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the light chain polypeptide is encoded by a nucleotide sequence at least 95% identical to SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

In one embodiment, the light chain polypeptide is encoded by a nucleotide sequence as set forth in SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and W094/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

For example, in one embodiment, the first recombinant nucleic acid sequence encodes a heavy chain polypeptide having an amino acid sequence at least 95% homologous to SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, or SEQ ID NO:131.

In one embodiment, the first recombinant nucleic acid sequence comprises a nucleic acid sequence at least 95% homologous to SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, or SEQ ID NO:132.

In one embodiment, the second recombinant nucleic acid sequence encodes a light chain polypeptide having an amino acid sequence at least 95% homologous to SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, or SEQ ID NO:133.

In one embodiment, the second recombinant nucleic acid sequence comprises a nucleic acid sequence at least 95% homologous to SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, or SEQ ID NO:134.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, or SEQ ID NO:133, or a variant thereof or a fragment thereof.

In another embodiment, the nucleotide sequence comprises an RNA sequence transcribed by a DNA sequence encoding a polypeptide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, or SEQ ID NO:134, or a variant thereof or a fragment thereof.

Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation (4) Circular and Linear Vector The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. ANTIBODY

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be an IgG1 antibody, an IgG2 antibody, an IgG3 antibody, or an IgG4 antibody. The antibody can be a chimera of any of an IgG1 antibody, an IgG2 antibody, an IgG3 antibody, or an IgG4 antibody. In some embodiments, the antibody hinge domain is modified. For example, in one embodiment, the antibody includes the amino acid substitution Ser288Pro. In one embodiment, includes the amino acid substitution Ser288Pro prevents IgG4 Fab arm switching.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

b. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

5. ANTIGEN

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with an HIV infection. In one embodiment, the antigen can be HIV antigen.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

a. Viral Antigens

The viral antigen can be a viral antigen or fragment or variant thereof. The virus can be a disease causing virus. The virus can be the Human Immunodeficiency virus.

The antigen may be an HIV viral antigen, or fragment thereof, or variant thereof. The HIV antigen can be from a factor that allows the virus to replicate, infect or survive. Factors that allow HIV to replicate or survive include, but are not limited to structural proteins and non-structural proteins. Such a protein can be an envelope protein or a glycoprotein.

In some embodiments, the HIV antigen can be a subtype A envelope protein, subtype B envelope protein, subtype C envelope protein, subtype D envelope protein, subtype B Nef-Rev protein, Gag subtype A, B, C, or D protein, MPol protein, a nucleic acid or amino acid sequences of Env A, Env B, Env C, Env D, B Nef-Rev, Gag, or any combination thereof. In one embodiment, an envelope protein is an HIV glycoprotein. In one embodiment, the HIV glycoprotein (gp) is HIV gp120, HIV gp41, or gp160.

A synthetic antibody specific for HIV can include a Fab fragment comprising the amino acid sequence of SEQ ID NO:3, which is encoded by the nucleic acid sequence of SEQ ID NO:4, SEQ ID NO: 5, which is encoded by the nucleic acid sequence of SEQ ID NO:6, amino acid sequence of SEQ ID NO:11, which is encoded by the nucleic acid sequence of SEQ ID NO:12, or SEQ ID NO: 13, which is encoded by the nucleic acid sequence of SEQ ID NO:14. The synthetic antibody can comprise the amino acid sequence of SEQ ID NO:1, which is encoded by the nucleic acid sequence of SEQ ID NO:2, the amino acid sequence of SEQ ID NO:7, which is encoded by the nucleic acid sequence of SEQ ID NO:8, or the amino acid sequence of SEQ ID NO:9, which is encoded by the nucleic acid sequence of SEQ ID NO:10.

A synthetic antibody specific for HIV can include a Fab fragment comprising the amino acid sequence of SEQ ID NO:17, which is encoded by the nucleic acid sequence of SEQ ID NO:18, SEQ ID NO: 19, which is encoded by the nucleic acid sequence of SEQ ID NO:20, amino acid sequence of SEQ ID NO:25, which is encoded by the nucleic acid sequence of SEQ ID NO:26, or SEQ ID NO: 27, which is encoded by the nucleic acid sequence of SEQ ID NO:28. The synthetic antibody can comprise the amino acid sequence of SEQ ID NO:15, which is encoded by the nucleic acid sequence of SEQ ID NO:16, the amino acid sequence of SEQ ID NO:21, which is encoded by the nucleic acid sequence of SEQ ID NO:22, or the amino acid sequence of SEQ ID NO:23, which is encoded by the nucleic acid sequence of SEQ ID NO:24.

A synthetic antibody specific for HIV can include a Fab fragment comprising the amino acid sequence of SEQ ID NO:39, which is encoded by the nucleic acid sequence of SEQ ID NO:40, SEQ ID NO: 41, which is encoded by the nucleic acid sequence of SEQ ID NO:42, amino acid sequence of SEQ ID NO:47, which is encoded by the nucleic acid sequence of SEQ ID NO:48, or SEQ ID NO: 49, which is encoded by the nucleic acid sequence of SEQ ID NO:50. The synthetic antibody can comprise the amino acid sequence of SEQ ID NO:37, which is encoded by the nucleic acid sequence of SEQ ID NO:38, the amino acid sequence of SEQ ID NO:43, which is encoded by the nucleic acid sequence of SEQ ID NO:44, the amino acid sequence of SEQ ID NO:45, which is encoded by the nucleic acid sequence of SEQ ID NO:46, the amino acid sequence of SEQ ID NO:51, which is encoded by the nucleic acid sequence of SEQ ID NO:52, or the amino acid sequence of SEQ ID NO:53, which is encoded by the nucleic acid sequence of SEQ ID NO:54.

The synthetic antibody can comprise the amino acid sequence of SEQ ID NO:29, which is encoded by the nucleic acid sequence of SEQ ID NO:30, the amino acid sequence of SEQ ID NO:31, which is encoded by the nucleic acid sequence of SEQ ID NO:32, the amino acid sequence of SEQ ID NO:33, which is encoded by the nucleic acid sequence of SEQ ID NO:34, or the amino acid sequence of SEQ ID NO:35 which is encoded by the nucleic acid sequence of SEQ ID NO:36.

A synthetic antibody specific for HIV can include an Ig comprising the amino acid sequence of SEQ ID NO:1.

The Ig can comprise the amino acid sequence of SEQ ID NO:7, which is encoded by the nucleic acid sequence of SEQ ID NO:8. The Ig can comprise the amino acid sequence of SEQ ID NO: 9, which is encoded by the nucleic acid sequence of SEQ ID NO:10. The Ig can comprise the amino acid sequence of SEQ ID NO:15, which is encoded by the nucleic acid sequence of SEQ ID NO:16. The Ig can comprise the amino acid sequence of SEQ ID NO: 21, which is encoded by the nucleic acid sequence of SEQ ID NO:22. The Ig can comprise the amino acid sequence of SEQ ID NO: 23, which is encoded by the nucleic acid sequence of SEQ ID NO: 24. The Ig can comprise the amino acid sequence of SEQ ID NO: 29, which is encoded by the nucleic acid sequence of SEQ ID NO: 30. The Ig can comprise the amino acid sequence of SEQ ID NO:31, which is encoded by the nucleic acid sequence of SEQ ID NO: 32. The Ig can comprise the amino acid sequence of SEQ ID NO:33, which is encoded by the nucleic acid sequence of SEQ ID NO: 34. The Ig can comprise the amino acid sequence of SEQ ID NO:35, which is encoded by the nucleic acid sequence of SEQ ID NO: 36. The Ig can comprise the amino acid sequence of SEQ ID NO:37, which is encoded by the nucleic acid sequence of SEQ ID NO: 38. The Ig can comprise the amino acid sequence of SEQ ID NO:43, which is encoded by the nucleic acid sequence of SEQ ID NO: 44. The Ig can comprise the amino acid sequence of SEQ ID NO:45, which is encoded by the nucleic acid sequence of SEQ ID NO: 46. The Ig can comprise the amino acid sequence of SEQ ID NO:51, which is encoded by the nucleic acid sequence of SEQ ID NO: 52. The Ig can comprise the amino acid sequence of SEQ ID NO:53, which is encoded by the nucleic acid sequence of SEQ ID NO:54. The Ig can comprise the amino acid sequence of SEQ ID NO:55, which is encoded by the nucleic acid sequence of SEQ ID NO: 56. The Ig can comprise the amino acid sequence of SEQ ID NO:57, which is encoded by the nucleic acid sequence of SEQ ID NO: 58. The Ig can comprise the amino acid sequence of SEQ ID NO:59, which is encoded by the nucleic acid sequence of SEQ ID NO: 60. The Ig can comprise the amino acid sequence of SEQ ID NO:61, which is encoded by the nucleic acid sequence of SEQ ID NO: 62. The Ig can comprise the amino acid sequence of SEQ ID NO:63, which is encoded by the nucleic acid sequence of SEQ ID NO: 64. The Ig can comprise the amino acid sequence of SEQ ID NO:65, which is encoded by the nucleic acid sequence of SEQ ID NO: 66. The Ig can comprise the amino acid sequence of SEQ ID NO:67, which is encoded by the nucleic acid sequence of SEQ ID NO: 68. The Ig can comprise the amino acid sequence of SEQ ID NO:69, which is encoded by the nucleic acid sequence of SEQ ID NO: 70. The Ig can comprise the amino acid sequence of SEQ ID NO:71, which is encoded by the nucleic acid sequence of SEQ ID NO: 72. The Ig can comprise the amino acid sequence of SEQ ID NO:73, which is encoded by the nucleic acid sequence of SEQ ID NO: 74. The Ig can comprise the amino acid sequence of SEQ ID NO:75, which is encoded by the nucleic acid sequence of SEQ ID NO: 76. The Ig can comprise the amino acid sequence of SEQ ID NO:77, which is encoded by the nucleic acid sequence of SEQ ID NO: 78. The Ig can comprise the amino acid sequence of SEQ ID NO:79, which is encoded by the nucleic acid sequence of SEQ ID NO: 80. The Ig can comprise the amino acid sequence of SEQ ID NO:81, which is encoded by the nucleic acid sequence of SEQ ID NO: 82. The Ig can comprise the amino acid sequence of SEQ ID NO:83, which is encoded by the nucleic acid sequence of SEQ ID NO: 84. The Ig can comprise the amino acid sequence of SEQ ID NO:85, which is encoded by the nucleic acid sequence of SEQ ID NO: 86. The Ig can comprise the amino acid sequence of SEQ ID NO:87, which is encoded by the nucleic acid sequence of SEQ ID NO: 88. The Ig can comprise the amino acid sequence of SEQ ID NO:89, which is encoded by the nucleic acid sequence of SEQ ID NO: 90. The Ig can comprise the amino acid sequence of SEQ ID NO:91, which is encoded by the nucleic acid sequence of SEQ ID NO: 92. The Ig can comprise the amino acid sequence of SEQ ID NO:93, which is encoded by the nucleic acid sequence of SEQ ID NO: 94. The Ig can comprise the amino acid sequence of SEQ ID NO:95, which is encoded by the nucleic acid sequence of SEQ ID NO: 96. The Ig can comprise the amino acid sequence of SEQ ID NO:97, which is encoded by the nucleic acid sequence of SEQ ID NO: 98. The Ig can comprise the amino acid sequence of SEQ ID NO:99, which is encoded by the nucleic acid sequence of SEQ ID NO: 100. The Ig can comprise the amino acid sequence of SEQ ID NO:101, which is encoded by the nucleic acid sequence of SEQ ID NO: 102. The Ig can comprise the amino acid sequence of SEQ ID NO:103, which is encoded by the nucleic acid sequence of SEQ ID NO: 104. The Ig can comprise the amino acid sequence of SEQ ID NO:105, which is encoded by the nucleic acid sequence of SEQ ID NO: 106. The Ig can comprise the amino acid sequence of SEQ ID NO:107, which is encoded by the nucleic acid sequence of SEQ ID NO: 108. The Ig can comprise the amino acid sequence of SEQ ID NO:109, which is encoded by the nucleic acid sequence of SEQ ID NO: 110. The Ig can comprise the amino acid sequence of SEQ ID NO:111, which is encoded by the nucleic acid sequence of SEQ ID NO: 112. The Ig can comprise the amino acid sequence of SEQ ID NO:113, which is encoded by the nucleic acid sequence of SEQ ID NO: 114. The Ig can comprise the amino acid sequence of SEQ ID NO:115, which is encoded by the nucleic acid sequence of SEQ ID NO: 116. The Ig can comprise the amino acid sequence of SEQ ID NO:117, which is encoded by the nucleic acid sequence of SEQ ID NO: 118. The Ig can comprise the amino acid sequence of SEQ ID NO:119, which is encoded by the nucleic acid sequence of SEQ ID NO: 120. The Ig can comprise the amino acid sequence of SEQ ID NO:121, which is encoded by the nucleic acid sequence of SEQ ID NO: 122. The Ig can comprise the amino acid sequence of SEQ ID NO:123, which is encoded by the nucleic acid sequence of SEQ ID NO: 124. The Ig can comprise the amino acid sequence of SEQ ID NO:125, which is encoded by the nucleic acid sequence of SEQ ID NO: 126. The Ig can comprise the amino acid sequence of SEQ ID NO:127, which is encoded by the nucleic acid sequence of SEQ ID NO: 128. The Ig can comprise the amino acid sequence of SEQ ID NO:129, which is encoded by the nucleic acid sequence of SEQ ID NO: 130. The Ig can comprise the amino acid sequence of SEQ ID NO:131, which is encoded by the nucleic acid sequence of SEQ ID NO: 132. The Ig can comprise the amino acid sequence of SEQ ID NO:133, which is encoded by the nucleic acid sequence of SEQ ID NO: 134.

6. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly- L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Applications Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. METHOD OF TREATMENT

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing a HIV infection. In one embodiment, the method treats, protects against, and/or prevents a disease associated with HIV.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. USE IN COMBINATION WITH ANTIRETROVIRALS

The present invention also provides a method of treating, protecting against, and/or preventing disease in a subject in need thereof by administering a combination of the synthetic antibody and a therapeutic antiretroviral agent.

The synthetic antibody and an antiretroviral agent may be administered using any suitable method such that a combination of the synthetic antibody and antiretroviral agent are both present in the subject. In one embodiment, the method may comprise administration of a first composition comprising a synthetic antibody of the invention by any of the methods described in detail above and administration of a second composition comprising an antiretroviral agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antiretroviral agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antiretroviral agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antiretroviral agent. In one embodiment, the method may comprise administration of a first composition comprising an antiretroviral agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antiretroviral agent. In one embodiment, the method may comprise administration of a first composition comprising a synthetic antibody of the invention by any of the methods described in detail above and a second composition comprising an antiretroviral agent concurrently. In one embodiment, the method may comprise administration of a first composition comprising a synthetic antibody of the invention by any of the methods described in detail above and a second composition comprising an antiretroviral agent concurrently. In one embodiment, the method may comprise administration of a single composition comprising a synthetic antibody of the invention and an antiretroviral agent.

Non-limiting examples of antiretrovirals that can be used in combination with the synthetic antibody of the invention include Nucleoside Reverse Transcriptase Inhibitors (NRTIs), Non-Nucleoside Reverse Transcriptase Inhibitors (NNRTIs), Protease Inhibitors (PIs), Fusion Inhibitors, CCRF Antagonists, Integrase Inhibitors, Post-Attachment Inhibitors, Pharmacokinetic Inhibitors, and any combination thereof. Exemplary antiretrovirals include, but are not limited to abacavir, emtricitabine, lamivudine, tenofovir, zidovudine, efavirenz, etravirine, nevirapine, rilpivirine, atazanavir, darunavir, fosamprenavir, ritonavir, saquinavir, tipranavir, enfuvirtide, maraviroc, dolutegravir, raltegravir, ibalizumab, and cobicistat. The present invention has multiple aspects, illustrated by the following non-limiting examples.

12. GENERATION OF SYNTHETIC ANTIBODIES IN VITRO AND EX VIVO

In one embodiment, the synthetic antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

13. USE IN COMBINATION WITH VACCINES

The present invention also provides a method of treating, protecting against, preventing disease, and/or inducing an immune response in a subject in need thereof by administering a combination of the synthetic antibody and a vaccine. In one embodiment, the vaccine is a DNA vaccine.

The synthetic antibody and vaccine may be administered using any suitable method such that a combination of the synthetic antibody and vaccine are both present in the subject. In one embodiment, the method may comprise administration of a first composition comprising a synthetic antibody of the invention by any of the methods described in detail above and administration of a second composition comprising an vaccine less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising a vaccine more than 1, more than 2, more than 3, more than 4, more than 5, more than 6, more than 7, more than 8, more than 9 or more than 10 days following administration of the synthetic antibody. In one embodiment, the method may comprise administration of a first composition comprising a vaccine and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the vaccine. In one embodiment, the method may comprise administration of a first composition comprising a vaccine and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the vaccine. In one embodiment, the method may comprise administration of a first composition comprising a synthetic antibody of the invention by any of the methods described in detail above and a second composition comprising a vaccine concurrently. In one embodiment, the method may comprise administration of a first composition comprising a synthetic antibody of the invention by any of the methods described in detail above and a second composition comprising a vaccine concurrently. In one embodiment, the method may comprise administration of a single composition comprising a synthetic antibody of the invention and a vaccine.

In one embodiment, the vaccine is a DNA vaccine. In one embodiment, the synthetic antibody is a DMAb.

The DNA vaccine and the DMAb may be administered at the same time or at different times. In one embodiment, the DNA vaccine and the DMAb are administered simultaneously. In one embodiment, the DNA vaccine is administered before the DMAb. In one embodiment, the DMAb is administered before the DNA vaccine.

In certain embodiments, the DNA vaccine is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DMAb is administered. In certain embodiments, the DNA vaccine is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DMAb is administered. In certain embodiments, the DNA vaccine is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DMAb is administered.

In certain embodiments, the DMAb is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DNA vaccine is administered. In certain embodiments, the DMAb is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DNA vaccine is administered. In certain embodiments, the DMAb is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DNA vaccine is administered.

In certain embodiments, the DMAb and DNA vaccine are administered once. In certain embodiments, the DMAb and/or the DNA vaccine are administered more than once. In certain embodiments, administration of the DMAb and DNA vaccine provides a persistent and systemic immune response.

The composition can comprise 1 or more, 2 or more, 3 or more, 4 or more, 5 or more, 6 or more, 7 or more, 8 or more, 9 or more, or 10 or more DNA vaccines encoding an antigen. The composition may comprise 1 or more, 2 or more, 3 or more, 4 or more, 5 or more, 6 or more, 7 or more, 8 or more, 9 or more, or 10 or more DNA encoded synthetic antibodies or fragments thereof.

a. DNA Vaccine

The vaccine can be a DNA vaccine, a peptide vaccine, or a combination DNA and peptide vaccine. The DNA vaccine can include a nucleic acid sequence encoding the antigen. The nucleic acid sequence can be DNA, RNA, cDNA, a variant thereof, a fragment thereof, or a combination thereof. The nucleic acid sequence can also include additional sequences that encode linker, leader, or tag sequences that are linked to the antigen by a peptide bond. The peptide vaccine can include an antigenic peptide, an antigenic protein, a variant thereof, a fragment thereof, or a combination thereof. The combination DNA and peptide vaccine can include the above described nucleic acid sequence encoding the antigen and the antigenic peptide or protein, in which the antigenic peptide or protein and the encoded antigen have the same amino acid sequence The vaccine can induce a humoral immune response in the subject administered the vaccine. The induced humoral immune response can be specific for the antigen. The induced humoral immune response can be reactive with the antigen. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the vaccine can include an increased level of neutralizing antibodies associated with the subject administered the vaccine as compared to a subject not administered the vaccine. The neutralizing antibodies can be specific for the antigen. The neutralizing antibodies can be reactive with the antigen. The neutralizing antibodies can provide protection against and/or treatment of infection and its associated pathologies in the subject administered the vaccine.

The humoral immune response induced by the vaccine can include an increased level of IgG antibodies associated with the subject administered the vaccine as compared to a subject not administered the vaccine. These IgG antibodies can be specific for the antigen. These IgG antibodies can be reactive with the antigen. Preferably, the humoral response is cross-reactive against two or more strains of the antigen. The level of IgG antibody associated with the subject administered the vaccine can be increased by about 1.5-fold to about 16-fold, about 2-fold to about 12-fold, or about 3-fold to about 10-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the vaccine.

The vaccine can induce a cellular immune response in the subject administered the vaccine. The induced cellular immune response can be specific for the antigen. The induced cellular immune response can be reactive to the antigen. Preferably, the cellular response is cross-reactive against two or more strains of the antigen. The induced cellular immune response can include eliciting a CD8+ T cell response. The elicited CD8+ T cell response can be reactive with the antigen. The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the vaccine as compared to the subject not administered the vaccine. The CD8+ T cell response associated with the subject administered the vaccine can be increased by about 2-fold to about 30-fold, about 3-fold to about 25-fold, or about 4-fold to about 20-fold as compared to the subject not administered the vaccine. The CD8+ T cell response associated with the subject administered the vaccine can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the vaccine.

The induced cellular immune response can include an increased frequency of CD3+CD8+ T cells that produce IFN-γ. The frequency of CD3+CD8+ IFN-γ+ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3+CD8+ T cells that produce TNF-α. The frequency of CD3+CD8+TNF-α+ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to the subject not administered the vaccine.

The induced cellular immune response can include an increased frequency of CD3+CD8+ T cells that produce IL-2. The frequency of CD3+CD8+IL-2+ T cells associated with the subject administered the vaccine can be increased by at least about 0.5-fold, 1.0-fold, 1.5-fold, 2.0-fold, 2.5-fold, 3.0-fold, 3.5-fold, 4.0-fold, 4.5-fold, or 5.0-fold as compared to the subject not administered the vaccine.

The induced cellular immune response can include an increased frequency of CD3+CD8+ T cells that produce both IFN-γ and TNF-α. The frequency of CD3+CD8+IFN-γ+ TNF-α+ T cells associated with the subject administered the vaccine can be increased by at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, or 180-fold as compared to the subject not administered the vaccine.

The cellular immune response induced by the vaccine can include eliciting a CD4+ T cell response. The elicited CD4+ T cell response can be reactive with the desired antigen. The elicited CD4⁺ T cell response can be polyfunctional. The induced cellular immune response can include eliciting a CD4⁺ T cell response, in which the CD4⁺ T cells produce IFN-γ, TNF-α, IL-2, or a combination of IFN-γ and TNF-α.

The induced cellular immune response can include an increased frequency of CD3⁺CD4⁺ T cells that produce IFN-γ. The frequency of CD3⁺CD4⁺IFN-γ⁺ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3⁺CD4⁺ T cells that produce TNF-α. The frequency of CD3⁺CD4⁺TNF-α⁺ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to the subject not administered the vaccine.

The induced cellular immune response can include an increased frequency of CD3⁺CD4⁺ T cells that produce IL-2. The frequency of CD3⁺CD4⁺IL-2⁺ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 45-fold, 50-fold, 55-fold, or 60-fold as compared to the subject not administered the vaccine.

The induced cellular immune response can include an increased frequency of CD3⁺CD4⁺ T cells that produce both IFN-γ and TNF-α. The frequency of CD3⁺CD4⁺IFN-γ⁺ TNF-α⁺ associated with the subject administered the vaccine can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to the subject not administered the vaccine.

The vaccine of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The vaccine can further induce an immune response when administered to different tissues such as the muscle or skin. The vaccine can further induce an immune response when administered via electroporation, or injection, or subcutaneously, or intramuscularly b. Antigen The antigen of the vaccine may be the same antigen across different subtypes of HIV. The vaccine may comprise 1 or more, 2 or more, 3 or more, 4 or more, or 5 or more DNA sequences encoding a particular protein sequence isolated from HIV subtypes A, B, C, D, or other HIV subtypes, or a combination or variant thereof. The antigen of the vaccine may be the same antigen across different subtypes of HIV. The vaccine may comprise 1 or more, 2 or more, 3 or more, 4 or more, or 5 or more consensus DNA sequences encoding a particular protein sequence isolated from HIV subtypes A, B, C, D, or other HIV subtypes, or a combination or variant thereof. The vaccine may comprise a DNA sequence encoding a particular protein sequence isolated from HIV subtype A, a second DNA sequence encoding a particular protein sequence isolated from HIV subtype B, a third DNA sequence encoding a particular protein sequence isolated from HIV subtype C, a fourth DNA sequence encoding a particular protein sequence isolated from HIV subtype D, or a combination thereof. The vaccine may comprise a consensus DNA sequence encoding a particular protein sequence isolated from HIV subtype A, a second consensus DNA sequence encoding a particular protein sequence isolated from HIV subtype B, a third consensus DNA sequence encoding a particular protein sequence isolated from HIV subtype C, a fourth consensus DNA sequence encoding a particular protein sequence isolated from HIV subtype D, or a combination thereof. The vaccine may comprise a consensus DNA sequence or variant thereof encoding a particular HIV subtype A protein sequence or variant thereof, a second consensus DNA sequence or variant thereof encoding a particular HIV subtype B protein sequence or variant thereof, a third consensus DNA sequence or variant thereof encoding a particular HIV subtype C protein sequence or variant thereof, a fourth consensus DNA sequence or variant thereof encoding a particular HIV subtype D protein sequence or variant thereof.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or a subtype B consensus Envelope protein sequence.

In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype A Nef-Rev consensus envelope DNA sequence construct, an IgE leader sequence linked to a consensus sequence for Subtype A Nef-Rev protein, or a Subtype A Nef-Rev consensus protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence.

In some embodiments, the HIV antigen can be a subtype C Nef-Rev consensus envelope DNA sequence construct, an IgE leader sequence linked to a consensus sequence for Subtype C Nef-Rev protein, or a Subtype C Nef-Rev consensus protein sequence.

In some embodiments, the HIV antigen can be a subtype D Nef-Rev consensus envelope DNA sequence construct, an IgE leader sequence linked to a consensus sequence for Subtype D Nef-Rev protein, or a Subtype D Nef-Rev consensus protein sequence.

In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments, the HIV antigen can be a MPol DNA sequence or a MPol protein sequence. The HIV antigen can be nucleic acid or amino acid sequences of Env A, Env B, Env C, Env D, B Nef-Rev, Gag, MPol, or any combination thereof.

In other embodiments, the HIV antigen may be a DNA sequence or consensus sequence of subtype A, B, C, or D encoding gp140 or consensus gp140 protein. In other embodiments, the HIV antigen may be a DNA sequence or consensus sequence of subtype A, B, C, or D encoding gp140 or consensus gp120 protein. In other embodiments, the HIV antigen gp140 peptide sequence or gp120 consensus peptide sequence of subtype A, B, C, or D. In other embodiments, the HIV antigen gp120 peptide sequence or gp140 consensus peptide sequence of subtype A, B, C, or D.

Examples of DNA vaccines encoding HIV antigens include those described in U.S. Pat. No. 8,168,769 and WO2015/073291, the contents of each are fully incorporated by reference In some embodiments, a DNA vaccine encoding a HIV antigen may include a nucleic acid sequence encoding an amino acid sequence comprising one of SEQ ID NO: 136, SEQ ID NO: 138, SEQ ID NO: 140, SEQ ID NO: 142, SEQ ID NO: 144, SEQ ID NO: 146, SEQ ID NO: 147, SEQ ID NO: 148, SEQ ID NO: 149, SEQ ID NO: 150, SEQ ID NO: 151, or SEQ ID NO: 152. In some embodiments, the DNA vaccine encoding a HIV antigen may include a nucleic acid sequence comprising the sequence of one of SEQ ID NO: 135, SEQ ID NO: 137, SEQ ID NO: 139, SEQ ID NO: 141, SEQ ID NO: 143, or SEQ ID NO: 145.

The antigen can affect a mammal, which can be a human, chimpanzee, dog, cat, horse, cow, mouse, or rat. The antigen can be contained in a protein from a mammal, which can be a human, chimpanzee, dog, cat, horse, cow, pig, sheep, mouse, or rat.

c. DNA

The composition may comprise the DNA. Also provided herein is a DNA that encodes the antigen as described above. The DNA can include an encoding sequence that encodes the antigen. The DNA can also include additional sequences that encode linker or tag sequences that are linked to the antigen by a peptide bond.

d. Vector

The composition may comprise a vector that includes the DNA encoding the antigen. The vector can be capable of expressing the antigen. The vector may be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

i. Expression Vectors

The vector may be circular plasmid or a linear nucleic acid vaccine. The circular plasmid and linear nucleic acid are capable of directing expression of a particular nucleotide sequence in an appropriate subject cell. The vector may have a promoter operably linked to the antigen-encoding nucleotide sequence, which may be operably linked to termination signals. The vector may also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

ii. Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing the DNA and enabling a cell to translate the sequence to a antigen that is recognized by the immune system. The vector can be combined with antigen at a mass ratio of between 5:1 and 1:5, or of between 1:1 and 2:1.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid may be pNP (Puerto Rico/34) or pM2 (New Caledonia/99). See FIG. 1. The plasmid may be pVAX, pcDNA3.0, or provax, or any other expression vector capable of expressing the DNA and enabling a cell to translate the sequence to a antigen that is recognized by the immune system.

The LEC may be perM2. The LEC may be perNP. perNP and perMR may be derived from pNP (Puerto Rico/34) and pM2 (New Caledonia/99), respectively. See FIG. 34. The LEC may be combined with antigen at a mass ratio of between 5:1 and 1:5, or of between 1:1 to 2:1.

iii. Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

e. Other Components of Vaccine-Adjuvants, Excipients

The composition may further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate is may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

14. EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The studies presented herein demonstrate in vivo production of broadly neutralizing and non-neutralizing antibodies against HIV-1 by novel DNA encoded mAb technology.

As described herein, an optimized, synthetic DNA vector platform (dMAb) to deliver encoding broadly neutralizing antibodies (bNabs) and non-neutralizing antibodies (non-Nabs) against HIV was designed. Plasmids encoding the heavy and light chain of numerous bNabs were designed. Using various optimization strategies including sequence, formulation, structural and delivery modifications, high levels (1-100 μg/ml) of serum bNabs are generated in mice. Antibody levels are detectable in the serum as early as two days after DNA injection with electroporation. Furthermore, these antibodies from the serum retain functional capabilities including binding to Env and neutralization as measured by the TZM-bl neutralization assay. To lower the possibility of viral escape in a clinical scenario, multiple HIV-1 bNabs can be encoded and expressed simultaneously.

Example 2—DMABs Encoding HIV bnAbs

The studies presented herein demonstrate DNA monoclonal antibodies are able to encode HIV bNabs and non-Nabs.

Figure 3:
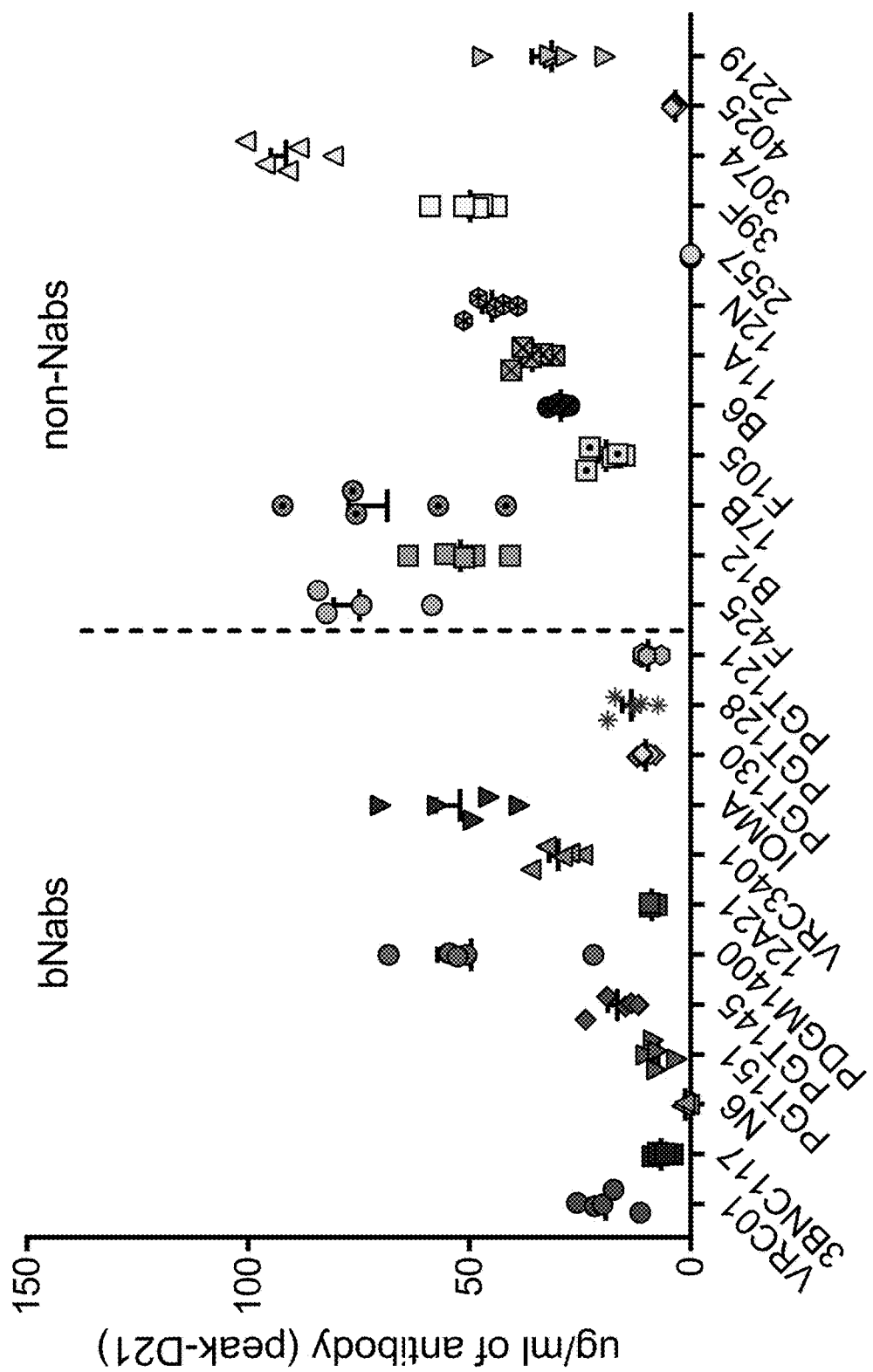
FIG. 3, depicts experimental results demonstrating in vivo expression of HIV dMAb constructs. BalbC mice were injected followed by electroporation with HIV dMAb constructs. Both broadly neutralizing antibodies and non-neutralizing antibodies express in mice.
Figure 4:
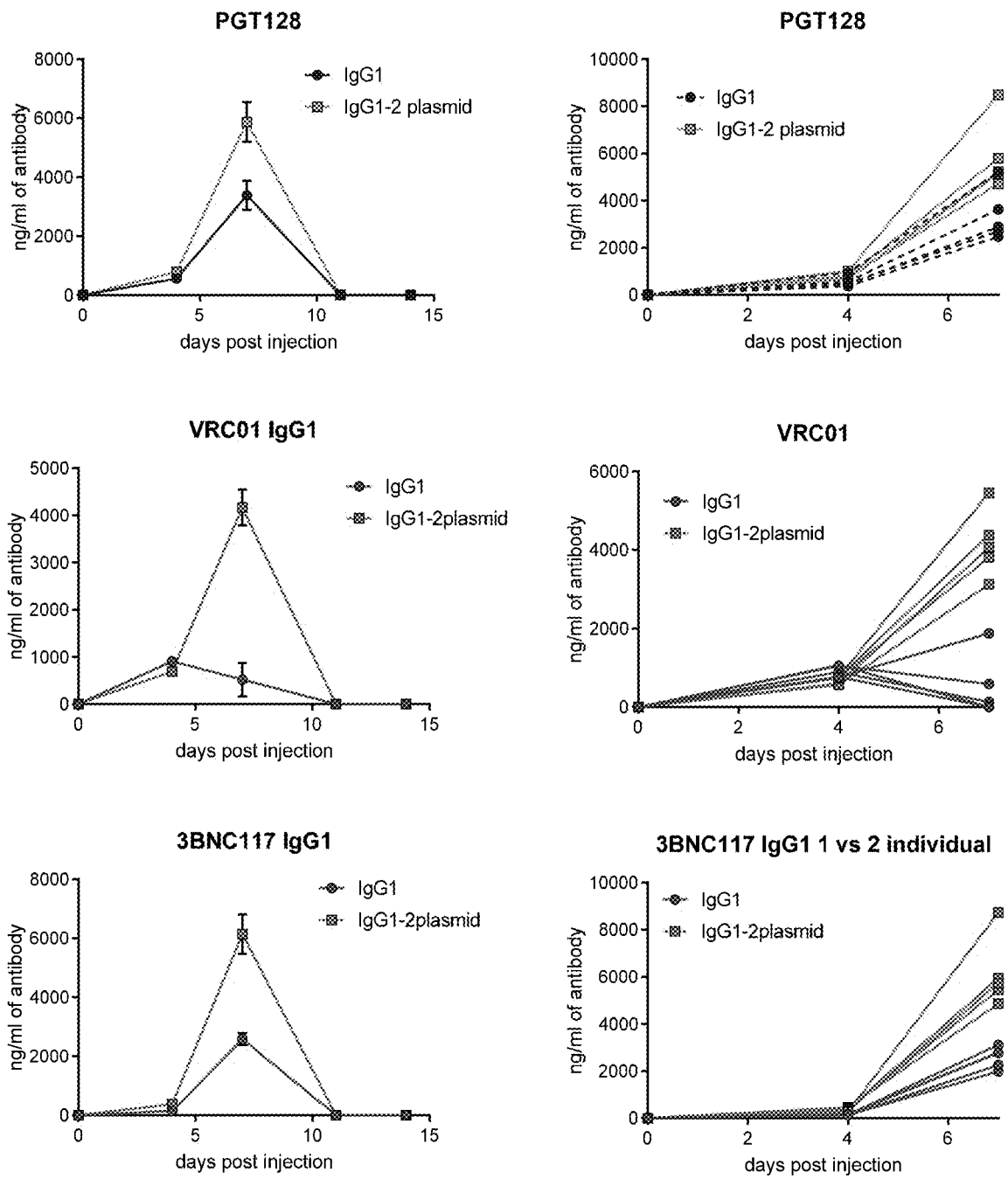
FIG. 4 depicts experimental results demonstrating how two plasmids expressing the heavy and light chain of the IgG1 on separate plasmids can increase expression levels over a single plasmid expressing both the heavy and light chain IgG1 across multiple HIV dMAbs.

Some HIV dMAbs express at very low levels (FIG. 3) thus we initially looked to determine if dMAb levels could be increases when the heavy and light change were encoded on separate plasmids. Encoding the heavy and light chain on two separate plasmids increases in vivo dMAb production of various HIV bNabs over that of single plasmid injection (FIG. 4).

Figures 5A, 5B, 5C:
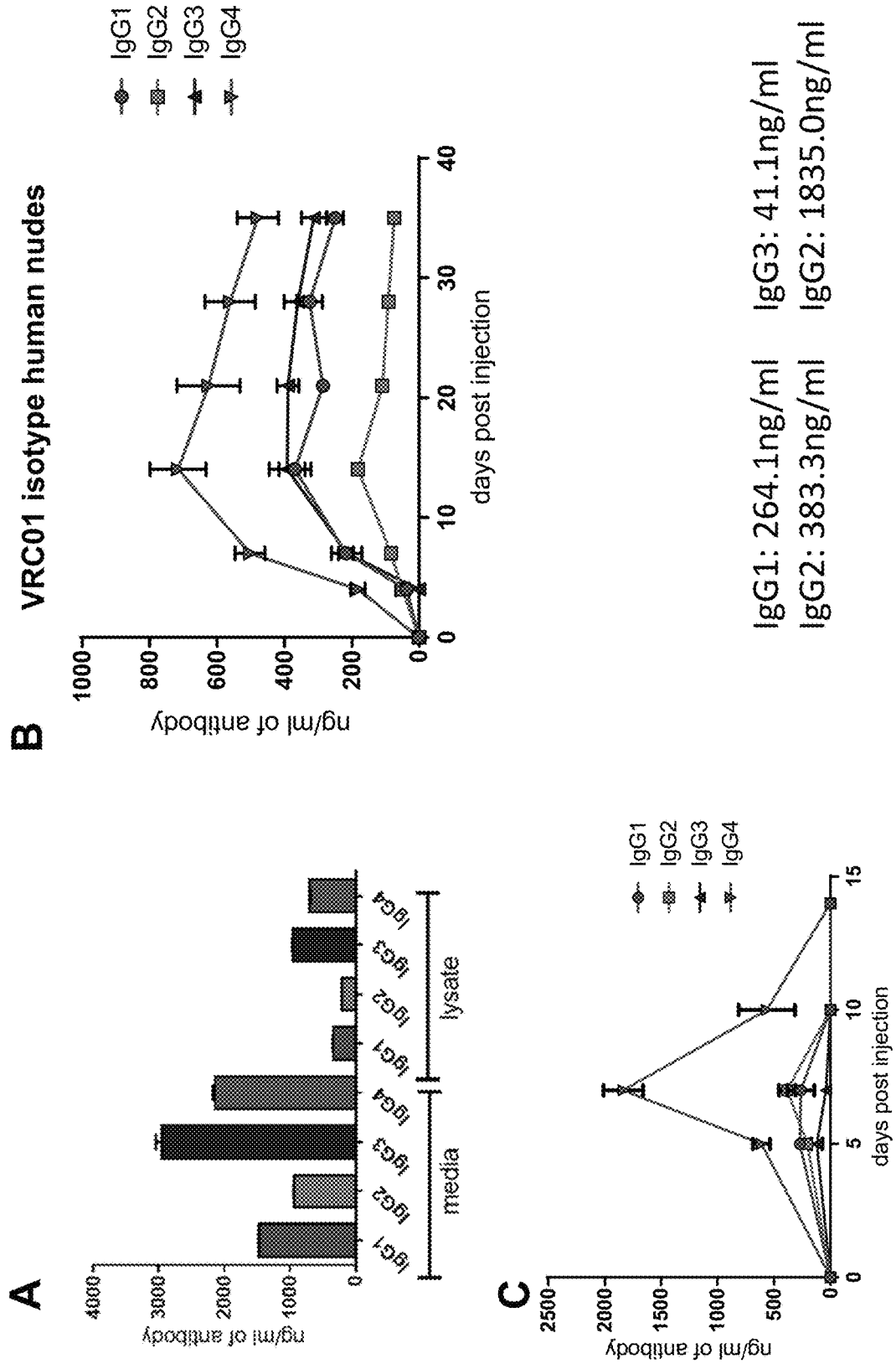
FIG. 5A depicts in vitro expression levels of human IgG1, IgG2, IgG3 and IgG4 isotypes for broadly neutralizing antibody VRC01 for both media and lysate.
FIG. 5B depicts expression levels of human IgG isotypes for VRC01 dMAbs in immune incompetent mice over the course of more than a month.
FIG. 5C depicts expression levels of human IgG isotypes for VRC01 dMAbs in immune competent balbC mice.
Figures 6A, 6B:
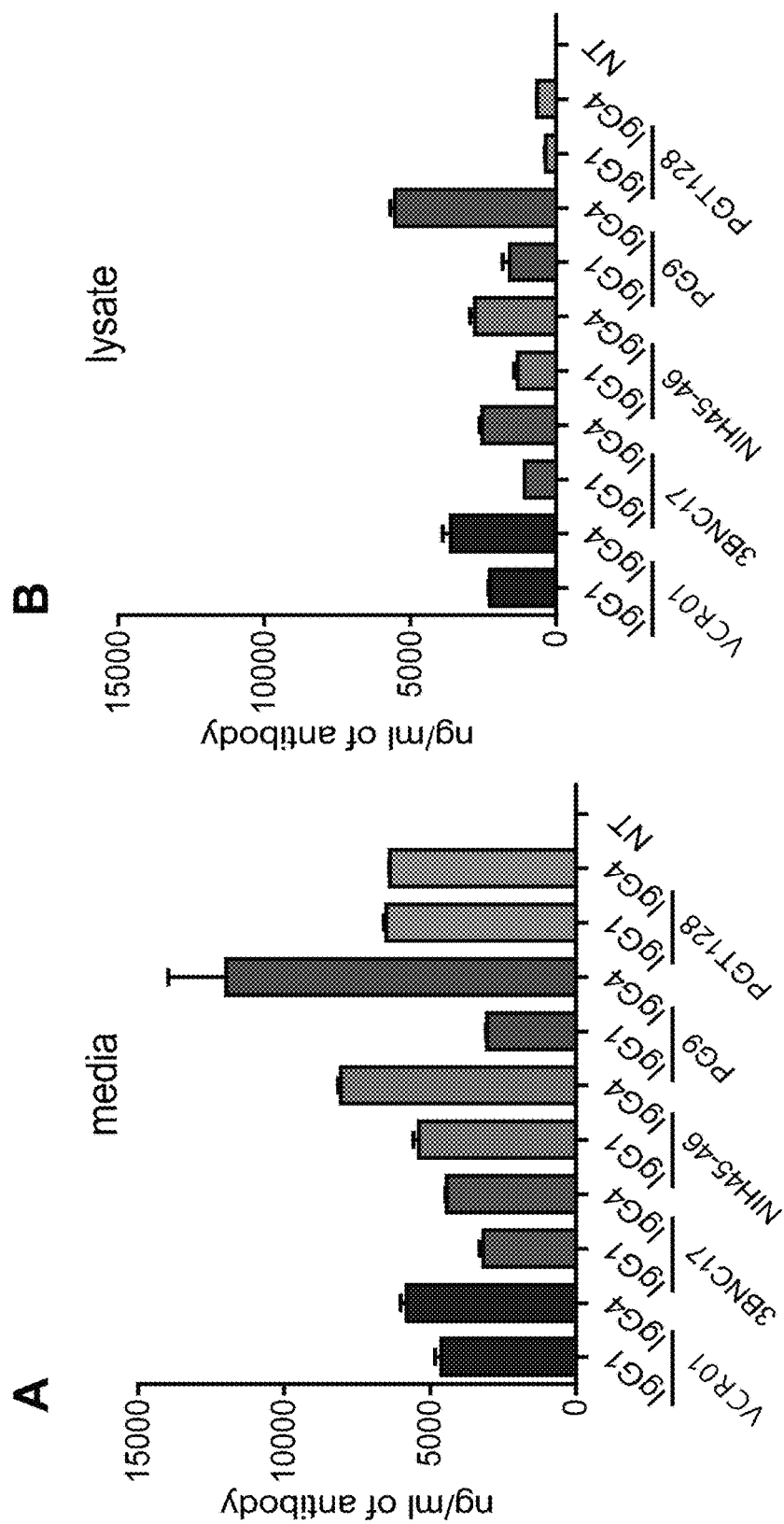
FIG. 6A depicts in vitro expression levels in 293T transfected cell media.
FIG. 6B depicts in vitro expression levels in 293T transfected cell lysate.
Figure 7A:
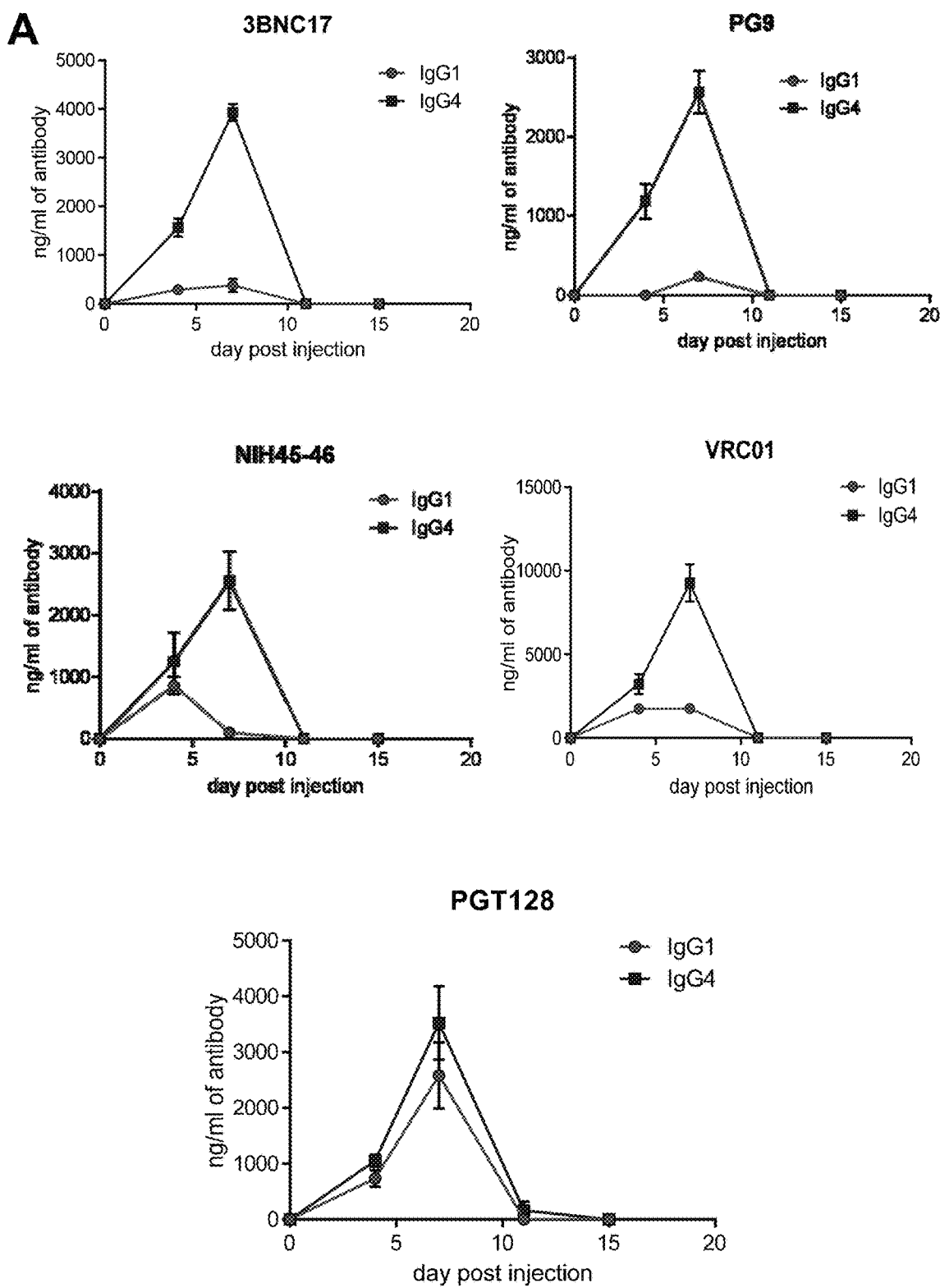
FIG. 7A depict in vivo expression levels over time for 5 HIV dMAbs, PG9, PGT128, 3BNC117, NIH45-46 and VRC01 comparing balbC mice injected with plasmids expressing either the IgG1 or IgG4 isoform.
Figure 7B:
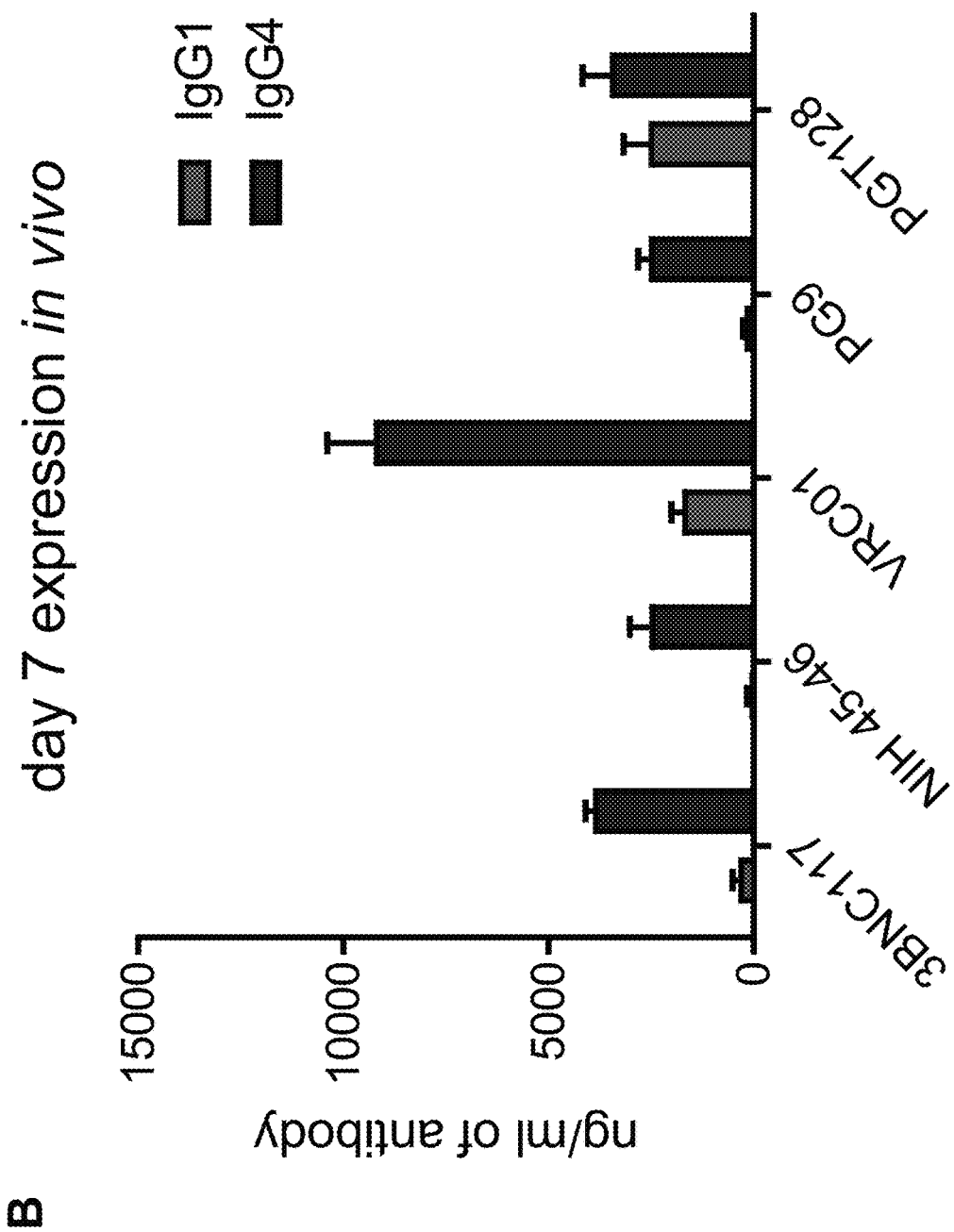
FIG. 7B, depicts peak expression levels on Day 7.

Different IgGs have different effector functions and distributions. Therefore, it was determined whether dMAbs expressing various IgGs have differential expression as well as effector functions. All isotypes of VRC01 express in vitro (FIG. 5A). In nude mice, IgG4 has the highest expression level (FIG. 5B). In BALB/c mice, IgG4 significantly increases VRC01 expression (FIG. 5C). Due to the limited expression in vivo of HIV dMAbs and the increase in VRC01 with IgG4 isotype, we next looked to see IgG4 optimization could be broadly applied to increase the levels of dMAb expression. All IgG4 constructs expressed in vitro in both the cell lysate and media of 293T transfected cells (FIG. 6). Furthermore, IgG4 increased the expression of each of PG9, 3BNC17, NIH 45-46, VRC01, PGT218 over IgG1 (FIG. 7).

Figure 8A:
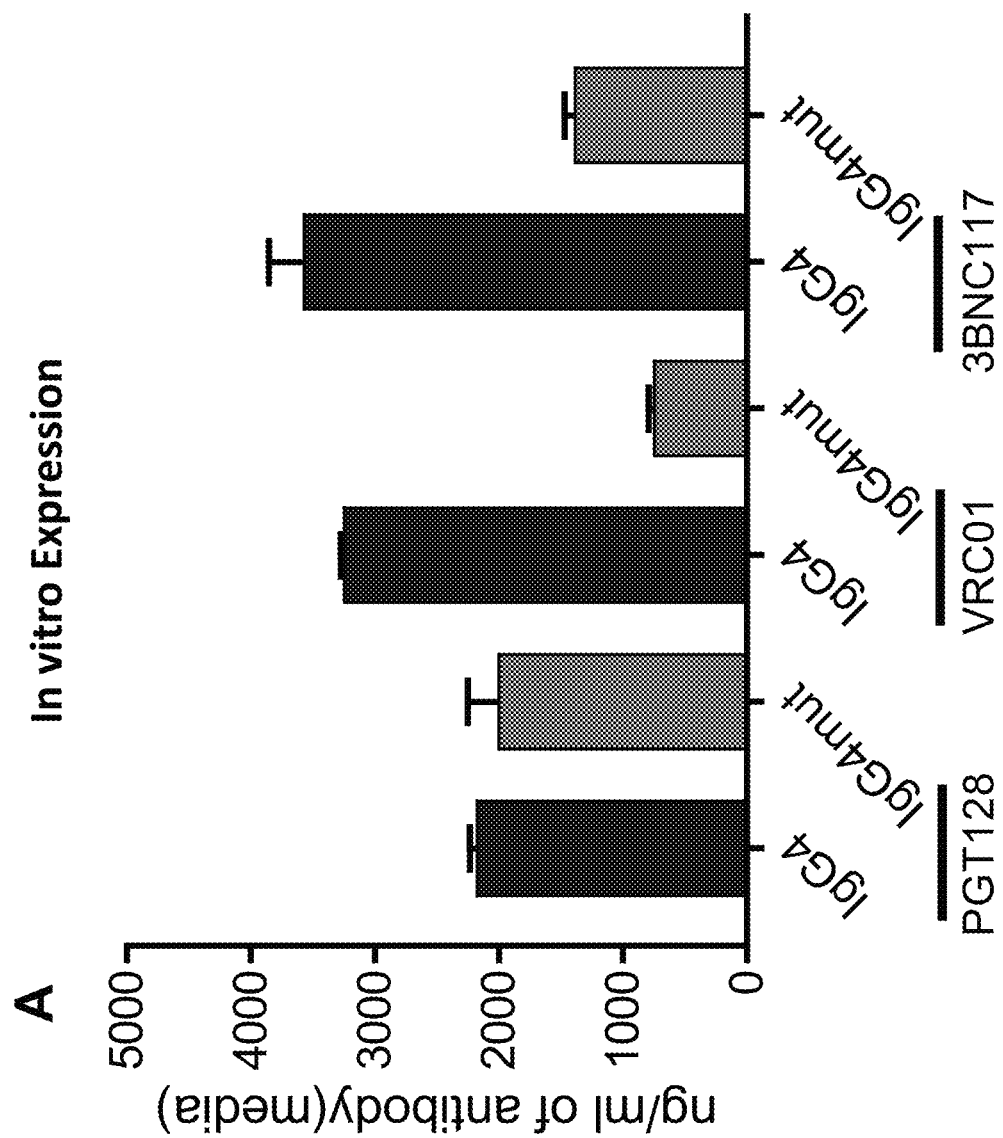
FIG. 8A depicts expression levels of IgG4 and IgG4mut (S228P) in vitro after 293T cells transfection.
Figure 8B:
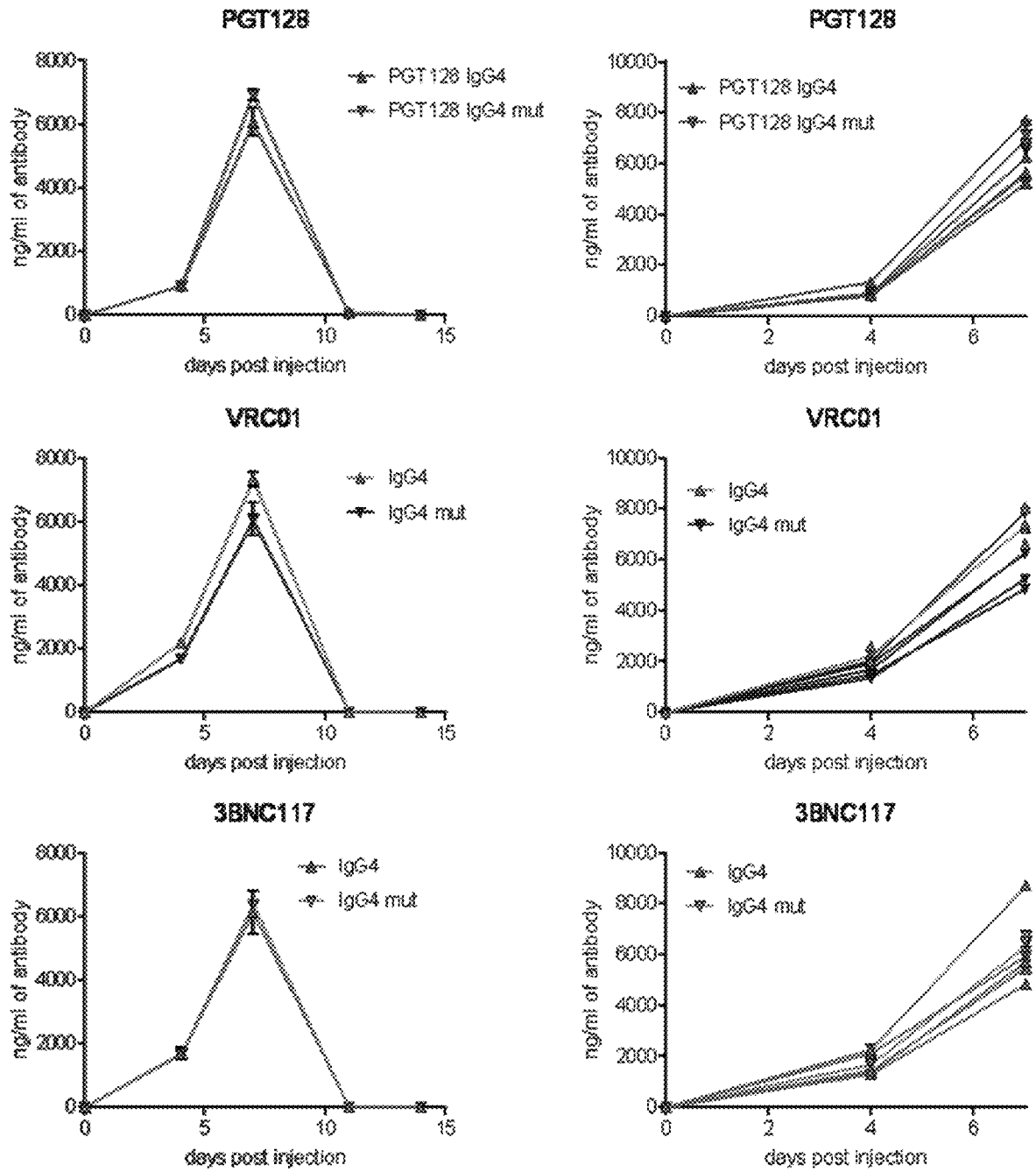
FIG. 8B depicts expression levels in vivo in balbC mice injected with either IgG4 or IgG4mut(S228P) plasmids for PGT128, VRC01, or 3BNC117.
Figure 9:
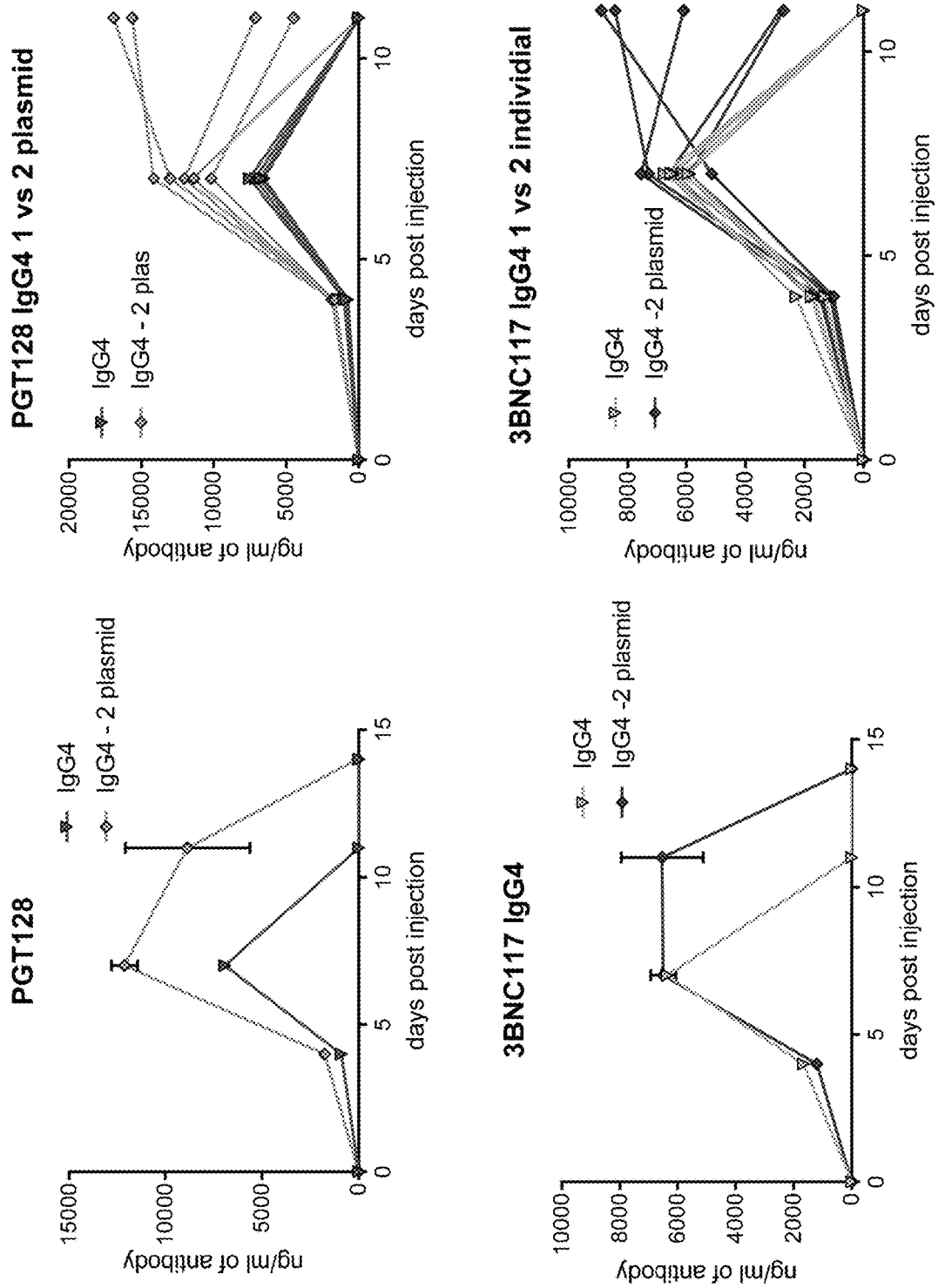
FIG. 9 depicts experimental results demonstrating that two plasmid system increases in vivo dMAb levels over that of single plasmid IgG4.
Figures 10A, 10B:
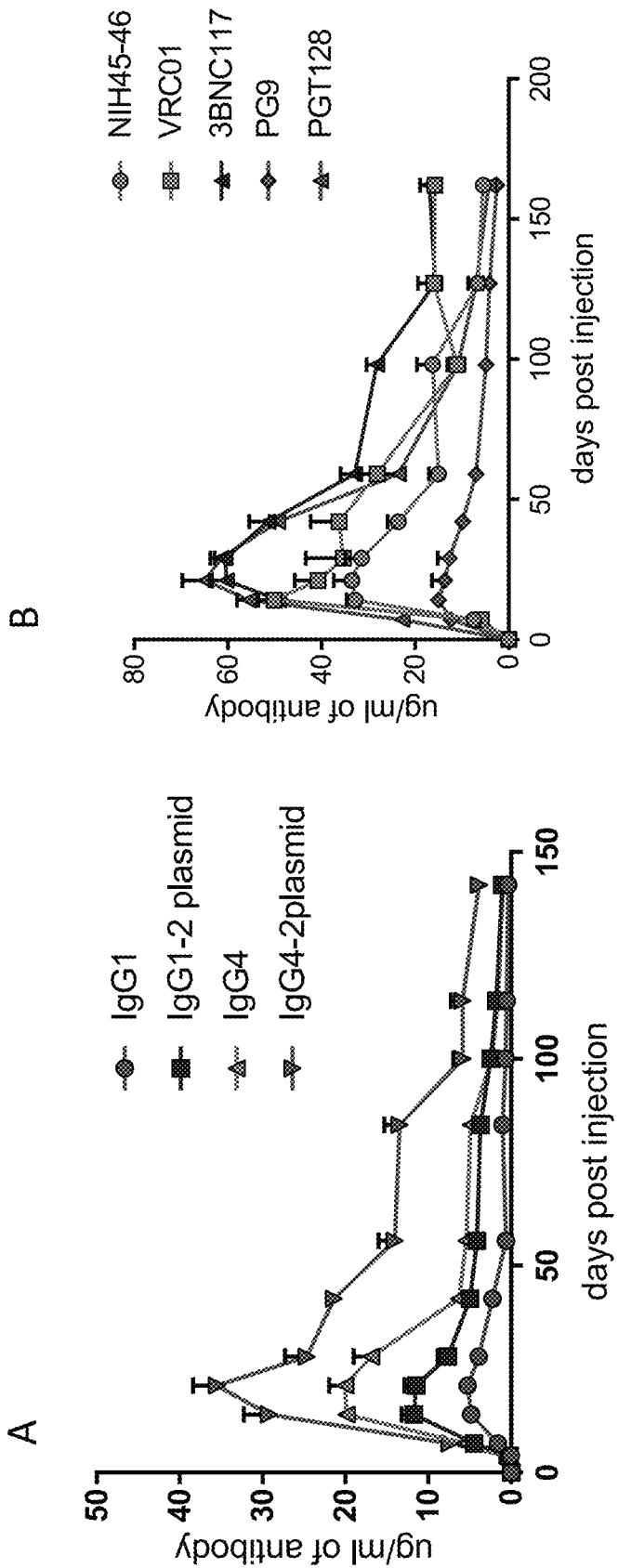
FIG. 10A depicts dMAb expression levels in vivo when balb C mice are immunocompromised and injected with plasmid expressing PGT128 on the IgG1 or IgG4 backbone delivered as either 1 or 2 plasmids.
FIG. 10B shows the generalization of IgG4 2 plasmid expression across 5 HIV dMAbs.
Figure 12:
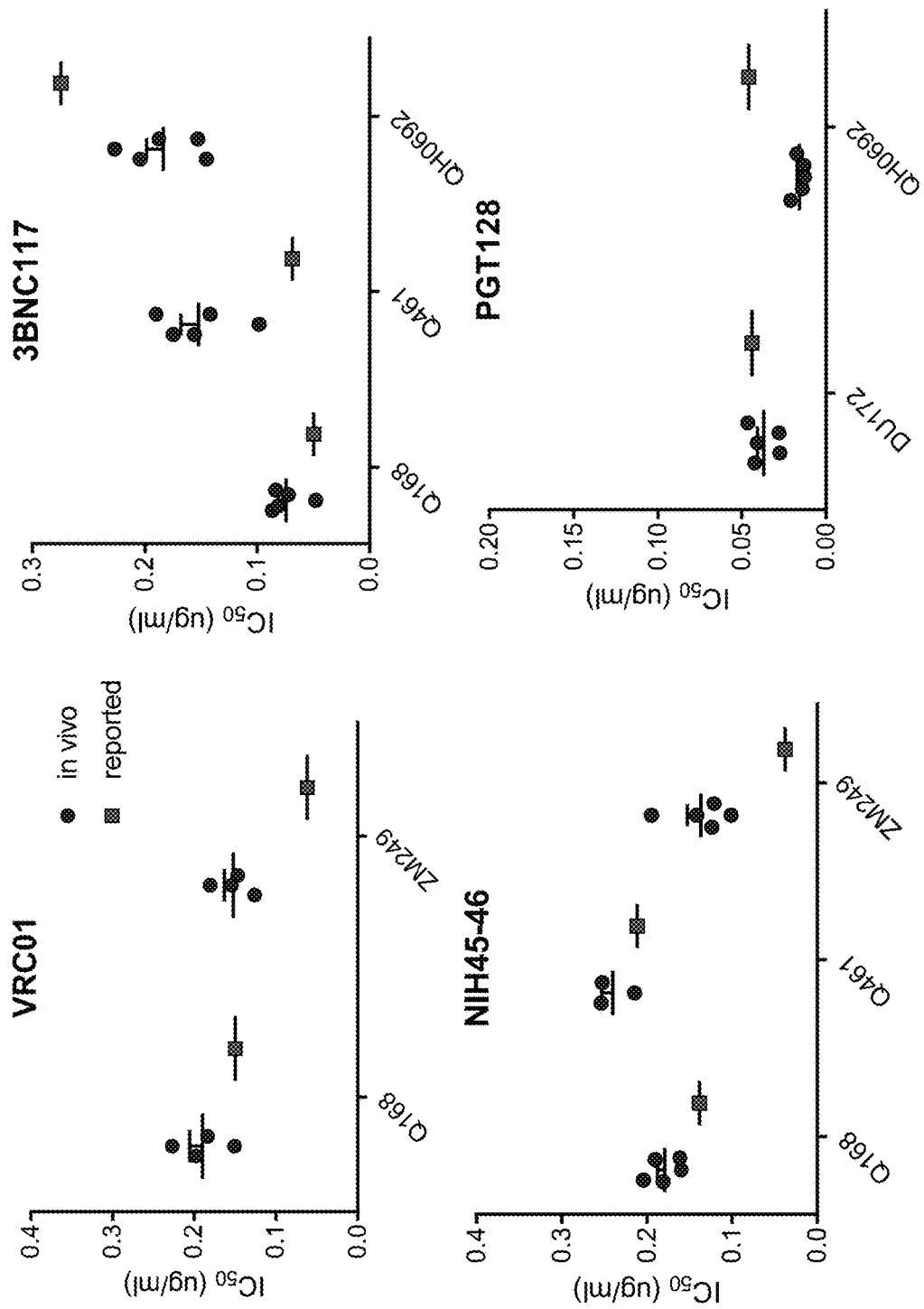
FIG. 12 depicts experimental results demonstrating that in vivo produced IgG4 HIV dMAbs are functional as measured by neutralization capacity in the TzmBl assay. Serum from balbC mice injected with VRC01, 3BNC117, NIH45-46 or PGT128 are able to neutralize multiple pseudotype viruses to similar levels as reported in the literature.

To further increase the level of dMAbs expression, a mutation was made the core-hinge region, Ser228Pro, to block Fab-arm exchange. FIG. 8 demonstrates, that the S228P mutation does not disrupt expression levels. Additionally, encoding the IgG4 heavy and light chain on separate plasmids further increased expression levels and kinetics of HIV dMAbs (FIG. 9). Importantly there was no change in the functionality of these antibodies when testing in the TzmBL assay (FIG. 11 and FIG. 12)

Figure 13:
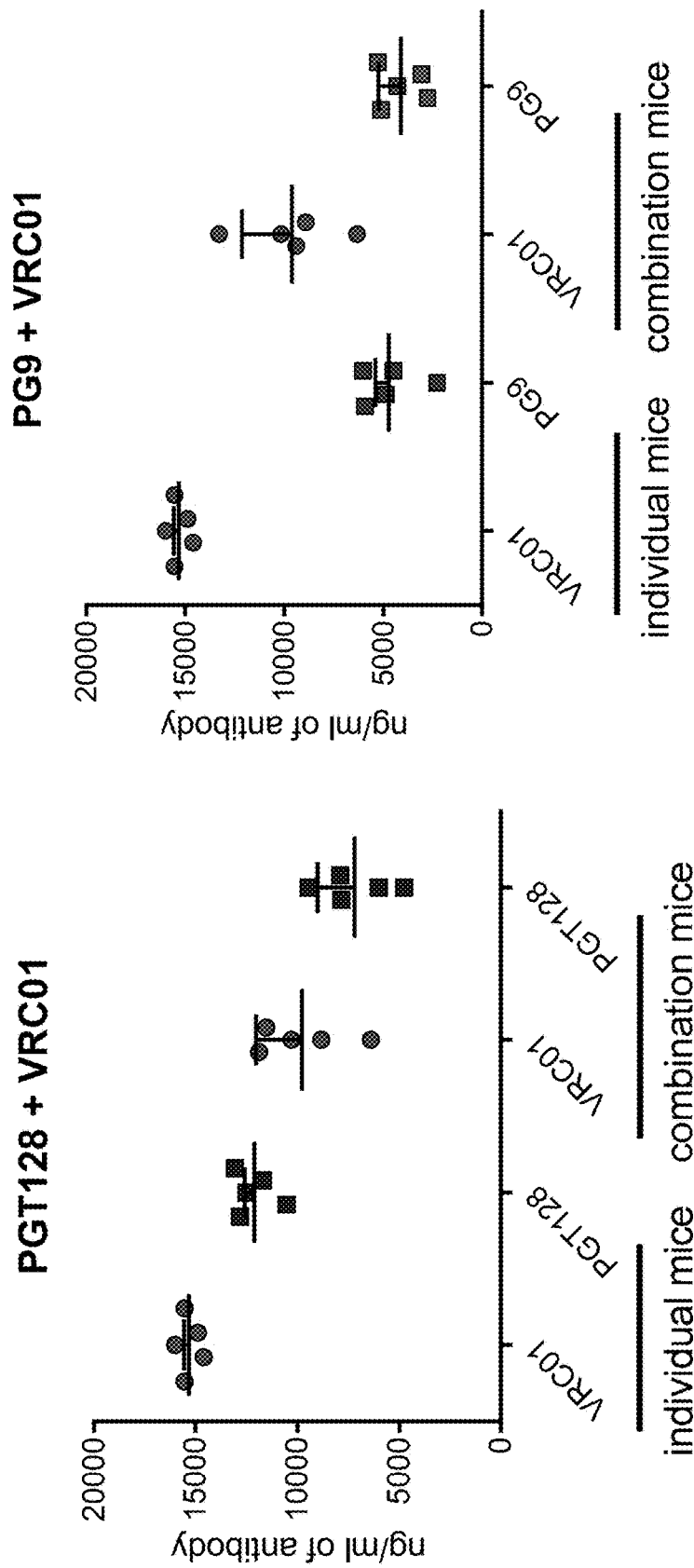
FIG. 13 depicts expression of multiple HIV dMAb in a single mouse. Mice were injected with single plasmid or two plasmids expressing different antibodies. Expression of hIgG was determined on day 7.

It may be beneficial to express multiple HIV bnAbs to have more than 1 site targeted which may decrease the likelihood of viral escape. We have demonstrated that multiple dMAbs expressing two different HIV bNab can be expressed in a single mouse (FIG. 13).

Example 3—Engineering HIV-1 Antibodies and Immunoadhesins for Increased In Vivo Production Using DNA Encoded Monoclonal Antibody Technology The ability of HIV specific broadly neutralizing antibodies (bNabs) to protect or control HIV-1 is well-established in animal models. Though these antibodies are powerful and can prevent infection or control viral loads, the cost of production could severely limit the ability to use these antibodies in the field. Additionally, current vaccine approaches have failed to induce similar antibodies. A novel way to encode and produce bNabs in vivo is described herein using a synthetic DNA encoded monoclonal antibody (dMab) platform.

Engineered plasmids encoding the heavy and light chain of over 20 HIV Envelope (Env) specific antibodies were produced and delivered intramuscularly to mice via electroporation. Initial production levels of many of the antibodies were low; however, using numerous optimization strategies including sequence, formulation, structural modifications and delivery, we can generate high levels (over 80 ug/ml) of serum dMabs in mice. dMabs are detectable in the serum as early as two days after injection and are sustained for over half a year. Additionally, these antibodies retain functional capabilities including binding to Env and neutralization as measured by the TZM-bl neutralization assay. The in vivo produced dMabs have similar neutralization profile and potency as reported with the recombinant purified monoclonal bNabs. To lower the possibility of viral escape, using the dMab platform, we can encode and express multiple HIV-1 bNabs simultaneously in a single mouse. Furthermore, we are exploring the ability to encode and produce bispecific antibodies or other immunoadhesins to increase potency and prevent escape.

The dMab platform represents a novel technique for in vivo antibody production against HIV-1 and possibly other immune targets.

Example 4—Rapid and Long-Term Immunity Elicited by DNA Encoded Antibody Prophylaxis and DNA Vaccination Against HIV Vaccination is known to exhibit a lag phase before generation of immunity; thus, there is a gap of time during infection before an immune response is in effect. The following provides specific novel approaches that utilize the benefit of vaccines and the native immune response along with a rapid generation of effective immunity using the DNA synthetic antibodies or dMabs.

An antibody-based prophylaxis/therapy entailing the electroporation mediated delivery of synthetic plasmids, encoding biologically active anti-Human Immunodeficiency virus (HIV) mAb (designated dMAb), is designed and evaluated for anti-viral efficacy as well as for the ability to overcome shortcomings inherent with conventional active vaccination by a novel passive immune-based strategy. One intramuscular injection of the HIV-dMAb produces antibodies in vivo more rapidly than active vaccination with an HIV-DNA vaccine. This dMAb neutralized diverse HIV clinical isolates and protected mice from viral challenge. Combinations of both afford rapid as well as long-lived protection.

A DNA based dMAb strategy induces rapid protection against an emerging viral infection, which can be combined with DNA vaccination providing a uniquely both short term and long-term protection against this emerging infectious disease. These studies have implications for pathogen treatment and control strategies.

dMAb IgG Quantification and Binding Assays

ELISA assays are performed with sera from subjects administered an HIV-dMAb to quantify expression kinetics and target antigen binding.

Analysis of dMAb Generated IgG

IgG expression of HIV infected cells are analyzed by western blot. For immunofluorescence analysis HIV infected cells are visually evaluated by confocal microscopy and quantitatively or semi-quantitatively analyzed.

dMAb DNA Plasmid Administration and In Vivo Analysis

Expression kinetics and functionality were evaluated in subjects following injection of control or HIV-dMAb. For studies that include the DNA vaccine, the HIV-DNA vaccine plasmid is administered.

Challenge Study

Subjects receive electroporation-enhanced injection of HIV-dMAb or control plasmids. The HIV-DNA vaccine was delivered as described above. After DNA delivery, subjects are challenged with HIV. The animals are monitored for survival and signs of infection. Serum samples are collected for cytokine quantification and other immune analysis. Blood samples are collected from after infection and viremia levels are measured.

Neutralizing Antibody Analysis

Anti-HIV neutralizing antibody titers from subjects administered HIV-dMAb are determined. Neutralization titers may be calculated as the reciprocal of the highest dilution mediating 100% reduction of the cytopathic effects in the cells.

Cytokine Quantitative Analysis

Sera is collected from HIV-dMAb, and HIV-DNA vaccine injected subjects as well as HIV challenged subjects. TNF-α, IL-1β and IL-6 sera cytokine levels are measured.

Anti-HIV dMAbs Design and Confirmation of Expression

The optimized synthetic plasmids constructed from the anti-HIV-neutralizing mAb were designed for the IgG and Fab antibodies. Cells are transfected with either the HIV-IgG plasmid or the HIV-Fab (VL, VH, or combined) plasmids to validate expression in vitro. The HIV-Fab and HIV-IgG expressed antibodies in the muscle that appeared to be properly assembled and biologically functional in vitro.

In Vivo Expression and Quantification of Anti-HIV dMAb

Following confirmation of in vitro expression, the ability of HIV-Fab or HIV-IgG to produce anti-HIV antibodies in vivo is measured. Both constructs generate mAbs. Subjects are administered either HIV-IgG or HIV-Fab, and sera antibody levels are evaluated through a binding ELISA. Sera collected after injection from both HIV-IgG and HIV-Fab bind to HIV protein but not to an unrelated control antigen. These data indicate that in vivo produced anti-HIV antibodies from HIV-IgG or HIV-Fab constructs have similar biological characteristics to conventionally produced antigen specific antibodies.

In Vivo Specificity and Broadly Neutralizing Activity in Sera from Anti-HIV dMAb Injected Subjects The anti-HIV dMAb generated mAbs are tested for binding specificity and anti-HIV neutralizing activity. Sera antibodies bind to HIV-infected cells. There is a strong specificity of the antibody generated from the anti-HIV dMAb plasmid.

Furthermore, the anti-HIV neutralizing activity in sera from subjects that received anti-HIV dMAb is measured against that in HIV strains. Sera from anti-HIV dMAb-injected subjects effectively neutralize HIV isolates, demonstrating that a single injection can produce significant neutralizing levels of human anti-HIV IgG. Thus, antibodies produced in vivo by anti-HIV dMAb constructs have relevant biological activity (i.e., binding and neutralizing activity against HIV).

Anti-HIV dMAb Injection Protects Mice from Lethal HIV Challenge

To determine whether antibodies generated from anti-HIV dMAb provide protection against early exposure to HIV, groups of 10 subjects receive of a control or anti-HIV dMAb on day 0. Each group subsequently is challenged subcutaneously with virus to mimic natural HIV infection. Subject survival and weight changes are subsequently recorded. Anti-HIV dMAb plasmids confer protective immunity.

The longevity of immune protection is next evaluated. A second group of subjects was challenged with HIV after injection with anti-HIV dMAb, or control plasmid on day 0. Subjects are monitored for survival. Anti-HIV dMAb provides a more durable degree of immune protection.

Anti-HIV dMAb protects subjects from both subcutaneous viral challenge and intranasal viral challenge compared with control-injected subjects, demonstrating that anti-HIV dMAbs can protect against systemic and mucosal infection.

An efficacy study comparing the protective efficacy of anti-HIV dMAb administration vs a HIV-DNA vaccine (HIV-DNA) is next performed. A novel consensus-based DNA vaccine was developed by our laboratory and is capable of providing protection against HIV challenge. The DNA vaccine also induced both measurable cellular immune responses, as well as potent neutralizing antibody responses. Groups of subjects are administered a single injection of anti-HIV dMAb, HIV-DNA, or the pVax1, followed by viral challenge. Anti-HIV dMAb confers protective immunity more rapidly than the HIV-DNA vaccine.

Comparison Between In Vivo Protective Immunity Conferred by Anti-HIV dMAb Administration and HIV-DNA Vaccination Next, a long-term HIV challenge protection study was performed following vaccination with the HIV-DNA vaccine or administration of anti-HIV dMAb on day 0. HIV-DNA confers longer protective immunity than anti-HIV dMAb.

Co-Delivery of Anti-HIV dMAb and the HIV-DNA Vaccine Produces Systemic Humoral Immunity, Cell-Mediated Immunity, and Protection In Vivo One potential issue of combining antibody delivery with vaccination approaches is that the antibodies can neutralize many traditional vaccines and thus are incompatible platforms. The effect of co-administration of anti-HIV dMAb and HIV-DNA on subject survival in the context of HIV challenge was is evaluated. Subjects are administered at day 0 anti-HIV dMAb and HIV-DNA. Subsequently, some animals are challenged with HIV at day 2 and the others at day 35. Survival in these groups is followed as a function of time. Anti-HIV dMAb mediates protection from infection, with the survival percentage decreasing to approximately 30% by 4 days after challenge in control (pVax1) animals. Both IgG induced by anti-HIV dMAb and HIV-DNA vaccine are detected. Anti-HIV dMAb mediates rapid protection from infection and death after HIV challenge.

Furthermore, T-cell responses induced in subjects injected with Anti-HIV dMAb, HIV-DNA, or anti-HIV dMAb plus HIV-DNA are evaluated. HIV-DNA elicits strong T-cell responses irrespective of co-delivery with anti-HIV dMAb, showing the lack of interference of these approaches. Conversely, animals administered only anti-HIV dMAb do not develop T-cell responses. Both anti-HIV dMAb and HIV-DNA vaccine can be administered simultaneously without reciprocal interference, providing immediate and long-lived protection via systemic humoral and cellular immunity.

Electroporation-Mediated Delivery of Optimized DNA Plasmids for the In Vivo Rapid Production of Biologically Functional mAbs Subjects administered anti-HIV dMAbs are fully protected from viral challenge shortly after administration, whereas subjects do not survive infection following a single immunization with HIV-DNA vaccine, owing presumably to an insufficient time to mount protective immunity. However, HIV-DNA provides complete protection after an immunization regimen followed by challenge at later time points. A similar level of protection occurs in subjects administered a single dose of anti-HIV dMAbs, although protection wanes over time. Notably, the co-delivery of anti-HIV dMAbs and HIV-DNA produces rapid and persistent humoral and cellular immunity, suggesting that a combination approach can have additive or synergistic effects. Importantly, co-delivery of anti-HIV dMAbs and HIV-DNA are not antagonistic in terms of the development of short- or long-term protective immune responses.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding one or more synthetic antibodies, wherein the nucleic acid molecule comprises at least one selected from the group consisting of a nucleotide sequence encoding an anti-HIV synthetic antibody, wherein the nucleotide sequence encodes one or more amino acid sequences at least 95% homologous to an amino acid sequence selected from the group consisting of SEQ ID NO:1, SEQ ID NO:3, SEQ ID NO:5, SEQ ID NO:7, SEQ ID NO:9, SEQ ID NO:11, or SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49 SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, and SEQ ID NO:133.

2. The nucleic acid molecule of claim 1, further comprising a nucleotide sequence encoding a cleavage domain.

3. The nucleic acid molecule of claim 1, comprising a nucleotide sequence that encodes one or more amino acid sequences selected from the group consisting of SEQ ID NO:1, SEQ ID NO:3, SEQ ID NO:5, SEQ ID NO:7, SEQ ID NO:9, SEQ ID NO:11, or SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39 SEQ ID NO:41, SEQ ID NO:43, SEQ ID NO:45, SEQ ID NO:47, SEQ ID NO:49 SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, and SEQ ID NO:133.

4. The nucleic acid molecule of claim 1, wherein the nucleic acid molecule comprises a nucleotide sequence at least 95% homologous to a nucleic acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, and SEQ ID NO:134.

5. The nucleic acid molecule of claim 4, wherein the nucleic acid molecule comprises a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO: 60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76, SEQ ID NO:78, SEQ ID NO: 80, SEQ ID NO:82, SEQ ID NO:84, SEQ ID NO:86, SEQ ID NO:88, SEQ ID NO: 90, SEQ ID NO:92, SEQ ID NO:94, SEQ ID NO:96, SEQ ID NO:98, SEQ ID NO: 100, SEQ ID NO:102, SEQ ID NO:104, SEQ ID NO:106, SEQ ID NO:108, SEQ ID NO: 110, SEQ ID NO:112, SEQ ID NO:114, SEQ ID NO:116, SEQ ID NO:118, SEQ ID NO: 120, SEQ ID NO:122, SEQ ID NO:124, SEQ ID NO:126, SEQ ID NO:128, SEQ ID NO: 130, SEQ ID NO:132, and SEQ ID NO:134.

6. The nucleic acid molecule of claim 1, wherein the nucleic acid molecule comprises a first nucleotide sequence encoding a synthetic anti-HIV heavy chain and a second nucleotide sequence encoding a synthetic anti-HIV light chain.

7. The nucleic acid molecule of claim 6, wherein the first nucleotide sequence encodes an amino acid sequence at least 90% homologous to an amino acid sequence selected from the group consisting of SEQ ID NO:3, SEQ ID NO:11, SEQ ID NO:17, SEQ ID NO:25, SEQ ID NO:39, SEQ ID NO:47, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, and SEQ ID NO:131.

8. The nucleic acid molecule of claim 7, wherein the first nucleotide sequence comprises a nucleotide sequence at least 90% homologous to a nucleotide sequence selected from the group consisting of SEQ ID NO:4, SEQ ID NO:12, SEQ ID NO:18, SEQ ID NO:26, SEQ ID NO:40, SEQ ID NO:48, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, and SEQ ID NO:132.

9. The nucleic acid molecule of claim 6, wherein the second nucleotide sequence encodes an amino acid sequence at least 90% homologous to an amino acid sequence selected from the group consisting of SEQ ID NO:5, SEQ ID NO:13, SEQ ID NO:19, SEQ ID NO:27, SEQ ID NO:41, SEQ ID NO:49, SEQ ID NO:57, SEQ ID NO:61, SEQ ID NO:65, SEQ ID NO:69, SEQ ID NO:73, SEQ ID NO:77, SEQ ID NO:81, SEQ ID NO:85, SEQ ID NO:89, SEQ ID NO:93, SEQ ID NO:97, SEQ ID NO:101, SEQ ID NO:105, SEQ ID NO:109, SEQ ID NO:113, SEQ ID NO:117, SEQ ID NO:121, SEQ ID NO:125, SEQ ID NO:129, and SEQ ID NO:133.

10. The nucleic acid molecule of claim 9, wherein the second nucleotide sequence comprises a nucleotide sequence at least 90% homologous to a nucleotide sequence selected from the group consisting of SEQ ID NO:6, SEQ ID NO:14, SEQ ID NO:20, SEQ ID NO:28, SEQ ID NO:42, SEQ ID NO:50, SEQ ID NO:58, SEQ ID NO:62, SEQ ID NO:66, SEQ ID NO:70, SEQ ID NO:74, SEQ ID NO:76, SEQ ID NO:82, SEQ ID NO:86, SEQ ID NO:90, SEQ ID NO:94, SEQ ID NO:98, SEQ ID NO:102, SEQ ID NO:106, SEQ ID NO:110, SEQ ID NO:114, SEQ ID NO:118, SEQ ID NO:122, SEQ ID NO:126, SEQ ID NO:130, and SEQ ID NO:134.

11. The nucleic acid molecule of claim 6, wherein
the first nucleotide sequence encodes an amino acid sequence at least 90% homologous to SEQ ID NO:3 and the second nucleotide sequence encodes an amino acid sequence at least 90% homologous to SEQ ID NO:5;
the first nucleotide sequence encodes an amino acid sequence at least 90% homologous to SEQ ID NO:11 and the second nucleotide sequence encodes an amino acid sequence at least 90% homologous to SEQ ID NO:13;
the first nucleotide sequence encodes an amino acid sequence at least 90% homologous to SEQ ID NO:17 and the second nucleotide sequence encodes an amino acid sequence at least 90% homologous to SEQ ID NO:19;
the first nucleotide sequence encodes an amino acid sequence at least 90% homologous to SEQ ID NO:25 and the second nucleotide sequence encodes an amino acid sequence at least 90% homologous to SEQ ID NO:27;

the first nucleotide sequence encodes an amino acid sequence at least 90% homologous to SEQ ID NO:39 and the second nucleotide sequence encodes an amino acid sequence at least 90% homologous to SEQ ID NO:41;
the first nucleotide sequence encodes an amino acid sequence at least 90% homologous to SEQ ID NO:47 and the second nucleotide sequence encodes an amino acid sequence at least 90% homologous to SEQ ID NO:49;
the first nucleotide sequence encodes an amino acid sequence at least 90% homologous to SEQ ID NO:55 and the second nucleotide sequence encodes an amino acid sequence at least 90% homologous to SEQ ID NO:57;
the first nucleotide sequence encodes an amino acid sequence at least 90% homologous to SEQ ID NO:59 and the second nucleotide sequence encodes an amino acid sequence at least 90% homologous to SEQ ID NO:61;
the first nucleotide sequence encodes an amino acid sequence at least 90% homologous to SEQ ID NO:63 and the second nucleotide sequence encodes an amino acid sequence at least 90% homologous to SEQ ID NO:65;
the first nucleotide sequence encodes an amino acid sequence at least 90% homologous to SEQ ID NO:67 and the second nucleotide sequence encodes an amino acid sequence at least 90% homologous to SEQ ID NO:69;
the first nucleotide sequence encodes an amino acid sequence at least 90% homologous to SEQ ID NO:71 and the second nucleotide sequence encodes an amino acid sequence at least 90% homologous to SEQ ID NO:73;
the first nucleotide sequence encodes an amino acid sequence at least 90% homologous to SEQ ID NO:75 and the second nucleotide sequence encodes an amino acid sequence at least 90% homologous to SEQ ID NO:77;
the first nucleotide sequence encodes an amino acid sequence at least 90% homologous to SEQ ID NO:79 and the second nucleotide sequence encodes an amino acid sequence at least 90% homologous to SEQ ID NO:81;
the first nucleotide sequence encodes an amino acid sequence at least 90% homologous to SEQ ID NO:83 and the second nucleotide sequence encodes an amino acid sequence at least 90% homologous to SEQ ID NO:85;
the first nucleotide sequence encodes an amino acid sequence at least 90% homologous to SEQ ID NO:87 and the second nucleotide sequence encodes an amino acid sequence at least 90% homologous to SEQ ID NO:89;
the first nucleotide sequence encodes an amino acid sequence at least 90% homologous to SEQ ID NO:91 and the second nucleotide sequence encodes an amino acid sequence at least 90% homologous to SEQ ID NO:93;
the first nucleotide sequence encodes an amino acid sequence at least 90% homologous to SEQ ID NO:95 and the second nucleotide sequence encodes an amino acid sequence at least 90% homologous to SEQ ID NO:97;
the first nucleotide sequence encodes an amino acid sequence at least 90% homologous to SEQ ID NO:99 and the second nucleotide sequence encodes an amino acid sequence at least 90% homologous to SEQ ID NO:101;
the first nucleotide sequence encodes an amino acid sequence at least 90% homologous to SEQ ID NO:103 and the second nucleotide sequence encodes an amino acid sequence at least 90% homologous to SEQ ID NO: 105;
the first nucleotide sequence encodes an amino acid sequence at least 90% homologous to SEQ ID NO: 107 and the second nucleotide sequence encodes an amino acid sequence at least 90% homologous to SEQ ID NO: 109;
the first nucleotide sequence encodes an amino acid sequence at least 90% homologous to SEQ ID NO:111 and the second nucleotide sequence encodes an amino acid sequence at least 90% homologous to SEQ ID NO: 113;
the first nucleotide sequence encodes an amino acid sequence at least 90% homologous to SEQ ID NO: 115 and the second nucleotide sequence encodes an amino acid sequence at least 90% homologous to SEQ ID NO: 117;
the first nucleotide sequence encodes an amino acid sequence at least 90% homologous to SEQ ID NO: 119 and the second nucleotide sequence encodes an amino acid sequence at least 90% homologous to SEQ ID NO: 121;
the first nucleotide sequence encodes an amino acid sequence at least 90% homologous to SEQ ID NO:123 and the second nucleotide sequence encodes an amino acid sequence at least 90% homologous to SEQ ID NO: 125;
the first nucleotide sequence encodes an amino acid sequence at least 90% homologous to SEQ ID NO: 1207 and the second nucleotide sequence encodes an amino acid sequence at least 90% homologous to SEQ ID NO: 129; or
the first nucleotide sequence encodes an amino acid sequence at least 90% homologous to SEQ ID NO:131 and the second nucleotide sequence encodes an amino acid sequence at least 90% homologous to SEQ ID NO: 133.

12. The nucleic acid molecule of claim 11, wherein
the first nucleotide sequence comprises a nucleotide sequence at least 90% homologous to SEQ ID NO:4 and the second nucleotide sequence comprises a nucleotide sequence at least 90% homologous to SEQ ID NO:6;
the first nucleotide sequence comprises a nucleotide sequence at least 90% homologous to SEQ ID NO:12 and the second nucleotide sequence comprises a nucleotide sequence at least 90% homologous to SEQ ID NO:14;
the first nucleotide sequence comprises a nucleotide sequence at least 90% homologous to SEQ ID NO:18 and the second nucleotide sequence comprises a nucleotide sequence at least 90% homologous to SEQ ID NO:20;
the first nucleotide sequence comprises a nucleotide sequence at least 90% homologous to SEQ ID NO:26 and the second nucleotide sequence comprises a nucleotide sequence at least 90% homologous to SEQ ID NO:28;
the first nucleotide sequence comprises a nucleotide sequence at least 90% homologous to SEQ ID NO:40 and the second nucleotide sequence comprises a nucleotide sequence at least 90% homologous to SEQ ID NO:42;

the first nucleotide sequence comprises a nucleotide sequence at least 90% homologous to SEQ ID NO:48 and the second nucleotide sequence comprises a nucleotide sequence at least 90% homologous to SEQ ID NO:50;

the first nucleotide sequence comprises a nucleotide sequence at least 90% homologous to SEQ ID NO:56 and the second nucleotide sequence comprises a nucleotide sequence at least 90% homologous to SEQ ID NO:58;

the first nucleotide sequence comprises a nucleotide sequence at least 90% homologous to SEQ ID NO:60 and the second nucleotide sequence comprises a nucleotide sequence at least 90% homologous to SEQ ID NO:62;

the first nucleotide sequence comprises a nucleotide sequence at least 90% homologous to SEQ ID NO:64 and the second nucleotide sequence comprises a nucleotide sequence at least 90% homologous to SEQ ID NO:66;

the first nucleotide sequence comprises a nucleotide sequence at least 90% homologous to SEQ ID NO:68 and the second nucleotide sequence comprises a nucleotide sequence at least 90% homologous to SEQ ID NO:70;

the first nucleotide sequence comprises a nucleotide sequence at least 90% homologous to SEQ ID NO:72 and the second nucleotide sequence comprises a nucleotide sequence at least 90% homologous to SEQ ID NO:74;

the first nucleotide sequence comprises a nucleotide sequence at least 90% homologous to SEQ ID NO:76 and the second nucleotide sequence comprises a nucleotide sequence at least 90% homologous to SEQ ID NO:78;

the first nucleotide sequence comprises a nucleotide sequence at least 90% homologous to SEQ ID NO:80 and the second nucleotide sequence comprises a nucleotide sequence at least 90% homologous to SEQ ID NO:82;

the first nucleotide sequence comprises a nucleotide sequence at least 90% homologous to SEQ ID NO:84 and the second nucleotide sequence comprises a nucleotide sequence at least 90% homologous to SEQ ID NO:86;

the first nucleotide sequence comprises a nucleotide sequence at least 90% homologous to SEQ ID NO:88 and the second nucleotide sequence comprises a nucleotide sequence at least 90% homologous to SEQ ID NO:90;

the first nucleotide sequence comprises a nucleotide sequence at least 90% homologous to SEQ ID NO:92 and the second nucleotide sequence comprises a nucleotide sequence at least 90% homologous to SEQ ID NO:94;

the first nucleotide sequence comprises a nucleotide sequence at least 90% homologous to SEQ ID NO:96 and the second nucleotide sequence comprises a nucleotide sequence at least 90% homologous to SEQ ID NO:98;

the first nucleotide sequence comprises a nucleotide sequence at least 90% homologous to SEQ ID NO:100 and the second nucleotide sequence comprises a nucleotide sequence at least 90% homologous to SEQ ID NO:102;

the first nucleotide sequence comprises a nucleotide sequence at least 90% homologous to SEQ ID NO:104 and the second nucleotide sequence comprises a nucleotide sequence at least 90% homologous to SEQ ID NO: 106;

the first nucleotide sequence comprises a nucleotide sequence at least 90% homologous to SEQ ID NO: 108 and the second nucleotide sequence comprises a nucleotide sequence at least 90% homologous to SEQ ID NO: 110;

the first nucleotide sequence comprises a nucleotide sequence at least 90% homologous to SEQ ID NO:112 and the second nucleotide sequence comprises a nucleotide sequence at least 90% homologous to SEQ ID NO: 114;

the first nucleotide sequence comprises a nucleotide sequence at least 90% homologous to SEQ ID NO: 116 and the second nucleotide sequence comprises a nucleotide sequence at least 90% homologous to SEQ ID NO: 118;

the first nucleotide sequence comprises a nucleotide sequence at least 90% homologous to SEQ ID NO: 120 and the second nucleotide sequence comprises a nucleotide sequence at least 90% homologous to SEQ ID NO: 122;

the first nucleotide sequence comprises a nucleotide sequence at least 90% homologous to SEQ ID NO:124 and the second nucleotide sequence comprises a nucleotide sequence at least 90% homologous to SEQ ID NO: 126;

the first nucleotide sequence comprises a nucleotide sequence at least 90% homologous to SEQ ID NO: 128 and the second nucleotide sequence comprises a nucleotide sequence at least 90% homologous to SEQ ID NO: 130; or the first nucleotide sequence comprises a nucleotide sequence at least 90% homologous to SEQ ID NO:132 and the second nucleotide sequence comprises a nucleotide sequence at least 90% homologous to SEQ ID NO: 134.

13. The nucleic acid molecule of claim 1, wherein the nucleotide sequence encodes a leader sequence.

14. The nucleic acid molecule of claim 1, wherein the nucleic acid molecule comprises an expression vector.

15. A composition comprising the nucleic acid molecule of claim 1.

16. The composition of claim 15, further comprising a pharmaceutically acceptable excipient.

* * * * *

```
SEQUENCE LISTING

<160> NUMBER OF SEQ ID NOS: 152

<210> SEQ ID NO 1
<211> LENGTH: 727
<212> TYPE: PRT
<213> ORGANISM: Artificial Sequence
<220> FEATURE:
<223> OTHER INFORMATION: 3BNC117 human IgG1 antibody

<400> SEQUENCE: 1

Met Asp Trp Thr Trp Arg Ile Leu Phe Leu Val Ala Ala Ala Thr Gly
1               5                   10                  15

Thr His Ala Gln Val Gln Leu Leu Gln Ser Gly Ala Ala Val Thr Lys
            20                  25                  30

Pro Gly Ala Ser Val Arg Val Ser Cys Glu Ala Ser Gly Tyr Asn Ile
        35                  40                  45

Arg Asp Tyr Phe Ile His Trp Trp Arg Gln Ala Pro Gly Gln Gly Leu
    50                  55                  60

Gln Trp Val Gly Trp Ile Asn Pro Lys Thr Gly Gln Pro Asn Asn Pro
65                  70                  75                  80

Arg Gln Phe Gln Gly Arg Val Ser Leu Thr Arg His Ala Ser Trp Asp
                85                  90                  95

Phe Asp Thr Phe Ser Phe Tyr Met Asp Leu Lys Ala Leu Arg Ser Asp
            100                 105                 110

Asp Thr Ala Val Tyr Phe Cys Ala Arg Gln Arg Ser Asp Tyr Trp Asp
        115                 120                 125

Phe Asp Val Trp Gly Ser Gly Thr Gln Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285
```

```
Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys Arg Gly Arg Lys Arg Arg Ser Gly
465                 470                 475                 480

Ser Gly Ala Thr Asn Phe Ser Leu Leu Lys Gln Ala Gly Asp Val Glu
                485                 490                 495

Glu Asn Pro Gly Pro Met Val Leu Gln Thr Gln Val Phe Ile Ser Leu
            500                 505                 510

Leu Leu Trp Ile Ser Gly Ala Tyr Gly Asp Ile Gln Met Thr Gln Ser
        515                 520                 525

Pro Ser Ser Leu Ser Ala Ser Val Gly Asp Thr Val Thr Ile Thr Cys
    530                 535                 540

Gln Ala Asn Gly Tyr Leu Asn Trp Tyr Gln Gln Arg Arg Gly Lys Ala
545                 550                 555                 560

Pro Lys Leu Leu Ile Tyr Asp Gly Ser Lys Leu Glu Arg Gly Val Pro
                565                 570                 575

Ser Arg Phe Ser Gly Arg Arg Trp Gly Gln Glu Tyr Asn Leu Thr Ile
            580                 585                 590

Asn Asn Leu Gln Pro Glu Asp Ile Ala Thr Tyr Phe Cys Gln Val Tyr
        595                 600                 605

Glu Phe Val Val Pro Gly Thr Arg Leu Asp Leu Lys Arg Thr Val Ala
    610                 615                 620

Ala Pro Ser Val Phe Ile Phe Pro Pro Ser Asp Glu Gln Leu Lys Ser
625                 630                 635                 640

Gly Thr Ala Ser Val Val Cys Leu Leu Asn Asn Phe Tyr Pro Arg Glu
                645                 650                 655

Ala Lys Val Gln Trp Lys Val Asp Asn Ala Leu Gln Ser Gly Asn Ser
            660                 665                 670

Gln Glu Ser Val Thr Glu Gln Asp Ser Lys Asp Ser Thr Tyr Ser Leu
        675                 680                 685

Ser Ser Thr Leu Thr Leu Ser Lys Ala Asp Tyr Glu Lys His Lys Val
    690                 695                 700
```

Tyr Ala Cys Glu Val Thr His Gln Gly Leu Arg Ser Pro Val Thr Lys
705                 710                 715                 720

Ser Phe Asn Arg Gly Glu Cys
            725

<210> SEQ ID NO 2
<211> LENGTH: 2205
<212> TYPE: DNA
<213> ORGANISM: Artificial Sequence
<220> FEATURE:
<223> OTHER INFORMATION: 3BNC117 human IgG1 antibody

<400> SEQUENCE: 2

```
ggatccgcca ccatggattg acatggaga attctgtttc tggtcgccgc cgctaccgga      60
actcacgctc aggtgcagct gctgcagtca ggggccgcag tgacaaagcc aggggcaagt    120
gtccgcgtgt catgcgaggc cagcggctac aacatccggg actatttcat tcactggtgg    180
cgacaggcac ctggacaggg actgcagtgg gtggggtgga tcaatccaaa gaccggccag    240
cccaacaatc taggcagtt ccagggcaga gtgagcctga cccggcatgc ttcctgggac     300
tttgatacat tctcttttta catggacctg aaggcactga ggagtgacga taccgccgtg    360
tacttctgcg ctagacagcg gtcagattat tgggactttg acgtgtgggg cagcggaact    420
caggtcaccg tgagctccgc cagtacaaag ggaccttcag tgtttccact ggctccctct    480
agtaaaagca catccggcgg aactgccgct ctggatgtc tggtgaagga ctacttccct    540
gagccagtca ccgtgtcctg gaactctgga gctctgacta gcggggtcca cacctttcca    600
gcagtgctgc agtcaagcgg cctgtactcc ctgtcctctg tggtcactgt ccccagttca    660
agcctgggaa ctcagaccta tatctgcaac gtgaatcaca gccaagtaa taccaaagtc    720
gacaagaaag tggagcccaa gtcctgtgat aaaacacata cttgccctcc ctgtccagct    780
cctgaactgc tgggcggccc aagcgtgttc ctgtttccac ccaagcctaa agacactctg    840
atgatttcta gaaccctga ggtcacatgc gtggtcgtgg acgtgagcca cgaggacccc     900
gaagtcaagt tcaactggta cgtggatggc gtcgaagtgc ataatgccaa gaccaaaccc    960
cgagaggaac agtacaactc tacttatagg gtcgtgagtg tcctgaccgt gctgcaccag   1020
gactggctga acggcaagga gtataagtgc aaagtgtcca ataaggctct gccagcaccc   1080
atcgaaaaaa caatttctaa ggccaaagga cagcctagag agccacaggt gtacactctg   1140
cctccatccc gggacgaact gacaaagaac caggtctctc tgacttgtct ggtgaaagga   1200
ttctatccca gcgatatcgc tgtggagtgg gaatccaatg gcagcctga gaacaattac   1260
aagaccacac cccctgtgct ggacagtgat gggtcattct ttctgtattc caagctgaca   1320
gtggacaaat tcggtggca gcagggcaac gtcttttctt gcagtgtgat gcatgaagcc   1380
ctgcacaatc attacacaca gaagtcactg agcctgtccc aggaaagcg aggacgaaaa   1440
aggagatctg ggagtggcgc tactaacttc tctctgctga acaggcagg agatgtggag   1500
gaaaatcctg gccaatggt cctgcagacc caggtgttta tctcactgct gctgtggatt   1560
agcggcgcat atggagacat ccagatgaca cagagcccct tctctctgtc agcaagcgtc   1620
ggcgataccg tgacaattac ttgtcaggcc aacggctacc tgaattggta tcagcagcgg   1680
cgcggaaagg ctcccaaact gctgatctac gacgctcca agctggagcg cggagtgcct   1740
agccgattct ccgggcgaag gtggggacag gagtataacc tgactatcaa caatctgcag   1800
cctgaagata ttgccaccta cttctgccag gtgtatgagt ttgtcgtgcc agggaccagg   1860
ctggacctga agagaacagt cgcagccccc agcgtgttca tctttccacc ctcagatgag   1920
```
cagctgaaat ccggaaccgc ctctgtggtg tgcctgctga caacttctac cccacgcgaa    1980
gccaaggtcc agtggaaagt ggacaacgct ctgcagtctg gcaatagtca ggagtcagtg    2040
acagaacagg acagcaagga ttccacttat tctctgagtt caaccctgac actgtccaaa    2100
gcagattacg agaagcacaa agtgtatgcc tgcgaggtca cccaccaggg gctgcggtca    2160
ccagtcacaa agtccttcaa cagaggggaa tgctgataac tcgag                    2205

```
<210> SEQ ID NO 3
<211> LENGTH: 472
<212> TYPE: PRT
<213> ORGANISM: Artificial Sequence
<220> FEATURE:
<223> OTHER INFORMATION: 3BNC117 human IgG1 antibody (heavy chain)
      (mod1)

<400> SEQUENCE: 3
```

Met Asp Trp Thr Trp Arg Ile Leu Phe Leu Val Ala Ala Ala Thr Gly
1               5                   10                  15

Thr His Ala Gln Val Gln Leu Leu Gln Ser Gly Ala Ala Val Thr Lys
            20                  25                  30

Pro Gly Ala Ser Val Arg Val Ser Cys Glu Ala Ser Gly Tyr Asn Ile
        35                  40                  45

Arg Asp Tyr Phe Ile His Trp Trp Arg Gln Ala Pro Gly Gln Gly Leu
    50                  55                  60

Gln Trp Val Gly Trp Ile Asn Pro Lys Thr Gly Gln Pro Asn Asn Pro
65                  70                  75                  80

Arg Gln Phe Gln Gly Arg Val Ser Leu Thr Arg His Ala Ser Trp Asp
                85                  90                  95

Phe Asp Thr Phe Ser Phe Tyr Met Asp Leu Lys Ala Leu Arg Ser Asp
            100                 105                 110

Asp Thr Ala Val Tyr Phe Cys Ala Arg Gln Arg Ser Asp Tyr Trp Asp
        115                 120                 125

Phe Asp Val Trp Gly Ser Gly Thr Gln Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 4
<211> LENGTH: 1440
<212> TYPE: DNA
<213> ORGANISM: Artificial Sequence
<220> FEATURE:
<223> OTHER INFORMATION: 3BNC117 human IgG1 antibody (heavy chain)
      (mod1)

<400> SEQUENCE: 4
ggatccgcca ccatggattg acatggaga attctgtttc tggtcgccgc cgctaccgga      60
actcacgctc aggtgcagct gctgcagtca ggggccgcag tgacaaagcc aggggcaagt     120
gtccgcgtgt catgcgaggc cagcggctac aacatccggg actatttcat tcactggtgg    180
cgacaggcac ctggacaggg actgcagtgg gtggggtgga tcaatccaaa gaccggccag    240
cccaacaatc ctaggcagtt ccagggcaga gtgagcctga cccggcatgc ttcctgggac    300
tttgatacat tctcttttta catggacctg aaggcactga ggagtgacga taccgccgtg    360
tacttctgcg ctagacagcg gtcagattat tgggactttg acgtgtgggg cagcggaact    420
caggtcaccg tgagctccgc cagtacaaag ggaccttcag tgtttccact ggctccctct    480
agtaaaagca catccggcgg aactgccgct ctgggatgtc tggtgaagga ctacttccct    540
gagccagtca ccgtgtcctg gaactctgga gctctgacta gcggggtcca cacctttcca    600
gcagtgctgc agtcaagcgg cctgtactcc ctgtcctctg tggtcactgt ccccagttca    660
agcctgggaa ctcagaccta tatctgcaac gtgaatcaca agccaagtaa taccaaagtc    720
gacaagaaag tggagcccaa gtcctgtgat aaaacacata cttgccctcc ctgtccagct    780
cctgaactgc tgggcggccc aagcgtgttc ctgtttccac ccaagcctaa agacactctg    840
atgatttcta gaacccctga ggtcacatgc gtggtcgtgg acgtgagcca cgaggacccc    900
gaagtcaagt tcaactggta cgtggatggc gtcgaagtgc ataatgccaa gaccaaaccc    960
cgagaggaac agtacaactc tactatagg gtcgtgagtg tcctgaccgt gctgcaccag   1020
gactggctga acggcaagga gtataagtgc aaagtgtcca ataaggctct gccagcaccc   1080

```
atcgaaaaaa caatttctaa ggccaaagga cagcctagag agccacaggt gtacactctg    1140
cctccatccc gggacgaact gacaaagaac caggtctctc tgacttgtct ggtgaaagga    1200
ttctatccca gcgatatcgc tgtggagtgg aatccaatg gcagcctga aacaattac       1260 aagaccacac ccctgtgct ggacagtgat gggtcattct ttctgtattc caagctgaca    1320
gtggacaaat ctcggtggca gcagggcaac gtcttttctt gcagtgtgat gcatgaagcc    1380
ctgcacaatc attacacaca gaagtcactg agcctgtccc caggaaagtg ataactcgag    1440
```

<210> SEQ ID NO 5
<211> LENGTH: 226
<212> TYPE: PRT
<213> ORGANISM: Artificial Sequence
<220> FEATURE:
<223> OTHER INFORMATION: 3BNC117 human IgG1 antibody (light chain) (mod1)

<400> SEQUENCE: 5

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Thr Val Thr Ile Thr Cys Gln Ala Asn Gly Tyr
        35                  40                  45

Leu Asn Trp Tyr Gln Gln Arg Gly Lys Ala Pro Lys Leu Leu Ile
    50                  55                  60

Tyr Asp Gly Ser Lys Leu Glu Arg Gly Val Pro Ser Arg Phe Ser Gly
65                  70                  75                  80

Arg Arg Trp Gly Gln Glu Tyr Asn Leu Thr Ile Asn Asn Leu Gln Pro
                85                  90                  95

Glu Asp Ile Ala Thr Tyr Phe Cys Gln Val Tyr Glu Phe Val Val Pro
            100                 105                 110

Gly Thr Arg Leu Asp Leu Lys Arg Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Arg Ser Pro Val Thr Lys Ser Phe Asn Arg Gly
    210                 215                 220

Glu Cys
225
```

<210> SEQ ID NO 6
<211> LENGTH: 702
<212> TYPE: DNA
<213> ORGANISM: Artificial Sequence
<220> FEATURE:
<223> OTHER INFORMATION: 3BNC117 human IgG1 antibody (light chain) (mod1)

<400> SEQUENCE: 6

```
ggatccgcca ccatggtcct gcagacccag gtgtttatct cactgctgct gtggattagc      60
ggcgcatatg agacatcca gatgacacag agcccttcct ctctgtcagc aagcgtcggc     120
gataccgtga caattacttg tcaggccaac ggctacctga attggtatca gcagcggcgc     180
ggaaaggctc ccaaactgct gatctacgac ggctccaagc tggagcgcgg agtgcctagc     240
cgattctccg gcgaaggtg gggacaggag tataacctga ctatcaacaa tctgcagcct     300
gaagatattg ccacctactt ctgccaggta tatgagtttg tcgtgccagg gaccaggctg     360
gacctgaaga gaacagtcgc agcccccagc gtgttcatct ttccaccctc agatgagcag     420
ctgaaatccg gaaccgcctc tgtggtgtgc ctgctgaaca acttctaccc acgcgaagcc     480
aaggtccagt ggaaagtgga caacgctctg cagtctggca atagtcagga gtcagtgaca     540
gaacaggaca gcaaggattc cacttattct ctgagttcaa ccctgacact gtccaaagca     600
gattacgaga agcacaaagt gtatgcctgc gaggtcaccc accaggggct gcggtcacca     660
gtcacaaagt ccttcaacag aggggaatgc tgataactcg ag                        702
```

<210> SEQ ID NO 7
<211> LENGTH: 724
<212> TYPE: PRT
<213> ORGANISM: Artificial Sequence
<220> FEATURE:
<223> OTHER INFORMATION: 3BNC117 human IgG4 (mod 2)

<400> SEQUENCE: 7

```
Met Asp Trp Thr Trp Arg Ile Leu Phe Leu Val Ala Ala Ala Thr Gly
1               5                   10                  15

Thr His Ala Gln Val Gln Leu Leu Gln Ser Gly Ala Ala Val Thr Lys
            20                  25                  30

Pro Gly Ala Ser Val Arg Val Ser Cys Glu Ala Ser Gly Tyr Asn Ile
        35                  40                  45

Arg Asp Tyr Phe Ile His Trp Trp Arg Gln Ala Pro Gly Gln Gly Leu
    50                  55                  60

Gln Trp Val Gly Trp Ile Asn Pro Lys Thr Gly Gln Pro Asn Asn Pro
65                  70                  75                  80

Arg Gln Phe Gln Gly Arg Val Ser Leu Thr Arg His Ala Ser Trp Asp
                85                  90                  95

Phe Asp Thr Phe Ser Phe Tyr Met Asp Leu Lys Ala Leu Arg Ser Asp
            100                 105                 110

Asp Thr Ala Val Tyr Phe Cys Ala Arg Gln Arg Ser Asp Tyr Trp Asp
        115                 120                 125

Phe Asp Val Trp Gly Ser Gly Thr Gln Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240
```

```
Glu Ser Lys Tyr Gly Pro Pro Cys Pro Ser Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys Arg Gly Arg Lys Arg Arg Ser Gly Ser Gly Ala
465                 470                 475                 480

Thr Asn Phe Ser Leu Leu Lys Gln Ala Gly Asp Val Glu Glu Asn Pro
                485                 490                 495

Gly Pro Met Val Leu Gln Thr Gln Val Phe Ile Ser Leu Leu Leu Trp
            500                 505                 510

Ile Ser Gly Ala Tyr Gly Asp Ile Gln Met Thr Gln Ser Pro Ser Ser
        515                 520                 525

Leu Ser Ala Ser Val Gly Asp Thr Val Thr Ile Thr Cys Gln Ala Asn
    530                 535                 540

Gly Tyr Leu Asn Trp Tyr Gln Gln Arg Gly Lys Ala Pro Lys Leu
545                 550                 555                 560

Leu Ile Tyr Asp Gly Ser Lys Leu Glu Arg Gly Val Pro Ser Arg Phe
                565                 570                 575

Ser Gly Arg Arg Trp Gly Gln Glu Tyr Asn Leu Thr Ile Asn Asn Leu
            580                 585                 590

Gln Pro Glu Asp Ile Ala Thr Tyr Phe Cys Gln Val Tyr Glu Phe Val
        595                 600                 605

Val Pro Gly Thr Arg Leu Asp Leu Lys Arg Thr Val Ala Ala Pro Ser
    610                 615                 620

Val Phe Ile Phe Pro Pro Ser Asp Glu Gln Leu Lys Ser Gly Thr Ala
625                 630                 635                 640

Ser Val Val Cys Leu Leu Asn Asn Phe Tyr Pro Arg Glu Ala Lys Val
                645                 650                 655
```

```
Gln Trp Lys Val Asp Asn Ala Leu Gln Ser Gly Asn Ser Gln Ser
            660                 665                 670

Val Thr Glu Gln Asp Ser Lys Asp Ser Thr Tyr Ser Leu Ser Asn Thr
        675                 680                 685

Leu Thr Leu Ser Lys Ala Asp Tyr Glu Lys His Lys Val Tyr Ala Cys
        690                 695                 700

Glu Val Thr His Gln Gly Leu Ser Ser Pro Val Thr Lys Ser Phe Asn
705                 710                 715                 720

Arg Gly Glu Cys

<210> SEQ ID NO 8
<211> LENGTH: 2196
<212> TYPE: DNA
<213> ORGANISM: Artificial Sequence
<220> FEATURE:
<223> OTHER INFORMATION: 3BNC117 human IgG4 (mod 2)

<400> SEQUENCE: 8
ggatccgcca ccatggactg gacctggcgc atcctgttcc tggtggcagc agcaaccgga      60
acacacgcac aggtgcagct gctgcagagc ggagcagcag tgacaaagcc aggagcatct     120
gtgagggtga gctgcgaggc atccggctac aacatccgcg attacttcat ccactggtgg     180
aggcaggcac aggacaggg actgcagtgg gtgggctgga tcaatcctaa gaccggccag     240
cctaacaatc aaggcagtt ccagggacgc gtgagcctga ccaggcacgc tcctgggac     300 tttgatacat tctcttttta catggacctg aaggccctgc gcagcgacga taccgccgtg     360
tacttctgtg cccggcagag gagcgattat tgggactttg acgtgtgggg ctctggcacc     420
caggtgacag tgagctccgc ctccacaaag ggaccaagcg tgttcccact ggcaccttgc     480
agcaggtcca cctctgagag cacagccgcc ctgggctgtc tggtgaagga ctacttccct     540
gagccagtga ccgtgagctg gaactccggc gccctgacca gcggagtgca cacatttccc     600
gccgtgctgc agtctagcgg cctgtactcc ctgtcctctg tggtgaccgt gcctagctcc     660
tctctgggca ccaagacata tacctgcaac gtggaccaca gccaagcaa tacaaaggtg     720 gataagagag tggagtccaa gtacggccct ccctgccctt cttgtccagc acctgagttc     780
ctgggcggcc cttccgtgtt cctgtttcca cccaagccaa aggacaccct gatgatctct     840
cggacccccg aggtgacatg cgtggtggtg gacgtgagcc aggaggaccc cgaggtgcag     900
ttcaactggt acgtggatgg cgtggaggtg cacaatgcca agacaaagcc cagagaggag     960
cagtttaact ctacctaccg ggtggtgagc gtgctgacag tgctgcacca ggactggctg    1020
aacggcaagg agtataagtg caaggtgtcc aataagggcc tgcctagctc catcgagaag    1080
accatctcta aggcaaaggg acagccacgg gagccacagg tgtacacact gcctccaagc    1140
caggaggaga tgaccaagaa ccaggtgtcc ctgacatgtc tggtgaaggg cttctatcca    1200
agcgacatcg ccgtggagtg ggagtccaat ggccagccg agaacaatta caagaccaca    1260
ccccctgtgc tggactctga tggcagcttc tttctgtata gcagactgac cgtggataag    1320
tcccggtggc aggagggcaa cgtgttttcc tgctctgtga tgcacgaggc cctgcacaat    1380
cactacaccc agaagagcct gtccctgtct ctgggcaaga gggcagaaa gaggagaagc    1440 ggctccggcg ccacaaaactt cagcctgctg aagcaggcag cgacgtgga ggagaatcca    1500 ggacccatgg tgctgcagac ccaggtgttt atctccctgc tgctgtggat ctctggcgcc    1560
tatgccgaca tccagatgac acagtccccc tctagcctgt ctgccagcgt gggcgataca    1620
gtgaccatca catgtcaggc caacggctac ctgaattggt atcagcagag gaggggcaag    1680
```

```
gcaccaaagc tgctgatcta cgacggcagc aagctggaga gaggcgtgcc ctcccggttc   1740
tctggcagga gatggggcca ggagtataac ctgaccatca acaatctgca gcctgaggat   1800
atcgccacat acttctgcca ggtgtatgag tttgtggtgc ctggcacccg cctggacctg   1860
aagaggacag tggccgcccc aagcgtgttc atctttccac ccagcgatga gcagctgaag   1920
tctggcaccg ccagcgtggt gtgcctgctg aacaatttct acccaagaga ggccaaggtg   1980
cagtggaagg tggacaacgc cctgcagagc ggcaattccc aggagtctgt gaccgagcag   2040
gacagcaagg attccacata ttccctgtct aacaccctga cactgagcaa ggccgattac   2100
gagaagcaca ggtgtatgc atgcgaggtg acccaccagg gactgtcctc tcctgtgaca   2160
aagtccttta tcggggcga gtgttgataa ctcgag                              2196
```

<210> SEQ ID NO 9
<211> LENGTH: 724
<212> TYPE: PRT
<213> ORGANISM: Artificial Sequence
<220> FEATURE:
<223> OTHER INFORMATION: 3BNC117 human IgG4 (S228P) (mod 3)

<400> SEQUENCE: 9

```
Met Asp Trp Thr Trp Arg Ile Leu Phe Leu Val Ala Ala Thr Gly
1               5                   10                  15

Thr His Ala Gln Val Gln Leu Leu Gln Ser Gly Ala Ala Val Thr Lys
            20                  25                  30

Pro Gly Ala Ser Val Arg Val Ser Cys Glu Ala Ser Gly Tyr Asn Ile
        35                  40                  45

Arg Asp Tyr Phe Ile His Trp Trp Arg Gln Ala Pro Gly Gln Gly Leu
    50                  55                  60

Gln Trp Val Gly Trp Ile Asn Pro Lys Thr Gly Gln Pro Asn Asn Pro
65                  70                  75                  80

Arg Gln Phe Gln Gly Arg Val Ser Leu Thr Arg His Ala Ser Trp Asp
                85                  90                  95

Phe Asp Thr Phe Ser Phe Tyr Met Asp Leu Lys Ala Leu Arg Ser Asp
            100                 105                 110

Asp Thr Ala Val Tyr Phe Cys Ala Arg Gln Arg Ser Asp Tyr Trp Asp
        115                 120                 125

Phe Asp Val Trp Gly Ser Gly Thr Gln Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Pro Cys Pro Ala Pro Glu Phe
                245                 250                 255

Leu Gly Gly Pro Ser Val Phe Leu Phe Pro Pro Lys Pro Lys Asp Thr
            260                 265                 270
```

-continued

```
Leu Met Ile Ser Arg Thr Pro Glu Val Thr Cys Val Val Asp Val
        275                 280                 285

Ser Gln Glu Asp Pro Glu Val Gln Phe Asn Trp Tyr Val Asp Gly Val
290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys Arg Gly Arg Lys Arg Arg Ser Gly Ser Gly Ala
465                 470                 475                 480

Thr Asn Phe Ser Leu Leu Lys Gln Ala Gly Asp Val Glu Glu Asn Pro
                485                 490                 495

Gly Pro Met Val Leu Gln Thr Gln Val Phe Ile Ser Leu Leu Leu Trp
            500                 505                 510

Ile Ser Gly Ala Tyr Gly Asp Ile Gln Met Thr Gln Ser Pro Ser Ser
        515                 520                 525

Leu Ser Ala Ser Val Gly Asp Thr Val Thr Ile Thr Cys Gln Ala Asn
    530                 535                 540

Gly Tyr Leu Asn Trp Tyr Gln Gln Arg Arg Gly Lys Ala Pro Lys Leu
545                 550                 555                 560

Leu Ile Tyr Asp Gly Ser Lys Leu Glu Arg Gly Val Pro Ser Arg Phe
                565                 570                 575

Ser Gly Arg Arg Trp Gly Gln Glu Tyr Asn Leu Thr Ile Asn Asn Leu
            580                 585                 590

Gln Pro Glu Asp Ile Ala Thr Tyr Phe Cys Gln Val Tyr Glu Phe Val
        595                 600                 605

Val Pro Gly Thr Arg Leu Asp Leu Lys Arg Thr Val Ala Ala Pro Ser
    610                 615                 620

Val Phe Ile Phe Pro Pro Ser Asp Glu Gln Leu Lys Ser Gly Thr Ala
625                 630                 635                 640

Ser Val Val Cys Leu Leu Asn Asn Phe Tyr Pro Arg Glu Ala Lys Val
                645                 650                 655

Gln Trp Lys Val Asp Asn Ala Leu Gln Ser Gly Asn Ser Gln Glu Ser
            660                 665                 670

Val Thr Glu Gln Asp Ser Lys Asp Ser Thr Tyr Ser Leu Ser Asn Thr
        675                 680                 685
```

```
Leu Thr Leu Ser Lys Ala Asp Tyr Glu Lys His Lys Val Tyr Ala Cys
    690                 695                 700
Glu Val Thr His Gln Gly Leu Ser Ser Pro Val Thr Lys Ser Phe Asn
705                 710                 715                 720
Arg Gly Glu Cys

<210> SEQ ID NO 10
<211> LENGTH: 2196
<212> TYPE: DNA
<213> ORGANISM: Artificial Sequence
<220> FEATURE:
<223> OTHER INFORMATION: 3BNC117 human IgG4 (S228P) (mod 3)

<400> SEQUENCE: 10
```

| | | | | |
|---|---|---|---|---|
| ggatccgcca | ccatggactg | gacctggcgc | atcctgttcc | tggtggcagc agcaaccgga | 60 |
| acacacgcac | aggtgcagct | gctgcagagc | ggagcagcag | tgacaaagcc aggagcatct | 120 |
| gtgagggtga | gctgcgaggc | atccggctac | aacatccgcg | attacttcat ccactggtgg | 180 |
| aggcaggcac | caggacaggg | actgcagtgg | gtgggctgga | tcaatcctaa gaccggccag | 240 |
| cctaacaatc | aaggcagtt | ccagggacgc | gtgagcctga | ccaggcacgc ctcctgggac | 300 |
| tttgatacat | tctcttttta | catggacctg | aaggccctgc | gcagcgacga taccgccgtg | 360 |
| tacttctgtg | cccggcagag | gagcgattat | tgggactttg | acgtgtgggg ctctggcacc | 420 |
| caggtgcacg | tgagctccgc | ctccacaaag | ggaccaagcg | tgttcccact ggcaccttgc | 480 |
| agcaggtcca | cctctgagag | cacagccgcc | ctgggctgtc | tggtgaagga ctacttccct | 540 |
| gagccagtga | ccgtgagctg | gaactccggc | gccctgacca | gcggagtgca cactttccc | 600 |
| gccgtgctgc | agtctagcgg | cctgtactcc | ctgtcctctg | tggtgaccgt gcctagctcc | 660 |
| tctctgggca | ccaagacata | tacctgcaac | gtggaccaca | agccaagcaa tacaaaggtg | 720 |
| gataagagag | tggagtccaa | gtacggccct | ccctgccctc | cctgtccagc acctgagttc | 780 |
| ctgggcggcc | cttccgtgtt | cctgtttcca | cccaagccaa | aggacaccct gatgatctct | 840 |
| cggacccccg | aggtgacatg | cgtggtggtg | gacgtgagcc | aggaggaccc cgaggtgcag | 900 |
| ttcaactggt | acgtggatgg | cgtggaggtg | cacaatgcca | agacaaagcc cagagaggag | 960 |
| cagtttaact | ctacctaccg | ggtggtgagc | gtgctgacag | tgctgcacca ggactggctg | 1020 |
| aacggcaagg | agtataagtg | caaggtgtcc | aataagggcc | tgcctagctc catcgagaag | 1080 |
| accatctcta | aggcaaaggg | acagccacgc | gagccacagg | tgtacacact gcctccaagc | 1140 |
| caggaggaga | tgaccaagaa | ccaggtgtcc | ctgacatgtc | tggtgaaggg cttctatcca | 1200 |
| agcgacatcg | ccgtggagtg | ggagtccaat | ggccagcccg | agaacaatta caagaccaca | 1260 |
| cccctgtgc | tggactctga | tggcagcttc | tttctgtata | gcagactgac cgtggataag | 1320 |
| tcccggtggc | aggagggcaa | cgtgttttcc | tgctctgtga | tgcacgaggc cctgcacaat | 1380 |
| cactacaccc | agaagagcct | gtccctgtct | ctgggcaaga | ggggcagaaa gaggagaagc | 1440 |
| ggctccggcg | ccacaaactt | cagcctgctg | aagcaggcag | cgacgtgga ggagaatcca | 1500 |
| ggacccatgg | tgctgcagac | ccaggtgttt | atctccctgc | tgctgtggat ctctggcgcc | 1560 |
| tatggcgaca | tccagatgac | acagtccccc | tctagcctgt | ctgccagcgt gggcgataca | 1620 |
| gtgaccatca | catgtcaggc | caacggctac | ctgaattggt | atcagcagag gaggggcaag | 1680 |
| gcaccaaagc | tgctgatcta | cgacggcagc | aagctggaga | gaggcgtgcc ctcccggttc | 1740 |
| tctggcagga | gatggggcca | ggagtataac | ctgaccatca | caatctgca gcctgaggat | 1800 |
| atcgccacat | acttctgcca | ggtgtatgag | tttgtggtgc | ctggcacccg cctggacctg | 1860 |

```
aagaggacag tggccgcccc aagcgtgttc atctttccac ccagcgatga gcagctgaag   1920
tctggcaccg ccagcgtggt gtgcctgctg aacaatttct acccaagaga ggccaaggtg   1980
cagtggaagg tggacaacgc cctgcagagc ggcaattccc aggagtctgt gaccgagcag   2040
gacagcaagg attccacata ttccctgtct aacaccctga cactgagcaa ggccgattac   2100
gagaagcaca aggtgtatgc atgcgaggtg acccaccagg gactgtcctc tcctgtgaca   2160
aagtccttta tcggggcga gtgttgataa ctcgag                              2196
```

<210> SEQ ID NO 11
<211> LENGTH: 469
<212> TYPE: PRT
<213> ORGANISM: Artificial Sequence
<220> FEATURE:
<223> OTHER INFORMATION: 3BNC117 human IgG4 (heavy chain) (mod 4)

<400> SEQUENCE: 11

```
Met Asp Trp Thr Trp Arg Ile Leu Phe Leu Val Ala Ala Ala Thr Gly
1               5                   10                  15

Thr His Ala Gln Val Gln Leu Leu Gln Ser Gly Ala Ala Val Thr Lys
            20                  25                  30

Pro Gly Ala Ser Val Arg Val Ser Cys Glu Ala Ser Gly Tyr Asn Ile
        35                  40                  45

Arg Asp Tyr Phe Ile His Trp Trp Arg Gln Ala Pro Gly Gln Gly Leu
    50                  55                  60

Gln Trp Val Gly Trp Ile Asn Pro Lys Thr Gly Gln Pro Asn Asn Pro
65                  70                  75                  80

Arg Gln Phe Gln Gly Arg Val Ser Leu Thr Arg His Ala Ser Trp Asp
                85                  90                  95

Phe Asp Thr Phe Ser Phe Tyr Met Asp Leu Lys Ala Leu Arg Ser Asp
            100                 105                 110

Asp Thr Ala Val Tyr Phe Cys Ala Arg Gln Arg Ser Asp Tyr Trp Asp
        115                 120                 125

Phe Asp Val Trp Gly Ser Gly Thr Gln Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Pro Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300
```

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Gly Leu Pro Ser
                340                 345                 350

Ser Ile Glu Lys Thr Ile Ser Lys Ala Lys Gly Gln Pro Arg Glu Pro
            355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
    435                 440                 445

Val Met His Glu Ala Leu His Asn His Tyr Thr Gln Lys Ser Leu Ser
450                 455                 460

Leu Ser Leu Gly Lys
465

<210> SEQ ID NO 12
<211> LENGTH: 1431
<212> TYPE: DNA
<213> ORGANISM: Artificial Sequence
<220> FEATURE:
<223> OTHER INFORMATION: 3BNC117 human IgG4 (heavy chain) (mod 4)

<400> SEQUENCE: 12
ggatccgcca ccatggactg gacctggcgc atcctgttcc tggtggcagc agcaaccgga      60
acacacgcac aggtgcagct gctgcagagc ggagcagcag tgacaaagcc aggagcatct     120
gtgagggtga gctgcgaggc atccggctac aacatccgcg attacttcat ccactggtgg     180
aggcaggcac aggacagggg actgcagtgg gtgggctgga tcaatcctaa gaccggccag     240
cctaacaatc aaggcagttt ccagggacgc gtgagcctga ccaggcacgc tcctgggac      300 tttgatacat tctctttta catggacctg aaggccctgc gcagcgacga taccgccgtg     360
tacttctgtg cccggcagag gagcgattat tgggactttg acgtgtgggg ctctggcacc     420
caggtgacag tgagctccgc ctccacaaag ggaccaagcg tgttcccact ggcaccttgc     480
agcaggtcca cctctgagag cacagccgcc ctgggctgtc tggtgaagga ctacttccct     540
gagccagtga ccgtgagctg gaactccggc gccctgacca gcggagtgca cacatttccc     600
gccgtgctgc agtctagcgg cctgtactcc ctgtcctctg tggtgaccgt gcctagctcc     660
tctctgggca ccaagacata cctgcaacgt ggaccaca agccaagcaa tacaaaggtg     720
gataagagag tggagtccaa gtacggccct ccctgccctc cctgtccagc acctgagttc     780
ctgggcggcc cttccgtgtt cctgttccca cccaagccaa aggacaccct gatgatctct     840 cggaccccg aggtgacatg cgtggtggtg gacgtgagcc aggaggaccc cgaggtgcag     900
ttcaactggt acgtggatgg cgtggaggtg cacaatgcca agacaaagcc agagaggag     960 cagtttaact ctacctaccg ggtggtgagc gtgctgacag tgctgcacca ggactggctg    1020
aacggcaagg agtataagtg caaggtgtcc aataagggcc tgcctagctc catcgagaag    1080

```
accatctcta aggcaaaggg acagccacgc gagccacagg tgtacacact gcctccaagc    1140
caggaggaga tgaccaagaa ccaggtgtcc ctgacatgtc tggtgaaggg cttctatcca    1200
agcgacatcg ccgtggagtg ggagtccaat ggccagcccg agaacaatta caagaccaca    1260 cccctgtgc tggactctga tggcagcttc tttctgtata gcagactgac cgtggataag    1320
tcccggtggc aggagggcaa cgtgttttcc tgctctgtga tgcacgaggc cctgcacaat    1380
cactacaccc agaagagcct gtccctgtct ctgggcaagt gataactcga g              1431
```

```
<210> SEQ ID NO 13
<211> LENGTH: 226
<212> TYPE: PRT
<213> ORGANISM: Artificial Sequence
<220> FEATURE:
<223> OTHER INFORMATION: 3BNC117 human IgG4 (light chain)(mod 4)

<400> SEQUENCE: 13
```

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Thr Val Thr Ile Thr Cys Gln Ala Asn Gly Tyr
        35                  40                  45

Leu Asn Trp Tyr Gln Gln Arg Arg Gly Lys Ala Pro Lys Leu Leu Ile
    50                  55                  60

Tyr Asp Gly Ser Lys Leu Glu Arg Gly Val Pro Ser Arg Phe Ser Gly
65                  70                  75                  80

Arg Arg Trp Gly Gln Glu Tyr Asn Leu Thr Ile Asn Asn Leu Gln Pro
                85                  90                  95

Glu Asp Ile Ala Thr Tyr Phe Cys Gln Val Tyr Glu Phe Val Val Pro
            100                 105                 110

Gly Thr Arg Leu Asp Leu Lys Arg Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Asn Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

```
<210> SEQ ID NO 14
<211> LENGTH: 702
<212> TYPE: DNA
<213> ORGANISM: Artificial Sequence
<220> FEATURE:
<223> OTHER INFORMATION: 3BNC117 human IgG4 (light chain)(mod 4)

<400> SEQUENCE: 14
ggatccgcca ccatggtgct gcagacccag gtgtttatct ccctgctgct gtggatctct    60
```

-continued

```
ggcgcctatg gcgacatcca gatgacacag tcccctcta gcctgtctgc cagcgtgggc      120
gatacagtga ccatcacatg tcaggccaac ggctacctga attggtatca gcagaggagg      180
ggcaaggcac caaagctgct gatctacgac ggcagcaagc tggagagagg cgtgccctcc      240
cggttctctg gcaggagatg gggccaggag tataacctga ccatcaacaa tctgcagcct      300
gaggatatcg ccacatactt ctgccaggtg tatgagtttg tggtgcctgg cacccgcctg      360
gacctgaaga ggacagtggc cgccccaagc gtgttcatct tccaccag cgatgagcag       420 ctgaagtctg gcaccgccag cgtggtgtgc ctgctgaaca atttctaccc aagagaggcc      480
aaggtgcagt ggaaggtgga caacgccctg cagagcggca attcccagga gtctgtgacc      540
gagcaggaca gcaaggattc cacatattcc ctgtctaaca ccctgacact gagcaaggcc      600
gattacgaga agcacaaggt gtatgcatgc gaggtgaccc accagggact gtcctctcct      660
gtgacaaagt cctttaatcg gggcgagtgt tgataactcg ag                        702
```

<210> SEQ ID NO 15
<211> LENGTH: 744
<212> TYPE: PRT
<213> ORGANISM: Artificial Sequence
<220> FEATURE:
<223> OTHER INFORMATION: PGT128 Human IgG1

<400> SEQUENCE: 15

```
Met Asp Trp Thr Trp Arg Ile Leu Phe Leu Val Ala Ala Thr Gly
1               5                   10                  15

Thr His Ala Gln Pro Gln Leu Gln Glu Ser Gly Pro Thr Leu Val Glu
                20                  25                  30

Ala Ser Glu Thr Leu Ser Leu Thr Cys Ala Val Ser Gly Asp Ser Thr
            35                  40                  45

Ala Ala Cys Asn Ser Phe Trp Gly Trp Val Arg Gln Pro Pro Gly Lys
        50                  55                  60

Gly Leu Glu Trp Val Gly Ser Leu Ser His Cys Ala Ser Tyr Trp Asn
65                  70                  75                  80

Arg Gly Trp Thr Tyr His Asn Pro Ser Leu Lys Ser Arg Leu Thr Leu
                85                  90                  95

Ala Leu Asp Thr Pro Lys Asn Leu Val Phe Leu Lys Leu Asn Ser Val
            100                 105                 110

Thr Ala Ala Asp Thr Ala Thr Tyr Tyr Cys Ala Arg Phe Gly Gly Glu
        115                 120                 125

Val Leu Arg Tyr Thr Asp Trp Pro Lys Pro Ala Trp Val Asp Leu Trp
    130                 135                 140

Gly Arg Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
```

```
            245                 250                 255
Cys Asp Lys Thr His Thr Cys Pro Pro Cys Pro Ala Pro Glu Leu Leu
            260                 265                 270
Gly Gly Pro Ser Val Phe Leu Phe Pro Pro Lys Pro Lys Asp Thr Leu
            275                 280                 285
Met Ile Ser Arg Thr Pro Glu Val Thr Cys Val Val Val Asp Val Ser
            290                 295                 300
His Glu Asp Pro Glu Val Lys Phe Asn Trp Tyr Val Asp Gly Val Glu
305                 310                 315                 320
Val His Asn Ala Lys Thr Lys Pro Arg Glu Glu Gln Tyr Asn Ser Thr
                325                 330                 335
Tyr Arg Val Val Ser Val Leu Thr Val Leu His Gln Asp Trp Leu Asn
                340                 345                 350
Gly Lys Glu Tyr Lys Cys Lys Val Ser Asn Lys Ala Leu Pro Ala Pro
            355                 360                 365
Ile Glu Lys Thr Ile Ser Lys Ala Lys Gly Gln Pro Arg Glu Pro Gln
            370                 375                 380
Val Tyr Thr Leu Pro Pro Ser Arg Asp Glu Leu Thr Lys Asn Gln Val
385                 390                 395                 400
Ser Leu Thr Cys Leu Val Lys Gly Phe Tyr Pro Ser Asp Ile Ala Val
                405                 410                 415
Glu Trp Glu Ser Asn Gly Gln Pro Glu Asn Asn Tyr Lys Thr Thr Pro
            420                 425                 430
Pro Val Leu Asp Ser Asp Gly Ser Phe Phe Leu Tyr Ser Lys Leu Thr
            435                 440                 445
Val Asp Lys Ser Arg Trp Gln Gln Gly Asn Val Phe Ser Cys Ser Val
450                 455                 460
Met His Glu Ala Leu His Asn His Tyr Thr Gln Lys Ser Leu Ser Leu
465                 470                 475                 480
Ser Pro Gly Lys Arg Gly Arg Lys Arg Arg Ser Gly Ser Gly Ala Thr
                485                 490                 495
Asn Phe Ser Leu Leu Lys Gln Ala Gly Asp Val Glu Glu Asn Pro Gly
            500                 505                 510
Pro Met Ala Trp Thr Pro Leu Phe Leu Phe Leu Leu Thr Cys Cys Pro
            515                 520                 525
Gly Gly Ser Asn Ser Gln Ser Ala Leu Thr Gln Pro Pro Ser Ala Ser
            530                 535                 540
Gly Ser Pro Gly Gln Ser Ile Thr Ile Ser Cys Thr Gly Thr Ser Asn
545                 550                 555                 560
Asn Phe Val Ser Trp Tyr Gln Gln His Ala Gly Lys Ala Pro Lys Leu
                565                 570                 575
Val Ile Tyr Asp Val Asn Lys Arg Pro Ser Gly Val Pro Asp Arg Phe
            580                 585                 590
Ser Gly Ser Lys Ser Gly Asn Thr Ala Ser Leu Thr Val Ser Gly Leu
            595                 600                 605
Gln Thr Asp Asp Glu Ala Val Tyr Tyr Cys Gly Ser Leu Val Gly Asn
            610                 615                 620
Trp Asp Val Ile Phe Gly Gly Gly Thr Lys Leu Thr Val Leu Gly Gln
625                 630                 635                 640
Pro Lys Ala Ala Pro Ser Val Thr Leu Phe Pro Pro Ser Ser Glu Glu
                645                 650                 655
Leu Gln Ala Asn Lys Ala Thr Leu Val Cys Leu Ile Ser Asp Phe Tyr
            660                 665                 670
```

```
Pro Gly Ala Val Thr Val Ala Trp Lys Ala Asp Ser Ser Pro Val Lys
        675                 680                 685

Ala Gly Val Glu Thr Thr Pro Ser Lys Gln Ser Asn Asn Lys Tyr
    690                 695                 700

Ala Ala Ser Ser Tyr Leu Ser Leu Thr Pro Glu Gln Trp Lys Ser His
705                 710                 715                 720

Lys Ser Tyr Ser Cys Gln Val Thr His Glu Gly Ser Thr Val Glu Lys
            725                 730                 735

Thr Val Ala Pro Thr Glu Cys Ser
            740
```

<210> SEQ ID NO 16
<211> LENGTH: 2256
<212> TYPE: DNA
<213> ORGANISM: Artificial Sequence
<220> FEATURE:
<223> OTHER INFORMATION: PGT128 Human IgG1

<400> SEQUENCE: 16

```
ggatccgcca ccatggactg gacctggaga atcctgttcc tggtggcagc agcaacagga      60
acccacgcac agccacagct gcaggagtcc ggacccaccc tggtggaggc ctccagaca     120
ctgtctctga cctgcgccgt gagcggcgat tccacagcag cctgtaactc cttctgggga    180
tgggtgcgcc agccccctgg caagggcctg agtgggtgg gctctctgag ccactgcgcc     240
agctactgga cagggctga cctatcac aatccctctc tgaagagcag actgaccctg       300
gccctggaca cacctaagaa cctggtgttc ctgaagctga atagcgtgac cgccgccgat    360
acagccacct actattgtgc caggtttggc ggcgaggtgc tgagatacac agactggcca    420
aagccagcat gggtggatct gtggggaagg ggcacactgg tgaccgtgag ctccgcctcc    480
accaagggac caagcgtgtt cccactggca ccttctagca gtccacatc tggcggcacc     540
gccgccctgg gatgcctggt gaaggactac ttccctgagc cagtgacagt gtcctggaac    600
tctggcgccc tgacctctgg cgtgcacaca tttcccgccg tgctgcagtc ctctggcctg    660
tacagcctga gctccgtggt gaccgtgcct tctagctccc tgggcacaca gacctatatc    720
tgcaacgtga atcacaagcc tagcaataca aaggtggaca gaaggtgga gccaaagtcc     780
tgtgataaga cacacacctg cccaccctgt ccagcacctg agctgctggg cggcccttcc    840
gtgttcctgt ttcctccaaa gccaaaggac accctgatga tctcccggac acctgaggtg    900
acctgcgtgg tggtggacgt gtctcacgag accccgagg tgaagtttaa ctggtacgtg    960
gatggcgtgg aggtgcacaa tgccaagacc aagcccaggg aggagcagta caactctacc  1020
tatagagtgg tgagcgtgct gacagtgctg caccaggatt ggctgaacgg caaggagtat  1080
aagtgcaagg tgagcaataa ggccctgcca gcccccatcg agaagaccat ctccaaggca  1140
aagggacagc cacgggagcc acaggtgtac acactgcccc cttcccgcga cgagctgacc  1200
aagaaccagg tgtctctgac atgtctggtg aagggcttct atcccagcga tatcgccgtg  1260
gagtgggagt ccaatggcca gcccgagaac aattacaaga ccacaccacc cgtgctggac  1320
agcgatggct ccttctttct gtattccaag ctgaccgtgg acaagtctag gtggcagcag  1380
ggcaacgtgt ttagctgctc cgtgatgcac gaggccctgc acaatcacta cacccagaag  1440
tctctgagcc tgtcccctgg caagagggga aggaagagga gatctggcag cggcgccaca  1500
aacttcagcc tgctgaagca ggccggcgat gtggaggaga tcctggccc aatggcctgg  1560
accctctgt tcctgttcct gctgacatgc tgtcctggcg gctccaactc tcagagcgcc  1620
```

-continued

```
ctgacccagc ctccatccgc ctctggcagc cctggacaga gcatcacaat ctcctgtaca    1680
ggcaccagca acaatttcgt gagctggtac cagcagcacg caggcaaggc accaaagctg    1740
gtcatctacg acgtgaacaa gcggccttcc ggcgtgccag atcgcttctc cggctctaag    1800
agcggcaata cagcctctct gaccgtgagc ggcctgcaga ccgacgatga ggccgtgtac    1860
tattgcggca gcctggtggg caactgggac gtgatcttcg gcggcggaac aaagctgacc    1920
gtgctgggac agccaaaggc agcaccttcc gtgaccctgt tccccccttc tagcgaggag    1980
ctgcaggcca ataaggccac cctggtgtgc ctgatcagcg acttctaccc tggagcagtg    2040
acagtggcat ggaaggccga ttcctctcca gtgaaggccg gcgtggagac acaaccccc    2100 tctaagcaga gcaacaataa gtacgccgcc agctcctatc tgtctctgac cccagagcag    2160
tggaagagcc acaagtccta ttcttgccag gtgacacacg agggctctac agtggagaag    2220
accgtggccc ccacagagtg tagctgataa ctcgag                              2256
```

<210> SEQ ID NO 17
<211> LENGTH: 484
<212> TYPE: PRT
<213> ORGANISM: Artificial Sequence
<220> FEATURE:
<223> OTHER INFORMATION: PGT128 HUMAN IgG1- (HEAVY CHAIN) (MOD 1)

<400> SEQUENCE: 17

```
Met Asp Trp Thr Trp Arg Ile Leu Phe Leu Val Ala Ala Thr Gly
1               5                   10                  15

Thr His Ala Gln Pro Gln Leu Gln Glu Ser Gly Pro Thr Leu Val Glu
            20                  25                  30

Ala Ser Glu Thr Leu Ser Leu Thr Cys Ala Val Ser Gly Asp Ser Thr
        35                  40                  45

Ala Ala Cys Asn Ser Phe Trp Gly Trp Val Arg Gln Pro Pro Gly Lys
    50                  55                  60

Gly Leu Glu Trp Val Gly Ser Leu Ser His Cys Ala Ser Tyr Trp Asn
65                  70                  75                  80

Arg Gly Trp Thr Tyr His Asn Pro Ser Leu Lys Ser Arg Leu Thr Leu
                85                  90                  95

Ala Leu Asp Thr Pro Lys Asn Leu Val Phe Leu Lys Leu Asn Ser Val
            100                 105                 110

Thr Ala Ala Asp Thr Ala Thr Tyr Tyr Cys Ala Arg Phe Gly Gly Glu
        115                 120                 125

Val Leu Arg Tyr Thr Asp Trp Pro Lys Pro Ala Trp Val Asp Leu Trp
    130                 135                 140

Gly Arg Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
```

```
                        245                 250                 255
        Cys Asp Lys Thr His Thr Cys Pro Pro Cys Pro Ala Pro Glu Leu Leu
                    260                 265                 270

Gly Gly Pro Ser Val Phe Leu Phe Pro Pro Lys Pro Lys Asp Thr Leu
                275                 280                 285

Met Ile Ser Arg Thr Pro Glu Val Thr Cys Val Val Val Asp Val Ser
            290                 295                 300

His Glu Asp Pro Glu Val Lys Phe Asn Trp Tyr Val Asp Gly Val Glu
        305                 310                 315                 320

Val His Asn Ala Lys Thr Lys Pro Arg Glu Glu Gln Tyr Asn Ser Thr
                        325                 330                 335

Tyr Arg Val Val Ser Val Leu Thr Val Leu His Gln Asp Trp Leu Asn
                    340                 345                 350

Gly Lys Glu Tyr Lys Cys Lys Val Ser Asn Lys Ala Leu Pro Ala Pro
                355                 360                 365

Ile Glu Lys Thr Ile Ser Lys Ala Lys Gly Gln Pro Arg Glu Pro Gln
            370                 375                 380

Val Tyr Thr Leu Pro Pro Ser Arg Asp Glu Leu Thr Lys Asn Gln Val
        385                 390                 395                 400

Ser Leu Thr Cys Leu Val Lys Gly Phe Tyr Pro Ser Asp Ile Ala Val
                        405                 410                 415

Glu Trp Glu Ser Asn Gly Gln Pro Glu Asn Asn Tyr Lys Thr Thr Pro
                    420                 425                 430

Pro Val Leu Asp Ser Asp Gly Ser Phe Phe Leu Tyr Ser Lys Leu Thr
                435                 440                 445

Val Asp Lys Ser Arg Trp Gln Gln Gly Asn Val Phe Ser Cys Ser Val
            450                 455                 460

Met His Glu Ala Leu His Asn His Tyr Thr Gln Lys Ser Leu Ser Leu
        465                 470                 475                 480

Ser Pro Gly Lys

<210> SEQ ID NO 18
<211> LENGTH: 1476
<212> TYPE: DNA
<213> ORGANISM: Artificial Sequence
<220> FEATURE:
<223> OTHER INFORMATION: PGT128 HUMAN IgG1- (HEAVY CHAIN) (MOD 1)

<400> SEQUENCE: 18
ggatccgcca ccatggactg gacctggaga atcctgttcc tggtggcagc agcaacagga      60
acccacgcac agccacagct gcaggagtcc ggacccaccc tggtggaggc ctccgagaca     120
ctgtctctga cctgcgccgt gagcggcgat ccacagcag cctgtaactc cttctgggga      180
tgggtgcgcc agcccctgg caagggcctg gagtgggtgg gctctctgag ccactgcgcc      240
agctactgga cagggggctg gacctatcac aatccctctc tgaagagcag actgaccctg     300
gccctggaca cacctaagaa cctggtgttc ctgaagctga atagcgtgac cgccgccgat     360
acagccacct actattgtgc caggtttggc ggcgaggtgc tgagatacac agactggcca     420
aagccagcat gggtggatct gtggggaagg ggcacactgg tgaccgtgag ctccgcctcc     480
accaagggac caagcgtgtt cccactggca ccttctagca gtccacatc tggcggcacc      540 gccgccctgg gatgcctggt gaaggactac ttccctgagc cagtgacagt gtcctggaac     600
tctggcgccc tgacctctgg cgtgcacaca tttcccgccg tgctgcagtc ctctggcctg     660
tacagcctga gctccgtggt gaccgtgcct tctagctccc tgggcacaca gacctatatc     720
```

-continued

```
tgcaacgtga atcacaagcc tagcaataca aaggtggaca agaaggtgga gccaaagtcc    780
tgtgataaga cacacacctg cccaccctgt ccagcacctg agctgctggg cggcccttcc    840
gtgttcctgt ttcctccaaa gccaaaggac accctgatga tctcccggac acctgaggtg    900
acctgcgtgg tggtggacgt gtctcacgag gaccccgagg tgaagtttaa ctggtacgtg    960
gatggcgtgg aggtgcacaa tgccaagacc aagcccaggg aggagcagta caactctacc   1020
tatagagtgg tgagcgtgct gacagtgctg caccaggatt ggctgaacgg caaggagtat   1080
aagtgcaagg tgagcaataa ggccctgcca gcccccatcg agaagaccat ctccaaggca   1140
aagggacagc cacgggagcc acaggtgtac acactgcccc cttcccgcga cgagctgacc   1200
aagaaccagg tgtctctgac atgtctggtg aagggcttct atccaagcga tatcgccgtg   1260
gagtgggagt ccaatggcca gcccgagaac aattacaaga ccacaccacc cgtgctggac   1320
agcgatggct ccttctttct gtattccaag ctgaccgtgg acaagtctag gtggcagcag   1380
ggcaacgtgt ttagctgctc cgtgatgcac gaggccctgc acaatcacta cacccagaag   1440
tctctgagcc tgtcccctgg caagtgataa ctcgag                             1476
```

<210> SEQ ID NO 19
<211> LENGTH: 231
<212> TYPE: PRT
<213> ORGANISM: Artificial Sequence
<220> FEATURE:
<223> OTHER INFORMATION: PGT128 human IgG1- (light chain) (mod 1)

<400> SEQUENCE: 19

```
Met Ala Trp Thr Pro Leu Phe Leu Phe Leu Leu Thr Cys Cys Pro Gly
1               5                   10                  15

Gly Ser Asn Ser Gln Ser Ala Leu Thr Gln Pro Pro Ser Ala Ser Gly
            20                  25                  30

Ser Pro Gly Gln Ser Ile Thr Ile Ser Cys Thr Gly Thr Ser Asn Asn
        35                  40                  45

Phe Val Ser Trp Tyr Gln Gln His Ala Gly Lys Ala Pro Lys Leu Val
    50                  55                  60

Ile Tyr Asp Val Asn Lys Arg Pro Ser Gly Val Pro Asp Arg Phe Ser
65                  70                  75                  80

Gly Ser Lys Ser Gly Asn Thr Ala Ser Leu Thr Val Ser Gly Leu Gln
                85                  90                  95

Thr Asp Asp Glu Ala Val Tyr Tyr Cys Gly Ser Leu Val Gly Asn Trp
            100                 105                 110

Asp Val Ile Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu
    130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Lys
        195                 200                 205

Ser Tyr Ser Cys Gln Val Thr His Glu Gly Ser Thr Val Glu Lys Thr
    210                 215                 220
```

Val Ala Pro Thr Glu Cys Ser
225                 230

<210> SEQ ID NO 20
<211> LENGTH: 717
<212> TYPE: DNA
<213> ORGANISM: Artificial Sequence
<220> FEATURE:
<223> OTHER INFORMATION: PGT128 human IgG1- (light chain) (mod 1)

<400> SEQUENCE: 20

```
ggatccgcca ccatggcctg gacccctctg ttcctgttcc tgctgacatg ctgtcctggc      60
ggctccaact ctcagagcgc cctgacccag cctccatccg cctctggcag ccctggacag     120
agcatcacaa tctcctgtac aggcaccagc aacaatttcg tgagctggta ccagcagcac     180
gcaggcaagg caccaaagct ggtcatctac gacgtgaaca gcggccttc cggcgtgcca     240
gatcgcttct ccggctctaa gagcggcaat acagcctctc tgaccgtgag cggcctgcag     300
accgacgatg aggccgtgta ctattgcggc agcctggtgg gcaactggga cgtgatcttc     360
ggcggcggaa caaagctgac cgtgctggga cagccaaagg cagcaccttc cgtgaccctg     420
tttccccctt ctagcgagga gctgcaggcc aataaggcca ccctggtgtg cctgatcagc     480
gacttctacc ctggagcagt gacagtggca tggaaggccg attcctctcc agtgaaggcc     540
ggcgtggaga ccacaacccc ctctaagcag agcaacaata gtacgccgc cagtccctat     600
ctgtctctga ccccagagca gtggaagagc cacaagtcct attcttgcca ggtgacacac     660
gagggctcta cagtggagaa gaccgtggcc cccacagagt gtagctgata actcgag       717
```

<210> SEQ ID NO 21
<211> LENGTH: 741
<212> TYPE: PRT
<213> ORGANISM: Artificial Sequence
<220> FEATURE:
<223> OTHER INFORMATION: PGT128 human IgG4 (mod 2)

<400> SEQUENCE: 21

Met Asp Trp Thr Trp Arg Ile Leu Phe Leu Val Ala Ala Ala Thr Gly
1               5                   10                  15

Thr His Ala Gln Pro Gln Leu Gln Glu Ser Gly Pro Thr Leu Val Glu
            20                  25                  30

Ala Ser Glu Thr Leu Ser Leu Thr Cys Ala Val Ser Gly Asp Ser Thr
        35                  40                  45

Ala Ala Cys Asn Ser Phe Trp Gly Trp Val Arg Gln Pro Pro Gly Lys
    50                  55                  60

Gly Leu Glu Trp Val Gly Ser Leu Ser His Cys Ala Ser Tyr Trp Asn
65                  70                  75                  80

Arg Gly Trp Thr Tyr His Asn Pro Ser Leu Lys Ser Arg Leu Thr Leu
                85                  90                  95

Ala Leu Asp Thr Pro Lys Asn Leu Val Phe Leu Lys Leu Asn Ser Val
            100                 105                 110

Thr Ala Ala Asp Thr Ala Thr Tyr Tyr Cys Ala Arg Phe Gly Gly Glu
        115                 120                 125

Val Leu Arg Tyr Thr Asp Trp Pro Lys Pro Ala Trp Val Asp Leu Trp
    130                 135                 140

Gly Arg Gly Thr Leu Val Thr Val Ser Ser Ala Ser Thr Lys Gly Pro
145                 150                 155                 160

Ser Val Phe Pro Leu Ala Pro Cys Ser Arg Ser Thr Ser Glu Ser Thr
                165                 170                 175

```
Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Lys Thr Tyr Thr Cys Asn Val Asp
225                 230                 235                 240

His Lys Pro Ser Asn Thr Lys Val Asp Lys Arg Val Glu Ser Lys Tyr
                245                 250                 255

Gly Pro Pro Cys Pro Ser Cys Pro Ala Pro Glu Phe Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser Gln Glu Asp
    290                 295                 300

Pro Glu Val Gln Phe Asn Trp Tyr Val Asp Gly Val Glu Val His Asn
305                 310                 315                 320

Ala Lys Thr Lys Pro Arg Glu Glu Gln Phe Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Gly Leu Pro Ser Ser Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Gln Glu Glu Met Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Arg Leu Thr Val Asp Lys
        435                 440                 445

Ser Arg Trp Gln Glu Gly Asn Val Phe Ser Cys Ser Val Met His Glu
    450                 455                 460

Ala Leu His Asn His Tyr Thr Gln Lys Ser Leu Ser Leu Ser Leu Gly
465                 470                 475                 480

Lys Arg Gly Arg Lys Arg Arg Ser Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Trp Thr Pro Leu Phe Leu Phe Leu Leu Thr Cys Cys Pro Gly Gly Ser
        515                 520                 525

Asn Ser Gln Ser Ala Leu Thr Gln Pro Pro Ser Ala Ser Gly Ser Pro
    530                 535                 540

Gly Gln Ser Ile Thr Ile Ser Cys Thr Gly Thr Ser Asn Asn Phe Val
545                 550                 555                 560

Ser Trp Tyr Gln Gln His Ala Gly Lys Ala Pro Lys Leu Val Ile Tyr
                565                 570                 575

Asp Val Asn Lys Arg Pro Ser Gly Val Pro Asp Arg Phe Ser Gly Ser
            580                 585                 590
```

-continued

```
Lys Ser Gly Asn Thr Ala Ser Leu Thr Val Ser Gly Leu Gln Thr Asp
            595                 600                 605
Asp Glu Ala Val Tyr Tyr Cys Gly Ser Leu Val Gly Asn Trp Asp Val
610                 615                 620
Ile Phe Gly Gly Gly Thr Lys Leu Thr Val Leu Gly Gln Pro Lys Ala
625                 630                 635                 640
Ala Pro Ser Val Thr Leu Phe Pro Pro Ser Ser Glu Glu Leu Gln Ala
            645                 650                 655
Asn Lys Ala Thr Leu Val Cys Leu Ile Ser Asp Phe Tyr Pro Gly Ala
            660                 665                 670
Val Thr Val Ala Trp Lys Ala Asp Ser Ser Pro Val Lys Ala Gly Val
            675                 680                 685
Glu Thr Thr Thr Pro Ser Lys Gln Ser Asn Asn Lys Tyr Ala Ala Ser
            690                 695                 700
Ser Tyr Leu Ser Leu Thr Pro Glu Gln Trp Lys Ser His Lys Ser Tyr
705                 710                 715                 720
Ser Cys Gln Val Thr His Glu Gly Ser Thr Val Glu Lys Thr Val Ala
            725                 730                 735
Pro Thr Glu Cys Ser
            740
```

<210> SEQ ID NO 22
<211> LENGTH: 2247
<212> TYPE: DNA
<213> ORGANISM: Artificial Sequence
<220> FEATURE:
<223> OTHER INFORMATION: PGT128 human IgG4 (mod 2)

<400> SEQUENCE: 22

```
ggatccgcca ccatggactg gacctggaga atcctgttcc tggtggcagc agcaacagga      60
acccacgcac agccccagct gcaggagtcc ggccctacac tggtggaggc cagcgagacc     120
ctgtccctga catgcgccgt gtctggcgat agcaccgcag catgtaactc cttctgggga     180
tgggtgcgcc agccccctgg caagggcctg gagtgggtgg ctctctgag ccactgcgcc      240
agctactgga cagggctg gacctatcac aatccatccc tgaagtctag actgacactg       300
gccctggaca cccccaagaa cctggtgttc ctgaagctga atagcgtgac agccgccgat     360
acagccacct actattgtgc caggtttggc ggcgaggtgc tgagatacac cgactggcca     420
aagccagcat gggtggatct gtggggaagg ggcaccctgg tgacagtgag ctccgccagc     480
acaaagggcc cttccgtgtt tcctctggcc ccatgctccc gctctaccag cgagtccaca     540
gccgccctgg gatgtctggt gaaggactat ttccctgagc cagtgaccgt gagctggaac     600
tccggcgccc tgacatccgg agtgcacacc tttccagccg tgctgcagtc tagcggcctg     660
tactctctgt cctctgtggt gacagtgcca agctcctctc tgggcacaaa gacctataca     720
tgcaacgtgg accacaagcc ctccaatacc aaggtggata gagggtgga gtctaagtac      780
ggcccaccct gcccaagctg tccagcacct gagttcctgg gcggcccaag cgtgttcctg     840
tttcctccaa agcccaagga caccctgatg atcagcagaa ccccgaggt gacatgcgtg      900
gtggtggacg tgtcccagga ggaccccgag gtgcagttca actggtacgt ggatggcgtg     960
gaggtgcaca atgccaagac caagccacgg gaggagcagt taattccac ataccgcgtg     1020
gtgtctgtgc tgaccgtgct gcaccaggac tggctgaacg gcaaggagta taagtgcaag    1080
gtgtctaata agggcctgcc cagctccatc gagaagacaa tcagcaaggc aaagggacag    1140
cccgggagc ctcaggtgta caccctgccc ccttctcagg aggagatgac aaagaaccag     1200
```

-continued

```
gtgagcctga cctgtctggt gaagggcttc tatccttccg acatcgccgt ggagtgggag    1260
tctaatggcc agccagagaa caattacaag accacaccac ccgtgctgga ctctgatggc    1320
agcttctttc tgtatagccg gctgaccgtg ataagtccc  gctggcagga gggcaacgtg    1380
ttttcttgca gcgtgatgca cgaggccctg cacaatcact acacacagaa gtccctgtct    1440
ctgagcctgg gcaagagggg aaggaagagg agatccggct ctggcgccac caacttcagc    1500
ctgctgaagc aggcaggcga cgtggaggag aatccaggac ccatggcctg gacacctctg    1560
ttcctgtttc tgctgacctg ctgtccaggc ggcagcaact cccagtctgc cctgacacag    1620
cctccaagcg cctccggctc tccaggacag tctatcacca tcagctgtac cggcacatct    1680
aacaattttg tgagctggta ccagcagcac gcaggcaagg cacctaagct ggtcatctac    1740
gacgtgaaca gaggccatc  cggcgtgccc gatagattca gcggctccaa gtctggcaat    1800
accgcctccc tgacagtgtc tggcctgcag acagacgatg aggccgtgta ctattgcggc    1860
agcctggtgg gcaactggga tgtgatcttc ggcggcggaa ccaagctgac agtgctggga    1920
cagcctaagg cagcaccatc cgtgaccctg tttccccctt ctagcgagga gctgcaggcc    1980
aataaggcca ccctggtgtg cctgatcagc gacttctacc ctggagcagt gaccgtggca    2040
tggaaggccg attcctctcc cgtgaaggcc ggcgtggaga ccacaacccc ttccaagcag    2100
tctaacaata gtacgccgc  cagctcctat ctgagcctga cacctgagca gtggaagtcc    2160
cacaagagct attcctgcca ggtgacccac gagggctcca ccgtggagaa gacagtggcc    2220
ccaaccgagt gttcttgata actcgag                                      2247
```

<210> SEQ ID NO 23
<211> LENGTH: 741
<212> TYPE: PRT
<213> ORGANISM: Artificial Sequence
<220> FEATURE:
<223> OTHER INFORMATION: PGT128 human IgG4mut (S228P) (mod3)

<400> SEQUENCE: 23

```
Met Asp Trp Thr Trp Arg Ile Leu Phe Leu Val Ala Ala Thr Gly
1               5                   10                  15

Thr His Ala Gln Pro Gln Leu Gln Glu Ser Gly Pro Thr Leu Val Glu
                20                  25                  30

Ala Ser Glu Thr Leu Ser Leu Thr Cys Ala Val Ser Gly Asp Ser Thr
            35                  40                  45

Ala Ala Cys Asn Ser Phe Trp Gly Trp Val Arg Gln Pro Pro Gly Lys
        50                  55                  60

Gly Leu Glu Trp Val Gly Ser Leu Ser His Cys Ala Ser Tyr Trp Asn
65                  70                  75                  80

Arg Gly Trp Thr Tyr His Asn Pro Ser Leu Lys Ser Arg Leu Thr Leu
                85                  90                  95

Ala Leu Asp Thr Pro Lys Asn Leu Val Phe Leu Lys Leu Asn Ser Val
            100                 105                 110

Thr Ala Ala Asp Thr Ala Thr Tyr Tyr Cys Ala Arg Phe Gly Gly Glu
        115                 120                 125

Val Leu Arg Tyr Thr Asp Trp Pro Lys Pro Ala Trp Val Asp Leu Trp
    130                 135                 140

Gly Arg Gly Thr Leu Val Thr Val Ser Ser Ala Ser Thr Lys Gly Pro
145                 150                 155                 160

Ser Val Phe Pro Leu Ala Pro Cys Ser Arg Ser Thr Ser Glu Ser Thr
                165                 170                 175
```

```
Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
        210                 215                 220

Val Pro Ser Ser Ser Leu Gly Thr Lys Thr Tyr Thr Cys Asn Val Asp
225                 230                 235                 240

His Lys Pro Ser Asn Thr Lys Val Asp Lys Arg Val Glu Ser Lys Tyr
                245                 250                 255

Gly Pro Pro Cys Pro Pro Cys Pro Ala Pro Glu Phe Leu Gly Gly Pro
                260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser Gln Glu Asp
        290                 295                 300

Pro Glu Val Gln Phe Asn Trp Tyr Val Asp Gly Val Glu Val His Asn
305                 310                 315                 320

Ala Lys Thr Lys Pro Arg Glu Glu Gln Phe Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Gly Leu Pro Ser Ser Ile Glu Lys
        355                 360                 365

Thr Ile Ser Lys Ala Lys Gly Gln Pro Arg Glu Pro Gln Val Tyr Thr
        370                 375                 380

Leu Pro Pro Ser Gln Glu Glu Met Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Arg Leu Thr Val Asp Lys
        435                 440                 445

Ser Arg Trp Gln Glu Gly Asn Val Phe Ser Cys Ser Val Met His Glu
        450                 455                 460

Ala Leu His Asn His Tyr Thr Gln Lys Ser Leu Ser Leu Ser Leu Gly
465                 470                 475                 480

Lys Arg Gly Arg Lys Arg Arg Ser Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Trp Thr Pro Leu Phe Leu Phe Leu Leu Thr Cys Cys Pro Gly Gly Ser
        515                 520                 525

Asn Ser Gln Ser Ala Leu Thr Gln Pro Pro Ser Ala Ser Gly Ser Pro
        530                 535                 540

Gly Gln Ser Ile Thr Ile Ser Cys Thr Gly Thr Ser Asn Asn Phe Val
545                 550                 555                 560

Ser Trp Tyr Gln Gln His Ala Gly Lys Ala Pro Lys Leu Val Ile Tyr
                565                 570                 575

Asp Val Asn Lys Arg Pro Ser Gly Val Pro Asp Arg Phe Ser Gly Ser
            580                 585                 590
```

```
Lys Ser Gly Asn Thr Ala Ser Leu Thr Val Ser Gly Leu Gln Thr Asp
            595                 600                 605

Asp Glu Ala Val Tyr Tyr Cys Gly Ser Leu Val Gly Asn Trp Asp Val
    610                 615                 620

Ile Phe Gly Gly Gly Thr Lys Leu Thr Val Leu Gly Gln Pro Lys Ala
625                 630                 635                 640

Ala Pro Ser Val Thr Leu Phe Pro Pro Ser Ser Glu Glu Leu Gln Ala
                645                 650                 655

Asn Lys Ala Thr Leu Val Cys Leu Ile Ser Asp Phe Tyr Pro Gly Ala
            660                 665                 670

Val Thr Val Ala Trp Lys Ala Asp Ser Ser Pro Val Lys Ala Gly Val
        675                 680                 685

Glu Thr Thr Thr Pro Ser Lys Gln Ser Asn Asn Lys Tyr Ala Ala Ser
    690                 695                 700

Ser Tyr Leu Ser Leu Thr Pro Glu Gln Trp Lys Ser His Lys Ser Tyr
705                 710                 715                 720

Ser Cys Gln Val Thr His Glu Gly Ser Thr Val Glu Lys Thr Val Ala
                725                 730                 735

Pro Thr Glu Cys Ser
            740
```

<210> SEQ ID NO 24
<211> LENGTH: 2247
<212> TYPE: DNA
<213> ORGANISM: Artificial Sequence
<220> FEATURE:
<223> OTHER INFORMATION: PGT128 human IgG4mut (S228P) (mod3)

<400> SEQUENCE: 24

```
ggatccgcca ccatggactg gacctggaga atcctgttcc tggtggcagc agcaacagga      60
acccacgcac agccccagct gcaggagtcc ggccctacac tggtggaggc cagcgagacc     120
ctgtccctga catgcgccgt gtctggcgat agcaccgcag catgtaactc cttctgggga     180
tgggtgcgcc agccccctgg caagggcctg gagtgggtgg gctctctgag ccactgcgcc     240
agctactgga caggggctg gacctatcac aatccatccc tgaagtctag actgacactg     300
gccctggaca cccccaagaa cctggtgttc ctgaagctga atagcgtgac agccgccgat     360
acagccacct actattgtgc caggtttggc ggcgaggtgc tgagatacac cgactggcca     420
aagccagcat gggtggatct gtggggaagg ggcaccctgg tgacagtgag ctccgccagc     480
acaaagggcc cttccgtgtt tcctctggcc ccatgctccc gctctaccag cgagtccaca     540
gccgccctgg gatgtctggt gaaggactat ttccctgagc cagtgaccgt gagctggaac     600
tccggcgccc tgacatccgg agtgcacacc tttccagccg tgctgcagtc tagcggcctg     660
tactctctgt cctctgtggt gacagtgcca agctcctctc tgggcacaaa gacctataca     720
tgcaacgtgg accacaagcc ctccaatacc aaggtggata gagggtgga gtctaagtac     780
ggcccaccct gcccaccctg tccagcacct gagttcctgg gcggcccaag cgtgttcctg     840
tttcctccaa agcccaagga caccctgatg atcagcagaa ccccgaggt gacatgcgtg     900
gtggtggacg tgtcccagga ggaccccgag gtgcagttca actggtacgt ggatggcgtg     960
gaggtgcaca atgccaagac caagccacgg gaggagcagt ttaattccac ataccgcgtg    1020
gtgtctgtgc tgaccgtgct gcaccaggac tggctgaacg gcaaggagta taagtgcaag    1080
gtgtctaata agggcctgcc cagctccatc gagaagacaa tcagcaaggc aaagggacag    1140
ccccgggagc ctcaggtgta caccctgccc ccttctcagg aggagatgac aaagaaccag    1200
```

```
gtgagcctga cctgtctggt gaagggcttc tatccttccg acatcgccgt ggagtgggag    1260
tctaatggcc agccagagaa caattacaag accacaccac ccgtgctgga ctctgatggc    1320
agcttctttc tgtatagccg gctgaccgtg gataagtccc gctggcagga gggcaacgtg    1380
ttttcttgca gcgtgatgca cgaggccctg cacaatcact acacacagaa gtccctgtct    1440
ctgagcctgg gcaagagggg aaggaagagg agatccggct ctggcgccac caacttcagc    1500
ctgctgaagc aggcaggcga cgtggaggag aatccaggac ccatggcctg gacacctctg    1560
ttcctgtttc tgctgacctg ctgtccaggc ggcagcaact cccagtctgc cctgacacag    1620
cctccaagcg cctccggctc tccaggacag tctatcacca tcagctgtac cggcacatct    1680
aacaattttg tgagctggta ccagcagcac gcaggcaagg cacctaagct ggtcatctac    1740
gacgtgaaca gaggccatcc ggcgtgccc gatagattca gcggctccaa gtctggcaat    1800
accgcctccc tgacagtgtc tggcctgcag acagacgatg aggccgtgta ctattgcggc    1860
agcctggtgg gcaactggga tgtgatcttc ggcggcggaa ccaagctgac agtgctggga    1920
cagcctaagg cagcaccatc cgtgaccctg tttccccctt ctagcgagga gctgcaggcc    1980
aataaggcca ccctggtgtg cctgatcagc gacttctacc ctggagcagt gaccgtggca    2040
tggaaggccg attcctctcc cgtgaaggcc ggcgtggaga ccacaacccc ttccaagcag    2100
tctaacaata gtacgccgc cagctcctat ctgagcctga cacctgagca gtggaagtcc    2160
cacaagagct attcctgcca ggtgacccac gagggctcca ccgtggagaa gacagtggcc    2220
ccaaccgagt gttcttgata actcgag                                      2247

<210> SEQ ID NO 25
<211> LENGTH: 481
<212> TYPE: PRT
<213> ORGANISM: Artificial Sequence
<220> FEATURE:
<223> OTHER INFORMATION: PGT128 human IgG4-heavy chain (mod 4)

<400> SEQUENCE: 25

Met Asp Trp Thr Trp Arg Ile Leu Phe Leu Val Ala Ala Ala Thr Gly
1               5                   10                  15

Thr His Ala Gln Pro Gln Leu Gln Glu Ser Gly Pro Thr Leu Val Glu
            20                  25                  30

Ala Ser Glu Thr Leu Ser Leu Thr Cys Ala Val Ser Gly Asp Ser Thr
        35                  40                  45

Ala Ala Cys Asn Ser Phe Trp Gly Trp Val Arg Gln Pro Pro Gly Lys
    50                  55                  60

Gly Leu Glu Trp Val Gly Ser Leu Ser His Cys Ala Ser Tyr Trp Asn
65                  70                  75                  80

Arg Gly Trp Thr Tyr His Asn Pro Ser Leu Lys Ser Arg Leu Thr Leu
                85                  90                  95

Ala Leu Asp Thr Pro Lys Asn Leu Val Phe Leu Lys Leu Asn Ser Val
            100                 105                 110

Thr Ala Ala Asp Thr Ala Thr Tyr Tyr Cys Ala Arg Phe Gly Gly Glu
        115                 120                 125

Val Leu Arg Tyr Thr Asp Trp Pro Lys Pro Ala Trp Val Asp Leu Trp
    130                 135                 140

Gly Arg Gly Thr Leu Val Thr Val Ser Ser Ala Ser Thr Lys Gly Pro
145                 150                 155                 160

Ser Val Phe Pro Leu Ala Pro Cys Ser Arg Ser Thr Ser Glu Ser Thr
                165                 170                 175
```

```
Ala Ala Leu Gly Cys Leu Val Lys Asp Tyr Phe Pro Glu Pro Val Thr
            180                 185                 190
Val Ser Trp Asn Ser Gly Ala Leu Thr Ser Gly Val His Thr Phe Pro
        195                 200                 205
Ala Val Leu Gln Ser Ser Gly Leu Tyr Ser Leu Ser Ser Val Val Thr
    210                 215                 220
Val Pro Ser Ser Leu Gly Thr Lys Thr Tyr Thr Cys Asn Val Asp
225                 230                 235                 240
His Lys Pro Ser Asn Thr Lys Val Asp Lys Arg Val Glu Ser Lys Tyr
                245                 250                 255
Gly Pro Pro Cys Pro Pro Cys Pro Ala Pro Glu Phe Leu Gly Gly Pro
            260                 265                 270
Ser Val Phe Leu Phe Pro Pro Lys Pro Lys Asp Thr Leu Met Ile Ser
        275                 280                 285
Arg Thr Pro Glu Val Thr Cys Val Val Val Asp Val Ser Gln Glu Asp
    290                 295                 300
Pro Glu Val Gln Phe Asn Trp Tyr Val Asp Gly Val Glu Val His Asn
305                 310                 315                 320
Ala Lys Thr Lys Pro Arg Glu Glu Gln Phe Asn Ser Thr Tyr Arg Val
                325                 330                 335
Val Ser Val Leu Thr Val Leu His Gln Asp Trp Leu Asn Gly Lys Glu
            340                 345                 350
Tyr Lys Cys Lys Val Ser Asn Lys Gly Leu Pro Ser Ser Ile Glu Lys
        355                 360                 365
Thr Ile Ser Lys Ala Lys Gly Gln Pro Arg Glu Pro Gln Val Tyr Thr
    370                 375                 380
Leu Pro Pro Ser Gln Glu Glu Met Thr Lys Asn Gln Val Ser Leu Thr
385                 390                 395                 400
Cys Leu Val Lys Gly Phe Tyr Pro Ser Asp Ile Ala Val Glu Trp Glu
                405                 410                 415
Ser Asn Gly Gln Pro Glu Asn Asn Tyr Lys Thr Thr Pro Pro Val Leu
            420                 425                 430
Asp Ser Asp Gly Ser Phe Phe Leu Tyr Ser Arg Leu Thr Val Asp Lys
        435                 440                 445
Ser Arg Trp Gln Glu Gly Asn Val Phe Ser Cys Ser Val Met His Glu
    450                 455                 460
Ala Leu His Asn His Tyr Thr Gln Lys Ser Leu Ser Leu Ser Leu Gly
465                 470                 475                 480
Lys

<210> SEQ ID NO 26
<211> LENGTH: 1467
<212> TYPE: DNA
<213> ORGANISM: Artificial Sequence
<220> FEATURE:
<223> OTHER INFORMATION: PGT128 human IgG4-heavy chain (mod 4)

<400> SEQUENCE: 26
ggatccgcca ccatggactg gacctggaga atcctgttcc tggtggcagc agcaacagga      60
acccacgcac agccccagct gcaggagtcc ggccctacac tggtggaggc cagcgagacc     120
ctgtccctga catgcgccgt gtctggcgat agcaccgcag catgtaactc cttctgggga     180
tgggtgcgcc agcccctggg caagggcctg gagtgggtgg ctctctctga gccactgcgcc    240 agctactgga acaggggctg gacctatcac aatccatccc tgaagtctag actgacactg     300
```

```
gccctggaca ccccccaagaa cctggtgttc ctgaagctga atagcgtgac agccgccgat    360
acagccacct actattgtgc caggtttggc ggcgaggtgc tgagatacac cgactggcca    420
aagccagcat gggtggatct gtggggaagg ggcaccctgg tgacagtgag ctccgccagc    480
acaaagggcc cttccgtgtt tcctctggcc ccatgctccc gctctaccag cgagtccaca    540
gccgccctgg gatgtctggt gaaggactat ttccctgagc cagtgaccgt gagctggaac    600
tccggcgccc tgacatccgg agtgcacacc tttccagccg tgctgcagtc tagcggcctg    660
tactctctgt cctctgtggt gacagtgcca agctcctctc tgggcacaaa gacctataca    720
tgcaacgtgg accacaagcc ctccaatacc aaggtggata gagggtgga gtctaagtac    780 ggcccaccct gcccaccctg tccagcacct gagttcctgg gcggcccaag cgtgttcctg    840
tttcctccaa agcccaagga caccctgatg atcagcagaa cccccgaggt gacatgcgtg    900
gtggtggacg tgtcccagga ggaccccgag gtgcagttca actggtacgt ggatggcgtg    960
gaggtgcaca atgccaagac caagccacgg gaggagcagt ttaattccac ataccgcgtg   1020
gtgtctgtgc tgaccgtgct gcaccaggac tggctgaacg gcaaggagta taagtgcaag   1080
gtgtctaata agggcctgcc cagctccatc gagaagacaa tcagcaaggc aaagggacag   1140
ccccgggagc ctcaggtgta caccctgccc ccttctcagg aggagatgac aaagaaccag   1200
gtgagcctga cctgtctggt gaagggcttc tatccttccg acatcgccgt ggagtgggag   1260
tctaatggcc agccagagaa caattacaag accacaccac ccgtgctgga ctctgatggc   1320
agcttctttc tgtatagccg gctgaccgtg gataagtccc gctggcagga gggcaacgtg   1380
ttttcttgca gcgtgatgca cgaggccctg cacaatcact acacacagaa gtccctgtct   1440
ctgagcctgg gcaagtgata actcgag                                        1467
```

<210> SEQ ID NO 27
<211> LENGTH: 231
<212> TYPE: PRT
<213> ORGANISM: Artificial Sequence
<220> FEATURE:
<223> OTHER INFORMATION: PGT128 human IgG4-light chain (mod 4)

<400> SEQUENCE: 27

```
Met Ala Trp Thr Pro Leu Phe Leu Phe Leu Leu Thr Cys Cys Pro Gly
1               5                   10                  15

Gly Ser Asn Ser Gln Ser Ala Leu Thr Gln Pro Ser Ala Ser Gly
            20                  25                  30

Ser Pro Gly Gln Ser Ile Thr Ile Ser Cys Thr Gly Thr Ser Asn Asn
        35                  40                  45

Phe Val Ser Trp Tyr Gln Gln His Ala Gly Lys Ala Pro Lys Leu Val
    50                  55                  60

Ile Tyr Asp Val Asn Lys Arg Pro Ser Gly Val Pro Asp Arg Phe Ser
65                  70                  75                  80

Gly Ser Lys Ser Gly Asn Thr Ala Ser Leu Thr Val Ser Gly Leu Gln
                85                  90                  95

Thr Asp Asp Glu Ala Val Tyr Tyr Cys Gly Ser Leu Val Gly Asn Trp
            100                 105                 110

Asp Val Ile Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu
    130                 135                 140

Gln Ala Asn Lys Ala Thr Leu Val Cys Leu Ile Ser Asp Phe Tyr Pro
```

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
                180                 185                 190

Ser Tyr Ser Cys Gln Val Thr His Glu Gly Ser Thr Val Glu Lys Thr
        195                 200                 205

Val Ala Pro Thr Glu Cys Ser
225                 230

<210> SEQ ID NO 28
<211> LENGTH: 717
<212> TYPE: DNA
<213> ORGANISM: Artificial Sequence
<220> FEATURE:
<223> OTHER INFORMATION: PGT128 human IgG4-light chain (mod 4)

<400> SEQUENCE: 28

```
ggatccgcca ccatggcctg gacacctctg ttcctgtttc tgctgacctg ctgtccaggc      60
ggcagcaact cccagtctgc cctgacacag cctccaagcg cctccggctc tccaggacag     120
tctatcacca tcagctgtac cggcacatct aacaattttg tgagctggta ccagcagcac     180
gcaggcaagg cacctaagct ggtcatctac gacgtgaaca gaggccatc cggcgtgccc      240
gatagattca gcggctccaa gtctggcaat accgcctccc tgacagtgtc tggcctgcag     300
acagacgatg aggccgtgta ctattgcggc agcctggtgg gcaactggga tgtgatcttc     360
ggcggcggaa ccaagctgac agtgctggga cagcctaagg cagcaccatc cgtgaccctg     420
tttccccctt ctagcgagga gctgcaggcc aataaggcca ccctggtgtg cctgatcagc     480
gacttctacc ctggagcagt gaccgtggca tggaaggccg attcctctcc cgtgaaggcc     540
ggcgtggaga ccacaacccc ttccaagcag tctaacaata gtacgccgc cagctcctat     600
ctgagcctga cacctgagca gtggaagtcc cacaagagct attcctgcca ggtgacccac     660
gagggctcca ccgtggagaa gacagtggcc caaccgagt gttcttgata actcgag        717
```

<210> SEQ ID NO 29
<211> LENGTH: 750
<212> TYPE: PRT
<213> ORGANISM: Artificial Sequence
<220> FEATURE:
<223> OTHER INFORMATION: PG9 IgG1

<400> SEQUENCE: 29

Met Asp Trp Thr Trp Arg Ile Leu Phe Leu Val Ala Ala Ala Thr Gly
1               5                   10                  15

Thr His Ala Gln Arg Leu Val Glu Ser Gly Gly Gly Val Val Gln Pro
                20                  25                  30

Gly Ser Ser Leu Arg Leu Ser Cys Ala Ala Ser Gly Phe Asp Phe Ser
            35                  40                  45

Arg Gln Gly Met His Trp Val Arg Gln Ala Pro Gly Gln Gly Leu Glu
        50                  55                  60

Trp Val Ala Phe Ile Lys Tyr Asp Gly Ser Glu Lys Tyr His Ala Asp
65                  70                  75                  80

Ser Val Trp Gly Arg Leu Ser Ile Ser Arg Asp Asn Ser Lys Asp Thr
                85                  90                  95

```
Leu Tyr Leu Gln Met Asn Ser Leu Arg Val Glu Asp Thr Ala Thr Tyr
                100                 105                 110

Phe Cys Val Arg Glu Ala Gly Gly Pro Asp Tyr Arg Asn Gly Tyr Asn
            115                 120                 125

Tyr Tyr Asp Phe Tyr Asp Gly Tyr Tyr Asn Tyr His Tyr Met Asp Val
        130                 135                 140

Trp Gly Lys Gly Thr Thr Val Thr Val Ser Ser Ala Ser Thr Lys Gly
145                 150                 155                 160

Pro Ser Val Phe Pro Leu Ala Pro Ser Ser Lys Ser Thr Ser Gly Gly
                165                 170                 175

Thr Ala Ala Leu Gly Cys Leu Val Lys Asp Tyr Phe Pro Glu Pro Val
            180                 185                 190

Thr Val Ser Trp Asn Ser Gly Ala Leu Thr Ser Gly Val His Thr Phe
        195                 200                 205

Pro Ala Val Leu Gln Ser Ser Gly Leu Tyr Ser Leu Ser Ser Val Val
            210                 215                 220

Thr Val Pro Ser Ser Leu Gly Thr Gln Thr Tyr Ile Cys Asn Val
225                 230                 235                 240

Asn His Lys Pro Ser Asn Thr Lys Val Asp Lys Lys Ala Glu Pro Lys
                245                 250                 255

Ser Cys Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys Arg Gly Arg Lys Arg Ser Gly Ser Gly Ala
                485                 490                 495

Thr Asn Phe Ser Leu Leu Lys Gln Ala Gly Asp Val Glu Glu Asn Pro
            500                 505                 510

Gly Pro Met Ala Trp Thr Pro Leu Phe Leu Phe Leu Leu Thr Cys Cys
```

```
          515                 520                 525
Pro Gly Gly Ser Asn Ser Gln Ser Ala Leu Thr Gln Pro Ala Ser Val
    530                 535                 540
Ser Gly Ser Pro Gly Gln Ser Ile Thr Ile Ser Cys Asn Gly Thr Ser
545                 550                 555                 560
Asn Asp Val Gly Gly Tyr Glu Ser Val Ser Trp Tyr Gln Gln His Pro
                565                 570                 575
Gly Lys Ala Pro Lys Val Val Ile Tyr Asp Val Ser Lys Arg Pro Ser
            580                 585                 590
Gly Val Ser Asn Arg Phe Ser Gly Ser Lys Ser Gly Asn Thr Ala Ser
        595                 600                 605
Leu Thr Ile Ser Gly Leu Gln Ala Glu Asp Glu Gly Asp Tyr Tyr Cys
    610                 615                 620
Lys Ser Leu Thr Ser Thr Arg Arg Arg Val Phe Gly Thr Gly Thr Lys
625                 630                 635                 640
Leu Thr Val Leu Gly Gln Pro Lys Ala Ala Pro Ser Val Thr Leu Phe
                645                 650                 655
Pro Pro Ser Ser Glu Glu Leu Gln Ala Asn Lys Ala Thr Leu Val Cys
            660                 665                 670
Leu Ile Ser Asp Phe Tyr Pro Gly Ala Val Thr Val Ala Trp Lys Ala
        675                 680                 685
Asp Ser Ser Pro Val Lys Ala Gly Val Glu Thr Thr Thr Pro Ser Lys
    690                 695                 700
Gln Ser Asn Asn Lys Tyr Ala Ala Ser Ser Tyr Leu Ser Leu Thr Pro
705                 710                 715                 720
Glu Gln Trp Lys Ser His Lys Ser Tyr Ser Cys Gln Val Thr His Glu
                725                 730                 735
Gly Ser Thr Val Glu Lys Thr Val Ala Pro Thr Glu Cys Ser
            740                 745                 750
```

<210> SEQ ID NO 30
<211> LENGTH: 2274
<212> TYPE: DNA
<213> ORGANISM: Artificial Sequence
<220> FEATURE:
<223> OTHER INFORMATION: PG9 IgG1

<400> SEQUENCE: 30

```
ggatccgcca ccatggactg gacttggaga atcctgttcc tggtcgccgc cgctaccggg     60
actcacgctc agaggctggt ggagagtggg ggaggggtcg tgcagccagg cagctccctg    120
cgactgagtt gcgccgcttc agggttcgac ttttcccgac agggaatgca ctgggtcagg    180
caggcacctg acagggact ggagtgggtg gcttttatca agtacgacgg aagtgaaaaa     240
tatcatgccg attcagtgtg ggggcggctg tcaattagcc gcgacaacag taaggatacc    300
ctgtacctgc agatgaatag cctgcgggtc gaggacacag ctacttattt ctgcgtgcgc    360
gaagcaggcg gaccagatta ccgaaacggg tataattact atgactttta cgatggctac    420
tataactacc actatatgga cgtgtggggc aagggaacca cagtcacagt gtctagtgca    480
tcaactaaag acccagcgt gttccccctg gccccttcaa gcaagtccac ttctgggggc    540
accgcagccc tgggatgtct ggtgaaggat tacttccctg agccagtcac cgtgagttgg    600
aactcaggcg ccctgactag cggagtccat acctttcctg ctgtgctgca gtcctctggg    660
ctgtactccc tgagttcagt ggtcactgtg ccaagctcct ctctgggcac ccagacatat    720
atctgcaacg tgaatcacaa gcctagcaat accaaagtcg acaagaaagt ggaaccaaag    780
```

-continued

```
tcctgtgata aaactcatac ctgccctccc tgtccagcac ctgagctgct gggagggcct      840
tccgtgttcc tgtttccacc caagccaaaa gacacactga tgatttctag gacaccagaa      900
gtcacttgcg tggtcgtgga cgtgagccac gaggaccccg aagtcaagtt taactggtac      960
gtggatggcg tcgaggtgca taatgccaag accaaacccc gcgaggaaca gtacaactcc     1020
acatataggg tcgtgtctgt cctgactgtg ctgcaccagg actggctgaa cggcaaggag     1080
tataagtgca aagtgtccaa taaggcactg ccagccccca tcgagaaaac catttctaag     1140
gccaaaggac agccaagaga accccaggtg tacacactgc ctccatcccg ggacgagctg     1200
actaagaacc aggtctctct gacctgtctg gtgaaaggct tctatccctc tgatatcgct     1260
gtggagtggg aaagtaatgg acagcctgaa aacaattaca agactacccc tcccgtgctg     1320
gacagcgatg gtccttctt tctgtatagc aagctgacag tggacaaatc cagatggcag     1380
cagggcaacg tctttagttg ctcagtgatg cacgaggccc tgcacaatca ttacacacag     1440
aaaagcctgt ccctgtctcc cggcaagagg ggaagaaaaa ggagaagtgg gtcaggcgca     1500
actaacttca gcctgctgaa gcaggccgga gatgtggagg aaaatcctgg gccaatggct     1560
tggacccctc tgttcctgtt cctgctgaca tgctgtcctg gcggaagcaa ctcccagtct     1620
gcactgaccc agccagcaag cgtgagcggg agcccaggcc agagcatcac catttcctgt     1680
aacggcacat ccaatgacgt gggcggctac gagtccgtgt cttggtatca gcagcatcct     1740
ggaaaggccc caaaagtcgt gatctacgat gtcagcaaaa gaccttctgg ggtgagtaac     1800
cggttcagtg gatcaaagag cgggaatacc gcttctctga caattagtgg cctgcaggca     1860
gaggacgaag gagattacta ttgcaagtca ctgacaagca ctcggcgccg agtcttcgga     1920
accgggacaa agctgactgt gctgggccag cccaaagctg caccttctgt gacccctgttt     1980 ccacccagtt cagaggaact gcaggctaac aaggccaccc tggtgtgcct gatcagcgac     2040
ttctaccctg gcgctgtcac tgtggcctgg aaggctgata gctccccagt caaagcagga     2100
gtggaaacaa ctacccctc caagcagtct aacaacaagt acgccgcttc tagttatctg     2160
tcactgaccc cagagcagtg gaagtctcac aaatcctatt cttgtcaggt cacccatgaa     2220
gggagcactg tggagaaaac cgtcgcacca accgaatgtt cctgataact cgag           2274
```

<210> SEQ ID NO 31
<211> LENGTH: 747
<212> TYPE: PRT
<213> ORGANISM: Artificial Sequence
<220> FEATURE:
<223> OTHER INFORMATION: PG9 human IgG4

<400> SEQUENCE: 31

```
Met Asp Trp Thr Trp Arg Ile Leu Phe Leu Val Ala Ala Ala Thr Gly
1               5                   10                  15

Thr His Ala Gln Arg Leu Val Glu Ser Gly Gly Gly Val Val Gln Pro
            20                  25                  30

Gly Ser Ser Leu Arg Leu Ser Cys Ala Ala Ser Gly Phe Asp Phe Ser
        35                  40                  45

Arg Gln Gly Met His Trp Val Arg Gln Ala Pro Gly Gln Gly Leu Glu
    50                  55                  60

Trp Val Ala Phe Ile Lys Tyr Asp Gly Ser Glu Lys Tyr His Ala Asp
65                  70                  75                  80

Ser Val Trp Gly Arg Leu Ser Ile Ser Arg Asp Asn Ser Lys Asp Thr
                85                  90                  95
```

```
Leu Tyr Leu Gln Met Asn Ser Leu Arg Val Glu Asp Thr Ala Thr Tyr
                100                 105                 110

Phe Cys Val Arg Glu Ala Gly Gly Pro Asp Tyr Arg Asn Gly Tyr Asn
            115                 120                 125

Tyr Tyr Asp Phe Tyr Asp Gly Tyr Tyr Asn Tyr His Tyr Met Asp Val
        130                 135                 140

Trp Gly Lys Gly Thr Thr Val Thr Val Ser Ser Ala Ser Thr Lys Gly
145                 150                 155                 160

Pro Ser Val Phe Pro Leu Ala Pro Cys Ser Arg Ser Thr Ser Glu Ser
                165                 170                 175

Thr Ala Ala Leu Gly Cys Leu Val Lys Asp Tyr Phe Pro Glu Pro Val
            180                 185                 190

Thr Val Ser Trp Asn Ser Gly Ala Leu Thr Ser Gly Val His Thr Phe
        195                 200                 205

Pro Ala Val Leu Gln Ser Ser Gly Leu Tyr Ser Leu Ser Ser Val Val
210                 215                 220

Thr Val Pro Ser Ser Ser Leu Gly Thr Lys Thr Tyr Thr Cys Asn Val
225                 230                 235                 240

Asp His Lys Pro Ser Asn Thr Lys Val Asp Lys Arg Val Glu Ser Lys
                245                 250                 255

Tyr Gly Pro Pro Cys Pro Ser Cys Pro Ala Pro Glu Phe Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser Gln Glu
290                 295                 300

Asp Pro Glu Val Gln Phe Asn Trp Tyr Val Asp Gly Val Glu Val His
305                 310                 315                 320

Asn Ala Lys Thr Lys Pro Arg Glu Glu Gln Phe Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Gly Leu Pro Ser Ser Ile Glu
        355                 360                 365

Lys Thr Ile Ser Lys Ala Lys Gly Gln Pro Arg Glu Pro Gln Val Tyr
370                 375                 380

Thr Leu Pro Pro Ser Gln Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Arg Leu Thr Val Asp
        435                 440                 445

Lys Ser Arg Trp Gln Glu Gly Asn Val Phe Ser Cys Ser Val Met His
450                 455                 460

Glu Ala Leu His Asn His Tyr Thr Gln Lys Ser Leu Ser Leu Ser Leu
465                 470                 475                 480

Gly Lys Arg Gly Arg Lys Arg Ser Gly Ser Gly Ala Thr Asn Phe
                485                 490                 495

Ser Leu Leu Lys Gln Ala Gly Asp Val Glu Glu Asn Pro Gly Pro Met
            500                 505                 510

Ala Trp Thr Pro Leu Phe Leu Phe Leu Leu Thr Cys Cys Pro Gly Gly
```

```
                515                 520                 525
Ser Asn Ser Gln Ser Ala Leu Thr Gln Pro Ala Ser Val Gly Ser
            530                 535                 540

Pro Gly Gln Ser Ile Thr Ile Ser Cys Asn Gly Thr Ser Asn Asp Val
545                 550                 555                 560

Gly Gly Tyr Glu Ser Val Ser Trp Tyr Gln Gln His Pro Gly Lys Ala
                565                 570                 575

Pro Lys Val Val Ile Tyr Asp Val Ser Lys Arg Pro Ser Gly Val Ser
            580                 585                 590

Asn Arg Phe Ser Gly Ser Lys Ser Gly Asn Thr Ala Ser Leu Thr Ile
            595                 600                 605

Ser Gly Leu Gln Ala Glu Asp Glu Gly Asp Tyr Tyr Cys Lys Ser Leu
    610                 615                 620

Thr Ser Thr Arg Arg Val Phe Gly Thr Gly Thr Lys Leu Thr Val
625                 630                 635                 640

Leu Gly Gln Pro Lys Ala Ala Pro Ser Val Thr Leu Phe Pro Pro Ser
            645                 650                 655

Ser Glu Glu Leu Gln Ala Asn Lys Ala Thr Leu Val Cys Leu Ile Ser
            660                 665                 670

Asp Phe Tyr Pro Gly Ala Val Thr Val Ala Trp Lys Ala Asp Ser Ser
    675                 680                 685

Pro Val Lys Ala Gly Val Glu Thr Thr Thr Pro Ser Lys Gln Ser Asn
690                 695                 700

Asn Lys Tyr Ala Ala Ser Ser Tyr Leu Ser Leu Thr Pro Glu Gln Trp
705                 710                 715                 720

Lys Ser His Lys Ser Tyr Ser Cys Gln Val Thr His Glu Gly Ser Thr
                725                 730                 735

Val Glu Lys Thr Val Ala Pro Thr Glu Cys Ser
            740                 745

<210> SEQ ID NO 32
<211> LENGTH: 2265
<212> TYPE: DNA
<213> ORGANISM: Artificial Sequence
<220> FEATURE:
<223> OTHER INFORMATION: PG9 human IgG4

<400> SEQUENCE: 32
ggatccgcca ccatggactg gacctggcgc atcctgtttc tggtggcagc agcaacagga      60
acccacgcac agaggctggt ggagagcggc ggcggcgtgg tgcagcctgg cagctccctg     120
agactgtcct gcgcagcatc tggcttcgac ttcagcaggc agggcatgca ctgggtgcgg     180
caggcaccag acagggact ggagtggtg gccttcatca gtacgacgg ctctgagaag        240 tatcacgcag atagcgtgtg gggccgcctg tccatctcta gggacaacag caaggatacc     300
ctgtacctgc agatgaattc cctgcgcgtg gaggacacag ccacctattt ctgcgtgagg     360
gaggccggcg gaccagatta caggaacggc tataattact atgacttta cgatggctac     420 tataactacc actatatgga cgtgtggggc aagggcacca gtgacagt gtctagcgcc       480 tccaccaagg gaccaagcgt gttccctctg gcaccatgca gcaggtccac ctctgagagc     540
acagccgccc tgggctgtct ggtgaaggat tatttccctg agccagtgac cgtgagctgg     600
aattccggcg ccctgacatc cggagtgcac acctttcctg ccgtgctgca gtcctctggc     660
ctgtacagct gagctccgt ggtgacagtg ccctctagct ccctgggcac aaagacctat     720
acatgcaacg tggaccacaa gccttccaat accaaggtgg ataagagagt ggagagcaag     780
```

```
tacggccctc cctgcccatc ctgtccagca cctgagttcc tgggcggccc aagcgtgttc    840
ctgtttccac ccaagcccaa ggacacactg atgatcagcc ggacccctga ggtgacatgc    900
gtggtggtgg acgtgtccca ggaggacccc gaggtgcagt tcaactggta cgtggatggc    960
gtggaggtgc acaatgccaa gaccaagccc agagaggagc agtttaacag cataccgg    1020 gtggtgtccg tgctgaccgt gctgcaccag gactggctga acggcaagga gtataagtgc   1080
aaggtgtcta ataagggcct gccttctagc atcgagaaga caatcagcaa ggcaaaggga   1140
cagccccggg agcctcaggt gtacaccctg cctccatctc aggaggagat gacaaagaac   1200
caggtgagcc tgacctgtct ggtgaagggc ttttatccat ctgacatcgc cgtggagtgg   1260
gagagcaatg ccagcccga gaacaattac aagaccacac ccctgtgct ggactctgat    1320 ggcagcttct ttctgtattc ccgcctgact gtggataagt ctaggtggca ggagggcaac   1380
gtgttttcct gctctgtgat gcacgaggcc ctgcacaatc actacacaca gaagagcctg   1440
tccctgtctc tgggcaagag aggaaggaag aggagaagcg ctccggagc aaccaacttc    1500 agcctgctga agcaggcagg cgacgtggag gagaatccag acccatggc ctggacacct    1560 ctgttcctgt ttctgctgac ctgctgtcca ggcggctcta acagccagtc cgccctgacc   1620
cagccagcat ctgtgagcgg ctcccctggc cagagcatca aatctcctg taacggcacc    1680 tccaatgacg tgggcggcta cgagtctgtg agctggtatc agcagcaccc aggcaaggcc   1740
cccaaggtgg tcatctacga tgtgagcaag agaccctccg gcgtgtctaa ccggttctcc   1800
ggctctaaga gcggcaatac cgcctctctg acaatcagcg gactgcaggc agaggacgag   1860
ggcgattact attgcaagag cctgacctcc acacggcgca gggtgttcgg aaccggcaca   1920
aagctgacag tgctgggaca gcctaaggca gcaccatccg tgaccctgtt tccaccctcc   1980
tctgaggagc tgcaggccaa caaggccacc ctggtgtgcc tgatcagcga cttctaccct   2040
ggagcagtga ccgtggcatg gaaggcagat agctccccag tgaaggcagg agtggagacc   2100
acaacccctt ctaagcagag caacaataag tacgccgcct ctagctatct gtccctgaca   2160
ccagagcagt ggaagtctca caagtcctat tcttgccagg tgacccacga gggctccacc   2220
gtggagaaga cagtggcccc caccgagtgt tcttgataac tcgag                   2265
```

<210> SEQ ID NO 33
<211> LENGTH: 733
<212> TYPE: PRT
<213> ORGANISM: Artificial Sequence
<220> FEATURE:
<223> OTHER INFORMATION: NIH45-46human IgG1 antibody

<400> SEQUENCE: 33

```
Met Asp Trp Thr Trp Arg Ile Leu Phe Leu Val Ala Ala Ala Thr Gly
1               5                   10                  15

Thr His Ala Gln Val Arg Leu Ser Gln Ser Gly Gly Gln Met Lys Lys
            20                  25                  30

Pro Gly Glu Ser Met Arg Leu Ser Cys Arg Ala Ser Gly Tyr Glu Phe
        35                  40                  45

Leu Asn Cys Pro Ile Asn Trp Ile Arg Leu Ala Pro Gly Arg Arg Pro
    50                  55                  60

Glu Trp Met Gly Trp Leu Lys Pro Arg Gly Gly Ala Val Asn Tyr Ala
65                  70                  75                  80

Arg Lys Phe Gln Gly Arg Val Thr Met Thr Arg Asp Val Tyr Ser Asp
                85                  90                  95
```

```
Thr Ala Phe Leu Glu Leu Arg Ser Leu Thr Ser Asp Asp Thr Ala Val
            100                 105                 110

Tyr Phe Cys Thr Arg Gly Lys Tyr Cys Thr Ala Arg Asp Tyr Tyr Asn
        115                 120                 125

Trp Asp Phe Glu His Trp Gly Arg Gly Ala Pro Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys Arg Gly Arg Lys Arg Arg
465                 470                 475                 480

Ser Gly Ser Gly Ala Thr Asn Phe Ser Leu Leu Lys Gln Ala Gly Asp
                485                 490                 495

Val Glu Glu Asn Pro Gly Pro Met Val Leu Gln Thr Gln Val Phe Ile
            500                 505                 510

Ser Leu Leu Leu Trp Ile Ser Gly Ala Tyr Gly Glu Ile Val Leu Thr
```

```
                515                 520                 525
Gln Ser Pro Ala Thr Leu Ser Leu Ser Pro Gly Glu Thr Ala Ile Ile
        530                 535                 540

Ser Cys Arg Thr Ser Gln Ser Gly Ser Leu Ala Trp Tyr Gln Gln Arg
545                 550                 555                 560

Pro Gly Gln Ala Pro Arg Leu Val Ile Tyr Ser Gly Ser Thr Arg Ala
                565                 570                 575

Ala Gly Ile Pro Asp Arg Phe Ser Gly Ser Arg Trp Gly Ala Asp Tyr
        580                 585                 590

Asn Leu Ser Ile Ser Asn Leu Glu Ser Gly Asp Phe Gly Val Tyr Tyr
                595                 600                 605

Cys Gln Gln Tyr Glu Phe Phe Gly Gln Gly Thr Lys Val Gln Val Asp
        610                 615                 620

Ile Lys Arg Thr Val Ala Ala Pro Ser Val Phe Ile Phe Pro Pro Ser
625                 630                 635                 640

Asp Glu Gln Leu Lys Ser Gly Thr Ala Ser Val Val Cys Leu Leu Asn
                645                 650                 655

Asn Phe Tyr Pro Arg Glu Ala Lys Val Gln Trp Lys Val Asp Asn Ala
        660                 665                 670

Leu Gln Ser Gly Asn Ser Gln Glu Ser Val Thr Glu Gln Asp Ser Lys
                675                 680                 685

Asp Ser Thr Tyr Ser Leu Ser Ser Thr Leu Thr Leu Ser Lys Ala Asp
        690                 695                 700

Tyr Glu Lys His Lys Val Tyr Ala Cys Glu Val Thr His Gln Gly Leu
705                 710                 715                 720

Arg Ser Pro Val Thr Lys Ser Phe Asn Arg Gly Glu Cys
                725                 730

<210> SEQ ID NO 34
<211> LENGTH: 2223
<212> TYPE: DNA
<213> ORGANISM: Artificial Sequence
<220> FEATURE:
<223> OTHER INFORMATION: NIH45-46human IgG1 antibody

<400> SEQUENCE: 34
ggatccgcca ccatggactg gacctggcgc atcctgttcc tggtggcagc agcaaccgga      60
acacacgcac aggtgaggct gtcccagtct ggcggccaga tgaagaagcc tggagagtct     120
atgaggctga gctgcagggc atccggatac gagttcctga actgtccaat caattggatc     180
agactggccc ctgcaggag accagagtgg atgggatggc tgaagcctcg ggcggcgcc     240 gtgaactacg caaggaagtt tcagggcaga gtgaccatga cacgggacgt gtatagcgat     300
accgccttcc tggagctgag atctctgacc agcgacgata cagccgtgta cttttgcacc     360
cgcggcaagt attgtacagc cagggactac tataattggg atttcgagca ctggggaagg     420
ggcgccccag tgaccgtgag ctccgcctcc acaaagggac ctagcgtgtt cccactggca     480
ccttctagca agagcacctc cggcggcaca gccgccctgg atgcctggt gaaggactac     540 ttccctgagc cagtgaccgt gtcctggaac tctggcgccc tgaccagcgg agtgcacaca     600
tttccagccg tgctgcagtc ctctggcctg tactccctga gctccgtggt gaccgtgccc     660
tctagctccc tgggcacccc agacatatat cgcaacgtga atcacaagcc atctaataca     720
aaggtggaca gaaggtgga gcccaagagc tgtgataaga cccacacatg ccctcccctgt     780 ccagcacctg agctgctggg cggccttcc gtgttcctgt ttccacccaa gccaaaggac     840
```

```
acactgatga tctccagaac ccccgaggtg acatgcgtgg tggtggacgt gtctcacgag    900
gaccccgagg tgaagttcaa ctggtacgtg gatggcgtgg aggtgcacaa tgccaagacc    960
aagccaagag aggagcagta caactctacc tatcgggtgg tgagcgtgct gacagtgctg   1020
caccaggatt ggctgaacgg caaggagtat aagtgcaagg tgagcaataa ggccctgcca   1080
gcccccatcg agaagaccat ctccaaggcc aagggccagc caagagagcc ccaggtgtac   1140
acactgcctc caagccggga cgagctgacc aagaaccagg tgtccctgac atgtctggtg   1200
aagggcttct atccttccga tatcgccgtg gagtgggagt ctaatggcca gccagagaac   1260
aattacaaga ccacaccccc tgtgctggac agcgatggct ccttctttct gtatagcaag   1320
ctgaccgtgg acaagtcccg gtggcagcag ggcaacgtgt ttcttgcag cgtgatgcac    1380
gaggccctgc acaatcacta cacccagaag tccctgtctc tgagcccagg caagagggga   1440
agaaagcggc gctccggctc tggagccaca aacttcagcc tgctgaagca ggccggcgat   1500
gtggaggaga atcctggccc aatggtgctg cagacccagg tgtttatctc cctgctgctg   1560
tggatctctg gcgcctacgg cgagatcgtg ctgacccagt ctccagccac actgagcctg   1620
tccccaggag agaccgcaat catctcctgt cgcacatctc agagcggctc cctggcatgg   1680
taccagcaga gaccaggaca ggcccctcgg ctggtcatct actctggcag cacaagggcc   1740
gcaggcatcc ccgaccgctt ctccggctct aggtggggcg ccgattacaa cctgagcatc   1800
tccaatctgg agagcggcga ctttggcgtg tactattgcc agcagtatga gttctttggc   1860
cagggcacca aggtgcaggt ggacatcaag cgcacagtgg ccgcccccag cgtgttcatc   1920
tttccaccca gcgatgagca gctgaagtct ggcaccgcca gcgtggtgtg cctgctgaac   1980
aatttctacc ctagggaggc caaggtgcag tggaaggtgg acaacgccct gcagtctggc   2040
aatagccagg agtccgtgac cgagcaggac tctaaggata gcacatattc cctgtctagc   2100
accctgacac tgtccaaggc cgattacgag aagcacaagg tgtatgcatg cgaggtgacc   2160
caccagggac tgcgcagccc cgtgacaaag tcctttaaca ggggcgagtg ttgataactc   2220
gag                                                                2223
```

<210> SEQ ID NO 35
<211> LENGTH: 730
<212> TYPE: PRT
<213> ORGANISM: Artificial Sequence
<220> FEATURE:
<223> OTHER INFORMATION: NIH45-46human IgG4 antibody

<400> SEQUENCE: 35

```
Met Asp Trp Thr Trp Arg Ile Leu Phe Leu Val Ala Ala Ala Thr Gly
1               5                   10                  15

Thr His Ala Gln Val Arg Leu Ser Gln Ser Gly Gly Gln Met Lys Lys
            20                  25                  30

Pro Gly Glu Ser Met Arg Leu Ser Cys Arg Ala Ser Gly Tyr Glu Phe
        35                  40                  45

Leu Asn Cys Pro Ile Asn Trp Ile Arg Leu Ala Pro Gly Arg Arg Pro
    50                  55                  60

Glu Trp Met Gly Trp Leu Lys Pro Arg Gly Gly Ala Val Asn Tyr Ala
65                  70                  75                  80

Arg Lys Phe Gln Gly Arg Val Thr Met Thr Arg Asp Val Tyr Ser Asp
                85                  90                  95

Thr Ala Phe Leu Glu Leu Arg Ser Leu Thr Ser Asp Asp Thr Ala Val
            100                 105                 110
```

-continued

```
Tyr Phe Cys Thr Arg Gly Lys Tyr Cys Thr Ala Arg Asp Tyr Tyr Asn
        115                 120                 125

Trp Asp Phe Glu His Trp Gly Arg Gly Ala Pro Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Ser Leu Gly Thr Lys Thr
210                 215                 220

Tyr Thr Cys Asn Val Asp His Lys Pro Ser Asn Thr Lys Val Asp Lys
225                 230                 235                 240

Arg Val Glu Ser Lys Tyr Gly Pro Pro Cys Pro Ser Cys Pro Ala Pro
            245                 250                 255

Glu Phe Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Gly Leu
        340                 345                 350

Pro Ser Ser Ile Glu Lys Thr Ile Ser Lys Ala Lys Gly Gln Pro Arg
    355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Arg Leu Thr Val Asp Lys Ser Arg Trp Gln Glu Gly Asn Val Phe Ser
    435                 440                 445

Cys Ser Val Met His Glu Ala Leu His Asn His Tyr Thr Gln Lys Ser
450                 455                 460

Leu Ser Leu Ser Leu Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
            485                 490                 495

Asn Pro Gly Pro Met Val Leu Gln Thr Gln Val Phe Ile Ser Leu Leu
        500                 505                 510

Leu Trp Ile Ser Gly Ala Tyr Gly Glu Ile Val Leu Thr Gln Ser Pro
    515                 520                 525

Ala Thr Leu Ser Leu Ser Pro Gly Glu Thr Ala Ile Ile Ser Cys Arg
```

Thr Ser Gln Ser Gly Ser Leu Ala Trp Tyr Gln Gln Arg Pro Gly Gln
545                 550                 555                 560

Ala Pro Arg Leu Val Ile Tyr Ser Gly Ser Thr Arg Ala Ala Gly Ile
            565                 570                 575

Pro Asp Arg Phe Ser Gly Ser Arg Trp Gly Ala Asp Tyr Asn Leu Ser
            580                 585                 590

Ile Ser Asn Leu Glu Ser Gly Asp Phe Gly Val Tyr Tyr Cys Gln Gln
            595                 600                 605

Tyr Glu Phe Phe Gly Gln Gly Thr Lys Val Gln Val Asp Ile Lys Arg
610                 615                 620

Thr Val Ala Ala Pro Ser Val Phe Ile Phe Pro Pro Ser Asp Glu Gln
625                 630                 635                 640

Leu Lys Ser Gly Thr Ala Ser Val Val Cys Leu Leu Asn Asn Phe Tyr
            645                 650                 655

Pro Arg Glu Ala Lys Val Gln Trp Lys Val Asp Asn Ala Leu Gln Ser
            660                 665                 670

Gly Asn Ser Gln Glu Ser Val Thr Glu Gln Asp Ser Lys Asp Ser Thr
            675                 680                 685

Tyr Ser Leu Ser Asn Thr Leu Thr Leu Ser Lys Ala Asp Tyr Glu Lys
690                 695                 700

His Lys Val Tyr Ala Cys Glu Val Thr His Gln Gly Leu Ser Ser Pro
705                 710                 715                 720

Val Thr Lys Ser Phe Asn Arg Gly Glu Cys
            725                 730

<210> SEQ ID NO 36
<211> LENGTH: 2214
<212> TYPE: DNA
<213> ORGANISM: Artificial Sequence
<220> FEATURE:
<223> OTHER INFORMATION: NIH45-46human IgG4 antibody

<400> SEQUENCE: 36
ggatccgcca ccatggactg gacctggaga atcctgttcc tggtggcagc agcaaccgga      60
acacacgcac aggtgcggct gtcccagtct ggcggccaga tgaagaagcc aggagagtct     120
atgaggctga gctgcagggc atccggatac gagttcctga actgtcctat caattggatc     180
aggctggcac caggcaggag acccgagtgg atgggatggc tgaagcccag ggcggcgcc      240 gtgaactacg caaggaagtt tcagggcaga gtgaccatga cacgggacgt gtattccgat     300
accgccttcc tggagctgag aagcctgaca tccgacgata ccgccgtgta cttttgcaca     360
cgcggcaagt attgtaccgc cagggactac tataattggg atttcgagca ctggggaaga     420
ggcgcccctg tgacagtgag ctccgcctcc accaagggcc caagcgtgtt ccctctggcc     480
ccatgcagcc ggtccacatc tgagagcacc gccgccctgg gatgtctggt gaaggactac     540
ttccctgagc cagtgaccgt gtcttggaac agcggcgccc tgacatctgg cgtgcacacc     600
tttcccgccg tgctgcagtc tagcggcctg tacagcctgt cctctgtggt gacagtgcct     660
agctcctctc tgggcaccaa gacatatacc tgcaacgtgg accacaagcc atccaatacc     720
aaggtggata agcgcgtgga gtctaagtac ggccctccct gccctagctg tccagcacct     780
gagttcctgg gcggcccaag cgtgttcctg tttccaccca gcccaaggaa caccctgatg     840
atctctagga caccagaggt gacctgcgtg gtggtggacg tgagccagga ggaccccgag     900
gtgcagttca actggtacgt ggatggcgtg gaggtgcaca atgccaagac aaagcctcgc     960

```
gaggagcagt taacagcac atacagggtg gtgtccgtgc tgaccgtgct gcaccaggat    1020
tggctgaacg gcaaggagta taagtgcaag gtgtccaata agggcctgcc aagctccatc    1080
gagaagacaa tctctaaggc aaagggacag ccccgggagc tcaggtgta caccctgcct    1140 ccaagccagg aggagatgac aaagaaccag gtgtccctga cctgtctggt gaagggcttc    1200
tatccctccg acatcgccgt ggagtgggag tctaatggcc agcctgagaa caattacaag    1260
accacacccc ctgtgctgga ctccgatggc tctttctttc tgtattccag actgaccgtg    1320
gataagtctc ggtggcagga gggcaacgtg ttttcctgct ctgtgatgca cgaggccctg    1380
cacaatcact acacacagaa gagcctgtcc ctgtctctgg gcaagagggg aagaaagcgg    1440
cgcagcggct ccggagcaac caacttctcc ctgctgaagc aggcaggcga cgtggaggag    1500
aatccaggac ccatggtgct gcagacacag gtgtttatct ctctgctgct gtggatcagc    1560
ggcgcctacg gcgagatcgt gctgacacag agcccagcca ccctgtctct gagccctgga    1620
gagacagcca tcatctcctg tcgcacctcc cagtctggca gcctggcatg gtaccagcag    1680
agacctggac aggccccacg gctggtcatc tactccggct ctaccagggc cgcaggcatc    1740
ccagaccgct tcagcggctc caggtggggc gccgattaca acctgtctat cagcaatctg    1800
gagagcggcg attttggcgt gtactattgc cagcagtatg agttctttgg ccagggcaca    1860
aaggtgcagg tggacatcaa agaaccgtg ccgccccaa gcgtgttcat ctttccaccc    1920
tccgatgagc agctgaagtc tggcacagcc agcgtggtgt gcctgctgaa caatttctac    1980
ccccgggagg ccaaggtgca gtggaaggtg gacaacgccc tgcagagcgg caattcccag    2040
gagtctgtga cagagcagga cagcaaggat tccacctatt ccctgtctaa cacactgacc    2100
ctgtccaagg ccgattacga gaagcacaag gtgtatgcct gcgaggtgac acaccagggc    2160
ctgtctagcc ctgtgaccaa gagctttaat cgcggcgagt gttgataact cgag           2214
```

<210> SEQ ID NO 37
<211> LENGTH: 729
<212> TYPE: PRT
<213> ORGANISM: Artificial Sequence
<220> FEATURE:
<223> OTHER INFORMATION: VRC01 human IgG1

<400> SEQUENCE: 37

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gln Met Lys Lys
            20                  25                  30

Pro Gly Glu Ser Met Arg Ile Ser Cys Arg Ala Ser Gly Tyr Glu Phe
        35                  40                  45

Ile Asp Cys Thr Leu Asn Trp Ile Arg Leu Ala Pro Gly Lys Arg Pro
    50                  55                  60

Glu Trp Met Gly Trp Leu Lys Pro Arg Gly Gly Ala Val Asn Tyr Ala
65                  70                  75                  80

Arg Pro Leu Gln Gly Arg Val Thr Met Thr Arg Asp Val Tyr Ser Asp
                85                  90                  95

Thr Ala Phe Leu Glu Leu Arg Ser Leu Thr Val Asp Asp Thr Ala Val
            100                 105                 110

Tyr Phe Cys Thr Arg Gly Lys Asn Cys Asp Tyr Asn Trp Asp Phe Glu
        115                 120                 125

His Trp Gly Arg Gly Thr Pro Val Ile Val Ser Ser Ala Ser Thr Lys
    130                 135                 140
```

```
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
            500                 505                 510

Trp Ile Ser Gly Ala Tyr Gly Glu Ile Val Leu Thr Gln Ser Pro Gly
        515                 520                 525

Thr Leu Ser Leu Ser Pro Gly Glu Thr Ala Ile Ile Ser Cys Arg Thr
    530                 535                 540

Ser Gln Tyr Gly Ser Leu Ala Trp Tyr Gln Gln Arg Pro Gly Gln Ala
545                 550                 555                 560
```

```
Pro Arg Leu Val Ile Tyr Ser Gly Ser Thr Arg Ala Ala Gly Ile Pro
            565                 570                 575
Asp Arg Phe Ser Gly Ser Arg Trp Gly Pro Asp Tyr Asn Leu Thr Ile
        580                 585                 590
Ser Asn Leu Glu Ser Gly Asp Phe Gly Val Tyr Tyr Cys Gln Gln Tyr
    595                 600                 605
Glu Phe Phe Gly Gln Gly Thr Lys Val Gln Val Asp Ile Lys Arg Thr
610                 615                 620
Val Ala Ala Pro Ser Val Phe Ile Phe Pro Pro Ser Asp Glu Gln Leu
625                 630                 635                 640
Lys Ser Gly Thr Ala Ser Val Val Cys Leu Leu Asn Asn Phe Tyr Pro
            645                 650                 655
Arg Glu Ala Lys Val Gln Trp Lys Val Asp Asn Ala Leu Gln Ser Gly
        660                 665                 670
Asn Ser Gln Glu Ser Val Thr Glu Gln Asp Ser Lys Asp Ser Thr Tyr
    675                 680                 685
Ser Leu Ser Asn Thr Leu Thr Leu Ser Lys Ala Asp Tyr Glu Lys His
690                 695                 700
Lys Val Tyr Ala Cys Glu Val Thr His Gln Gly Leu Ser Ser Pro Val
705                 710                 715                 720
Thr Lys Ser Phe Asn Arg Gly Glu Cys
            725

<210> SEQ ID NO 38
<211> LENGTH: 2211
<212> TYPE: DNA
<213> ORGANISM: Artificial Sequence
<220> FEATURE:
<223> OTHER INFORMATION: VRC01 human IgG1

<400> SEQUENCE: 38
ggatccgcca ccatggattg acatggagg attctgtttc tggtcgccgc cgccacagga      60
actcatgctc aggtgcagct ggtgcagtca ggagggcaga tgaagaaacc tggcgagagt    120
atgcgaatct catgcagggc tagcggatac gaattcatcg actgtaccct gaactggatt    180
agactggcac ctggaaagcg gccagagtgg atggggtggc tgaaaccaag aggcggagca    240
gtgaattacg ccagaccact gcagggacga gtcactatga cccgcgacgt gtatagcgat    300
accgcattcc tggaactgcg atccctgaca gtcgacgata ctgccgtgta cttctgcaca    360
aggggcaaga actgtgacta taattgggat tttgagcact ggggccgggg aacaccagtc    420
attgtgagct ccgcaagtac taaggggccc tcagtgtttc ccctggctcc ttctagtaaa    480
agtacctcag ggggcacagc cgctctggga tgcctggtga aggattactt ccctgagcca    540
gtcacagtga gttggaactc aggcgccctg acatctggag tccatacttt tcccgctgtg    600
ctgcagtcaa gcggactgta cagcctgtcc tctgtggtca cagtgcctag ttcaagcctg    660
gggacacaga cttatatctg caacgtcaat cacaagccca gcaatactaa gtgtgacaag    720
aaagtggaac taagtcctg tgataaaacc catacatgcc ctccctgtcc agctcctgag    780
ctgctgggag gccaagcgt gttcctgttt ccacccaagc ctaaagacac cctgatgatt    840
tctcggactc tgaagtcac ctgcgtggtc gtggacgtga gccacgagga ccccgaagtc    900
aagtttaact ggtacgtgga tggcgtcgag gtgcataatg ccaagacaaa acccagggag    960
gaacagtaca acagcaccta tagagtcgtg tccgtcctga cagtgctgca ccaggactgg   1020
ctgaacggaa aggagtataa gtgcaaagtg agcaataagg ccctgccagc tcccatcgag   1080
```

-continued

```
aaaacaattt ccaaggcaaa agggcagcca cgggaacccc agtgtacac tctgcctcca    1140
tctcgcgacg agctgactaa gaaccaggtc agcctgacct gtctggtgaa agggttctat   1200
ccaagtgata tcgccgtgga gtgggaaagc aatggccagc cgaaaacaa ttacaagacc    1260
acaccccctg tgctggacag cgatggctcc ttctttctgt attctaagct gaccgtggat   1320
aaaagtcgct ggcagcaggg aaacgtcttt agctgctccg tgatgcacga ggctctgcac   1380
aatcattaca cccagaagtc tctgagtctg tcacctggca agcggggacg caaaaggaga   1440
agcgggtccg gcgctacaaa cttcagcctg ctgaagcagg caggcgacgt ggaggaaaat   1500
cctggaccaa tggtcctgca gacccaggtg ttcatctccc tgctgctgtg gatttctggg   1560
gcatacggcg aaattgtgct gacccagagc cctgggacac tgtctctgag tccaggcgag   1620
acagccatca tttcctgtcg gacttctcag tacggaagtc tggcatggta tcagcagcga   1680
ccaggacagg ctcctcgact ggtcatctac tcagggagca ctagggcagc cggcattcct   1740
gaccgattct ccggatctag gtgggggcct gattacaacc tgaccatctc aaatctggaa   1800
agcgggact ttggcgtgta ctattgccag cagtatgagt tctttggaca ggggaccaag    1860
gtccaggtgg acatcaaacg cacagtcgct gcaccatccg tgttcatttt tccaccctct   1920
gatgaacagc tgaagtccgg caccgcctct gtggtgtgcc tgctgaacaa tttctacccc   1980
agggaggcaa aggtccagtg gaaagtggac aacgccctgc agtctggaaa tagtcaggag   2040
tcagtgactg aacaggacag caaggattcc acctattctc tgtccaacac tctgaccctg   2100
tccaaagctg attacgagaa gcacaaagtg tatgcatgcg aggtcactca ccaggggctg   2160
tcatcaccag tcacaaaatc cttcaacaga ggggaatgct gataactcga g            2211
```

<210> SEQ ID NO 39
<211> LENGTH: 470
<212> TYPE: PRT
<213> ORGANISM: Artificial Sequence
<220> FEATURE:
<223> OTHER INFORMATION: VRC01 human IgG1(heavy chain) (mod1)

<400> SEQUENCE: 39

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gln Met Lys Lys
                20                  25                  30

Pro Gly Glu Ser Met Arg Ile Ser Cys Arg Ala Ser Gly Tyr Glu Phe
            35                  40                  45

Ile Asp Cys Thr Leu Asn Trp Ile Arg Leu Ala Pro Gly Lys Arg Pro
        50                  55                  60

Glu Trp Met Gly Trp Leu Lys Pro Arg Gly Gly Ala Val Asn Tyr Ala
65                  70                  75                  80

Arg Pro Leu Gln Gly Arg Val Thr Met Thr Arg Asp Val Tyr Ser Asp
                85                  90                  95

Thr Ala Phe Leu Glu Leu Arg Ser Leu Thr Val Asp Asp Thr Ala Val
            100                 105                 110

Tyr Phe Cys Thr Arg Gly Lys Asn Cys Asp Tyr Asn Trp Asp Phe Glu
        115                 120                 125

His Trp Gly Arg Gly Thr Pro Val Ile Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
```

165                 170                 175
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 40
<211> LENGTH: 1434
<212> TYPE: DNA
<213> ORGANISM: Artificial Sequence
<220> FEATURE:
<223> OTHER INFORMATION: VRC01 human IgG1(heavy chain) (mod1)

<400> SEQUENCE: 40
ggatccgcca ccatggattg acatggagg attctgtttc tggtcgccgc cgccacagga      60
actcatgctc aggtgcagct ggtgcagtca ggagggcaga tgaagaaacc tggcgagagt     120
atgcgaatct catgcagggc tagcggatac gaattcatcg actgtaccct gaactggatt     180
agactggcac ctggaaagcg gccagagtgg atggggtggc tgaaaccaag aggcggagca     240
gtgaattacg ccagaccact gcagggacga gtcactatga cccgcgacgt gtatagcgat     300

```
accgcattcc tggaactgcg atccctgaca gtcgacgata ctgccgtgta cttctgcaca    360
agggggcaaga actgtgacta taattgggat tttgagcact ggggccgggg aacaccagtc   420
attgtgagct ccgcaagtac taaggggccc tcagtgtttc ccctggctcc ttctagtaaa    480
agtacctcag ggggcacagc cgctctggga tgcctggtga aggattactt ccctgagcca    540
gtcacagtga gttggaactc aggcgccctg acatctggag tccatacttt tcccgctgtg    600
ctgcagtcaa gcggactgta cagcctgtcc tctgtggtca cagtgcctag ttcaagcctg    660
gggacacaga cttatatctg caacgtcaat cacaagccca gcaatactaa agtggacaag    720
aaagtggaac ctaagtcctg tgataaaacc catcatgcc ctccctgtcc agctcctgag     780
ctgctgggag ggccaagcgt gttcctgttt ccacccaagc ctaaagacac cctgatgatt    840
tctcggactc ctgaagtcac ctgcgtggtc gtggacgtga gccacgagga ccccgaagtc    900
aagtttaact ggtacgtgga tggcgtcgag gtgcataatg ccaagacaaa acccagggag   960
gaacagtaca acagcaccta tagagtcgtg tccgtcctga cagtgctgca ccaggactgg   1020
ctgaacggaa aggagtataa gtgcaaagtg agcaataagg ccctgccagc tcccatcgag   1080
aaaacaattt ccaaggcaaa agggcagcca cgggaacccc aggtgtacac tctgcctcca   1140
tctcgcgacg agctgactaa gaaccaggtc agcctgacct gtctggtgaa agggttctat   1200
ccaagtgata tcgccgtgga gtgggaaagc aatggccagc cgaaaacaa ttacaagacc    1260
acaccccctg tgctggacag cgatggctcc ttctttctgt attctaagct gaccgtggat   1320
aaaagtcgct ggcagcaggg aaacgtcttt agctgctccg tgatgcacga ggctctgcac   1380
aatcattaca cccagaagtc tctgagtctg tcacctggca agtgataact cgag          1434
```

<210> SEQ ID NO 41
<211> LENGTH: 230
<212> TYPE: PRT
<213> ORGANISM: Artificial Sequence
<220> FEATURE:
<223> OTHER INFORMATION: VRC01 human IgG1(light chain)(mod1)

<400> SEQUENCE: 41

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Thr Ala Ile Ile Ser Cys Arg Thr Ser Gln Tyr
        35                  40                  45

Gly Ser Leu Ala Trp Tyr Gln Gln Arg Pro Gly Gln Ala Pro Arg Leu
    50                  55                  60

Val Ile Tyr Ser Gly Ser Thr Arg Ala Ala Gly Ile Pro Asp Arg Phe
65                  70                  75                  80

Ser Gly Ser Arg Trp Gly Pro Asp Tyr Asn Leu Thr Ile Ser Asn Leu
                85                  90                  95

Glu Ser Gly Asp Phe Gly Val Tyr Tyr Cys Gln Gln Tyr Glu Phe Phe
            100                 105                 110

Gly Gln Gly Thr Lys Val Gln Val Asp Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
```

```
                    165                 170                 175
Glu Ser Val Thr Glu Gln Asp Ser Lys Asp Ser Thr Tyr Ser Leu Ser
            180                 185                 190

Asn Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
210                 215                 220

Phe Asn Arg Gly Glu Cys
225                 230

<210> SEQ ID NO 42
<211> LENGTH: 714
<212> TYPE: DNA
<213> ORGANISM: Artificial Sequence
<220> FEATURE:
<223> OTHER INFORMATION: VRC01 human IgG1(light chain)(mod1)

<400> SEQUENCE: 42
ggatccgcca ccatggtcct gcagacccag gtgttcatct ccctgctgct gtggatttct      60
ggggcatacg gcgaaattgt gctgacccag agccctggga cactgtctct gagtccaggc     120
gagacagcca tcatttcctg tcggacttct cagtacggaa gtctggcatg gtatcagcag     180
cgaccaggac aggctcctcg actggtcatc tactcaggga gcactagggc agccggcatt     240
cctgaccgat tctccggatc taggtggggg cctgattaca acctgaccat ctcaaatctg     300
gaaagcgggg actttggcgt gtactattgc cagcagtatg agttctttgg acaggggacc     360
aaggtccagg tggacatcaa acgcacagtc gctgcaccat ccgtgttcat ttttccaccc     420
tctgatgaac agctgaagtc cggcaccgcc tctgtggtgt gcctgctgaa caatttctac     480
cccagggagg caaaggtcca gtggaaagtg acaacgccc tgcagtctgg aaatagtcag      540
gagtcagtga ctgaacagga cagcaaggat ccacctatt ctctgtccaa cactctgacc      600
ctgtccaaag ctgattacga aagcacaaa gtgtatgcat gcgaggtcac tcaccagggg      660
ctgtcatcac cagtcacaaa atccttcaac agaggggaat gctgataact cgag            714

<210> SEQ ID NO 43
<211> LENGTH: 726
<212> TYPE: PRT
<213> ORGANISM: Artificial Sequence
<220> FEATURE:
<223> OTHER INFORMATION: VRC01 human IgG4 (mod 2)

<400> SEQUENCE: 43

Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gln Met Lys Lys
            20                  25                  30

Pro Gly Glu Ser Met Arg Ile Ser Cys Arg Ala Ser Gly Tyr Glu Phe
        35                  40                  45

Ile Asp Cys Thr Leu Asn Trp Ile Arg Leu Ala Pro Gly Lys Arg Pro
    50                  55                  60

Glu Trp Met Gly Trp Leu Lys Pro Arg Gly Gly Ala Val Asn Tyr Ala
65                  70                  75                  80

Arg Pro Leu Gln Gly Arg Val Thr Met Thr Arg Asp Val Tyr Ser Asp
                85                  90                  95

Thr Ala Phe Leu Glu Leu Arg Ser Leu Thr Val Asp Asp Thr Ala Val
            100                 105                 110
```

```
Tyr Phe Cys Thr Arg Gly Lys Asn Cys Asp Tyr Asn Trp Asp Phe Glu
            115                 120                 125

His Trp Gly Arg Gly Thr Pro Val Ile Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Lys Thr Tyr Thr Cys Asn
            210                 215                 220

Val Asp His Lys Pro Ser Asn Thr Lys Val Asp Lys Arg Val Glu Ser
225                 230                 235                 240

Lys Tyr Gly Pro Pro Cys Pro Ser Cys Pro Ala Pro Glu Phe Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
            290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
450                 455                 460

Leu Gly Lys Arg Gly Arg Lys Arg Arg Ser Gly Ser Gly Ala Thr Asn
465                 470                 475                 480

Phe Ser Leu Leu Lys Gln Ala Gly Asp Val Glu Glu Asn Pro Gly Pro
            485                 490                 495

Met Val Leu Gln Thr Gln Val Phe Ile Ser Leu Leu Leu Trp Ile Ser
            500                 505                 510

Gly Ala Tyr Gly Glu Ile Val Leu Thr Gln Ser Pro Gly Thr Leu Ser
            515                 520                 525

Leu Ser Pro Gly Glu Thr Ala Ile Ile Ser Cys Arg Thr Ser Gln Tyr
```

```
                530             535             540
Gly Ser Leu Ala Trp Tyr Gln Gln Arg Pro Gly Gln Ala Pro Arg Leu
545                 550                 555                 560

Val Ile Tyr Ser Gly Ser Thr Arg Ala Ala Gly Ile Pro Asp Arg Phe
                565                 570                 575

Ser Gly Ser Arg Trp Gly Pro Asp Tyr Asn Leu Thr Ile Ser Asn Leu
                580                 585                 590

Glu Ser Gly Asp Phe Gly Val Tyr Tyr Cys Gln Gln Tyr Glu Phe Phe
                595                 600                 605

Gly Gln Gly Thr Lys Val Gln Val Asp Ile Lys Arg Thr Val Ala Ala
                610                 615                 620

Pro Ser Val Phe Ile Phe Pro Pro Ser Asp Glu Gln Leu Lys Ser Gly
625                 630                 635                 640

Thr Ala Ser Val Val Cys Leu Leu Asn Asn Phe Tyr Pro Arg Glu Ala
                645                 650                 655

Lys Val Gln Trp Lys Val Asp Asn Ala Leu Gln Ser Gly Asn Ser Gln
                660                 665                 670

Glu Ser Val Thr Glu Gln Asp Ser Lys Asp Ser Thr Tyr Ser Leu Ser
                675                 680                 685

Asn Thr Leu Thr Leu Ser Lys Ala Asp Tyr Glu Lys His Lys Val Tyr
690                 695                 700

Ala Cys Glu Val Thr His Gln Gly Leu Ser Ser Pro Val Thr Lys Ser
705                 710                 715                 720

Phe Asn Arg Gly Glu Cys
                725

<210> SEQ ID NO 44
<211> LENGTH: 2202
<212> TYPE: DNA
<213> ORGANISM: Artificial Sequence
<220> FEATURE:
<223> OTHER INFORMATION: VRC01 human IgG4 (mod 2)

<400> SEQUENCE: 44
ggatccgcca ccatggattg gacttggagg attctgtttc tggtcgccgc cgctactgga      60
acccatgctc aggtgcagct ggtgcagtca ggagggcaga tgaagaaacc tggagagagc     120
atgcgaatct cctgcagggc ctctgggtac gaattcatcg actgtacact gaactggatt     180
agactggctc ctgggaagcg gccagagtgg atgggctggc tgaaaccaag aggcggagca     240
gtgaattacg ccagaccact gcagggacga gtcactatga cccgcgacgt gtattctgat     300
actgcttttc tggaactgcg aagtctgacc gtcgacgata cagcagtgta cttctgcacc     360
aggggcaaga actgtgacta taattgggat tttgagcact ggggaagagg gactcctgtc     420
attgtgagct ccgcaagcac caagggacca tccgtgttcc cactggcacc ttgcagtcgg     480
tcaactagcg agtccaccgc cgctctggga tgtctggtga aggattactt cccagaaccc     540
gtcaccgtga gctggaactc cggagccctg accagcggag tccatacatt tcctgctgtg     600
ctgcagtcta gtggactgta ctccctgtca agcgtggtca ccgtcccttc ctctagtctg     660
gggacaaaga cttatacctg caacgtgac cacaaaccat ccaatacaaa ggtcgataaa     720
cgcgtggagt caaagtacgg ccctccctgc cctagctgtc cagctcctga gttcctgggc     780
ggcccaagcg tgttcctgtt tccccctaag cctaaagaca cactgatgat ctctaggaca     840
ccagaagtca cttgcgtggt cgtggacgtg agccaggagg accccgaagt ccagttcaac     900
tggtacgtgg atggcgtcga ggtgcacaat gccaagacca aacctcggga ggaacagttt     960
```

```
aactctactt accgcgtcgt gagtgtcctg accgtgctgc atcaggactg gctgaacggc    1020
aaggagtata agtgcaaagt gtccaataag ggactgccat caagcatcga gaaaaccatt    1080
tctaaggcaa aaggccagcc aagagaaccc caggtgtaca cactgccacc cagccaggag    1140
gaaatgacaa agaaccaggt ctccctgact tgtctggtga aagggtttta tccaagcgac    1200
attgccgtgg agtgggaatc caatggccag cccgagaaca attacaagac cacacctcca    1260
gtgctggact ctgatggcag tttcttctg tattcaaggc tgaccgtgga taaaagcaga    1320
tggcaggagg gaaacgtctt ctcttgcagt gtgatgcacg aagctctgca caatcattac    1380
actcagaagt cactgagcct gtccctggga aagcgaggac gaaaaaggag atctggcagt    1440
ggagctacca acttcagcct gctgaagcag gcaggagacg tggaggaaaa tcctgggcca    1500
atggtcctgc agactcaggt gttcatcagt ctgctgctgt ggatttcagg cgcctacgga    1560
gagattgtgc tgactcagtc tcccggcacc ctgtcactga gccctggaga aaccgccatc    1620
attagttgtc gaacatcaca gtacgggagc tggcatggt atcagcagcg accaggacag    1680
gctccccgac tggtcatcta ctccggctct acacgggcag ccggaattcc cgaccgattc    1740
agtgggtcaa ggtggggccc tgattacaac ctgactatct ccaatctgga gtctggcgac    1800
tttggagtgt actattgcca gcagtatgaa ttctttgggc agggcaccaa ggtccaggtg    1860
gacatcaaaa gaacagtcgc tgcaccaagc gtgttcatct tcccccttc agatgagcag    1920 ctgaagagtg gaaccgcctc agtggtgtgc ctgctgaaca atttctaccc ccgggaagca    1980
aaggtccagt ggaaagtgga caacgccctg cagtcaggca atagccagga gtccgtgaca    2040
gaacaggact ctaaggatag tacttattca ctgtccaaca cactgactct gtccaaagct    2100
gattacgaga agcacaaagt gtatgcatgc gaggtcaccc accagggct gtcatcaccc    2160 gtcaccaagt ctttcaatag gggcgaatgt tgataactcg ag                      2202
```

<210> SEQ ID NO 45
<211> LENGTH: 726
<212> TYPE: PRT
<213> ORGANISM: Artificial Sequence
<220> FEATURE:
<223> OTHER INFORMATION: VRC01 human IgG4 mut (S228P) (mod 3)

<400> SEQUENCE: 45

```
Met Asp Trp Thr Trp Arg Ile Leu Phe Leu Val Ala Ala Ala Thr Gly
  1               5                  10                  15

Thr His Ala Gln Val Gln Leu Val Gln Ser Gly Gly Gln Met Lys Lys
             20                  25                  30

Pro Gly Glu Ser Met Arg Ile Ser Cys Arg Ala Ser Gly Tyr Glu Phe
         35                  40                  45

Ile Asp Cys Thr Leu Asn Trp Ile Arg Leu Ala Pro Gly Lys Arg Pro
     50                  55                  60

Glu Trp Met Gly Trp Leu Lys Pro Arg Gly Gly Ala Val Asn Tyr Ala
 65                  70                  75                  80

Arg Pro Leu Gln Gly Arg Val Thr Met Thr Arg Asp Val Tyr Ser Asp
                 85                  90                  95

Thr Ala Phe Leu Glu Leu Arg Ser Leu Thr Val Asp Asp Thr Ala Val
            100                 105                 110

Tyr Phe Cys Thr Arg Gly Lys Asn Cys Asp Tyr Asn Trp Asp Phe Glu
        115                 120                 125

His Trp Gly Arg Gly Thr Pro Val Ile Val Ser Ser Ala Ser Thr Lys
    130                 135                 140
```

```
Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys Arg Gly Arg Lys Arg Arg Ser Gly Ser Gly Ala Thr Asn
465                 470                 475                 480

Phe Ser Leu Leu Lys Gln Ala Gly Asp Val Glu Glu Asn Pro Gly Pro
                485                 490                 495

Met Val Leu Gln Thr Gln Val Phe Ile Ser Leu Leu Leu Trp Ile Ser
            500                 505                 510

Gly Ala Tyr Gly Glu Ile Val Leu Thr Gln Ser Pro Gly Thr Leu Ser
        515                 520                 525

Leu Ser Pro Gly Glu Thr Ala Ile Ile Ser Cys Arg Thr Ser Gln Tyr
    530                 535                 540

Gly Ser Leu Ala Trp Tyr Gln Gln Arg Pro Gly Gln Ala Pro Arg Leu
545                 550                 555                 560
```

```
Val Ile Tyr Ser Gly Ser Thr Arg Ala Ala Gly Ile Pro Asp Arg Phe
            565                 570                 575

Ser Gly Ser Arg Trp Gly Pro Asp Tyr Asn Leu Thr Ile Ser Asn Leu
        580                 585                 590

Glu Ser Gly Asp Phe Gly Val Tyr Tyr Cys Gln Gln Tyr Glu Phe Phe
        595                 600                 605

Gly Gln Gly Thr Lys Val Gln Val Asp Ile Lys Arg Thr Val Ala Ala
        610                 615                 620

Pro Ser Val Phe Ile Phe Pro Pro Ser Asp Glu Gln Leu Lys Ser Gly
625                 630                 635                 640

Thr Ala Ser Val Val Cys Leu Leu Asn Asn Phe Tyr Pro Arg Glu Ala
                645                 650                 655

Lys Val Gln Trp Lys Val Asp Asn Ala Leu Gln Ser Gly Asn Ser Gln
            660                 665                 670

Glu Ser Val Thr Glu Gln Asp Ser Lys Asp Ser Thr Tyr Ser Leu Ser
        675                 680                 685

Asn Thr Leu Thr Leu Ser Lys Ala Asp Tyr Glu Lys His Lys Val Tyr
        690                 695                 700

Ala Cys Glu Val Thr His Gln Gly Leu Ser Ser Pro Val Thr Lys Ser
705                 710                 715                 720

Phe Asn Arg Gly Glu Cys
                725

<210> SEQ ID NO 46
<211> LENGTH: 2202
<212> TYPE: DNA
<213> ORGANISM: Artificial Sequence
<220> FEATURE:
<223> OTHER INFORMATION: VRC01 human IgG4 mut (S228P) (mod 3)

<400> SEQUENCE: 46
ggatccgcca ccatggattg gacttggagg attctgtttc tggtcgccgc cgctactgga      60
acccatgctc aggtgcagct ggtgcagtca ggagggcaga tgaagaaacc tggagagagc     120
atgcgaatct cctgcagggc ctctgggtac gaattcatcg actgtacact gaactggatt     180
agactggctc ctgggaagcg gccagagtgg atgggctggc tgaaaccaag aggcggagca     240
gtgaattacg ccagaccact gcagggacga gtcactatga cccgcgacgt gtattctgat     300
actgcttttc tggaactgcg aagtctgacc gtcgacgata cagcagtgta cttctgcacc     360 agggggcaaga actgtgacta taattgggat tttgagcact ggggaagagg gactcctgtc     420
attgtgagct ccgcaagcac caagggacca tccgtgttcc cactggcacc ttgcagtcgg     480
tcaactagcg agtccaccgc cgctctggga tgtctggtga aggattactt cccagaaccc     540
gtcaccgtga gctggaactc cggagccctg accagcggag tccatacatt tcctgctgtg     600
ctgcagtcta gtggactgta ctccctgtca gcgtggtca ccgtcccttc tctagtctg      660 gggacaaaga cttatacctg caacgtggac cacaaaccat ccatacaaa ggtcgataaa     720 cgcgtggagt caaagtacgg ccctccctgc cctccctgtc cagctcctga gttcctgggc     780
ggcccaagcg tgttcctgtt tcccctaag cctaaagaca cactgatgat ctctaggaca     840
ccagaagtca cttgcgtggt cgtggacgtg agccaggagg accccgaagt ccagttcaac     900
tggtacgtgg atggcgtcga ggtgcacaat gccaagacca acctcgggga ggaacagttt     960
aactctactt accgcgtcgt gagtgtcctg accgtgctgc atcaggactg gctgaacggc    1020
aaggagtata agtgcaaagt gtccaataag ggactgccat caagcatcga gaaaccatt    1080
```

-continued

```
tctaaggcaa aaggccagcc aagagaaccc caggtgtaca cactgccacc cagccaggag    1140
gaaatgacaa agaaccaggt ctccctgact tgtctggtga aagggtttta tccaagcgac    1200
attgccgtgg agtgggaatc caatggccag cccgagaaca attacaagac cacacctcca    1260
gtgctggact ctgatggcag tttctttctg tattcaaggc tgaccgtgga taaaagcaga    1320
tggcaggagg gaaacgtctt ctcttgcagt gtgatgcacg aagctctgca caatcattac    1380
actcagaagt cactgagcct gtccctggga aagcgaggac gaaaaaggag atctggcagt    1440
ggagctacca acttcagcct gctgaagcag gcaggagacg tggaggaaaa tcctgggcca    1500
atggtcctgc agactcaggt gttcatcagt ctgctgctgt ggatttcagg cgcctacgga    1560
gagattgtgc tgactcagtc tcccggcacc ctgtcactga gccctggaga aaccgccatc    1620
attagttgtc gaacatcaca gtacgggagc ctggcatggt atcagcagcg accaggacag    1680
gctccccgac tggtcatcta ctccggctct acacgggcag ccggaattcc cgaccgattc    1740
agtgggtcaa ggtggggccc tgattacaac ctgactatct ccaatctgga gtctggcgac    1800
tttggagtgt actattgcca gcagtatgaa ttctttgggc agggcaccaa ggtccaggtg    1860
gacatcaaaa gaacagtcgc tgcaccaagc gtgttcatct tccccccttc agatgagcag    1920
ctgaagagtg gaaccgcctc agtggtgtgc ctgctgaaca atttctaccc ccgggaagca    1980
aaggtccagt ggaaagtgga caacgccctg cagtcaggca atagccagga gtccgtgaca    2040
gaacaggact ctaaggatag tacttattca ctgtccaaca cactgactct gtccaaagct    2100
gattacgaga agcacaaagt gtatgcatgc gaggtcaccc accagggggct gtcatcaccc    2160 gtcaccaagt ctttcaatag ggcgaatgt tgataactcg ag                        2202
```

<210> SEQ ID NO 47
<211> LENGTH: 467
<212> TYPE: PRT
<213> ORGANISM: Artificial Sequence
<220> FEATURE:
<223> OTHER INFORMATION: VRC01 human IgG4 (heavy chain) (mod4)

<400> SEQUENCE: 47

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gln Met Lys Lys
            20                  25                  30

Pro Gly Glu Ser Met Arg Ile Ser Cys Arg Ala Ser Gly Tyr Glu Phe
        35                  40                  45

Ile Asp Cys Thr Leu Asn Trp Ile Arg Leu Ala Pro Gly Lys Arg Pro
    50                  55                  60

Glu Trp Met Gly Trp Leu Lys Pro Arg Gly Gly Ala Val Asn Tyr Ala
65                  70                  75                  80

Arg Pro Leu Gln Gly Arg Val Thr Met Thr Arg Asp Val Tyr Ser Asp
                85                  90                  95

Thr Ala Phe Leu Glu Leu Arg Ser Leu Thr Val Asp Asp Thr Ala Val
            100                 105                 110

Tyr Phe Cys Thr Arg Gly Lys Asn Cys Asp Tyr Asn Trp Asp Phe Glu
        115                 120                 125

His Trp Gly Arg Gly Thr Pro Val Ile Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
```

```
              165                 170                 175
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Lys Thr Tyr Thr Cys Asn
            210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
            450                 455                 460

Leu Gly Lys
465

<210> SEQ ID NO 48
<211> LENGTH: 1425
<212> TYPE: DNA
<213> ORGANISM: Artificial Sequence
<220> FEATURE:
<223> OTHER INFORMATION: VRC01 human IgG4 (heavy chain) (mod4)

<400> SEQUENCE: 48
ggatccgcca ccatggattg gacttggagg attctgtttc tggtcgccgc cgctactgga      60
acccatgctc aggtgcagct ggtgcagtca ggagggcaga tgaagaaacc tggagagagc     120
atgcgaatct cctgcagggc ctctgggtac gaattcatcg actgtacact gaactggatt     180
agactggctc ctgggaagcg gccagagtgg atgggctggc tgaaaccaag aggcggagca     240
gtgaattacg ccagaccact gcagggacga gtcactatga cccgcgacgt gtattctgat     300
```

```
actgctttc  tggaactgcg  aagtctgacc  gtcgacgata  cagcagtgta  cttctgcacc       360 agggggcaaga  actgtgacta  taattgggat  tttgagcact  ggggaagagg  gactcctgtc      420
attgtgagct  ccgcaagcac  caagggacca  tccgtgttcc  cactggcacc  ttgcagtcgg      480
tcaactagcg  agtccaccgc  cgctctggga  tgtctggtga  aggattactt  cccagaaccc      540
gtcaccgtga  gctggaactc  cggagccctg  accagcggag  tccatacatt  tcctgctgtg      600
ctgcagtcta  gtggactgta  ctccctgtca  agcgtggtca  ccgtcccttc  ctctagtctg      660
gggacaaaga  cttatacctg  caacgtggac  cacaaaccat  ccaatacaaa  ggtcgataaa      720
cgcgtggagt  caaagtacgg  ccctcccctgc  cctcccctgtc  cagctcctga  gttcctgggc    780
ggcccaagcg  tgttcctgtt  tcccctaag  cctaaagaca  cactgatgat  ctctaggaca       840
ccagaagtca  cttgcgtggt  cgtggacgtg  agccaggagg  accccgaagt  ccagttcaac      900
tggtacgtgg  atggcgtcga  ggtgcacaat  gccaagacca  accctcggga  ggaacagttt      960
aactctactt  accgcgtcgt  gagtgtcctg  accgtgctgc  atcaggactg  gctgaacggc    1020
aaggagtata  agtgcaaagt  gtccaataag  ggactgccat  caagcatcga  gaaaaccatt   1080
tctaaggcaa  aaggccagcc  aagagaaccc  caggtgtaca  cactgccacc  cagccaggag   1140
gaaatgacaa  agaaccaggt  ctccctgact  tgtctggtga  aagggttta  tccaagcgac     1200 attgccgtgg  agtgggaatc  caatggccag  cccgagaaca  attacaagac  cacacctcca   1260
gtgctggact  ctgatggcag  tttcttctg  tattcaaggc  tgaccgtgga  taaaagcaga    1320
tggcaggagg  gaaacgtctt  ctcttgcagt  gtgatgcacg  aagctctgca  caatcattac   1380
actcagaagt  cactgagcct  gtccctggga  aagtgataac  tcgag                    1425
```

<210> SEQ ID NO 49
<211> LENGTH: 230
<212> TYPE: PRT
<213> ORGANISM: Artificial Sequence
<220> FEATURE:
<223> OTHER INFORMATION: VRC01 human IgG4 (light chain)(mod4)

<400> SEQUENCE: 49

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Thr Ala Ile Ile Ser Cys Arg Thr Ser Gln Tyr
        35                  40                  45

Gly Ser Leu Ala Trp Tyr Gln Gln Arg Pro Gly Gln Ala Pro Arg Leu
    50                  55                  60

Val Ile Tyr Ser Gly Ser Thr Arg Ala Ala Gly Ile Pro Asp Arg Phe
65                  70                  75                  80

Ser Gly Ser Arg Trp Gly Pro Asp Tyr Asn Leu Thr Ile Ser Asn Leu
                85                  90                  95

Glu Ser Gly Asp Phe Gly Val Tyr Tyr Cys Gln Gln Tyr Glu Phe Phe
            100                 105                 110

Gly Gln Gly Thr Lys Val Gln Val Asp Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
```

```
                165                 170                 175
Glu Ser Val Thr Glu Gln Asp Ser Lys Asp Ser Thr Tyr Ser Leu Ser
            180                 185                 190

Asn Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys
225                 230

<210> SEQ ID NO 50
<211> LENGTH: 714
<212> TYPE: DNA
<213> ORGANISM: Artificial Sequence
<220> FEATURE:
<223> OTHER INFORMATION: VRC01 human IgG4 (light chain)(mod4)

<400> SEQUENCE: 50
ggatccgcca ccatggtcct gcagactcag gtgttcatca gtctgctgct gtggatttca      60
ggcgcctacg gagagattgt gctgactcag tctcccggca ccctgtcact gagccctgga     120
gaaaccgcca tcattagttg tcgaacatca cagtacggga gctggcatg gtatcagcag      180 cgaccaggac aggctccccg actggtcatc tactccggct ctacacgggc agccggaatt     240
cccgaccgat tcagtgggtc aaggtggggc cctgattaca acctgactat ctccaatctg     300
gagtctggcg actttggagt gtactattgc cagcagtatg aattctttgg cagggcacc      360 aaggtccagg tggacatcaa agaacagtc gctgcaccaa gcgtgttcat ctttccccct      420
tcagatgagc agctgaagag tggaaccgcc tcagtggtgt gcctgctgaa caatttctac     480
ccccgggaag caaggtcca gtggaaagtg acaacgccc tgcagtcagg caatagccag      540
gagtccgtga cagaacagga ctctaaggat agtacttatt cactgtccaa cacactgact     600
ctgtccaaag ctgattacga aagcacaaaa gtgtatgcat gcgaggtcac ccaccagggg     660
ctgtcatcac ccgtcaccaa gtctttcaat aggggcgaat gttgataact cgag           714

<210> SEQ ID NO 51
<211> LENGTH: 725
<212> TYPE: PRT
<213> ORGANISM: Artificial Sequence
<220> FEATURE:
<223> OTHER INFORMATION: VRC01 human IgG2_New

<400> SEQUENCE: 51

Met Asp Trp Thr Trp Arg Ile Leu Phe Leu Val Ala Ala Thr Gly
1               5                   10                  15

Thr His Ala Gln Val Gln Leu Val Gln Ser Gly Gly Gln Met Lys Lys
            20                  25                  30

Pro Gly Glu Ser Met Arg Ile Ser Cys Arg Ala Ser Gly Tyr Glu Phe
        35                  40                  45

Ile Asp Cys Thr Leu Asn Trp Ile Arg Leu Ala Pro Gly Lys Arg Pro
    50                  55                  60

Glu Trp Met Gly Trp Leu Lys Pro Arg Gly Gly Ala Val Asn Tyr Ala
65                  70                  75                  80

Arg Pro Leu Gln Gly Arg Val Thr Met Thr Arg Asp Val Tyr Ser Asp
            85                  90                  95

Thr Ala Phe Leu Glu Leu Arg Ser Leu Thr Val Asp Asp Thr Ala Val
            100                 105                 110
```

```
Tyr Phe Cys Thr Arg Gly Lys Asn Cys Asp Tyr Asn Trp Asp Phe Glu
            115                 120                 125

His Trp Gly Arg Gly Thr Pro Val Ile Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys Arg Gly Arg Lys Arg Arg Ser Gly Ser Gly Ala Thr Asn Phe
465                 470                 475                 480

Ser Leu Leu Lys Gln Ala Gly Asp Val Glu Glu Asn Pro Gly Pro Met
                485                 490                 495

Val Leu Gln Thr Gln Val Phe Ile Ser Leu Leu Leu Trp Ile Ser Gly
                500                 505                 510

Ala Tyr Gly Glu Ile Val Leu Thr Gln Ser Pro Gly Thr Leu Ser Leu
            515                 520                 525

Ser Pro Gly Glu Thr Ala Ile Ile Ser Cys Arg Thr Ser Gln Tyr Gly
```

```
                530             535             540
Ser Leu Ala Trp Tyr Gln Gln Arg Pro Gly Gln Ala Pro Arg Leu Val
545                 550                 555                 560

Ile Tyr Ser Gly Ser Thr Arg Ala Ala Gly Ile Pro Asp Arg Phe Ser
                    565                 570                 575

Gly Ser Arg Trp Gly Pro Asp Tyr Asn Leu Thr Ile Ser Asn Leu Glu
                580                 585                 590

Ser Gly Asp Phe Gly Val Tyr Tyr Cys Gln Gln Tyr Glu Phe Phe Gly
                    595                 600                 605

Gln Gly Thr Lys Val Gln Val Asp Ile Lys Arg Thr Val Ala Ala Pro
                610                 615                 620

Ser Val Phe Ile Phe Pro Pro Ser Asp Glu Gln Leu Lys Ser Gly Thr
625                 630                 635                 640

Ala Ser Val Val Cys Leu Leu Asn Asn Phe Tyr Pro Arg Glu Ala Lys
                    645                 650                 655

Val Gln Trp Lys Val Asp Asn Ala Leu Gln Ser Gly Asn Ser Gln Glu
                660                 665                 670

Ser Val Thr Glu Gln Asp Ser Lys Asp Ser Thr Tyr Ser Leu Ser Asn
            675                 680                 685

Thr Leu Thr Leu Ser Lys Ala Asp Tyr Glu Lys His Lys Val Tyr Ala
690                 695                 700

Cys Glu Val Thr His Gln Gly Leu Ser Ser Pro Val Thr Lys Ser Phe
705                 710                 715                 720

Asn Arg Gly Glu Cys
                725

<210> SEQ ID NO 52
<211> LENGTH: 2199
<212> TYPE: DNA
<213> ORGANISM: Artificial Sequence
<220> FEATURE:
<223> OTHER INFORMATION: VRC01 human IgG2_New

<400> SEQUENCE: 52
ggatccgcca ccatggattg gacatggagg attctgtttc tggtcgccgc cgccactgga     60
actcatgctc aggtgcagct ggtgcagtct ggagggcaga tgaagaaacc aggggagtct    120
atgcgaatca gttgcagggc ttcaggctac gaattcatcg actgtaccct gaactggatt    180
agactggcac ctggcaagcg accagagtgg atgggatggc tgaaacccag aggcggagcc    240
gtgaattacg ctagacctct gcagggacgg gtcactatga cccgcgacgt gtatagcgat    300
acagcttttc tggagctgcg aagcctgacc gtcgacgata cagcagtgta cttctgcact    360
aggggcaaga actgtgacta taattgggat tttgaacact ggggagagg cacccccagtc    420 attgtgagct ccgcatctac aaaaggacct agcgtgttcc cactggcacc ttgcagccgg    480
tccacttctg agagtaccgc cgctctggga tgtctggtga aggattactt ccccgaacct    540
gtcacagtgt cttggaacag tggggccctg actagcggcg tccacacctt tcccgctgtg    600
ctgcagtcta gtgggctgta cagcctgtca agcgtggtca ctgtgccatc ctctaatttt    660
ggcacacaga cttatacctg caacgtgac cataagccct ccaatacaaa ggtcgataaa    720
actgtggaga gaaaatgctg cgtggaatgc cctccctgtc cagcaccacc cgtcgcagga    780
ccaagcgtgt tcctgtttcc tccaaagcca aagacacac tgatgatcag ccggacaccc    840
gaggtcactt gcgtggtcgt ggacgtgagc cacgaggacc ccgaagtcca gttcaactgg    900
tacgtggatg gcgtcgaagt gcataatgct aagaccaaac caagggagga acagttcaac    960
```

-continued

```
tcaacccttta gagtcgtgag cgtgctgaca gtcgtgcatc aggactggct gaacggaaag    1020
gagtataagt gcaaagtgtc caataagggg ctgccagccc ccatcgagaa aaccatttct    1080
aagacaaaag gccagccacg ggaacccag gtgtacacac tgccccttc ccgcgaggaa    1140 atgactaaga accaggtctc tctgacctgt ctggtgaaag ctttatcc ctctgacatt    1200 gccgtggagt gggaaagtaa tggacagcct gagaacaatt acaagaccac accacccatg    1260
ctggactcag atgaagctt ctttctgtat tccaagctga ccgtggataa atctagatgg    1320
cagcagggga acgtcttctc atgcagcgtg atgcacgagg ccctgcacaa tcattacact    1380
cagaagtccc tgtctctgag tcctgggaag cggggccgca aaaggagatc aggaagcggg    1440
gctaccaact tcagcctgct gaagcaggca ggggacgtgg aggaaaatcc tggcccaatg    1500
gtcctgcaga ctcaggtgtt catcagcctg ctgctgtgga tttccggagc atacggggag    1560
attgtgctga cccagtcacc tggaacactg tccctgtctc aggggaaaac agccatcatt    1620
agctgtcgaa cttcccagta cggctctctg catggtatc agcagcgacc aggacaggct    1680
cctcgactgg tcatctacag tggatcaacc cgggcagccg ggattcctga ccgattcagc    1740
ggctccaggt ggggacctga ttacaacctg acaatcagta atctggagtc aggagactt    1800 ggggtgtact attgccagca gtatgaattc ttgggccagg gaacaaaggt ccaggtggac    1860
atcaaacgca ctgtcgctgc acccagcgtg ttcatttttc ctccatccga tgagcagctg    1920
aagagcggaa ccgcatccgt ggtgtgcctg ctgaacaatt tctaccctag ggaagcaaag    1980
gtccagtgga agtggacaa cgccctgcag tccggcaatt ctcaggagag tgtgactgaa    2040
caggactcaa aggatagcac ctattccctg agtaacacac tgactctgag caaagctgat    2100
tacgagaagc acaaagtgta tgcatgcgaa gtcaccccacc aggggctgag ctctccagtc    2160
actaagtctt ttaatcgggg cgaatgctga taactcgag                            2199
```

<210> SEQ ID NO 53
<211> LENGTH: 776
<212> TYPE: PRT
<213> ORGANISM: Artificial Sequence
<220> FEATURE:
<223> OTHER INFORMATION: VRC01 human IgG3_new

<400> SEQUENCE: 53

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gln Met Lys Lys
            20                  25                  30

Pro Gly Glu Ser Met Arg Ile Ser Cys Arg Ala Ser Gly Tyr Glu Phe
        35                  40                  45

Ile Asp Cys Thr Leu Asn Trp Ile Arg Leu Ala Pro Gly Lys Arg Pro
    50                  55                  60

Glu Trp Met Gly Trp Leu Lys Pro Arg Gly Gly Ala Val Asn Tyr Ala
65                  70                  75                  80

Arg Pro Leu Gln Gly Arg Val Thr Met Thr Arg Asp Val Tyr Ser Asp
                85                  90                  95

Thr Ala Phe Leu Glu Leu Arg Ser Leu Thr Val Asp Asp Thr Ala Val
            100                 105                 110

Tyr Phe Cys Thr Arg Gly Lys Asn Cys Asp Tyr Asn Trp Asp Phe Glu
        115                 120                 125

His Trp Gly Arg Gly Thr Pro Val Ile Val Ser Ser Ala Ser Thr Lys
    130                 135                 140
```

-continued

```
Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Thr Cys Asn
210                 215                 220

Val Asn His Lys Pro Ser Asn Thr Lys Val Asp Lys Arg Val Glu Leu
225                 230                 235                 240

Lys Thr Pro Leu Gly Asp Thr Thr His Thr Cys Pro Arg Cys Pro Glu
                245                 250                 255

Pro Lys Ser Cys Asp Thr Pro Pro Cys Pro Arg Cys Pro Glu Pro
            260                 265                 270

Lys Ser Cys Asp Thr Pro Pro Cys Pro Arg Cys Pro Glu Pro Lys
        275                 280                 285

Ser Cys Asp Thr Pro Pro Cys Pro Arg Cys Pro Ala Pro Glu Leu
290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Asp Val
                325                 330                 335

Ser His Glu Asp Pro Glu Val Gln Phe Lys Trp Tyr Val Asp Gly Val
            340                 345                 350

Glu Val His Asn Ala Lys Thr Lys Pro Arg Glu Glu Gln Tyr Asn Ser
        355                 360                 365

Thr Phe Arg Val Val Ser Val Leu Thr Val Leu His Gln Asp Trp Leu
370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Thr Lys Gly Gln Pro Arg Glu Pro
                405                 410                 415

Gln Val Tyr Thr Leu Pro Pro Ser Arg Glu Glu Met Thr Lys Asn Gln
            420                 425                 430

Val Ser Leu Thr Cys Leu Val Lys Gly Phe Tyr Pro Ser Asp Ile Ala
        435                 440                 445

Val Glu Trp Glu Ser Ser Gly Gln Pro Glu Asn Asn Tyr Asn Thr Thr
450                 455                 460

Pro Pro Met Leu Asp Ser Asp Gly Ser Phe Phe Leu Tyr Ser Lys Leu
465                 470                 475                 480

Thr Val Asp Lys Ser Arg Trp Gln Gln Gly Asn Ile Phe Ser Cys Ser
                485                 490                 495

Val Met His Glu Ala Leu His Asn Arg Phe Thr Gln Lys Ser Leu Ser
            500                 505                 510

Leu Ser Pro Gly Lys Arg Gly Arg Lys Arg Arg Ser Gly Ser Gly Ala
        515                 520                 525

Thr Asn Phe Ser Leu Leu Lys Gln Ala Gly Asp Val Glu Glu Asn Pro
530                 535                 540

Gly Pro Met Val Leu Gln Thr Gln Val Phe Ile Ser Leu Leu Leu Trp
545                 550                 555                 560
```

```
Ile Ser Gly Ala Tyr Gly Glu Ile Val Leu Thr Gln Ser Pro Gly Thr
              565                 570                 575
Leu Ser Leu Ser Pro Gly Glu Thr Ala Ile Ile Ser Cys Arg Thr Ser
        580                 585                 590
Gln Tyr Gly Ser Leu Ala Trp Tyr Gln Gln Arg Pro Gly Gln Ala Pro
    595                 600                 605
Arg Leu Val Ile Tyr Ser Gly Ser Thr Arg Ala Ala Gly Ile Pro Asp
610                 615                 620
Arg Phe Ser Gly Ser Arg Trp Gly Pro Asp Tyr Asn Leu Thr Ile Ser
625                 630                 635                 640
Asn Leu Glu Ser Gly Asp Phe Gly Val Tyr Tyr Cys Gln Gln Tyr Glu
                645                 650                 655
Phe Phe Gly Gln Gly Thr Lys Val Gln Val Asp Ile Lys Arg Thr Val
            660                 665                 670
Ala Ala Pro Ser Val Phe Ile Phe Pro Pro Ser Asp Glu Gln Leu Lys
        675                 680                 685
Ser Gly Thr Ala Ser Val Val Cys Leu Leu Asn Asn Phe Tyr Pro Arg
    690                 695                 700
Glu Ala Lys Val Gln Trp Lys Val Asp Asn Ala Leu Gln Ser Gly Asn
705                 710                 715                 720
Ser Gln Glu Ser Val Thr Glu Gln Asp Ser Lys Asp Ser Thr Tyr Ser
                725                 730                 735
Leu Ser Asn Thr Leu Thr Leu Ser Lys Ala Asp Tyr Glu Lys His Lys
            740                 745                 750
Val Tyr Ala Cys Glu Val Thr His Gln Gly Leu Ser Ser Pro Val Thr
        755                 760                 765
Lys Ser Phe Asn Arg Gly Glu Cys
    770                 775

<210> SEQ ID NO 54
<211> LENGTH: 2352
<212> TYPE: DNA
<213> ORGANISM: Artificial Sequence
<220> FEATURE:
<223> OTHER INFORMATION: VRC01 human IgG3_new

<400> SEQUENCE: 54
ggatccgcca ccatggattg acatggagg attctgttcc tggtcgccgc cgccacagga    60
acccatgctc aggtgcagct ggtgcagtct ggagggcaga tgaagaaacc cggcgagtca   120
atgcgaatca gctgcagggc ttccggatac gaattcatcg attgtaccct gaactggatt   180
agactggcac caggaaagcg gcccgagtgg atggggtggc tgaaaccacg cggcggagca   240
gtgaattacg ccagacccct gcagggccgg gtcacaatga ctcgcgacgt gtattcagat   300
accgcattcc tggagctgcg aagcctgact gtcgacgata ccgccgtgta cttctgcaca   360
agggcaaaa actgtgacta caactggat ttcgaacact ggggccgcgg aaccccagtc   420
attgtgagct ccgcatcaac aaagggcct agcgtgtttc ctctggcccc atgcagtagg   480
tcaacaagcg ggggcactgc cgctctggga tgtctggtga aggactattt cccagagccc   540
gtcaccgtgt catggaacag cggcgccctg acatccggag tccatacttt tcccgctgtg   600
ctgcagtcta gtggactgta ctctctgtca agcgtggtca cagtcccttc ctctagtctg   660
gggacccaga catatacttg taacgtgaat cacaagccaa gcaacactaa ggtcgacaaa   720
agagtggagc tgaaaccccc tctgggcgat accacacata catgcccaag atgtcctgag   780
ccaaagtcct gcgacacgcc tccaccatgc cctcggtgtc ccgaacctaa atcttgtgat   840
```

```
acacccctc catgcccacg atgtccagag ccaaagagct gcgacactcc cctccatgt    900
cctcgatgtc ctgctccaga actgctggga gggccctccg tgttcctgtt tccccctaag   960
cctaaagata ccctgatgat cagtcggacc ccagaggtca catgcgtggt cgtggacgtg  1020
tcccacgagg accccgaagt ccagttcaag tggtacgtgg acggcgtcga agtgcataac  1080
gccaagacaa aacctaggga ggaacagtat aattccactt ttagagtcgt gtctgtcctg  1140
accgtgctgc accaggactg gctgaacgga aggagtaca agtgtaaagt gtctaataag  1200
gccctgcccg ctcctatcga aaaactatt agcaagacca aagggcagcc ccgggaacct  1260
caggtgtaca ccctgccacc ctcccgcgag aaatgactta gaaccaggt ctctctgacc  1320
tgcctggtga aagggttcta tcccagcgat atcgctgtgg agtgggaatc aagcggccag  1380
cctgagaaca attacaatac tacccctcca atgctggact ccgatggctc tttctttctg  1440
tatagtaagc tgacagtgga caaatcaaga tggcagcagg aaacatttt ctcctgttct  1500
gtgatgcacg aagcccctgca taatcggttt acccagaaga gtctgtcact gagcccaggc  1560
aagcggggac gcaaaaggag atccgggtct ggcgctacaa acttctccct gctgaagcag  1620
gcaggcgacg tggaggaaaa tccaggacct atggtcctgc agacccaggt gttcatctct  1680
ctgctgctgt ggattagtgg ggcatacggc gaaattgtgc tgacccagtc cccagggaca  1740
ctgagtctgt cacccggcga gacagccatc atttcttgcc ggactagtca gtacggatca  1800
ctggcatggt atcagcagcg acctggacag gctccacgac tggtcatcta cagcgggtcc  1860
actagggcag ccggcattcc tgaccgattc tctggaagta ggtgggggcc tgattacaac  1920
ctgaccatca gcaatctgga gtccggggac ttggcgtgt actattgtca gcagtatgaa  1980
ttctttggac aggggactaa ggtccaggtg gatatcaaac gcaccgtcgc tgcacccagc  2040
gtgttcatct ttccccctag tgacgaacag ctgaagtctg gcaccgccag tgtcgtgtgc  2100
ctgctgaaca acttctaccc taggggaggca aaggtccagt ggaaagtgga taacgccctg  2160
cagagtggaa attcacagga gagcgtgaca gaacaggact ccaaggattc tacttatagt  2220
ctgtccaaca ccctgacact gagcaaaagct gactacgaga agcacaaagt gtatgcatgt  2280
gaggtcaccc accagggggct gagctcacca gtcacaaaat ccttcaatag gggagaatgt  2340
tgataactcg ag                                                      2352
```

<210> SEQ ID NO 55
<211> LENGTH: 489
<212> TYPE: PRT
<213> ORGANISM: Artificial Sequence
<220> FEATURE:
<223> OTHER INFORMATION: PGT145 Heavy Chain

<400> SEQUENCE: 55

Met Asp Trp Thr Trp Arg Ile Leu Phe Leu Val Ala Ala Thr Gly
1               5                   10                  15

Thr His Ala Gln Val Gln Leu Val Gln Ser Gly Ala Glu Val Lys Lys
            20                  25                  30

Pro Gly Ser Ser Val Lys Val Ser Cys Lys Ala Ser Gly Asn Ser Phe
        35                  40                  45

Ser Asn His Asp Val His Trp Val Arg Gln Ala Thr Gly Gln Gly Leu
    50                  55                  60

Glu Trp Met Gly Trp Met Ser His Glu Gly Asp Lys Thr Gly Leu Ala
65                  70                  75                  80

Gln Lys Phe Gln Gly Arg Val Thr Ile Thr Arg Asp Ser Gly Ala Ser

```
                    85                  90                  95
Thr Val Tyr Met Glu Leu Arg Gly Leu Thr Ala Asp Asp Thr Ala Ile
                100                 105                 110
Tyr Tyr Cys Leu Thr Gly Ser Lys His Arg Leu Arg Asp Tyr Phe Leu
                115                 120                 125
Tyr Asn Glu Tyr Gly Pro Asn Tyr Glu Leu Trp Gly Asp Tyr Leu Ala
130                 135                 140
Thr Leu Asp Val Trp Gly His Gly Thr Ala Val Thr Val Ser Ser Ala
145                 150                 155                 160
Ser Thr Lys Gly Pro Ser Val Phe Pro Leu Ala Pro Ser Ser Lys Ser
                165                 170                 175
Thr Ser Gly Gly Thr Ala Ala Leu Gly Cys Leu Val Lys Asp Tyr Phe
                180                 185                 190
Pro Glu Pro Val Thr Val Ser Trp Asn Ser Gly Ala Leu Thr Ser Gly
                195                 200                 205
Val His Thr Phe Pro Ala Val Leu Gln Ser Ser Gly Leu Tyr Ser Leu
                210                 215                 220
Ser Ser Val Val Thr Val Pro Ser Ser Ser Leu Gly Thr Gln Thr Tyr
225                 230                 235                 240
Ile Cys Asn Val Asn His Lys Pro Ser Asn Thr Lys Val Asp Lys Lys
                245                 250                 255
Val Glu Pro Lys Ser Cys Asp Lys Thr His Thr Cys Pro Pro Cys Pro
                260                 265                 270
Ala Pro Glu Leu Leu Gly Gly Pro Ser Val Phe Leu Phe Pro Pro Lys
                275                 280                 285
Pro Lys Asp Thr Leu Met Ile Ser Arg Thr Pro Glu Val Thr Cys Val
290                 295                 300
Val Val Asp Val Ser His Glu Asp Pro Glu Val Lys Phe Asn Trp Tyr
305                 310                 315                 320
Val Asp Gly Val Glu Val His Asn Ala Lys Thr Lys Pro Arg Glu Glu
                325                 330                 335
Gln Tyr Asn Ser Thr Tyr Arg Val Val Ser Val Leu Thr Val Leu His
                340                 345                 350
Gln Asp Trp Leu Asn Gly Lys Glu Tyr Lys Cys Lys Val Ser Asn Lys
                355                 360                 365
Ala Leu Pro Ala Pro Ile Glu Lys Thr Ile Ser Lys Ala Lys Gly Gln
                370                 375                 380
Pro Arg Glu Pro Gln Val Tyr Thr Leu Pro Pro Ser Arg Asp Glu Leu
385                 390                 395                 400
Thr Lys Asn Gln Val Ser Leu Thr Cys Leu Val Lys Gly Phe Tyr Pro
                405                 410                 415
Ser Asp Ile Ala Val Glu Trp Glu Ser Asn Gly Gln Pro Glu Asn Asn
                420                 425                 430
Tyr Lys Thr Thr Pro Pro Val Leu Asp Ser Asp Gly Ser Phe Phe Leu
                435                 440                 445
Tyr Ser Lys Leu Thr Val Asp Lys Ser Arg Trp Gln Gln Gly Asn Val
                450                 455                 460
Phe Ser Cys Ser Val Met His Glu Ala Leu His Asn His Tyr Thr Gln
465                 470                 475                 480
Lys Ser Leu Ser Leu Ser Pro Gly Lys
                485

<210> SEQ ID NO 56
```

<211> LENGTH: 1467
<212> TYPE: DNA
<213> ORGANISM: Artificial Sequence
<220> FEATURE:
<223> OTHER INFORMATION: PGT145 Heavy Chain

<400> SEQUENCE: 56

```
atggattgga catggaggat tctgtttctg gtcgccgccg ccactggaac tcacgctcag      60
gtgcagctgg tgcagtcagg ggccgaagtg aagaagcccg gcagctccgt gaaggtgtcc     120
tgcaaggcct ctggcaactc cttctctaat cacgacgtgc actgggtgag gcaggcaacc     180
ggacagggcc tggagtggat gggctggatg tcccacgagg cgacaagac aggcctggca     240
cagaagtttc agggccgggt gaccatcaca cgcgattccg gcgcctctac cgtgtatatg     300
gagctgagag gcctgaccgc cgacgataca gccatctact attgcctgac aggcagcaag     360
cacaggctga gagactactt cctgtataac gagtacggcc taattatga ggagtggggc     420
gactacctgg ccaccctgga cgtgtgggga cacggaaccg cagtgacagt gtctagcgcc     480
agcacaaagg gcccatccgt gtttccactg gcaccctcct ctaagagcac ctccggcggc     540
acagccgccc tgggctgtct ggtgaaggat tacttcccag agccagtgac cgtgagctgg     600
aactccggcg ccctgacctc cggagtgcac acatttccag ccgtgctgca gagctccggc     660
ctgtatagcc tgtctagcgt ggtgaccgtg ccctcctcta gcctgggcac ccagacatac     720
atctgcaacg tgaatcacaa gccatccaat acaaaggtgg acaagaaggt ggagcccaag     780
tcttgtgata agacccacac atgccctccc tgtcctgcac cagagctgct gggcggccca     840
tccgtgttcc tgtttccacc caagcctaag gacaccctga tgatcagccg gaccccagag     900
gtgacatgcg tggtggtgga cgtgtcccac gaggaccccg aggtgaagtt caactggtac     960
gtggatggcg tggaggtgca caatgccaag accaagccta gggaggagca gtataactct    1020
acctacagag tggtgagcgt gctgacagtg ctgcaccagg actggctgaa cggcaaggag    1080
tacaagtgca aggtgtctaa taaggccctg cccgccccta tcgagaagac catcagcaag    1140
gcaaagggac agcctcggga gccacaggtg tatacactgc ctccatctcg cgacgagctg    1200
accaagaacc aggtgagcct gacatgtctg gtgaagggct tctaccctag cgatatcgcc    1260
gtggagtggg agtccaatgg ccagccagag aacaattata agaccacacc ccctgtgctg    1320
gactctgatg gcagcttctt tctgtactcc aagctgaccg tggataagtc tcgctggcag    1380
cagggcaacg tgttcagctg tagcgtgatg cacgaagccc tgcacaacca ctacacccag    1440
aaaagcctgt cactgagccc cggaaaa                                       1467
```

<210> SEQ ID NO 57
<211> LENGTH: 239
<212> TYPE: PRT
<213> ORGANISM: Artificial Sequence
<220> FEATURE:
<223> OTHER INFORMATION: PGT145 Kappa Light Chain

<400> SEQUENCE: 57

```
Met Val Leu Gln Thr Gln Val Phe Ile Ser Leu Leu Trp Ile Ser
1               5                   10                  15

Gly Ala Tyr Gly Glu Val Val Ile Thr Gln Ser Pro Leu Phe Leu Pro
            20                  25                  30

Val Thr Pro Gly Glu Ala Ala Ser Leu Ser Cys Lys Cys Ser His Ser
        35                  40                  45

Leu Gln His Ser Thr Gly Ala Asn Tyr Leu Ala Trp Tyr Leu Gln Arg
    50                  55                  60
```

Pro Gly Gln Thr Pro Arg Leu Leu Ile His Leu Ala Thr His Arg Ala
65                  70                  75                  80

Ser Gly Val Pro Asp Arg Phe Ser Gly Ser Gly Thr Asp Phe
                85                  90                  95

Thr Leu Lys Ile Ser Arg Val Glu Ser Asp Asp Val Gly Thr Tyr Tyr
            100                 105                 110

Cys Met Gln Gly Leu His Ser Pro Trp Thr Phe Gly Gln Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 58
<211> LENGTH: 717
<212> TYPE: DNA
<213> ORGANISM: Artificial Sequence
<220> FEATURE:
<223> OTHER INFORMATION: PGT145 Kappa Light Chain

<400> SEQUENCE: 58
atggtgctgc agacccaggt gttcatttca ctgctgctgt ggatttcagg agcctacgga      60
gaagtcgtca ttacccagtc ccctctgttc ctgccagtga ccccaggaga ggcagcatct    120
ctgagctgca gtgttccca ctctctgcag cacagcacag cgccaactac ctggcctgg     180
tatctgcaga ggcctggcca gaccccaaga ctgctgatcc acctggcaac acagggca      240
tccggagtgc cagaccgctt cagcggctcc ggctctggaa ccgacttcac cctgaagatc    300
agcagggtgg agtccgacga tgtgggcacc tactattgca tgcagggcct gcactctccc    360
tggaccttcg gccagggcac aaaggtggag atcaagagga ccgtggcagc accttccgtg    420
ttcatctttc cccttctga cgagcagctg aagtctggca cagccagcgt ggtgtgcctg    480
ctgaacaact ctaccccag ggaggccaag gtgcagtgga aggtggataa cgccctgcag    540
agcggcaatt cccaggagtc tgtgaccgag caggacagca aggattccac atattctctg    600
agctccaccc tgacactgag caaggccgac tacgagaagc acaaggtgta tgcctgcgag    660
gtcacccatc agggggctgtc aagtccagtc acaaagtcct tcaataggggg cgaatgc     717

<210> SEQ ID NO 59
<211> LENGTH: 484
<212> TYPE: PRT
<213> ORGANISM: Artificial Sequence
<220> FEATURE:
<223> OTHER INFORMATION: PGT151 Heavy Chain

<400> SEQUENCE: 59

Met Asp Trp Thr Trp Arg Ile Leu Phe Leu Val Ala Ala Ala Thr Gly

```
1               5                   10                  15
Thr His Ala Arg Val Gln Leu Val Glu Ser Gly Gly Val Val Gln
            20                  25                  30
Pro Gly Lys Ser Val Arg Leu Ser Cys Val Val Ser Asp Phe Pro Phe
        35                  40                  45
Ser Lys Tyr Pro Met Tyr Trp Val Arg Gln Ala Pro Gly Lys Gly Leu
    50                  55                  60
Glu Trp Val Ala Ala Ile Ser Gly Asp Ala Trp His Val Val Tyr Ser
65                  70                  75                  80
Asn Ser Val Gln Gly Arg Phe Leu Val Ser Arg Asp Asn Val Lys Asn
                85                  90                  95
Thr Leu Tyr Leu Glu Met Asn Ser Leu Lys Ile Glu Asp Thr Ala Val
                100                 105                 110
Tyr Arg Cys Ala Arg Met Phe Gln Glu Ser Gly Pro Pro Arg Leu Asp
                115                 120                 125
Arg Trp Ser Gly Arg Asn Tyr Tyr Tyr Ser Gly Met Asp Val Trp
    130                 135                 140
Gly Gln Gly Thr Thr Val Thr Val Ser Ser Ala Ser Thr Lys Gly Pro
145                 150                 155                 160
Ser Val Phe Pro Leu Ala Pro Ser Ser Lys Ser Thr Ser Gly Gly Thr
                165                 170                 175
Ala Ala Leu Gly Cys Leu Val Lys Asp Tyr Phe Pro Glu Pro Val Thr
                180                 185                 190
Val Ser Trp Asn Ser Gly Ala Leu Thr Ser Gly Val His Thr Phe Pro
                195                 200                 205
Ala Val Leu Gln Ser Ser Gly Leu Tyr Ser Leu Ser Ser Val Val Thr
                210                 215                 220
Val Pro Ser Ser Ser Leu Gly Thr Gln Thr Tyr Ile Cys Asn Val Asn
225                 230                 235                 240
His Lys Pro Ser Asn Thr Lys Val Asp Lys Lys Val Glu Pro Lys Ser
                245                 250                 255
Cys Asp Lys Thr His Thr Cys Pro Pro Cys Pro Ala Pro Glu Leu Leu
                260                 265                 270
Gly Gly Pro Ser Val Phe Leu Phe Pro Pro Lys Pro Lys Asp Thr Leu
                275                 280                 285
Met Ile Ser Arg Thr Pro Glu Val Thr Cys Val Val Val Asp Val Ser
                290                 295                 300
His Glu Asp Pro Glu Val Lys Phe Asn Trp Tyr Val Asp Gly Val Glu
305                 310                 315                 320
Val His Asn Ala Lys Thr Lys Pro Arg Glu Glu Gln Tyr Asn Ser Thr
                325                 330                 335
Tyr Arg Val Val Ser Val Leu Thr Val Leu His Gln Asp Trp Leu Asn
                340                 345                 350
Gly Lys Glu Tyr Lys Cys Lys Val Ser Asn Lys Ala Leu Pro Ala Pro
                355                 360                 365
Ile Glu Lys Thr Ile Ser Lys Ala Lys Gly Gln Pro Arg Glu Pro Gln
                370                 375                 380
Val Tyr Thr Leu Pro Pro Ser Arg Asp Glu Leu Thr Lys Asn Gln Val
385                 390                 395                 400
Ser Leu Thr Cys Leu Val Lys Gly Phe Tyr Pro Ser Asp Ile Ala Val
                405                 410                 415
Glu Trp Glu Ser Asn Gly Gln Pro Glu Asn Asn Tyr Lys Thr Thr Pro
                420                 425                 430
```

Pro Val Leu Asp Ser Asp Gly Ser Phe Phe Leu Tyr Ser Lys Leu Thr
    435                 440                 445

Val Asp Lys Ser Arg Trp Gln Gln Gly Asn Val Phe Ser Cys Ser Val
450                 455                 460

Met His Glu Ala Leu His Asn His Tyr Thr Gln Lys Ser Leu Ser Leu
465                 470                 475                 480

Ser Pro Gly Lys

<210> SEQ ID NO 60
<211> LENGTH: 1452
<212> TYPE: DNA
<213> ORGANISM: Artificial Sequence
<220> FEATURE:
<223> OTHER INFORMATION: PGT151 Heavy Chain

<400> SEQUENCE: 60

| | | | | | |
|---|---|---|---|---|---|
| atggactgga | cttggcgcat | tctgtttctg | gtcgcagccg | caaccgggac | tcacgctcgg | 60 |
| gtgcagctgg | tcgaatcagg | aggaggagtg | gtgcagccag | gcaagagcgt | gcggctgtcc | 120 |
| tgcgtggtgt | ctgacttccc | cttcagcaag | tacccaatgt | attgggtgcg | ccaggcacca | 180 |
| ggcaagggcc | tggagtgggt | ggcagcaatc | tccggcgatg | catggcacgt | ggtgtactct | 240 |
| aacagcgtgc | agggcaggtt | cctggtgagc | agagacaacg | tgaagaatac | cctgtacctg | 300 |
| gagatgaatt | ccctgaagat | cgaggataca | gccgtgtata | ggtgcgccag | aatgtttcag | 360 |
| gagagcggcc | ctcccaggct | ggacaggtgg | agcggaagga | actactatta | ctattccgga | 420 |
| atggacgtgt | ggggacaggg | aaccacagtg | accgtgagct | ccgccagcac | aaagggccct | 480 |
| tccgtgttcc | ctctggcccc | atctagcaag | tccacctctg | gcggcacagc | cgccctgggc | 540 |
| tgtctggtga | aggactactt | ccctgagcca | gtgaccgtgt | cttggaacag | cggcgccctg | 600 |
| acctctggag | tgcacacatt | tcccgccgtg | ctgcagtcct | ctggcctgta | ctccctgagc | 660 |
| tccgtggtga | ccgtgccttc | tagctccctg | ggcacccaga | catatatctg | caacgtgaat | 720 |
| cacaagccca | gcaatacaaa | ggtggacaag | aaggtggagc | ctaagtcctg | tgataagacc | 780 |
| cacacatgcc | caccctgtcc | agcacctgag | ctgctgggcg | gccctagcgt | gttcctgttt | 840 |
| cctccaaagc | caaaggacac | cctgatgatc | tctagaaccc | ctgaggtgac | atgcgtggtg | 900 |
| gtggacgtga | gccacgagga | ccccgaggtg | aagtttaact | ggtacgtgga | tggcgtggag | 960 |
| gtgcacaatg | ccaagacaaa | gccccgggag | gagcagtaca | actctaccta | tcgcgtggtg | 1020 |
| agcgtgctga | cagtgctgca | ccaggactgg | ctgaacggca | aggagtataa | gtgcaaggtg | 1080 |
| tccaataagg | ccctgccagc | ccccatcgag | aagaccatct | ctaaggcaaa | gggacagccc | 1140 |
| agggagcctc | aggtgtacac | actgcccccct | tccagagacg | agctgaccaa | gaaccaggtg | 1200 |
| tctctgacat | gtctggtgaa | gggcttctat | ccatctgata | tcgccgtgga | gtgggagagc | 1260 |
| aatggccagc | ccgagaacaa | ttacaagacc | acaccaccg | tgctggactc | cgatggctct | 1320 |
| ttctttctgt | attccaagct | gaccgtggat | aagtctaggt | ggcagcaggg | caacgtgttc | 1380 |
| agctgttccg | tgatgcacga | agcactgcac | aaccattaca | cccagaagag | cctgagcctg | 1440 |
| agccccggca | ag | | | | | 1452 |

<210> SEQ ID NO 61
<211> LENGTH: 239
<212> TYPE: PRT
<213> ORGANISM: Artificial Sequence
<220> FEATURE:
<223> OTHER INFORMATION: PGT151 Kappa Light Chain

<400> SEQUENCE: 61

Met Val Leu Gln Thr Gln Val Phe Ile Ser Leu Leu Trp Ile Ser
1               5                   10                  15

Gly Ala Tyr Gly Asp Ile Val Met Thr Gln Thr Pro Leu Ser Leu Ser
            20                  25                  30

Val Thr Pro Gly Gln Pro Ala Ser Ile Ser Cys Lys Ser Ser Glu Ser
        35                  40                  45

Leu Arg Gln Ser Asn Gly Lys Thr Ser Leu Tyr Trp Tyr Arg Gln Lys
    50                  55                  60

Pro Gly Gln Ser Pro Gln Leu Leu Val Phe Glu Val Ser Asn Arg Phe
65                  70                  75                  80

Ser Gly Val Ser Asp Arg Phe Val Gly Ser Gly Ser Gly Thr Asp Phe
                85                  90                  95

Thr Leu Arg Ile Ser Arg Val Glu Ala Glu Asp Val Gly Phe Tyr Tyr
            100                 105                 110

Cys Met Gln Ser Lys Asp Phe Pro Leu Thr Phe Gly Gly Gly Thr Lys
        115                 120                 125

Val Asp Leu Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 62
<211> LENGTH: 717
<212> TYPE: DNA
<213> ORGANISM: Artificial Sequence
<220> FEATURE:
<223> OTHER INFORMATION: PGT151 Kappa Light Chain

<400> SEQUENCE: 62
atggtgctgc agactcaggt gtttattagc ctgctgctgt ggatttccgg ggcctacggg      60
gacattgtga tgacccagac tcctctgtcc ctgtctgtga ccccaggaca gccagcaagc     120
atctcctgca gagctccga gagcctgagg cagtccaacg gcaagacaag cctgtactgg     180
tatagacaga agcctggcca gagcccacag ctgctggtgt tcgaggtgtc caatcggttt     240
tccggcgtgt ctgacaggtt cgtgggctct ggcagcggaa ccgacttcac cctgaggatc     300
tctagagtgg aggccgagga cgtgggcttc tactattgca tgcagtccaa ggatttcccc     360
ctgaccttcg gcggcggcac aaaggtggac ctgaagagga ccgtggcagc accttccgtg     420
ttcatctttc cccttctga tgagcagctg aagtctggca gccagcgt ggtgtgcctg       480 ctgaacaact ctaccccccg cgaggccaag gtgcagtgga aggtggacaa cgccctgcag     540
agcggcaatt cccaggagtc tgtgaccgag caggacagca aggattccac atattctctg     600
tctagcaccc tgacactgtc caaggccgat tacgagaagc acaaggtgta tgcctgtgag     660
gtcacccacc aggggctgtc cagtccagtc acaaaatcct tcaatcgggg agaatgt     717

<210> SEQ ID NO 63
<211> LENGTH: 490
<212> TYPE: PRT
<213> ORGANISM: Artificial Sequence
<220> FEATURE:
<223> OTHER INFORMATION: PGDM1400 Heavy Chain

<400> SEQUENCE: 63

Met Asp Trp Thr Trp Arg Ile Leu Phe Leu Val Ala Ala Ala Thr Gly
1               5                   10                  15

Thr His Ala Gln Ala Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
         355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490

<210> SEQ ID NO 64
<211> LENGTH: 1470
<212> TYPE: DNA
<213> ORGANISM: Artificial Sequence
<220> FEATURE:
<223> OTHER INFORMATION: PGDM1400 Heavy Chain

<400> SEQUENCE: 64

| | | | | | |
|---|---|---|---|---|---|
| atggattgga | catggaggat | tctgtttctg | gtcgccgccg | caaccggaac | tcacgctcag | 60 |
| gctcagctgg | tgcagtctgg | acctgaagtg | aggaagccag | gcacctccgt | gaaggtgtct | 120 |
| tgcaaggccc | ccggcaacac | cctgaagaca | tacgatctgc | actgggtgag | atctgtgcca | 180 |
| ggacagggcc | tgcagtggat | gggatggatc | agccacgagg | gcgacaagaa | agtgatcgtg | 240 |
| gagaggttca | aggccaaggt | gaccatcgat | tgggacagat | ccaccaatac | agcctacctg | 300 |
| cagctgagcg | gcctgacctc | cggcgataca | gccgtgtact | attgcgccaa | gggcagcaag | 360 |
| cacaggctga | gagactacgc | cctgtatgac | gatgacggcg | ccctgaactg | gccgtggat | 420 |
| gtggactatc | tgtccaatct | ggagttctgg | ggacagggaa | ccgcagtgac | agtgagctcc | 480 |
| gcctctacca | agggccctag | cgtgtttcca | ctggcccctc | tagcaagtc | taccagcggc | 540 |
| ggcacagccg | ccctgggatg | tctggtgaag | gactacttcc | cagagcccgt | gacagtgagc | 600 |
| tggaactccg | gcgccctgac | ctctggagtg | cacacatttc | ctgccgtgct | gcagtcctct | 660 |
| ggcctgtaca | gcctgagctc | cgtggtgacc | gtgccatcta | gctccctggg | cacccagaca | 720 |
| tatatctgca | acgtgaatca | caagcctagc | aatacaaagg | tggataagaa | ggtggagcca | 780 |
| aagtcctgtg | acaagaccca | cacatgccct | ccctgtcctg | caccagagct | gctgggcggc | 840 |
| ccaagcgtgt | tcctgttccc | acccaagcct | aaggatacc | tgatgatctc | ccggaccca | 900 |
| gaggtgacat | gcgtggtggt | ggacgtgagc | cacgaggacc | ccgaggtgaa | gtttaactgg | 960 |
| tacgtggacg | gcgtggaggt | gcacaatgcc | aagacaaagc | ccggggagga | gcagtacaac | 1020 |
| tccacctatc | gcgtggtgtc | tgtgctgaca | gtgctgcacc | aggattggct | gaacggcaag | 1080 |
| gagtataagt | gcaaggtgag | caataaggcc | ctgcccgccc | ctatcgagaa | gaccatctcc | 1140 |
| aaggcaaagg | gacagcctcg | ggagccacag | gtgtacacac | tgcctccatc | ccgcgatgag | 1200 |
| ctgaccaaga | accaggtgtc | tctgacatgt | ctggtgaagg | gcttctatcc | ctctgacatc | 1260 |

```
gccgtggagt gggagagcaa tggccagcct gagaacaatt acaagaccac accccctgtg    1320
ctggattctg acggcagctt ctttctgtat agcaagctga ccgtggacaa gtcccgctgg    1380
cagcagggca acgtgttcag ctgttctgtg atgcacgaag cactgcacaa ccactacacc    1440
cagaagtcac tgtcactgtc accaggaaaa                                      1470
```

<210> SEQ ID NO 65
<211> LENGTH: 239
<212> TYPE: PRT
<213> ORGANISM: Artificial Sequence
<220> FEATURE:
<223> OTHER INFORMATION: PGDM1400 Kappa Light Chain

<400> SEQUENCE: 65

```
Met Val Leu Gln Thr Gln Val Phe Ile Ser Leu Leu Leu Trp Ile Ser
1               5                   10                  15

Gly Ala Tyr Gly Asp Phe Val Leu Thr Gln Ser Pro His Ser Leu Ser
            20                  25                  30

Val Thr Pro Gly Glu Ser Ala Ser Ile Ser Cys Lys Ser Ser His Ser
        35                  40                  45

Leu Ile His Gly Asp Arg Asn Asn Tyr Leu Ala Trp Tyr Val Gln Lys
    50                  55                  60

Pro Gly Arg Ser Pro Gln Leu Leu Ile Tyr Leu Ala Ser Ser Arg Ala
65                  70                  75                  80

Ser Gly Val Pro Asp Arg Phe Ser Gly Ser Gly Ser Asp Lys Asp Phe
                85                  90                  95

Thr Leu Lys Ile Ser Arg Val Glu Thr Glu Asp Val Gly Thr Tyr Tyr
            100                 105                 110

Cys Met Gln Gly Arg Glu Ser Pro Trp Thr Phe Gly Gln Gly Thr Lys
        115                 120                 125

Val Asp Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 66
<211> LENGTH: 717
<212> TYPE: DNA
<213> ORGANISM: Artificial Sequence
<220> FEATURE:
<223> OTHER INFORMATION: PGDM1400 Kappa Light Chain

<400> SEQUENCE: 66

```
atggtgctgc agacccaggt gttcatttca ctgctgctgt ggatttccgg ggcatacggg      60
gacttcgtgc tgactcagag ccctcatagc ctgtccgtga ccccaggaga gtctgccagc     120
atctcctgca agagctccca cagcctgatc acggcgacc ggaacaatta cctggcctgg     180
```

```
tacgtgcaga agccaggccg cagcccccag ctgctgatct acctggcctc tagcagggcc      240
tccggagtgc ctgacagatt ctctggcagc ggctccgaca aggacttcac cctgaagatc      300
tctagggtgg agacagagga tgtgggcaca tactattgca tgcagggcag agagtcccct      360
tggaccttcg gccagggcac aaaggtggac atcaagagga ccgtggcagc accatccgtg      420
ttcatctttc cccttctga tgagcagctg aagtctggca cagccagcgt ggtgtgcctg      480
ctgaacaact ctaccccccg cgaggccaag gtgcagtgga aggtggacaa cgccctgcag      540
tctggcaata gccaggagtc cgtgaccgag caggactcta aggatagcac atattccctg      600
tcctctaccc tgacactgtc caaggccgat tacgagaagc acaaggtgta tgcctgtgag      660
gtcacccacc aggggctgtc cagtcccgtc acaaagtcct tcaatagggg cgaatgc       717
```

<210> SEQ ID NO 67
<211> LENGTH: 471
<212> TYPE: PRT
<213> ORGANISM: Artificial Sequence
<220> FEATURE:
<223> OTHER INFORMATION: 12A21 Heavy Chain

<400> SEQUENCE: 67

```
Met Asp Trp Thr Trp Arg Ile Leu Phe Leu Val Ala Ala Ala Thr Gly
1               5                   10                  15

Thr His Ala Ser Gln His Leu Val Gln Ser Gly Thr Gln Val Lys Lys
            20                  25                  30

Pro Gly Ala Ser Val Arg Val Ser Cys Gln Ala Ser Gly Tyr Thr Phe
        35                  40                  45

Thr Asn Tyr Ile Leu His Trp Trp Arg Gln Ala Pro Gly Gln Gly Leu
    50                  55                  60

Glu Trp Met Gly Leu Ile Lys Pro Val Phe Gly Ala Val Asn Tyr Ala
65                  70                  75                  80

Arg Gln Phe Gln Gly Arg Ile Gln Leu Thr Arg Asp Ile Tyr Arg Glu
                85                  90                  95

Ile Ala Phe Leu Asp Leu Ser Gly Leu Arg Ser Asp Thr Ala Val
            100                 105                 110

Tyr Tyr Cys Ala Arg Asp Glu Ser Gly Asp Leu Lys Trp His Leu
        115                 120                 125

His Pro Trp Gly Gln Gly Thr Gln Val Ile Val Ser Pro Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270
```

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 68
<211> LENGTH: 1413
<212> TYPE: DNA
<213> ORGANISM: Artificial Sequence
<220> FEATURE:
<223> OTHER INFORMATION: 12A21 Heavy Chain

<400> SEQUENCE: 68
atggattgga catggcgcat tctgtttctg gtcgcagccg ctactggaac ccacgcatca      60
cagcatctgg tgcagtctgg aactcaggtg aagaagccag gagcatccgt gcgggtgtct     120
tgccaggcaa gcggctacac cttcacaaac tatatcctgc actggtggag gcaggccaca     180
ggacagggcc tggagtggat gggcctgatc aagcccgtgt cggcgccgt gaattacgcc      240 cggcagtttc agggccgcat ccagctgacc agggacatct atagagagat cgcctttctg     300
gatctgtccg gcctgcggtc tgacgataca gccgtgtact attgcgcccg cgacgagagc     360
ggcgacgatc tgaagtggca cctgcaccct ggggacagg gaacccaggt catcgtgagc      420
ccagcatcta caagggacc ttccgtgttc ccactggcac ccagctccaa gagcacctcc     480
ggcggcacag ccgccctggg ctgtctggtg aaggattact cccagagcc agtgaccgtg     540 agctggaact ccggcgccct gacctctgga gtgcacacat tcccgccgt gctgcagtct      600 agcggcctgt actccctgtc ctctgtggtg accgtgccta gctcctctct gggcacccag     660
acatatatct gcaacgtgaa tcacaagcct tctaatacaa aggtggacaa gaaggtggag     720
ccaaagagct gtgataagac ccacacatgc cctccctgtc ctgcaccaga gctgctgggc     780
ggcccaagcg tgttcctgtt tccacccaag cccaaggaca ccctgatgat ctccaggacc     840
cctgaggtga catgcgtggt ggtggacgtg tctcacgagg accccgaggt gaagtttaac     900

```
tggtacgtgg atggcgtgga ggtgcacaat gccaagacaa agcccaggga ggagcagtac   960
aacagcacct atagagtggt gtccgtgctg acagtgctgc accaggactg gctgaacggc  1020
aaggagtata agtgcaaggt gagcaataag gccctgcccg cccctatcga aagaccatc   1080 tccaaggcca agggccagcc tagggagcca caggtgtaca cactgcctcc aagcagagac  1140
gagctgacca agaaccaggt gtccctgaca tgtctggtga agggctttta tccatccgat  1200
atcgccgtgg agtgggagtc taatggccag cccgagaaca attacaagac cacacccct   1260 gtgctggact ctgatggcag cttctttctg tattctaagc tgaccgtgga taagagcaga  1320
tggcagcagg gcaacgtgtt cagctgtagc gtgatgcacg aagcactgca caaccactac  1380
acccagaagt cactgtcact gagcccagga aaa                                1413
```

<210> SEQ ID NO 69
<211> LENGTH: 230
<212> TYPE: PRT
<213> ORGANISM: Artificial Sequence
<220> FEATURE:
<223> OTHER INFORMATION: 12A21 Kappa Light Chain

<400> SEQUENCE: 69

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Asn Cys Gln Ala Gly Gln Gly
        35                  40                  45

Ile Gly Ser Ser Leu Asn Trp Tyr Gln Lys Lys Pro Gly Arg Ala Pro
    50                  55                  60

Lys Leu Leu Val His Gly Ala Ser Asn Leu Gln Arg Gly Val Pro Ser
65                  70                  75                  80

Arg Phe Ser Gly Ser Gly Phe His Thr Thr Phe Thr Leu Thr Ile Ser
                85                  90                  95

Ser Leu Gln Pro Asp Asp Val Ala Thr Tyr Phe Cys Ala Val Phe Gln
            100                 105                 110

Trp Phe Gly Pro Gly Thr Lys Val Asp Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys
225                 230
```

<210> SEQ ID NO 70
<211> LENGTH: 690
<212> TYPE: DNA
<213> ORGANISM: Artificial Sequence
<220> FEATURE:

<223> OTHER INFORMATION: 12A21 Kappa Light Chain

<400> SEQUENCE: 70

```
atggtgctgc agactcaggt gtttatttca ctgctgctgt ggatttcagg agcctacggc      60
gacattcaga tgactcagag cccctcaagc ctgtccgcct ctgtgggcga ccgggtgacc     120
atcaactgcc aggcaggaca gggaatcggc agctccctga attggtacca gaagaagcca     180
ggaagggcac aaagctgct ggtgcacgga gcatccaacc tgcagagggg cgtgcccagc      240
agattcagcg gctccggctt ccacaccacc ttcaccctga caatctctag cctgcagcct     300
gacgatgtgg ccacctattt ttgcgccgtg ttccagtggt ttggccctgg caccaaggtg     360
gacatcaaga ggacagtggc cgccccatcc gtgttcatct tcccccttc tgatgagcag      420
ctgaagtctg gcacagccag cgtggtgtgc ctgctgaaca atttctaccc ccggggaggcc    480
aaggtgcagt ggaaggtgga caacgccctg cagtctggca atagccagga gtccgtgacc     540
gagcaggact ctaaggatag cacatattcc ctgtcctcta ccctgacact gtccaaggcc     600
gattacgaga agcacaaggt gtatgcctgt gaggtcaccc accagggct gtcaagtcca      660
gtcacaaaat ccttcaatcg gggagaatgc                                      690
```

<210> SEQ ID NO 71
<211> LENGTH: 471
<212> TYPE: PRT
<213> ORGANISM: Artificial Sequence
<220> FEATURE:
<223> OTHER INFORMATION: VRC3401 Heavy Chain

<400> SEQUENCE: 71

```
Met Asp Trp Thr Trp Arg Ile Leu Phe Leu Val Ala Ala Thr Gly
1               5                   10                  15

Thr His Ala Gln Glu Val Leu Val Gln Ser Gly Ala Glu Val Lys Lys
            20                  25                  30

Pro Gly Ala Ser Val Lys Val Ser Cys Arg Ala Phe Gly Tyr Thr Phe
        35                  40                  45

Thr Gly Asn Ala Leu His Trp Val Arg Gln Ala Pro Gly Gln Gly Leu
    50                  55                  60

Glu Trp Leu Gly Trp Ile Asn Pro His Ser Gly Asp Thr Thr Thr Ser
65                  70                  75                  80

Gln Lys Phe Gln Gly Arg Val Tyr Met Thr Arg Asp Lys Ser Ile Asn
                85                  90                  95

Thr Ala Phe Leu Asp Val Thr Arg Leu Thr Ser Asp Thr Gly Ile
            100                 105                 110

Tyr Tyr Cys Ala Arg Asp Lys Tyr Tyr Gly Asn Glu Ala Val Gly Met
        115                 120                 125

Asp Val Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220
```

```
Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
        340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 72
<211> LENGTH: 1413
<212> TYPE: DNA
<213> ORGANISM: Artificial Sequence
<220> FEATURE:
<223> OTHER INFORMATION: VRC3401 Heavy Chain

<400> SEQUENCE: 72
atggattgga catggcgcat tctgtttctg gtcgcagccg ctaccggaac ccacgctcag      60
gaagtgctgg tgcagtcagg ggccgaagtg aagaagcccg gcgcctccgt gaaggtgtct     120
tgcagggcct tcggctacac cttcaccggc aacgcactgc actgggtgag acaggcacct     180
ggacagggcc tggagtggct gggatggatc aatccacact ctggcgacac cacaaccagc     240
cagaagttcc agggcagggt gtatatgaca agagacaagt ctatcaacac cgcctttctg     300
gatgtgacac ggctgaccag cgacgataca ggcatctact attgcgcccg cgacaagtac     360
tatggcaatg aggcagtggg aatggacgtg tggggacagg gcacatccgt gaccgtgagc     420
tccgccagca ccaagggacc ttccgtgttc ccactggcac cctctagcaa gtctacaagc     480
ggcggcaccg ccgccctggg atgtctggtg aaggattact tcccagagcc agtgaccgtg     540
agctggaact ccggcgccct gacatctggc gtgcacacct ttcctgccgt gctgcagtcc     600
```

```
tctggcctgt acagcctgag ctccgtggtg acagtgccat ctagctccct gggcacacag    660
acctatatct gcaacgtgaa tcacaagcca agcaatacca aggtggacaa gaaggtggag    720
cccaagtcct gtgataagac acacacctgc cctccctgtc ctgcaccaga gctgctgggc    780
ggcccaagcg tgttcctgtt tccacccaag cctaaggaca cactgatgat ctcccggaca    840
ccagaggtga cctgcgtggt ggtggacgtg tctcacgagg accccgaggt gaagtttaac    900
tggtacgtgg atggcgtgga ggtgcacaat gccaagacca gccccggga ggagcagtac    960
aactccacat atcgcgtggt gtctgtgctg accgtgctgc accaggactg gctgaacggc   1020
aaggagtata agtgcaaggt gagcaataag gccctgcccg cccctatcga agacaatc    1080
tccaaggcca agggccagcc tagggagcca caggtgtaca ccctgcctcc atccagagac   1140
gagctgacaa agaaccaggt gtctctgacc tgtctggtga agggcttcta tccctctgat   1200
atcgccgtgg agtgggagag caatggccag cctgagaaca attacaagac aaacccctccc   1260
gtgctggact ctgatggcag cttctttctg tatagcaagc tgaccgtgga taagtcccgc   1320
tggcagcagg gcaacgtgtt cagctgttct gtgatgcacg aagcactgca caaccactac   1380
acccagaagt cactgtcact gagcccagga aag                                1413
```

<210> SEQ ID NO 73
<211> LENGTH: 232
<212> TYPE: PRT
<213> ORGANISM: Artificial Sequence
<220> FEATURE:
<223> OTHER INFORMATION: VRC3401 Kappa Light Chain

<400> SEQUENCE: 73

```
Met Val Leu Gln Thr Gln Val Phe Ile Ser Leu Leu Trp Ile Ser
1               5                   10                  15

Gly Ala Tyr Gly Gln Leu Thr Gln Ser Pro Ser Phe Leu Ser Ala Ser
            20                  25                  30

Val Gly Asp Lys Val Thr Ile Thr Cys Arg Ala Ser Gln Gly Val Arg
        35                  40                  45

Asn Glu Leu Ala Trp Tyr Gln Gln Lys Pro Gly Lys Ala Pro Asn Leu
    50                  55                  60

Leu Ile Tyr Tyr Ala Ser Thr Leu Gln Ser Gly Val Pro Ser Arg Phe
65                  70                  75                  80

Ser Ala Thr Gly Ser Gly Thr His Phe Thr Leu Thr Val Ser Ser Leu
                85                  90                  95

Gln Pro Glu Asp Phe Ala Thr Tyr Phe Cys Gln His Met Ser Ser Tyr
            100                 105                 110

Pro Leu Thr Phe Gly Gly Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220
```

Lys Ser Phe Asn Arg Gly Glu Cys
225                 230

<210> SEQ ID NO 74
<211> LENGTH: 696
<212> TYPE: DNA
<213> ORGANISM: Artificial Sequence
<220> FEATURE:
<223> OTHER INFORMATION: VRC3401 Kappa Light Chain

<400> SEQUENCE: 74

| | | |
|---|---|---|
| atggtgctgc agacccaggt gtttatttca ctgctgctgt ggattagcgg agcctacggc | 60 |
| cagctgaccc agagcccaag tttcctgagc gcctccgtgg gcgacaaggt gaccatcaca | 120 |
| tgcagggcct cccagggcgt gagaaacgag ctggcctggt accagcagaa gccaggcaag | 180 |
| gcccccaatc tgctgatcta ctatgcctcc accctgcagc tggagtgcc ctctaggttc | 240 |
| agcgccaccg gctctggcac acactttacc ctgacagtga gctccctgca gcctgaggat | 300 |
| ttcgccacat acttttgcca gcacatgtct agctatccac tgaccttcgg cggcggcaca | 360 |
| aaggtggaga tcaagaggac cgtggcagca ccaagcgtgt tcatctttcc ccctagcgac | 420 |
| gagcagctga gagcggcac agcctccgtg gtgtgcctgc tgaacaactt ctaccctcgc | 480 |
| gaggccaagg tgcagtggaa ggtggataac gccctgcagt ccggcaattc tcaggagagc | 540 |
| gtgaccgagc aggactccaa ggattctaca tatagcctgt cctctaccct gacactgagc | 600 |
| aaggccgact acgagaagca caaggtgtat gcctgtgagg tcacccacca ggggctgagc | 660 |
| agtccagtca ccaagtcctt caatcggggc gaatgt | 696 |

<210> SEQ ID NO 75
<211> LENGTH: 475
<212> TYPE: PRT
<213> ORGANISM: Artificial Sequence
<220> FEATURE:
<223> OTHER INFORMATION: IOMA Heavy Chain

<400> SEQUENCE: 75

Met Asp Trp Thr Trp Arg Ile Leu Phe Leu Val Ala Ala Ala Thr Gly
1               5                   10                  15

Thr His Ala Glu Val Gln Leu Val Glu Ser Gly Ala Gln Val Lys Lys
            20                  25                  30

Pro Gly Ala Ser Val Thr Val Ser Cys Thr Ala Ser Gly Tyr Lys Phe
        35                  40                  45

Thr Gly Tyr His Met His Trp Val Arg Gln Ala Pro Gly Arg Gly Leu
    50                  55                  60

Glu Trp Met Gly Trp Ile Asn Pro Phe Arg Gly Ala Val Lys Tyr Pro
65                  70                  75                  80

Gln Asn Phe Arg Gly Arg Val Ser Met Thr Arg Asp Thr Ser Met Glu
                85                  90                  95

Ile Phe Tyr Met Glu Leu Ser Arg Leu Thr Ser Asp Asp Thr Ala Val
            100                 105                 110

Tyr Tyr Cys Ala Arg Glu Met Phe Asp Ser Ser Ala Asp Trp Ser Pro
        115                 120                 125

Trp Arg Gly Met Val Ala Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp

```
                    165                 170                 175
Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 76
<211> LENGTH: 1425
<212> TYPE: DNA
<213> ORGANISM: Artificial Sequence
<220> FEATURE:
<223> OTHER INFORMATION: IOMA Heavy Chain

<400> SEQUENCE: 76
atggactgga catggagaat cctgttcctg gtcgcagcag caaccggcac ccacgcagaa      60
gtgcagctgg tcgaaagcgg ggctcaggtg aagaagccag gagcaagcgt gaccgtgtcc     120
tgcacagcat ctggctacaa gttcaccggc tatcacatgc actgggtgcg caggcacct     180 ggaaggggcc tggagtggat gggatggatc aaccccttca ggggcgccgt gaagtaccct     240
cagaacttca ggggcagagt gtccatgacc aggacacat ctatggagat cttctatatg     300
```

```
gagctgagca gactgaccct cgacgataca gccgtgtact attgcgcccg ggagatgttt    360
gacagctccg ccgattggag cccctggagg ggaatggtgg catggggaca gggcaccctg    420
gtgacagtgt ctagcgcctc taccaagggc cctagcgtgt tccactggc ccctcctct     480 aagtccacct ctggcggcac agccgccctg ggctgtctgg tgaaggatta cttcccagag    540
cccgtgacag tgtcttggaa cagcggcgcc ctgaccagcg gagtgcacac atttcctgcc    600
gtgctgcaga gctccggcct gtactccctg tctagcgtgg tgaccgtgcc atcctctagc    660
ctgggcaccc agacatatat ctgcaacgtg aatcacaagc cttctaatac aaaggtggac    720
aagaaggtgg agccaaagag ctgtgataag acccacacat gccctcctg tcctgcacca    780 gagctgctgg gcggcccatc cgtgttcctg tttccaccca gcccaagga caccctgatg    840 atctccagga ccccagaggt gacatgcgtg gtggtggacg tgtctcacga ggaccccgag    900
gtgaagttca actggtacgt ggatggcgtg gaggtgcaca atgccaagac aaagcccagg    960
gaggagcagt acaacagcac ctatagagtg gtgtccgtgc tgacagtgct gcaccaggac    1020
tggctgaacg gcaaggagta taagtgcaag gtgagcaata aggccctgcc cgcccctatc    1080
gagaagacca tctccaaggc aaagggacag cctcgggagc acaggtgta cacactgcct    1140 ccaagccgcg acgagctgac caagaaccag gtgtccctga catgtctggt gaagggcttc    1200 tatcctcc gatatcgccgt ggagtgggag tctaatggcc agcctgagaa caattacaag    1260
accacacccc ctgtgctgga ctccgatggc tctttctttc tgtattctaa gctgaccgtg    1320
gataagagca gatggcagca gggcaacgtg ttcagctgtt ccgtgatgca cgaagcactg    1380
cacaaccatt acactcagaa gtcactgtca ctgtcaccag ggaag                   1425
```

<210> SEQ ID NO 77
<211> LENGTH: 234
<212> TYPE: PRT
<213> ORGANISM: Artificial Sequence
<220> FEATURE:
<223> OTHER INFORMATION: IOMA Lambda Light Chain

<400> SEQUENCE: 77

```
Met Ala Trp Thr Pro Leu Phe Leu Phe Leu Leu Thr Cys Cys Pro Gly
  1               5                  10                  15

Gly Ser Asn Ser Gln Ser Ala Leu Thr Gln Pro Ala Ser Val Ser Gly
             20                  25                  30

Ser Pro Gly Gln Ser Ile Thr Ile Ser Cys Ala Gly Ser Ser Arg Asp
         35                  40                  45

Val Gly Gly Phe Asp Leu Val Ser Trp Tyr Gln Gln His Pro Gly Lys
     50                  55                  60

Ala Pro Lys Leu Ile Ile Tyr Glu Val Asn Lys Arg Pro Ser Gly Ile
 65                  70                  75                  80

Ser Ser Arg Phe Ser Ala Ser Lys Ser Gly Asn Thr Ala Ser Leu Thr
                 85                  90                  95

Ile Ser Gly Leu Gln Glu Glu Asp Glu Ala His Tyr Tyr Cys Tyr Ser
            100                 105                 110

Tyr Ala Asp Gly Val Ala Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
```

165                 170                 175
Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Lys Ser Tyr Ser Cys Gln Val Thr His Glu Gly Ser Thr Val
        210                 215                 220

Glu Lys Thr Val Ala Pro Thr Glu Cys Ser
225                 230

<210> SEQ ID NO 78
<211> LENGTH: 702
<212> TYPE: DNA
<213> ORGANISM: Artificial Sequence
<220> FEATURE:
<223> OTHER INFORMATION: IOMA Lambda Light Chain

<400> SEQUENCE: 78
atggcttgga cccctctgtt tctgtttctg ctgacctgtt gccccggagg aagtaattcc       60
cagtctgccc tgacccagcc tgcatcagtg tccggctctc ctggccagtc catcacaatc      120
tcttgcgcag gcagctccag ggacgtgggc ggctttgatc tggtgtcctg gtaccagcag      180
cacccaggca aggcccccaa gctgatcatc tatgaggtga acaagaggcc ctctggcatc      240
tctagcagat tcagcgcctc caagtctggc aatacagcca gcctgaccat ctccggcctg      300
caggaggagg acgaggcaca ctactattgc tactcctatg cagatggagt ggccttcggc      360
ggcggcacaa agctgaccgt gctgggacag cctaaggcag caccatccgt gacactgttt      420 ccccccttcct ctgaggagct gcaggccaac aaggccaccc tggtgtgcct gatcagcgac      480
ttctacccag agcagtgac cgtggcatgg aaggcagata gctcccccagt gaaggcagga      540 gtggagacaa caacccctttc taagcagagc aacaataagt acgccgcctc tagctatctg      600
tctctgaccc ccgagcagtg gaagagccac aagagctatt cctgccaggt cacccatgaa      660
ggctcaaccg tggagaaaac agtcgcccct accgaatgct ca                        702

<210> SEQ ID NO 79
<211> LENGTH: 478
<212> TYPE: PRT
<213> ORGANISM: Artificial Sequence
<220> FEATURE:
<223> OTHER INFORMATION: PGT130 Heavy Chain

<400> SEQUENCE: 79

Met Asp Trp Thr Trp Arg Ile Leu Phe Leu Val Ala Ala Thr Gly
1               5                   10                  15

Thr His Ala Gln Val Gln Leu Gln Glu Ser Gly Pro Gly Leu Val Lys
                20                  25                  30

Pro Ala Glu Thr Leu Ser Leu Thr Cys Ser Val Ser Gly Glu Ser Ile
            35                  40                  45

Asn Thr Gly His Tyr Tyr Trp Gly Trp Val Arg Gln Val Pro Gly Lys
        50                  55                  60

Gly Leu Glu Trp Ile Gly His Ile His Tyr Thr Thr Ala Val Leu His
65                  70                  75                  80

Asn Pro Ser Leu Lys Ser Arg Leu Thr Ile Lys Ile Tyr Thr Leu Arg
                85                  90                  95

Asn Gln Ile Thr Leu Arg Leu Ser Asn Val Thr Ala Ala Asp Thr Ala
            100                 105                 110

Val Tyr His Cys Val Arg Ser Gly Gly Asp Ile Leu Tyr Tyr Glu
115                 120                 125

Trp Gln Lys Pro His Trp Phe Ser Pro Trp Gly Pro Gly Ile His Val
130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Ile Cys Asn Val Asn His Lys Pro Ser Asn Thr
225                 230                 235                 240

Lys Val Asp Lys Lys Val Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 80
<211> LENGTH: 1434
<212> TYPE: DNA
<213> ORGANISM: Artificial Sequence
<220> FEATURE:
<223> OTHER INFORMATION: PGT130 Heavy Chain

<400> SEQUENCE: 80

```
atggactgga cttggaggat tctgtttctg gtcgccgccg ctactggaac tcacgctcag    60
gtgcagctgc aggaatctgg ccccggactg gtgaagcctg ccgagacact gtccctgaca   120
tgctctgtga gcggcgagtc tatcaacacc ggccactact attggggatg ggtgcggcag   180
gtgccaggca agggcctgga gtggatcggc cacatccact ataccacagc cgtgctgcac   240
aatccttctc tgaagagccg cctgaccatc aagatctaca cactgaggaa ccagatcacc   300
ctgagactgt ctaatgtgac cgccgccgac acagccgtgt atcactgcgt gagaagcggc   360
ggcgatatcc tgtactatta cgagtggcag aagccacact ggttctcccc atggggacca   420
ggcatccacg tgaccgtgag ctccgcctct acaaagggcc ccagcgtgtt cctctggcc    480
ccatctagca agtccacctc tggcggcaca gccgccctgg gctgtctggt gaaggactac   540
ttcccagagc ccgtgaccgt gtcctggaac tctggcgccc tgacctccgg agtgcacaca   600
tttcctgccg tgctgcagtc ctctggcctg tatagcctga gctccgtggt gaccgtgcca   660
tctagctccc tgggcaccca gacatacatc tgcaacgtga atcacaagcc ttctaataca   720
aaggtggaca agaaggtgga gccaaagagc tgtgataaga cccacacatg ccctccctgt   780
cctgcaccag agctgctggg cggcccaagc gtgttcctgt ttccacccaa gcccaaggac   840
accctgatga tctccaggac cccagaggtg acatgcgtgg tggtggacgt gtctcacgag   900
gaccccgagg tgaagttcaa ctggtacgtg gatggcgtgg aggtgcacaa tgccaagaca   960
aagcccgggg aggagcagta taactccacc taccgcgtgg tgtctgtgct gacagtgctg  1020
caccaggact ggctgaacgg caaggagtac aagtgcaagg tgagcaataa ggccctgccc  1080
gcccctatcg agaagaccat ctccaaggca agggacagc ccaggagcc tcaggtgtat   1140
acactgcctc caagcagaga cgagctgacc aagaaccagg tgtccctgac atgtctggtg  1200
aagggcttct accctctga tatcgccgtg gagtgggaga gcaatggcca gcctgagaac  1260
aattataaga ccacaccccc tgtgctggac agcgatggct ccttctttct gtacagcaag  1320
ctgaccgtgg ataagtccag gtggcagcag ggcaacgtgt tcagctgttc cgtgatgcac  1380
gaagcactgc acaaccatta cacccagaag tccctgtcac tgtcacccgg caaa          1434
```

<210> SEQ ID NO 81
<211> LENGTH: 236
<212> TYPE: PRT
<213> ORGANISM: Artificial Sequence
<220> FEATURE:
<223> OTHER INFORMATION: PGT130 Lambda Light Chain

<400> SEQUENCE: 81

Met Ala Trp Thr Pro Leu Phe Leu Phe Leu Leu Thr Cys Cys Pro Gly
1               5                   10                  15

Gly Ser Asn Ser Gln Ser Ala Leu Thr Gln Pro Pro Ser Ala Ser Gly
            20                  25                  30

Ser Leu Gly Gln Ser Val Thr Ile Ser Cys Asn Gly Thr Ser Ser Asp
        35                  40                  45

Ile Gly Gly Trp Asn Phe Val Ser Trp Tyr Gln Gln Phe Pro Gly Arg
    50                  55                  60

Ala Pro Arg Leu Ile Ile Phe Glu Val Asn Lys Arg Pro Ser Gly Val
65                  70                  75                  80

Pro Gly Arg Phe Ser Gly Ser Lys Ser Gly Asn Ser Ala Ser Leu Thr
                85                  90                  95

Val Ser Gly Leu Gln Ser Asp Asp Glu Gly Gln Tyr Phe Cys Ser Ser
            100                 105                 110

Leu Phe Gly Arg Trp Asp Val Val Phe Gly Gly Thr Lys Leu Thr
    115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Lys Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 82
<211> LENGTH: 708
<212> TYPE: DNA
<213> ORGANISM: Artificial Sequence
<220> FEATURE:
<223> OTHER INFORMATION: PGT130 Lambda Light Chain

<400> SEQUENCE: 82
atggcatgga caccctgtt tctgttcctg ctgacctgtt gccccggagg ctcaaatagc      60
cagtctgccc tgacccagcc cccaagcgcc tccggctctc tgggccagag cgtgacaatc     120
tcctgcaacg gcaccagctc cgacatcggc ggatggaatt cgtgagctg gtaccagcag     180 tttccaggca gggccccag actgatcatc ttcgaggtga acaagcggcc ttccggagtg     240
ccaggccgct ttagcggctc aagtctggca aatagcgcct ccctgacagt gtctggcctg     300
cagagcgacg atgagggcca gtatttctgc tctagcctgt ttggcaggtg ggatgtggtg     360
ttcggcggcg gaacaaagct gaccgtgctg ggacagccaa aggcagcacc ttctgtgacc     420
ctgtttcccc cttcctctga ggagctgcag gccaacaagg ccaccctggt gtgcctgatc     480
agcgacttct accctggagc agtgaccgtg gcatggaagg ccgatagctc cccagtgaag     540
gccggcgtgg agacaacaac ccctccaag cagtctaaca ataagtacgc cgcctctagc     600
tatctgtccc tgacacccga gcagtggaag tctcacaagt cttatagctg ccaggtcacc     660
catgaaggaa gcacagtgga aaaaaccgtc gcaccaaccg aatgtagc                  708

<210> SEQ ID NO 83
<211> LENGTH: 481
<212> TYPE: PRT
<213> ORGANISM: Artificial Sequence
<220> FEATURE:
<223> OTHER INFORMATION: PGT121 Heavy Chain

<400> SEQUENCE: 83

Met Asp Trp Thr Trp Arg Ile Leu Phe Leu Val Ala Ala Ala Thr Gly
1               5                   10                  15

Thr His Ala Gln Met Gln Leu Gln Glu Ser Gly Pro Gly Leu Val Lys
            20                  25                  30

Pro Ser Glu Thr Leu Ser Leu Thr Cys Ser Val Ser Gly Ala Ser Ile
        35                  40                  45

Ser Asp Ser Tyr Trp Ser Trp Ile Arg Arg Ser Pro Gly Lys Gly Leu
    50                  55                  60

```
Glu Trp Ile Gly Tyr Val His Lys Ser Gly Asp Thr Asn Tyr Ser Pro
 65                  70                  75                  80

Ser Leu Lys Ser Arg Val Asn Leu Ser Leu Asp Thr Ser Lys Asn Gln
                 85                  90                  95

Val Ser Leu Ser Leu Val Ala Ala Thr Ala Ala Asp Ser Gly Lys Tyr
            100                 105                 110

Tyr Cys Ala Arg Thr Leu His Gly Arg Arg Ile Tyr Gly Ile Val Ala
        115                 120                 125

Phe Asn Glu Trp Phe Thr Tyr Phe Tyr Met Asp Val Trp Gly Asn Gly
    130                 135                 140

Thr Gln Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480
```

Lys

<210> SEQ ID NO 84
<211> LENGTH: 1443
<212> TYPE: DNA
<213> ORGANISM: Artificial Sequence
<220> FEATURE:
<223> OTHER INFORMATION: PGT121 Heavy Chain

<400> SEQUENCE: 84

| | | | | | |
|---|---|---|---|---|---|
| atggattgga | catggaggat | tctgtttctg | gtcgccgccg | ctactggaac | ccacgctcag | 60 |
| atgcagctgc | aggagtcagg | ccccggactg | gtgaagccct | ccgagacact | gtctctgaca | 120 |
| tgctctgtga | gcggcgcctc | catctctgac | agctactggt | cttggatcag | agaagccct | 180 |
| ggcaagggcc | tggagtggat | cggctacgtg | cacaagtctg | cgacaccaa | ctattcccca | 240 |
| tctctgaaga | gcagggtgaa | cctgagcctg | gatacatcca | agaatcaggt | gagcctgtcc | 300 |
| ctggtggcag | caaccgcagc | agacagcggc | aagtactatt | gcgccagaac | actgcacggc | 360 |
| aggaggatct | acggcatcgt | ggccttcaac | gagtggttca | cctacttta | tatggacgtg | 420 |
| tggggcaatg | gcacccaggt | gacagtgagc | tccgcctcca | caagggacc | tagcgtgttc | 480 |
| ccactggcac | cctctagcaa | gtctaccagc | ggcggcacag | ccgccctggg | atgtctggtg | 540 |
| aaggattatt | cccagagcc | agtgaccgtg | agctggaact | ccggcgccct | gaccagcgga | 600 |
| gtgcacacat | ttcagccgt | gctgcagtcc | tctggcctgt | actccctgag | ctccgtggtg | 660 |
| accgtgccct | ctagctccct | gggcacccag | acatatatct | gcaacgtgaa | tcacaagcca | 720 |
| tccaatacaa | aggtggacaa | gaaggtggag | cccaagtctt | gtgataagac | ccacacatgc | 780 |
| cctccctgtc | ctgcaccaga | gctgctgggc | ggcccaagcg | tgttcctgtt | tccacccaag | 840 |
| cctaaggaca | ccctgatgat | cagccggacc | ccagaggtga | catgcgtggt | ggtggacgtg | 900 |
| tcccacgagg | accccgaggt | gaagttcaac | tggtacgtgg | atggcgtgga | ggtgcacaat | 960 |
| gccaagacaa | agcccaggga | ggagcagtac | aacagcacct | atagagtggt | gtccgtgctg | 1020 |
| acagtgctgc | accaggactg | gctgaacggc | aaggagtata | agtgcaaggt | gtctaataag | 1080 |
| gccctgcccg | cccctatcga | gaagaccatc | tccaaggcaa | agggacagcc | tcgggagcca | 1140 |
| caggtgtaca | cactgcctcc | aagccgcgac | gagctgacca | agaaccaggt | gtccctgaca | 1200 |
| tgtctggtga | agggcttcta | tccttccgat | atcgccgtgg | agtgggagtc | taatggccag | 1260 |
| ccagagaaca | attacaagac | cacaccccct | gtgctggact | ctgatggcag | cttctttctg | 1320 |
| tattctaagc | tgaccgtgga | taagagccgc | tggcagcagg | gcaacgtgtt | cagctgttct | 1380 |
| gtgatgcacg | aagcactgca | caaccactac | actcagaagt | ccctgtccct | gtccctggc | 1440 |
| aag | | | | | | 1443 |

<210> SEQ ID NO 85
<211> LENGTH: 230
<212> TYPE: PRT
<213> ORGANISM: Artificial Sequence
<220> FEATURE:
<223> OTHER INFORMATION: PGT121 Lambda Light Chain

<400> SEQUENCE: 85

Met Ala Trp Thr Pro Leu Phe Leu Phe Leu Leu Thr Cys Cys Pro Gly
1               5                   10                  15

Gly Ser Asn Ser Asp Ile Ser Val Ala Pro Gly Glu Thr Ala Arg Ile
            20                  25                  30

Ser Cys Gly Glu Lys Ser Leu Gly Ser Arg Ala Val Gln Trp Tyr Gln

```
                35                  40                  45
His Arg Ala Gly Gln Ala Pro Ser Leu Ile Ile Tyr Asn Asn Gln Asp
            50                  55                  60

Arg Pro Ser Gly Ile Pro Glu Arg Phe Ser Gly Ser Pro Asp Ser Pro
65                  70                  75                  80

Phe Gly Thr Thr Ala Thr Leu Thr Ile Thr Ser Val Glu Ala Gly Asp
                85                  90                  95

Glu Ala Asp Tyr Tyr Cys His Ile Trp Asp Ser Arg Val Pro Thr Lys
            100                 105                 110

Trp Val Phe Gly Gly Gly Thr Thr Leu Thr Val Leu Gly Gln Pro Lys
        115                 120                 125

Ala Ala Pro Ser Val Thr Leu Phe Pro Pro Ser Ser Glu Glu Leu Gln
    130                 135                 140

Ala Asn Lys Ala Thr Leu Val Cys Leu Ile Ser Asp Phe Tyr Pro Gly
145                 150                 155                 160

Ala Val Thr Val Ala Trp Lys Ala Asp Ser Ser Pro Val Lys Ala Gly
                165                 170                 175

Val Glu Thr Thr Thr Pro Ser Lys Gln Ser Asn Asn Lys Tyr Ala Ala
            180                 185                 190

Ser Ser Tyr Leu Ser Leu Thr Pro Glu Gln Trp Lys Ser His Lys Ser
        195                 200                 205

Tyr Ser Cys Gln Val Thr His Glu Gly Ser Thr Val Glu Lys Thr Val
    210                 215                 220

Ala Pro Thr Glu Cys Ser
225                 230

<210> SEQ ID NO 86
<211> LENGTH: 690
<212> TYPE: DNA
<213> ORGANISM: Artificial Sequence
<220> FEATURE:
<223> OTHER INFORMATION: PGT121 Lambda Light Chain

<400> SEQUENCE: 86
atggcttgga ctcccctgtt cctgttcctg ctgacttgtt gccctggcgg ctctaactct      60
gacatttccg tcgctcctgg cgagactgcc aggatcagct gcggagagaa gtccctgggc     120
tctcgggccg tgcagtggta ccagcacagg gcaggacagg caccatccct gatcatctat     180
aacaatcagg acaggccttc tggcatccca gagagattca gcggctcccc agatagcccc     240
tttggcacca cagccacact gaccatcaca tccgtggagg caggcgacga ggcagattac     300
tattgccaca tctgggactc ccgggtgcct accaagtggg tgttcggcgg cggaaccaca     360
ctgacagtgc tgggacagcc aaaggcagca ccttctgtga ccctgtttcc cctagctcc      420 gaggagctgc aggccaacaa ggccaccctg gtgtgcctga tctccgactt ctaccctgga     480
gcagtgacag tggcatggaa ggccgattct agcccagtga aggccggcgt ggagacaaca     540
acccccagca gcagtccaa caataagtac gccgcctcct cttatctgtc tctgacacca      600
gagcagtgga agagccacaa gtcttatagc tgccaggtca cccatgaagg aagcaccgtg     660
gagaaaacag tcgccccaac agaatgtagc                                     690

<210> SEQ ID NO 87
<211> LENGTH: 473
<212> TYPE: PRT
<213> ORGANISM: Artificial Sequence
<220> FEATURE:
<223> OTHER INFORMATION: 2219 Heavy Chain
```

<400> SEQUENCE: 87

Met Asp Trp Thr Trp Arg Ile Leu Phe Leu Val Ala Ala Thr Gly
1               5                   10                  15

Thr His Ala Glu Ile Gln Leu Glu Gln Ser Gly Ala Glu Val Lys Lys
            20                  25                  30

Ser Gly Glu Ser Leu Lys Ile Ser Cys Gln Thr Ser Gly Tyr Ser Phe
        35                  40                  45

Ser Asp Tyr Trp Ile Gly Trp Val Arg Gln Met Pro Gly Lys Gly Leu
50                  55                  60

Glu Trp Met Gly Ile Phe Tyr Pro Gly Asp Ser Asp Ser Arg Tyr Ser
65                  70                  75                  80

Pro Ser Phe Glu Gly Gln Val Thr Met Ser Ala Asp Arg Ser Thr Asn
                85                  90                  95

Thr Ala His Leu Gln Trp Ser Ser Leu Lys Pro Ser Asp Thr Ala Leu
            100                 105                 110

Tyr Tyr Cys Ala Arg Leu Gly Gly Asp Tyr Glu Asp Ser Gly Ala Asp
        115                 120                 125

Ala Phe Asp Phe Trp Gly Gln Gly Thr Leu Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn

| | | 405 | | | | 410 | | | | 415 | | |
|---|---|---|---|---|---|---|---|---|---|---|---|---|

Tyr Lys Thr Thr Pro Val Leu Asp Ser Asp Gly Ser Phe Phe Leu
            420              425              430

Tyr Ser Lys Leu Thr Val Asp Lys Ser Arg Trp Gln Gln Gly Asn Val
        435              440              445

Phe Ser Cys Ser Val Met His Glu Ala Leu His Asn His Tyr Thr Gln
    450              455              460

Lys Ser Leu Ser Leu Ser Pro Gly Lys
465              470

<210> SEQ ID NO 88
<211> LENGTH: 1419
<212> TYPE: DNA
<213> ORGANISM: Artificial Sequence
<220> FEATURE:
<223> OTHER INFORMATION: 2219 Heavy Chain

<400> SEQUENCE: 88

```
atggattgga catggaggat tctgtttctg gtcgccgccg ccactggaac tcacgctgag      60
attcagctgg agcagagtgg agcagaagtc aagaagagcg gggagagcct gaagattagt     120
tgccagacaa gcggatacag tttctctgac tactggatcg gatgggtgcg gcagatgcca     180
ggcaagggcc tggagtggat gggcatcttc taccccggcg actctgatag caggtattcc     240
ccttcttttg agggccaggt gaccatgagc gccgatagat ccaccaacac agcccacctg     300
cagtggagct ccctgaagcc ctccgacaca gccctgtact attgcgcaag gctgggcggc     360
gattatgagg acagcggagc cgacgccttt gattttggg gcaggggac tctggtgacc      420
gtgagcagcg ccagcacaaa gggcccatcc gtgtttccac tggcacctc ctctaagagc     480
acctccggcg gcacagccgc cctgggctgt ctggtgaagg attacttccc agagccagtg     540
accgtgagct ggaactccgg cgccctgacc tccggagtgc acacatttcc agccgtgctg     600
cagagctccg gcctgtatag cctgtctagc gtggtgaccg tgccctcctc tagcctgggc     660
acccagacat acatctgcaa cgtgaatcac aagccatcca atacaaaggt ggacaagaag     720
gtggagccca gtcttgtga taagacccac acatgccctc cctgtcctgc accagagctg     780
ctgggcggcc catccgtgtt cctgtttcca cccaagccta aggacaccct gatgatcagc     840
cggaccccag aggtgacatg cgtggtggtg gacgtgtccc acgaggaccc cgaggtgaag     900
ttcaactggt acgtggatgg cgtggaggtg cacaatgcca agaccaagcc tagggaggag     960
cagtataact ctacctacag agtggtgagc gtgctgacag tgctgcacca ggactggctg    1020
aacggcaagg agtacaagtg caaggtgtct aataaggccc tgcccgcccc tatcgagaag    1080
accatcagca aggcaaaggg acagcctcgg gagccacagg tgtatacact gcctccatct    1140
cgcgacgagc tgaccaagaa ccaggtgagc ctgacatgtc tggtgaaggg cttctaccct    1200
agcgatatcg ccgtggagtg ggagtccaat ggccagccag agaacaatta taagaccaca    1260
cccctgtgc tggactctga tggcagcttc tttctgtact ccaagctgac cgtggataag    1320
tctcgctggc agcagggcaa cgtgttcagc tgtagcgtga tgcacgaagc cctgcacaac    1380
cactacaccc agaaaagcct gtcactgagc cccggaaaa                           1419
```

<210> SEQ ID NO 89
<211> LENGTH: 238
<212> TYPE: PRT
<213> ORGANISM: Artificial Sequence
<220> FEATURE:
<223> OTHER INFORMATION: 2219 Lambda Light Chain

<400> SEQUENCE: 89

Met Ala Trp Thr Pro Leu Phe Leu Phe Leu Thr Cys Cys Pro Gly
1               5                   10                  15

Gly Ser Asn Ser Gln Ser Val Leu Thr Gln Pro Pro Ser Ala Ser Gly
            20                  25                  30

Thr Pro Gly Gln Arg Ile Ser Ile Ser Cys Ser Gly Thr Ser Ser Asn
        35                  40                  45

Val Glu Asn Asn Tyr Val Tyr Trp Tyr Gln His Leu Pro Gly Thr Ala
 50                  55                  60

Pro Lys Leu Leu Ile Tyr Arg Asn Asp His Arg Ser Ser Gly Ile Pro
65                  70                  75                  80

Asp Arg Phe Ser Ala Ser Lys Ser Gly Thr Ser Ala Ser Leu Ala Ile
                85                  90                  95

Ser Gly Leu Arg Pro Glu Asp Glu Gly Asp Tyr Tyr Cys Ala Ala Trp
            100                 105                 110

Asp Asp Ser Arg Gly Gly Pro Asp Trp Val Phe Gly Gly Gly Thr Lys
        115                 120                 125

Leu Thr Val Leu Gly Gln Pro Lys Ala Ala Pro Ser Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Ser Ser Pro Val Lys Ala Gly Val Glu Thr Thr Thr Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Lys Ser Tyr Ser Cys Gln Val Thr His Glu
210                 215                 220

Gly Ser Thr Val Glu Lys Thr Val Ala Pro Thr Glu Cys Ser
225                 230                 235

<210> SEQ ID NO 90
<211> LENGTH: 714
<212> TYPE: DNA
<213> ORGANISM: Artificial Sequence
<220> FEATURE:
<223> OTHER INFORMATION: 2219 Lambda Light Chain

<400> SEQUENCE: 90

```
atggcttgga cccctctgtt tctgtttctg ctgacctgtt gccccggagg aagtaattcc    60
cagtccgtcc tgacccagcc tcctctgcc agtggaacac ccggccagcg aatctctatc    120
tcctgtagtg gaacttcatc taatgtcgag aacaattacg tgtattggta ccagcacctg   180
ccaggaaccg cacctaagct gctgatctat aggaacgacc acagaagctc cggcatccca   240
gatcggttct ctgccagcaa gtccggcaca tctgccagcc tggcaatctc cggcctgcgc   300
cccgaggacg agggcgatta ctattgcgcc gcctgggatg attccagagg aggaccagat   360
tgggtgttcg gcgcgggac taaactgacc gtgctggac agcctaaggc agcaccatcc    420
gtgacactgt tccccccttc ctctgaggag ctgcaggcca acaaggccac cctggtgtgc   480
ctgatcagcg acttctaccc aggagcagtg accgtggcat ggaaggcaga tagctcccca   540
gtgaaggcag gagtggagac aacaaccct tctaagcaga gcaacaataa gtacgccgcc    600
tctagctatc tgtctctgac ccccgagcag tggaagagcc acaagagcta tccctgccag   660
```
gtcacccatg aaggctcaac cgtggagaaa acagtcgccc taccgaatg ctca        714

<210> SEQ ID NO 91
<211> LENGTH: 476
<212> TYPE: PRT
<213> ORGANISM: Artificial Sequence
<220> FEATURE:
<223> OTHER INFORMATION: 3074 Heavy Chain

<400> SEQUENCE: 91

```
Met Asp Trp Thr Trp Arg Ile Leu Phe Leu Val Ala Ala Ala Thr Gly
1               5                   10                  15

Thr His Ala Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Gly Phe His Trp Ser Trp Ile Arg Gln Pro Pro Gly Lys Gly Leu
    50                  55                  60

Glu Tyr Ile Gly Tyr Ile Tyr Tyr Ser Gly Ser Thr Ser Tyr Asn Pro
65                  70                  75                  80

Ser Leu Lys Ser Arg Val Ser Met Ser Val Asp Thr Ser Arg Asn Gln
                85                  90                  95

Phe Ser Leu Glu Leu Ser Ser Val Thr Ala Ala Asp Thr Ala Val Tyr
            100                 105                 110

Tyr Cys Ala Arg Asp Phe Gly Glu Tyr His Tyr Asp Gly Arg Gly Phe
        115                 120                 125

Gln Cys Glu Gly Phe Asp Leu Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350
```

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
        370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 92
<211> LENGTH: 1428
<212> TYPE: DNA
<213> ORGANISM: Artificial Sequence
<220> FEATURE:
<223> OTHER INFORMATION: 3074 Heavy Chain

<400> SEQUENCE: 92
atggattgga catggaggat tctgtttctg gtcgccgccg ccactggaac tcacgctcag    60
gtgcagctgc aggaaagcgg gcctggactg gtgaagccta gtgaaactct gagcctgact   120
tgtaccgtga gcggaggaag cattagcggc ttccactggt cctggatcag cagccccct   180 ggcaaggccc tggagtacat cggctatatc tactattctg cagcacctc ctacaacccc   240 tccctgaagt ctagggtgtc tatgagcgtg acacatcta gaaatcagtt cagcctggag   300
ctgagctccg tgaccgcagc agatacagcc gtgtactatt gcgcccggga ctttggcgag   360
taccactatg atggccgcgg cttttcagtgc gagggctttg atctgtgggg cagggaact   420 ctggtgaccg tgagcagcgc cagcacaaag ggcccatccg tgtttccact ggcaccctcc   480
tctaagagca cctccggcgg cacagccgcc ctgggctgtc tggtgaagga ttacttccca   540
gagccagtga ccgtgagctg gaactccggc gccctgacct ccggagtgca cattttcca   600 gccgtgctgc agagctccgg cctgtatagc ctgtctagcg tggtgaccgt gccctcctct   660
agcctgggca cccagacata catctgcaac gtgaatcaca agccatccaa tacaaaggtg   720
gacaagaagg tggagcccaa gtcttgtgat aagacccaca catgccctcc ctgtcctgca   780
ccagagctgc tgggcggccc atccgtgttc ctgtttccac ccaagcctaa ggacaccctg   840
atgatcagcc ggacccccaga ggtgacatgc gtggtggtgg acgtgtccca cgaggacccc   900
gaggtgaagt tcaactggta cgtggatggc gtggaggtgc acaatgccaa gaccaagcct   960
agggaggagc agtataactc tacctacaga gtggtgagcg tgctgacagt gctgcaccag  1020
gactggctga acggcaagga gtacaagtgc aaggtgtcta ataaggccct gcccgcccct  1080
atcgagaaga ccatcagcaa ggcaaaggga cagcctcggg agccacaggt gtatacactg  1140
cctccatctc gcgacgagct gaccaagaac caggtgagcc tgacatgtct ggtgaagggc  1200 ttctaccta gcgatatcgc cgtggagtgg gagtccaatg ccagccaga gaacaattat  1260 aagaccacac cccctgtgct ggactctgat ggcagcttct ttctgtactc caagctgacc  1320
gtggataagt ctcgctggca gcagggcaac gtgttcagct gtagcgtgat gcacgaagcc  1380
ctgcacaacc actacaccca gaaaagcctg tcactgagcc ccggaaaa                1428

<210> SEQ ID NO 93
<211> LENGTH: 235
<212> TYPE: PRT
<213> ORGANISM: Artificial Sequence
<220> FEATURE:
<223> OTHER INFORMATION: 3074 Lambda Light Chain

<400> SEQUENCE: 93

```
Met Ala Trp Thr Pro Leu Phe Leu Phe Leu Thr Cys Cys Pro Gly
1               5                   10                  15

Gly Ser Asn Ser Gln Ser Val Leu Thr Gln Pro Pro Ser Val Ser Ala
            20                  25                  30

Ala Pro Gly Gln Lys Val Thr Ile Ser Cys Ser Gly Ser Ser Ser Asn
        35                  40                  45

Ile Gly Asn Asn Met Val Ser Trp Tyr Gln Gln His Pro Gly Thr Ala
    50                  55                  60

Pro Lys Leu Leu Ile Tyr Glu Asn Ser Lys Arg Pro Ser Gly Ile Pro
65                  70                  75                  80

Asp Arg Phe Ser Gly Ser Arg Ser Gly Thr Ser Ala Thr Leu Gly Ile
                85                  90                  95

Ile Gly Leu Gln Thr Gly Asp Glu Ala Glu Tyr Tyr Cys Ala Thr Trp
            100                 105                 110

Asp Gly Ser Leu Arg Thr Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235
```

<210> SEQ ID NO 94
<211> LENGTH: 705
<212> TYPE: DNA
<213> ORGANISM: Artificial Sequence
<220> FEATURE:
<223> OTHER INFORMATION: 3074 Lambda Light Chain

<400> SEQUENCE: 94
atggcttgga cccctctgtt tctgtttctg ctgacctgtt gccccggagg aagtaattcc    60
cagagcgtcc tgactcagcc tccaagcgtg tccgcagccc tgggcagaa ggtgaccatt    120 agttgtagcg gcagcagcag caatatcggc aacaatatgg tgtcttggta ccagcagcac    180
ccaggaaccg cacctaagct gctgatctat gagaacagca gaggccatc cggcatcccc    240 gacaggttca gcggctccag atctggcacc agcgccacac tgggcatcat cggcctgcag    300
acaggcgatg aggccgagta ctattgcgct acttgggatg ggagcctgcg gaccgtcttt    360

-continued

```
ggggggaggaa ctaaactgac tgtgctggga cagcctaagg cagcaccatc cgtgacactg    420
tttccccctt cctctgagga gctgcaggcc aacaaggcca ccctggtgtg cctgatcagc    480
gacttctacc caggagcagt gaccgtggca tggaaggcag atagctcccc agtgaaggca    540
ggagtggaga caacaacccc ttctaagcag agcaacaata agtacgccgc ctctagctat    600
ctgtctctga cccccgagca gtggaagagc cacaagagct attcctgcca ggtcacccat    660
gaaggctcaa ccgtggagaa aacagtcgcc cctaccgaat gctca                    705

<210> SEQ ID NO 95
<211> LENGTH: 473
<212> TYPE: PRT
<213> ORGANISM: Artificial Sequence
<220> FEATURE:
<223> OTHER INFORMATION: 4028 Heavy Chain

<400> SEQUENCE: 95

Met Asp Trp Thr Trp Arg Ile Leu Phe Leu Val Ala Ala Thr Gly
1               5                   10                  15

Thr His Ala Glu Val Gln Leu Val Gln Ser Gly Ala Glu Val Lys Lys
            20                  25                  30

Pro Gly Glu Ser Leu Lys Ile Ser Cys Lys Ala Ser Gly Tyr Ser Phe
        35                  40                  45

Ser Ser Tyr Trp Ile Ala Trp Val Arg Gln Met Pro Gly Lys Gly Leu
    50                  55                  60

Glu Trp Met Gly Phe Ile Tyr Pro Ala Asp Ser Asp Thr Arg Tyr Ser
65                  70                  75                  80

Pro Ser Phe Gln Gly Gln Gly Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Ile Leu Gly Phe Trp Gly Ala Asn Arg Gly Gly Gly
        115                 120                 125

Gly Met Asp Val Trp Gly Gln Gly Thr Thr Val Ile Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300
```

| | | | | | | | | | | | |
|---|---|---|---|---|---|---|---|---|---|---|---|
| Val | Asp | Gly | Val | Glu | Val | His | Asn | Ala | Lys | Thr | Lys | Pro | Arg | Glu | Glu |
| 305 | | | | 310 | | | | 315 | | | | 320 | | | |
| Gln | Tyr | Asn | Ser | Thr | Tyr | Arg | Val | Val | Ser | Val | Leu | Thr | Val | Leu | His |
| | | | 325 | | | | | 330 | | | | | 335 | | |
| Gln | Asp | Trp | Leu | Asn | Gly | Lys | Glu | Tyr | Lys | Cys | Lys | Val | Ser | Asn | Lys |
| | | 340 | | | | | 345 | | | | | 350 | | | |
| Ala | Leu | Pro | Ala | Pro | Ile | Glu | Lys | Thr | Ile | Ser | Lys | Ala | Lys | Gly | Gln |
| | 355 | | | | | 360 | | | | | 365 | | | | |
| Pro | Arg | Glu | Pro | Gln | Val | Tyr | Thr | Leu | Pro | Pro | Ser | Arg | Asp | Glu | Leu |
| 370 | | | | | 375 | | | | | 380 | | | | | |
| Thr | Lys | Asn | Gln | Val | Ser | Leu | Thr | Cys | Leu | Val | Lys | Gly | Phe | Tyr | Pro |
| 385 | | | | | 390 | | | | | 395 | | | | | 400 |
| Ser | Asp | Ile | Ala | Val | Glu | Trp | Glu | Ser | Asn | Gly | Gln | Pro | Glu | Asn | Asn |
| | | | | 405 | | | | | 410 | | | | | 415 | |
| Tyr | Lys | Thr | Thr | Pro | Pro | Val | Leu | Asp | Ser | Asp | Gly | Ser | Phe | Phe | Leu |
| | | | 420 | | | | | 425 | | | | | 430 | | |
| Tyr | Ser | Lys | Leu | Thr | Val | Asp | Lys | Ser | Arg | Trp | Gln | Gln | Gly | Asn | Val |
| | | 435 | | | | | 440 | | | | | 445 | | | |
| Phe | Ser | Cys | Ser | Val | Met | His | Glu | Ala | Leu | His | Asn | His | Tyr | Thr | Gln |
| | 450 | | | | | 455 | | | | | 460 | | | | |
| Lys | Ser | Leu | Ser | Leu | Ser | Pro | Gly | Lys | | | | | | | |
| 465 | | | | 470 | | | | | | | | | | | |

<210> SEQ ID NO 96
<211> LENGTH: 1419
<212> TYPE: DNA
<213> ORGANISM: Artificial Sequence
<220> FEATURE:
<223> OTHER INFORMATION: 4028 Heavy Chain

<400> SEQUENCE: 96

| | |
|---|---|
| atggattgga catggaggat tctgtttctg gtcgccgccg ccactggaac tcacgctgaa | 60 |
| gtgcagctgg tgcagagcgg agccgaggtc aagaagcctg gcgaaagcct gaaaatctca | 120 |
| tgtaaagcaa gcggatactc attcagctcc tactggatcg catgggtgag gcagatgcca | 180 |
| ggcaagggcc tggagtggat gggcttcatc taccccgccg actctgatac agatatattcc | 240 |
| ccttctttc agggccaggg caccatcagc gccgacaaga gcatctccac agcctatctg | 300 |
| cagtggtcta gcctgaaggc ctccgataca gccatgtact attgcgccat cctgggcttc | 360 |
| tggggcgcca atcggggcgg aggcgggatg gatgtctggg gcagggaac accgtcatt | 420 |
| gtcagcagtg ccagcacaaa gggcccatcc gtgtttccac tggcaccctc ctctaagagc | 480 |
| acctccggcg gcacagccgc cctgggctgt ctggtgaagg attacttccc agagccagtg | 540 |
| accgtgagct ggaactccgg cgccctgacc tccggagtgc acacatttcc agccgtgctg | 600 |
| cagagctccg gcctgtatag cctgtctagc gtggtgaccg tgccctcctc tagcctgggc | 660 |
| acccagacat acatctgcaa cgtgaatcac aagccatcca tacaaaggt ggacaagaag | 720 |
| gtggagccca gtcttgtga taagacccac acatgccctc cctgtcctgc accagagctg | 780 |
| ctgggcggcc catccgtgtt cctgtttcca cccaagccta aggacaccct gatgatcagc | 840 |
| cggacccag aggtgacatg cgtggtggtg acgtgtccc acgaggaccc cgaggtgaag | 900 |
| ttcaactggt acgtggatgg cgtggaggtg cacaatgcca agaccaagcc tagggaggag | 960 |
| cagtataact ctacctacag agtggtgagc gtgctgacag tgctgcacca ggactggctg | 1020 |
| aacggcaagg agtacaagtg caaggtgtct aataaggccc tgcccgcccc tatcgagaag | 1080 |

| accatcagca aggcaaaggg acagcctcgg gagccacagg tgtatacact gcctccatct | 1140 |
| cgcgacgagc tgaccaagaa ccaggtgagc ctgacatgtc tggtgaaggg cttctaccct | 1200 |
| agcgatatcg ccgtggagtg ggagtccaat ggccagccag agaacaatta taagaccaca | 1260 |
| cccccctgtgc tggactctga tggcagcttc tttctgtact ccaagctgac cgtggataag | 1320 |
| tctcgctggc agcagggcaa cgtgttcagc tgtagcgtga tgcacgaagc cctgcacaac | 1380 |
| cactacaccc agaaaagcct gtcactgagc cccggaaaa | 1419 |

<210> SEQ ID NO 97
<211> LENGTH: 235
<212> TYPE: PRT
<213> ORGANISM: Artificial Sequence
<220> FEATURE:
<223> OTHER INFORMATION: 4028 Lambda Light Chain

<400> SEQUENCE: 97

```
Met Ala Trp Thr Pro Leu Phe Leu Phe Leu Leu Thr Cys Cys Pro Gly
1               5                   10                  15

Gly Ser Asn Ser Gln Ser Tyr Glu Leu Thr Gln Pro Pro Ser Val Ser
            20                  25                  30

Val Ser Pro Gly Gln Thr Ala Arg Ile Thr Cys Ser Gly Asp Ala Leu
        35                  40                  45

Pro Glu Lys Tyr Ala Tyr Trp Tyr Gln Gln Lys Ser Gly Gln Ala Pro
    50                  55                  60

Val Leu Ile Ile Tyr Glu Asp Ser Lys Arg Pro Ser Gly Ile Pro Glu
65                  70                  75                  80

Arg Phe Ser Gly Ser Arg Ser Gly Thr Met Ala Thr Leu Thr Ile Ser
                85                  90                  95

Gly Ala Gln Val Asp Asp Glu Ala Asp Tyr Tyr Cys Tyr Ser Thr Asn
            100                 105                 110

Ser Gly Gly Thr Phe Phe Val Phe Gly Thr Gly Thr Lys Val Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235
```

<210> SEQ ID NO 98
<211> LENGTH: 705
<212> TYPE: DNA
<213> ORGANISM: Artificial Sequence
<220> FEATURE:
<223> OTHER INFORMATION: 4028 Lambda Light Chain

<400> SEQUENCE: 98

| atggcttgga cccctctgtt tctgtttctg ctgacctgtt gccccggagg aagtaattcc | 60 |

```
cagagctacg aactgactca gcctcccagc gtgtccgtgt cccccggcca gactgccaga    120
atcacttgca gcggcgatgc cctgccagag aagtacgcct attggtacca gcagaagtct    180
ggccaggccc ccgtgctgat catctatgag gacagcaaga ggccctccgg catccctgag    240
aggttcagcg gctccagatc tggcaccatg gccaccctga caatcagcgg agcacaggtg    300
gacgatgagg cagattacta ttgctactcc actaactcag gcgggacatt tttcgtgttt    360
gggacaggga ctaaggtcac cgtgctggga cagcctaagg cagcaccatc cgtgacactg    420
tttccccctt cctctgagga gctgcaggcc aacaaggcca ccctggtgtg cctgatcagc    480
gacttctacc caggagcagt gaccgtggca tggaaggcag atagctcccc agtgaaggca    540
ggagtggaga caacaacccc ttctaagcag agcaacaata gtacgccgc ctctagctat    600 ctgtctctga cccccgagca gtggaagagc cacaagagct attcctgcca ggtcacccat    660
gaaggctcaa ccgtggagaa aacagtcgcc cctaccgaat gctca               705
```

<210> SEQ ID NO 99
<211> LENGTH: 473
<212> TYPE: PRT
<213> ORGANISM: Artificial Sequence
<220> FEATURE:
<223> OTHER INFORMATION: 2557 Heavy Chain

<400> SEQUENCE: 99

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Glu Val Lys Gln
            20                  25                  30

Pro Gly Gln Ser Leu Lys Ile Ser Cys Lys Ser Ser Gly Tyr Asn Phe
        35                  40                  45

Leu Asp Ser Trp Ile Gly Trp Val Arg Gln Ile Pro Gly Lys Gly Leu
    50                  55                  60

Glu Trp Ile Gly Ile Ile Tyr Pro Asp Ser Asp Ala His Tyr Ser
65                  70                  75                  80

Pro Ser Phe Glu Gly Gln Val Thr Met Ser Val Asp Lys Ser Ile Ser
                85                  90                  95

Thr Ala Tyr Leu Gln Trp Thr Thr Leu Gln Ala Ser Asp Thr Gly Lys
            100                 105                 110

Tyr Phe Cys Thr Arg Leu Tyr Leu Phe Glu Gly Ala Gln Ser Ser Asn
        115                 120                 125

Ala Phe Asp Leu Trp Gly Gln Gly Thr Met Ile Leu Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
```

```
            245                 250                 255
Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
        340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
    435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 100
<211> LENGTH: 1419
<212> TYPE: DNA
<213> ORGANISM: Artificial Sequence
<220> FEATURE:
<223> OTHER INFORMATION: 2557 Heavy Chain

<400> SEQUENCE: 100
atggattgga catggaggat tctgtttctg gtcgccgccg ccactggaac tcacgctgaa    60
gtgcagctgg tggaatccgg gggcgaggtc aaacagcctg gcagagcctg aagatcagt   120 tgtaaaagta gtgggtataa tttcctggac agctggatcg gatgggtgag gcagatccca   180
ggcaagggcc tggagtggat cggcatcatc tacccgacg attccgacgc cactatagc    240 ccttccttcg agggccaggt gaccatgtct gtggataagt ctatcagcac agcctacctg   300
cagtggacca cactgcaggc ctccgatacc ggcaagtact ctgcacaag actgtatctg   360 tttgagggcg ctcagtcaag caacgcattc gatctgtggg gcagggaac tatgattctg   420 gtgtcaagcg ccagcacaaa gggcccatcc gtgtttccac tggcaccctc ctctaagagc   480
acctccggcg gcacagccgc cctgggctgt ctggtgaagg attacttccc agagccagtg   540
accgtgagct ggaactccgg cgccctgacc tccggagtgc acatttcc agccgtgctg    600 cagagctccg gcctgtatag cctgtctagc gtggtgaccg tgccctcctc tagcctgggc   660
acccagacat acatctgcaa cgtgaatcac aagccatcca atacaaaggt ggacaagaag   720
gtggagccca gtcttgtga taagacccac acatgcccc cctgtcctgc accagagctg   780
```

```
ctgggcggcc catccgtgtt cctgtttcca cccaagccta aggacaccct gatgatcagc    840
cggaccccag aggtgacatg cgtggtggtg gacgtgtccc acgaggaccc cgaggtgaag    900
ttcaactggt acgtggatgg cgtggaggtg cacaatgcca agaccaagcc tagggaggag    960
cagtataact ctacctacag agtggtgagc gtgctgacag tgctgcacca ggactggctg   1020
aacggcaagg agtacaagtg caaggtgtct aataaggccc tgcccgcccc tatcgagaag   1080
accatcagca aggcaaaggg acagcctcgg gagccacagg tgtatacact gcctccatct   1140
cgcgacgagc tgaccaagaa ccaggtgagc ctgacatgtc tggtgaaggg cttctaccct   1200
agcgatatcg ccgtggagtg ggagtccaat ggccagccag agaacaatta taagaccaca   1260 cccctgtgc tggactctga tggcagcttc tttctgtact ccaagctgac cgtggataag   1320
tctcgctggc agcagggcaa cgtgttcagc tgtagcgtga tgcacgaagc cctgcacaac   1380
cactacaccc agaaaagcct gtcactgagc cccggaaaa                          1419
```

<210> SEQ ID NO 101
<211> LENGTH: 233
<212> TYPE: PRT
<213> ORGANISM: Artificial Sequence
<220> FEATURE:
<223> OTHER INFORMATION: 2557 Lambda Light Chain

<400> SEQUENCE: 101

```
Met Ala Trp Thr Pro Leu Phe Leu Phe Leu Leu Thr Cys Cys Pro Gly
1               5                   10                  15

Gly Ser Asn Ser Gln Ser Tyr Leu Leu Thr Gln Pro Pro Ser Val Ser
            20                  25                  30

Val Ser Pro Gly Gln Thr Ala Ser Ile Ser Cys Ser Gly Asp Lys Leu
        35                  40                  45

Asp Asp Lys Tyr Val Ser Trp Tyr Gln Arg Pro Gly Gln Ser Pro
    50                  55                  60

Val Leu Leu Met Tyr Gln Asp Phe Lys Arg Pro Ser Gly Ile Pro Glu
65                  70                  75                  80

Arg Leu Ser Gly Ser Lys Ser Gly Lys Thr Ala Thr Leu Thr Ile Ser
                85                  90                  95

Gly Thr Gln Ser Leu Asp Glu Gly Asp Tyr Tyr Cys Gln Ala Trp Asp
            100                 105                 110

Ala Ser Thr Gly Val Ser Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Lys Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 102
<211> LENGTH: 699
<212> TYPE: DNA
<213> ORGANISM: Artificial Sequence
<220> FEATURE:
<223> OTHER INFORMATION: 2557 Lambda Light Chain

<400> SEQUENCE: 102

```
atggcttgga cccctctgtt tctgtttctg ctgacctgtt gccccggagg aagtaattcc      60
cagagctacc tgctgaccca gcctccttcc gtgagcgtga ccctggaca gaccgcatca     120
atttcttgtt ccggcgataa actggatgac aagtacgtgt cttggtacta tcagaggccc     180
ggacagagcc ctgtgctgct gatgtatcag gatttcaaga ggccatccgg catccccgag     240
agactgagcg gctccaagtc tggcaagacc gccacactga ccatcagcgg cacacagtcc     300
ctggacgagg cgattacta ttgccaggct tgggatgctt caacaggcgt ctctggggga     360
ggaacaaaac tgaccgtgct gggacagcct aaggcagcac catccgtgac actgtttccc     420
cttcctctg aggagctgca ggccaacaag gccaccctgg tgtgcctgat cagcgacttc     480
tacccaggag cagtgaccgt ggcatggaag gcagatagct ccccagtgaa ggcaggagtg     540
gagacaacaa ccccttctaa gcagagcaac aataagtacg ccgcctctag ctatctgtct     600
ctgaccccg agcagtggaa gagccacaag agctattcct gccaggtcac ccatgaaggc     660
tcaaccgtgg agaaaacagt cgcccctacc gaatgctca                           699
```

<210> SEQ ID NO 103
<211> LENGTH: 472
<212> TYPE: PRT
<213> ORGANISM: Artificial Sequence
<220> FEATURE:
<223> OTHER INFORMATION: F425-B4e8 Heavy Chain

<400> SEQUENCE: 103

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Gly Gly Leu Val Gln
            20                  25                  30

Pro Gly Gly Ser Leu Arg Leu Ser Cys Ala Ala Phe Gly Phe Asn Phe
        35                  40                  45

Ser Ser Tyr Val Met His Trp Val Arg Gln Ala Pro Gly Gln Gly Leu
    50                  55                  60

Glu Tyr Leu Ser Ala Ile Ser Ser Asp Gly Glu Thr Thr Tyr His Ala
65                  70                  75                  80

Asn Ser Val Lys Gly Arg Phe Thr Ser Ser Arg Asp Asn Ser Lys Asn
                85                  90                  95

Thr Leu Phe Leu Gln Met Gly Ser Leu Arg Thr Glu Asp Val Ala Val
            100                 105                 110

Tyr Tyr Cys Ala Arg Asp Arg Tyr Tyr Glu Thr Ser Gly Ser Asn Ala
        115                 120                 125

Phe Asp Val Trp Gly Gln Gly Thr Met Val Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190
```

```
His Thr Phe Pro Ala Val Leu Gln Ser Ser Gly Leu Tyr Ser Leu Ser
            195                 200                 205

Ser Val Val Thr Val Pro Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 104
<211> LENGTH: 1416
<212> TYPE: DNA
<213> ORGANISM: Artificial Sequence
<220> FEATURE:
<223> OTHER INFORMATION: F425-B4e8 Heavy Chain

<400> SEQUENCE: 104
atggattgga catggaggat tctgtttctg gtcgccgccg ccactggaac tcacgctcag     60
gtgcagctgg tgcagagcgg gggcggcctg gtgcagcctg agggtcact  gagactgtcc    120 tgtgccgcat cgggttcaa tttcagctcc tacgtgatgc actgggtgag caggcacca    180 ggacagggcc tggagtacct gtctgccatc tctagcgacg gcgagacaac atatcacgcc    240
aactccgtga agggccggtt cacctcctct cgcgataaca gcaagaatac actgtttctg    300
cagatgggct ccctgaggac cgaggacgtg gccgtgtact attgcgccag ggatagatac    360
tatgagacaa gcgaagcaa cgcctttgac gtgggggc agggaacaat ggtggtggtc    420
tcctcagcca gcacaaaggg cccatccgtg tttccactgg caccctcctc taagagcacc    480
```

| | |
|---|---|
| tccggcggca cagccgccct gggctgtctg gtgaaggatt acttcccaga gccagtgacc | 540 |
| gtgagctgga actccggcgc cctgacctcc ggagtgcaca catttccagc cgtgctgcag | 600 |
| agctccggcc tgtatagcct gtctagcgtg gtgaccgtgc cctcctctag cctgggcacc | 660 |
| cagacataca tctgcaacgt gaatcacaag ccatccaata caaaggtgga caagaaggtg | 720 |
| gagcccaagt cttgtgataa gacccacaca tgccctccct gtcctgcacc agagctgctg | 780 |
| ggcggcccat ccgtgttcct gtttccaccc aagcctaagg acaccctgat gatcagccgg | 840 |
| accccagagg tgacatgcgt ggtggtggac gtgtcccacg aggaccccga ggtgaagttc | 900 |
| aactggtacg tggatggcgt ggaggtgcac aatgccaaga ccaagcctag ggaggagcag | 960 |
| tataactcta cctacagagt ggtgagcgtg ctgacagtgc tgcaccagga ctggctgaac | 1020 |
| ggcaaggagt acaagtgcaa ggtgtctaat aaggccctgc ccgcccctat cgagaagacc | 1080 |
| atcagcaagg caagggaca gcctcgggag ccacaggtgt atacactgcc tccatctcgc | 1140 |
| gacgagctga ccaagaacca ggtgagcctg acatgtctgg tgaagggctt ctaccctagc | 1200 |
| gatatcgccg tggagtggga gtccaatggc cagccagaga caattataa gaccacaccc | 1260 |
| cctgtgctgg actctgatgg cagcttcttt ctgtactcca agctgaccgt ggataagtct | 1320 |
| cgctggcagc agggcaacgt gttcagctgt agcgtgatgc acgaagccct gcacaaccac | 1380 |
| tacacccaga aaagcctgtc actgagcccc ggaaaa | 1416 |

<210> SEQ ID NO 105
<211> LENGTH: 235
<212> TYPE: PRT
<213> ORGANISM: Artificial Sequence
<220> FEATURE:
<223> OTHER INFORMATION: F425 Kappa Light Chain

<400> SEQUENCE: 105

Met Val Leu Gln Thr Gln Val Phe Ile Ser Leu Leu Trp Ile Ser
1               5                   10                  15

Gly Ala Tyr Gly Asn Ser Val Leu Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Ser Asn Tyr Leu Asn Trp Tyr Gln His Lys Pro Gly Lys Ala Pro
    50                  55                  60

Lys Leu Leu Ile Tyr Thr Ala Ser Asn Leu Glu Thr Gly Val Pro Ser
65                  70                  75                  80

Arg Phe Ser Gly Gly Gly Ser Gly Thr His Phe Ser Phe Thr Ile Thr
                85                  90                  95

Ser Leu Gln Pro Glu Asp Ala Ala Thr Tyr Phe Cys Gln Gln Tyr Asp
            100                 105                 110

Asn Leu Gly Asp Leu Ser Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 106
<211> LENGTH: 705
<212> TYPE: DNA
<213> ORGANISM: Artificial Sequence
<220> FEATURE:
<223> OTHER INFORMATION: F425 Kappa Light Chain

<400> SEQUENCE: 106
atggtgctgc agacccaggt gttcatttca ctgctgctgt ggatttcagg agcctacgga      60
aactctgtgc tgacccagtc tccatcttct ctgagcgcat ccgtcggcga ccgcgtgacc     120
atcacttgcc aggcttccca ggacatttct aactacctga ttggtatca gcacaagccc      180 ggcaaggccc ctaagctgct gatctacacc gccagcaacc tggagacagg agtgcccagc     240
aggttcagcg gcggcggcag cggcacccac ttcagctttta ccatcacatc cctgcagcca     300
gaggacgcag caacatattt ttgccagcag tacgataatc tgggggacct gtcattcggc     360
ggcgggacca agtggaaat caagcggacc gtggcagcac cttccgtgtt catctttccc       420
ccttctgacg agcagctgaa gtctggcaca gccagcgtgg tgtgcctgct gaacaacttc     480
tacccagggg aggccaaggt gcagtggaag gtggataacg ccctgcagag cggcaattcc     540
caggagtctg tgaccgagca ggacagcaag gattccacat attctctgag ctccaccctg     600
acactgagca aggccgacta cgagaagcac aaggtgtatg cctgcgaggt cacccatcag     660
gggctgtcaa gtccagtcac aaagtccttc aatagggggcg aatgc                    705

<210> SEQ ID NO 107
<211> LENGTH: 477
<212> TYPE: PRT
<213> ORGANISM: Artificial Sequence
<220> FEATURE:
<223> OTHER INFORMATION: 17B Heavy Chain

<400> SEQUENCE: 107

Met Asp Trp Thr Trp Arg Ile Leu Phe Leu Val Ala Ala Thr Gly
1               5                   10                  15

Thr His Ala Glu Val Gln Leu Val Glu Ser Gly Ala Glu Val Lys Lys
            20                  25                  30

Pro Gly Ser Ser Val Lys Val Ser Cys Lys Ala Ser Gly Asp Thr Phe
        35                  40                  45

Ile Arg Tyr Ser Phe Thr Trp Val Arg Gln Ala Pro Gly Gln Gly Leu
    50                  55                  60

Glu Trp Met Gly Arg Ile Ile Thr Ile Leu Asp Val Ala His Tyr Ala
65                  70                  75                  80

Pro His Leu Gln Gly Arg Val Thr Ile Thr Ala Asp Lys Ser Thr Ser
            85                  90                  95

Thr Val Tyr Leu Glu Leu Arg Asn Leu Arg Ser Asp Asp Thr Ala Val
            100                 105                 110

Tyr Phe Cys Ala Gly Val Tyr Glu Gly Glu Ala Asp Glu Gly Glu Tyr
        115                 120                 125

Asp Asn Asn Gly Phe Leu Lys His Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
            165                 170                 175

Lys Asp Tyr Phe Pro Glu Pro Val Thr Val Ser Trp Asn Ser Gly Ala
        180                 185                 190

Leu Thr Ser Gly Val His Thr Phe Pro Ala Val Leu Gln Ser Ser Gly
    195                 200                 205

Leu Tyr Ser Leu Ser Ser Val Val Thr Val Pro Ser Ser Ser Leu Gly
210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 108
<211> LENGTH: 1431
<212> TYPE: DNA
<213> ORGANISM: Artificial Sequence
<220> FEATURE:
<223> OTHER INFORMATION: 17B Heavy Chain

<400> SEQUENCE: 108
atggattgga catggaggat tctgtttctg gtcgccgccg ccactggaac tcacgctgaa    60
gtgcagctgg tggaaagcgg agccgaagtc aaaaaacctg ggtcaagcgt caaagtcagt   120
tgtaaggcaa gcggggatac attcatccgg tactctttca cctgggtgcg ccaggcacca   180

```
ggacagggcc tggagtggat gggcaggatc atcacaatcc tggacgtggc acactacgcc    240
cctcacctgc agggaagggt gaccatcaca gccgataaga gcacctccac agtgtatctg    300
gagctgagga acctgagaag cgacgatacc gccgtgtact tttgcgcagg cgtgtatgag    360
ggagaggcag acgagggcga gtacgacaac aacggatttc tgaagcattg gggacagggg    420
actctggtga cagtgagcag cgccagcaca aagggcccat ccgtgtttcc actggcaccc    480
tcctctaaga gcacctccgg cggcacagcc gccctgggct gtctggtgaa ggattacttc    540
ccagagccag tgaccgtgag ctggaactcc ggcgccctga cctccggagt gcacacattt    600
ccagccgtgc tgcagagctc cggcctgtat agcctgtcta gcgtggtgac cgtgccctcc    660
tctagcctgg gcacccagac atacatctgc aacgtgaatc acaagccatc caatacaaag    720
gtggacaaga aggtggagcc caagtcttgt gataagaccc acacatgccc tccctgtcct    780
gcaccagagc tgctgggcgg cccatccgtg ttcctgtttc cacccaagcc taaggacacc    840
ctgatgatca gccggacccc agaggtgaca tgcgtggtgg tggacgtgtc ccacgaggac    900
cccgaggtga agttcaactg gtacgtggat ggcgtggagg tgcacaatgc caagaccaag    960
cctagggagg agcagtataa ctctacctac agagtggtga gcgtgctgac agtgctgcac   1020
caggactggc tgaacggcaa ggagtacaag tgcaaggtgt ctaataaggc cctgcccgcc   1080
cctatcgaga gaccatcag caaggcaaag ggacagcctc gggagccaca ggtgtataca   1140
ctgcctccat ctcgcgacga gctgaccaag aaccaggtga gcctgacatg tctggtgaag   1200
ggcttctacc ctagcgatat cgccgtggag tgggagtcca atggccagcc agagaacaat   1260
tataagacca cccccctgt gctggactct gatggcagct tctttctgta ctccaagctg   1320
accgtggata gtctcgctg gcagcagggc aacgtgttca gctgtagcgt gatgcacgaa   1380
gccctgcaca accactacac ccagaaaagc ctgtcactga gccccggaaa a            1431
```

<210> SEQ ID NO 109
<211> LENGTH: 236
<212> TYPE: PRT
<213> ORGANISM: Artificial Sequence
<220> FEATURE:
<223> OTHER INFORMATION: 17B Kappa Light Chain

<400> SEQUENCE: 109

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Ala Thr Leu Ser
            20                  25                  30

Val Ser Pro Gly Glu Arg Ala Thr Leu Ser Cys Arg Ala Ser Glu Ser
        35                  40                  45

Val Ser Ser Asp Leu Ala Trp Tyr Gln Gln Lys Pro Gly Gln Ala Pro
    50                  55                  60

Arg Leu Leu Ile Tyr Gly Ala Ser Thr Arg Ala Thr Gly Val Pro Ala
65                  70                  75                  80

Arg Phe Ser Gly Ser Gly Ser Gly Ala Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Pro Arg Tyr Thr Phe Gly Gln Gly Thr Arg Leu Glu Ile
        115                 120                 125

Lys Arg Thr Val Ala Ala Pro Ser Val Phe Ile Phe Pro Pro Ser Asp
    130                 135                 140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 110
<211> LENGTH: 708
<212> TYPE: DNA
<213> ORGANISM: Artificial Sequence
<220> FEATURE:
<223> OTHER INFORMATION: 17B Kappa Light Chain

<400> SEQUENCE: 110
atggtgctgc agacccaggt gttcatttca ctgctgctgt ggatttcagg agcctacgga      60
gatattgtga tgacccagag cccagccacc ctgtccgtga gccccggcga gagagccacc     120
ctgtcctgta gagcctccga gagcgtgagc tccgacctgg catggtacca gcagaagcca     180
ggacaggccc ctaggctgct gatctatgga gcatccacca gggccacagg agtgccagca     240
agattctccg gctctggcag cggagcagag tttaccctga catctctag cctgcagtct     300 gaggatttcg ccgtgtacta ttgccagcag tacaataact ggcctcctcg ctacaccttc     360
gggcagggca cacggctgga aatcaaaaga accgtggcag caccttccgt gttcatcttt     420 ccccccttctg acgagcagct gaagtctggc acagccagcg tggtgtgcct gctgaacaac     480
ttctacccca gggaggccaa ggtgcagtgg aaggtggata cgccctgca gagcggcaat     540 tcccaggagt ctgtgaccga gcaggacagc aaggattcca catattctct gagctccacc     600
ctgacactga gcaaggccga ctacgagaag cacaaggtgt atgcctgcga ggtcacccat     660 cagggggctgt caagtccagt cacaaagtcc ttcaataggg gcgaatgc                 708

<210> SEQ ID NO 111
<211> LENGTH: 472
<212> TYPE: PRT
<213> ORGANISM: Artificial Sequence
<220> FEATURE:
<223> OTHER INFORMATION: F105 Heavy Chain

<400> SEQUENCE: 111

Met Asp Trp Thr Trp Arg Ile Leu Phe Leu Val Ala Ala Ala Thr Gly
1               5                   10                  15

Thr His Ala Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser His Tyr Trp Ser Trp Ile Arg Gln Ser Pro Gly Lys Gly Leu
    50                  55                  60

Gln Trp Ile Gly Tyr Ile Tyr Tyr Ser Gly Ser Thr Asn Tyr Ser Pro
65                  70                  75                  80

Ser Leu Lys Ser Arg Val Thr Ile Ser Val Glu Thr Ala Lys Asn Gln
```

```
                    85                  90                  95
Phe Ser Leu Lys Leu Thr Ser Met Thr Ala Ala Asp Thr Ala Val Tyr
            100                 105                 110

Tyr Cys Ala Arg Gly Pro Val Pro Ala Val Phe Tyr Gly Asp Tyr Arg
            115                 120                 125

Leu Asp Pro Trp Gly Gln Gly Thr Leu Val Thr Val Ser Ser Ala Ser
        130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 112
<211> LENGTH: 1416
<212> TYPE: DNA
<213> ORGANISM: Artificial Sequence
```

<220> FEATURE:
<223> OTHER INFORMATION: F105 Heavy Chain

<400> SEQUENCE: 112

| | | | | | |
|---|---|---|---|---|---|
| atggattgga | catggaggat | tctgtttctg | gtcgccgccg | ccactggaac | tcacgctcag | 60 |
| gtgcagctgc | aggaaagcgg | acccggcctg | gtgaagccct | ctgaaactct | gtcactgact | 120 |
| tgtaccgtct | ctgggggaag | catcagctcc | cactactgga | gctggatcag | gcagtcccca | 180 |
| ggcaagggcc | tgcagtggat | cggctacatc | tactattctg | gcagcaccaa | ctattccccc | 240 |
| tctctgaagt | ctagagtgac | catcagcgtg | gagacagcca | agaatcagtt | ctccctgaag | 300 |
| ctgacctcta | tgacagccgc | cgacacagcc | gtgtactatt | gcgccagggg | ccccgtgcct | 360 |
| gccgtgtttt | acggagatta | tcggctggac | ccttgggggc | agggaacact | ggtgactgtg | 420 |
| agtagcgcca | gcacaaaggg | cccatccgtg | tttccactgg | cacccteete | taagagcacc | 480 |
| tccggcggca | cagccgccct | gggctgtctg | gtgaaggatt | acttcccaga | gccagtgacc | 540 |
| gtgagctgga | actccggcgc | cctgacctcc | ggagtgcaca | catttccagc | cgtgctgcag | 600 |
| agctccggcc | tgtatagcct | gtctagcgtg | gtgaccgtgc | cctcctctag | cctgggcacc | 660 |
| cagacataca | tctgcaacgt | gaatcacaag | ccatccaata | caaggtgga | caagaaggtg | 720 |
| gagcccaagt | cttgtgataa | gacccacaca | tgccctccct | gtcctgcacc | agagctgctg | 780 |
| ggcggcccat | ccgtgttcct | gtttccaccc | aagcctaagg | acaccctgat | gatcagccgg | 840 |
| accccagagg | tgacatgcgt | ggtggtggac | gtgtcccacg | aggaccccga | ggtgaagttc | 900 |
| aactggtacg | tggatggcgt | ggaggtgcac | aatgccaaga | ccaagcctag | ggaggagcag | 960 |
| tataactcta | cctacagagt | ggtgagcgtg | ctgacagtgc | tgcaccagga | ctggctgaac | 1020 |
| ggcaaggagt | acaagtgcaa | ggtgtctaat | aaggccctgc | cgccccctat | cgagaagacc | 1080 |
| atcagcaagg | caagggaca | gcctcgggag | ccacaggtgt | atacactgcc | tccatctcgc | 1140 |
| gacgagctga | ccaagaacca | ggtgagcctg | acatgtctgg | tgaagggctt | ctaccctagc | 1200 |
| gatatcgccg | tggagtggga | gtccaatggc | cagccagaga | caattataa | gaccacaccc | 1260 |
| cctgtgctgg | actctgatgg | cagcttcttt | ctgtactcca | agctgaccgt | ggataagtct | 1320 |
| cgctggcagc | agggcaacgt | gttcagctgt | agcgtgatgc | acgaagccct | gcacaaccac | 1380 |
| tacacccaga | aaagcctgtc | actgagcccc | ggaaaa | | | 1416 |

<210> SEQ ID NO 113
<211> LENGTH: 235
<212> TYPE: PRT
<213> ORGANISM: Artificial Sequence
<220> FEATURE:
<223> OTHER INFORMATION: F105 Kappa Light Chain

<400> SEQUENCE: 113

Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Ala Gly Glu Arg Ala Thr Leu Ser Cys Arg Ala Ser Gln Ser
        35                  40                  45

Val Ser Ser Arg Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile

```
                    85                  90                  95
Ser Arg Val Glu Pro Glu Asp Phe Ala Val Tyr Tyr Cys Gln Gln Tyr
                100                 105                 110

Asp Asn Ser Val Cys Thr Phe Gly Gln Gly Thr Lys Leu Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 114
<211> LENGTH: 705
<212> TYPE: DNA
<213> ORGANISM: Artificial Sequence
<220> FEATURE:
<223> OTHER INFORMATION: F105 Kappa Light Chain

<400> SEQUENCE: 114

```
atggtgctgc agacccaggt gttcatttca ctgctgctgt ggatttcagg agcctacgga    60
gaaatcgtcc tgacccagtc ccccggaacc ctgagtctga gcgccggaga gcgagccacc   120
ctgagttgta gagcatcaca gagtgtcagc tcccggtacc tggcctggta tcagcagaag   180
ccaggacagg cccctcgcct gctgatctac ggagcctcta gcagggccac cggcatccca   240
gacagattct ccggctctgg cagcggcaca gacttcaccc tgacaatctc cagggtggag   300
cccgaggact tcgccgtgta ctattgccag cagtatgaca atagcgtctg taccttcggg   360
cagggcacca aactggaaat caagaggacc gtggcagcac cttccgtgtt catctttccc   420
ccttctgacg agcagctgaa gtctggcaca gccagcgtgg tgtgcctgct gaacaacttc   480
taccccaggg aggccaaggt gcagtggaag gtggataacg ccctgcagag cggcaattcc   540
caggagtctg tgaccgagca ggacagcaag gattccacat attctctgag ctccaccctg   600
acactgagca aggccgacta cgagaagcac aaggtgtatg cctgcgaggt cacccatcag   660
gggctgtcaa gtccagtcac aaagtccttc aatagggggcg aatgc                  705
```

<210> SEQ ID NO 115
<211> LENGTH: 476
<212> TYPE: PRT
<213> ORGANISM: Artificial Sequence
<220> FEATURE:
<223> OTHER INFORMATION: b12 Heavy Chain

<400> SEQUENCE: 115

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
            20                  25                  30
```

-continued

```
Pro Gly Ala Ser Val Lys Val Ser Cys Gln Ala Ser Gly Tyr Arg Phe
            35                  40                  45
Ser Asn Phe Val Ile His Trp Val Arg Gln Ala Pro Gly Gln Arg Phe
 50                  55                  60
Glu Trp Met Gly Trp Ile Asn Pro Tyr Asn Gly Asn Lys Glu Phe Ser
 65                  70                  75                  80
Ala Lys Phe Gln Asp Arg Val Thr Phe Thr Ala Asp Thr Ser Ala Asn
                85                  90                  95
Thr Ala Tyr Met Glu Leu Arg Ser Leu Arg Ser Ala Asp Thr Ala Val
            100                 105                 110
Tyr Tyr Cys Ala Arg Val Gly Pro Tyr Ser Trp Asp Asp Ser Pro Gln
            115                 120                 125
Asp Asn Tyr Tyr Met Asp Val Trp Gly Lys Gly Thr Thr Val Ile Val
    130                 135                 140
Ser Ser Ala Ser Thr Lys Gly Pro Ser Val Phe Pro Leu Ala Pro Ser
145                 150                 155                 160
Ser Lys Ser Thr Ser Gly Gly Thr Ala Ala Leu Gly Cys Leu Val Lys
                165                 170                 175
Asp Tyr Phe Pro Glu Pro Val Thr Val Ser Trp Asn Ser Gly Ala Leu
            180                 185                 190
Thr Ser Gly Val His Thr Phe Pro Ala Val Leu Gln Ser Ser Gly Leu
            195                 200                 205
Tyr Ser Leu Ser Ser Val Val Thr Val Pro Ser Ser Ser Leu Gly Thr
    210                 215                 220
Gln Thr Tyr Ile Cys Asn Val Asn His Lys Pro Ser Asn Thr Lys Val
225                 230                 235                 240
Asp Lys Lys Val Glu Pro Lys Ser Cys Asp Lys Thr His Thr Cys Pro
                245                 250                 255
Pro Cys Pro Ala Pro Glu Leu Leu Gly Gly Pro Ser Val Phe Leu Phe
            260                 265                 270
Pro Pro Lys Pro Lys Asp Thr Leu Met Ile Ser Arg Thr Pro Glu Val
            275                 280                 285
Thr Cys Val Val Val Asp Val Ser His Glu Asp Pro Glu Val Lys Phe
    290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
            340                 345                 350
Ser Asn Lys Ala Leu Pro Ala Pro Ile Glu Lys Thr Ile Ser Lys Ala
            355                 360                 365
Lys Gly Gln Pro Arg Glu Pro Gln Val Tyr Thr Leu Pro Pro Ser Arg
    370                 375                 380
Asp Glu Leu Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
            420                 425                 430
Phe Phe Leu Tyr Ser Lys Leu Thr Val Asp Lys Ser Arg Trp Gln Gln
            435                 440                 445
Gly Asn Val Phe Ser Cys Ser Val Met His Glu Ala Leu His Asn His
```

```
              450                 455                 460
Tyr Thr Gln Lys Ser Leu Ser Leu Ser Pro Gly Lys
465                 470                 475
```

<210> SEQ ID NO 116
<211> LENGTH: 1428
<212> TYPE: DNA
<213> ORGANISM: Artificial Sequence
<220> FEATURE:
<223> OTHER INFORMATION: b12 Heavy Chain

<400> SEQUENCE: 116

```
atggattgga catggaggat tctgtttctg gtcgccgccg ccactggaac tcacgctcag    60
gtgcagctgg tccagtcagg agcagaagtg aagaaacccg agcatcagt gaaagtcagt    120
tgtcaggcaa gcggatacag atttagcaac ttcgtgatcc actgggtgcg gcaggcacca    180
ggacagaggt tcgagtggat gggctggatc aatccttaca cggcaataa ggagttctcc     240
gccaagtttc aggacagggt gaccttcaca gccgatacct ctgccaacac agcctacatg    300
gagctgagga gcctgagatc cgccgacacc gccgtgtact attgcgcccg ggtgggacca    360
tattcttggg acgatagccc tcaggataac tattacatgg acgtgtgggg aagggaaca     420
acagtcatcg tgtcatcagc cagcacaaag ggcccatccg tgtttccact ggcaccctcc    480
tctaagagca cctccggcgg cacagccgcc ctgggctgtc tggtgaagga ttacttccca    540
gagccagtga ccgtgagctg gaactccggc gccctgacct ccggagtgca cacatttcca    600
gccgtgctgc agagctccgg cctgtatagc ctgtctagcg tggtgaccgt gccctcctct    660
agcctgggca cccagacata catctgcaac gtgaatcaca gccatccaa tacaaaggtg    720
gacaagaagg tggagcccaa gtcttgtgat aagacccaca catgcccctcc ctgtcctgca    780
ccagagctgc tgggcggccc atccgtgttc ctgtttccac ccaagcctaa ggacaccctg    840
atgatcagcc ggaccccaga ggtgacatgc gtggtggtgg acgtgtccca cgaggacccc    900
gaggtgaagt tcaactggta cgtggatggc gtggaggtgc acaatgccaa gaccaagcct    960
agggaggagc agtataactc tacctacaga gtggtgagcg tgctgacagt gctgcaccag   1020
gactggctga acggcaagga gtacaagtgc aaggtgtcta ataaggccct gcccgcccct   1080
atcgagaaga ccatcagcaa ggcaaaggga cagcctcggg agccacaggt gtatacactg   1140
cctccatctc gcgacgagct gaccaagaac caggtgagcc tgacatgtct ggtgaagggc   1200
ttctacccta gcgatatcgc cgtggagtgg gagtccaatg ccagccaga gaacaattat   1260
aagaccacac cccctgtgct ggactctgat ggcagcttct ttctgtactc caagctgacc   1320
gtggataagt ctcgctggca gcaggcaac gtgttcagct gtagcgtgat gcacgaagcc   1380
ctgcacaacc actacaccca gaaaagcctg tcactgagcc ccggaaaa              1428
```

<210> SEQ ID NO 117
<211> LENGTH: 235
<212> TYPE: PRT
<213> ORGANISM: Artificial Sequence
<220> FEATURE:
<223> OTHER INFORMATION: b12 Kappa Light Chain

<400> SEQUENCE: 117

```
Met Val Leu Gln Thr Gln Val Phe Ile Ser Leu Leu Leu Trp Ile Ser
1               5                   10                  15
Gly Ala Tyr Gly Glu Ile Val Leu Thr Gln Ser Pro Gly Thr Leu Ser
            20                  25                  30
```

Leu Ser Pro Gly Glu Arg Ala Thr Phe Ser Cys Arg Ser Ser His Ser
            35                  40                  45

Ile Arg Ser Arg Arg Val Ala Trp Tyr Gln His Lys Pro Gly Gln Ala
 50                  55                  60

Pro Arg Leu Val Ile His Gly Val Ser Asn Arg Ala Ser Gly Ile Ser
 65                  70                  75                  80

Asp Arg Phe Ser Gly Ser Gly Ser Gly Thr Asp Phe Thr Leu Thr Ile
                85                  90                  95

Thr Arg Val Glu Pro Glu Asp Phe Ala Leu Tyr Tyr Cys Gln Val Tyr
            100                 105                 110

Gly Ala Ser Ser Tyr Thr Phe Gly Gln Gly Thr Lys Leu Glu Arg Lys
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 118
<211> LENGTH: 705
<212> TYPE: DNA
<213> ORGANISM: Artificial Sequence
<220> FEATURE:
<223> OTHER INFORMATION: b12 Kappa Light Chain

<400> SEQUENCE: 118
atggtgctgc agacccaggt gttcatttca ctgctgctgt ggatttcagg agcctacgga      60
gagattgtgc tgacccagag tcctggaacc ctgtccctga gtcctggaga acgggccacc     120
ttttcatgcc gatcatccca tagtatcagg tctaggagat ggcatggta ccagcacaag      180 ccaggacagg cccctcggct ggtcatccac ggcgtgagca cagggcaag cggaatctcc      240 gaccgcttca gcggctccgg ctctggcaca gacttcaccc tgacaatcac cagggtggag     300
cccgaggact cgccctgta ctattgccag gtctacgggg catcctccta cattcgga       360 cagggcacaa aactggaacg gaaaagaacc gtggcagcac cttccgtgtt catctttccc     420
ccttctgacg agcagctgaa gtctggcaca gccagcgtgg tgtgcctgct gaacaacttc     480 tacccccaggg aggccaaggt gcagtggaag gtggataacg ccctgcagag cggcaattcc    540
caggagtctg tgaccgagca ggacagcaag gattccacat attctctgag ctccaccctg    600
acactgagca aggccgacta cgagaagcac aaggtgtatg cctgcgaggt cacccatcag    660
gggctgtcaa gtccagtcac aaagtccttc aatagggggcg aatgc                  705

<210> SEQ ID NO 119
<211> LENGTH: 482
<212> TYPE: PRT
<213> ORGANISM: Artificial Sequence
<220> FEATURE:

<223> OTHER INFORMATION: b6 Heavy Chain

<400> SEQUENCE: 119

```
Met Asp Trp Thr Trp Arg Ile Leu Phe Leu Val Ala Ala Thr Gly
1               5                   10                  15

Thr His Ala Asn Ser Gln Leu Glu Glu Ser Gly Gly Gly Leu Val Lys
            20                  25                  30

Pro Gly Gly Ser Leu Arg Leu Ser Cys Val Gly Ser Gly Phe Thr Phe
        35                  40                  45

Ser Ser Ala Trp Met Ala Trp Val Arg Gln Ala Pro Gly Arg Gly Leu
    50                  55                  60

Glu Trp Val Gly Leu Ile Lys Ser Lys Ala Asp Gly Thr Thr Asp
65                  70                  75                  80

Tyr Ala Thr Pro Val Lys Gly Arg Phe Ser Ile Ser Arg Asn Asn Leu
                85                  90                  95

Lys Asp Thr Val Tyr Leu Gln Met Asp Ser Leu Arg Ala Asp Asp Thr
            100                 105                 110

Ala Val Tyr Tyr Cys Ala Thr Gln Lys Pro Arg Tyr Phe Asp Leu Leu
        115                 120                 125

Ser Gly Gln Tyr Arg Arg Val Ala Gly Ala Phe Asp Val Trp Gly His
    130                 135                 140

Gly Thr Thr Val Thr Val Ser Pro Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400
```

```
Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 120
<211> LENGTH: 1446
<212> TYPE: DNA
<213> ORGANISM: Artificial Sequence
<220> FEATURE:
<223> OTHER INFORMATION: b6 Heavy Chain

<400> SEQUENCE: 120
atggattgga catggaggat tctgtttctg gtcgccgccg ccactggaac tcacgctaac      60
tcacagctgg aggagagcgg cggcggcctg gtcaaacctg gcgggtccct gcgactgtct     120
tgcgtggggt ctggctttac tttcagctcc gcctggatgg catgggtgag gcaggcacca     180
ggaagaggcc tggagtgggt gggcctgatc aagagcaagg ccgacggcga gacaacagat     240
tacgccaccc ctgtgaaggg ccggttctct atcagccgca acaatctgaa ggacacagtg     300
tatctgcaga tggattccct gagggccgac gataccgccg tgtactattg cgccacacag     360 aagcccggt actttgacct gctgtctggc cagtatcgga gagtcgcagg gcttttgat     420 gtctggggc acggcacaac agtcacagtg tcaccagcca gcacaaaggg cccatccgtg     480
tttccactgg caccctcctc taagagcacc tccggcggca cagccgccct gggctgtctg     540
gtgaaggatt acttcccaga gccagtgacc gtgagctgga actccggcgc cctgacctcc     600
ggagtgcaca catttccagc cgtgctgcag agctccggcc tgtatagcct gtctagcgtg     660
gtgaccgtgc cctcctctag cctgggcacc cagacataca tctgcaacgt gaatcacaag     720
ccatccaata caaaggtgga caagaaggtg agcccaagt cttgtgataa gacccacaca     780
tgccctccct gtcctgcacc agagctgctg ggcggcccat ccgtgttcct gtttccaccc     840
aagcctaagg acaccctgat gatcagccgg accccagagg tgacatgcgt ggtggtggac     900
gtgtcccacg aggaccccga ggtgaagttc aactggtacg tggatggcgt ggaggtgcac     960
aatgccaaga ccaagcctag ggaggagcag tataactcta cctacagagt ggtgagcgtg    1020
ctgacagtgc tgcaccagga ctggctgaac ggcaaggagt acaagtgcaa ggtgtctaat    1080
aaggccctgc cgcccctat cgagaagacc atcagcaagg caaagggaca gcctcgggag    1140
ccacaggtgt atacactgcc tccatctcgc gacgagctga ccaagaacca ggtgagcctg    1200
acatgtctgg tgaagggctt ctaccctagc gatatcgccg tggagtggga gtccaatggc    1260
cagccagaga caattataa gaccacaccc ctgtgctgg actctgatgg cagcttcttt    1320
ctgtactcca agctgaccgt ggataagtct cgctggcagc agggcaacgt gttcagctgt    1380
agcgtgatgc acgaagccct gcacaaccac tacacccaga aaagcctgtc actgagcccc    1440
ggaaaa                                                              1446

<210> SEQ ID NO 121
```

<211> LENGTH: 235
<212> TYPE: PRT
<213> ORGANISM: Artificial Sequence
<220> FEATURE:
<223> OTHER INFORMATION: b6 Kappa Light Chain

<400> SEQUENCE: 121

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Arg Ala Thr Leu Ser Cys Arg Ala Gly Gln Ser
        35                  40                  45

Ile Ser Ser Asn Tyr Leu Ala Trp Tyr Gln Gln Lys Pro Gly Gln Ala
    50                  55                  60

Pro Arg Leu Leu Ile Tyr Gly Ala Ser Asn Arg Ala Thr Gly Ile Pro
65                  70                  75                  80

Asp Arg Phe Ser Gly Ser Gly Ser Gly Thr Asp Phe Thr Leu Ser Ile
                85                  90                  95

Ser Arg Leu Glu Pro Glu Asp Phe Ala Val Tyr Tyr Cys Gln Gln Tyr
            100                 105                 110

Gly Thr Ser Pro Tyr Thr Phe Gly Gln Gly Thr Gln Leu Asp Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 122
<211> LENGTH: 705
<212> TYPE: DNA
<213> ORGANISM: Artificial Sequence
<220> FEATURE:
<223> OTHER INFORMATION: b6 Kappa Light Chain

<400> SEQUENCE: 122
atggtgctgc agacccaggt gttcatttca ctgctgctgt ggatttcagg agcctacgga      60
gaaatcgtcc tgacccagtc ccctggcacc ctgtccctgt cccctggaga aagagccacc     120
ctgagttgta gagccgggca gagcattagc tccaactacc tggcctggta tcagcagaag     180
ccaggacagg cccctcggct gctgatctac ggagcatcca atagggcaac cggcatccca     240
gacagattct ctggcagcgg ctccggaacc gacttcaccc tgtctatcag ccgcctggag     300
ccagaggact cgccgtgta ctattgccag cagtatggca cttcacctta cttttttgga      360
cagggaactc agctggacat caagcgaacc gtggcagcac cttccgtgtt catctttccc     420
ccttctgacg agcagctgaa gtctggcaca gccagcgtgg tgtgcctgct gaacaacttc     480

```
taccccaggg aggccaaggt gcagtggaag gtggataacg ccctgcagag cggcaattcc      540
caggagtctg tgaccgagca ggacagcaag gattccacat attctctgag ctccaccctg      600
acactgagca aggccgacta cgagaagcac aaggtgtatg cctgcgaggt cacccatcag      660
gggctgtcaa gtccagtcac aaagtccttc aatagggggcg aatgc                     705
```

<210> SEQ ID NO 123
<211> LENGTH: 471
<212> TYPE: PRT
<213> ORGANISM: Artificial Sequence
<220> FEATURE:
<223> OTHER INFORMATION: 11A Heavy Chain

<400> SEQUENCE: 123

```
Met Asp Trp Thr Trp Arg Ile Leu Phe Leu Val Ala Ala Ala Thr Gly
1               5                   10                  15

Thr His Ala Asn Ser Gln Leu Val Glu Ser Gly Gly Gly Leu Val Lys
            20                  25                  30

Pro Gly Thr Ser Leu Ser Leu Thr Cys Lys Ala Ser Gly Phe Asp Phe
        35                  40                  45

Ser Asp Asn Tyr Tyr Ile Cys Trp Val Arg Gln Ala Pro Gly Lys Gly
    50                  55                  60

Leu Glu Trp Ile Gly Cys Ile Phe Thr Gln Asn Val Arg Thr Tyr Tyr
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Val Ala Asp Thr Ala Thr
            100                 105                 110

Tyr Phe Cys Ala Arg Phe Ser Asp Thr Gly Pro Asp Tyr Gly Leu Gly
        115                 120                 125

Asn Leu Trp Gly Pro Gly Ser Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
```

```
            325                 330                 335
Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 124
<211> LENGTH: 1413
<212> TYPE: DNA
<213> ORGANISM: Artificial Sequence
<220> FEATURE:
<223> OTHER INFORMATION: 11A Heavy Chain

<400> SEQUENCE: 124
atggattgga catgaggat tctgtttctg gtcgccgccg ccactggaac tcacgctaat      60
agccagctgg tggagagcgg cggcggcctg gtgaaacctg gaacctcact gtccctgacc    120
tgtaaggcaa gcggatttga cttctccgac aactactata tctgctgggt gcggcaggca    180
ccaggcaagg gcctggagtg gatcggctgt atcttcaccc agaacgtgag acatactat     240 gccaattggg ccaagggcag gttcaccatc tctaagacaa gctccaccac agtgaccctg    300
cagatgacca gcctgacagt ggccgacacc gccacatact tctgcgcccg cttttctgat    360
acaggacctg actacggact gggaaatctg tggggacctg ggagcctggt gactgtctca    420
tcagccagca aagggccc atccgtgttt ccactggcac cctcctctaa gagcacctcc      480
ggcggcacag ccgccctggg ctgtctggtg aaggattact cccagagcc agtgaccgtg     540 agctggaact ccggcgccct gacctccgga gtgcacacat tccagccgt gctgcagagc     600 tccggcctgt atagcctgtc tagcgtggtg accgtgccct cctctagcct gggcacccag    660
acatacatct gcaacgtgaa tcacaagcca tccaatacaa aggtggacaa gaaggtggag    720
cccaagtctt gtgataagac ccacacatgc cctccctgtc ctgcaccaga gctgctgggc    780
ggcccatccg tgttcctgtt ccacccaag cctaaggaca ccctgatgat cagccggacc     840
ccagaggtga catgcgtggt ggtggacgtg tcccacgagg accccgaggt gaagttcaac    900
tggtacgtgg atggcgtgga ggtgcacaat gccaagacca gcctaggga ggagcagtat     960 aactctacct acagagtggt gagcgtgctg acagtgctgc accaggactg gctgaacggc    1020
aaggagtaca gtgcaaggt gtctaataag gccctgcccg cccctatcga gaagaccatc    1080
agcaaggcaa aggacagcc tcgggagcca caggtgtata cactgcctcc atctcgcgac    1140
gagctgacca gaaccaggt gagcctgaca tgtctggtga agggcttcta ccctagcgat    1200
```

```
atcgccgtgg agtgggagtc caatggccag ccagagaaca attataagac cacacccct    1260 gtgctggact ctgatggcag cttctttctg tactccaagc tgaccgtgga taagtctcgc    1320
tggcagcagg gcaacgtgtt cagctgtagc gtgatgcacg aagccctgca caaccactac    1380
acccagaaaa gcctgtcact gagccccgga aaa                                 1413
```

<210> SEQ ID NO 125
<211> LENGTH: 240
<212> TYPE: PRT
<213> ORGANISM: Artificial Sequence
<220> FEATURE:
<223> OTHER INFORMATION: 11A Kappa Light Chain

<400> SEQUENCE: 125

```
Met Val Leu Gln Thr Gln Val Phe Ile Ser Leu Leu Trp Ile Ser
1               5                   10                  15

Gly Ala Tyr Gly Asp Ile Gly Met Thr Gln Thr Pro Ala Ser Glu
            20                  25                  30

Ala Ala Val Gly Gly Thr Val Thr Ile Lys Cys Gln Ala Ser Gln Arg
        35                  40                  45

Ile Gly Ser His Val Ser Trp Tyr Gln Gln Lys Pro Gly Gln Arg Pro
    50                  55                  60

Lys Leu Leu Ile Tyr Gly Ala Ser Asn Leu Glu Ser Gly Val Pro Ser
65                  70                  75                  80

Arg Phe Ser Gly Arg Gly Ser Gly Thr Gln Phe Thr Leu Thr Ile Ser
                85                  90                  95

Asp Leu Glu Cys Ala Asp Ala Ala Thr Tyr Tyr Cys Gln Ala Thr Tyr
            100                 105                 110

Asp Pro Tyr Thr Gly Gly Ser Tyr Gly Ala Gly Phe Gly Gly Gly Thr
        115                 120                 125

Ala Val Val Val Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 126
<211> LENGTH: 720
<212> TYPE: DNA
<213> ORGANISM: Artificial Sequence
<220> FEATURE:
<223> OTHER INFORMATION: 11A Kappa Light Chain

<400> SEQUENCE: 126

```
atggtgctgc agacccaggt gttcatttca ctgctgctgt ggatttcagg agcctacgga    60
gacatcggaa tgacccagac accagccagc ggggaagcag ccgtcggggg aacagtgaca    120
atcaagtgcc aggccagcca gagaatcggc agccacgtgt cctggtacca gcagaagccc    180
```

```
ggccagaggc ctaagctgct gatctatggc gcctccaacc tggagtctgg cgtgccatct    240
aggttcagcg gcagaggcag cggcacccag tttaccctga caatctccga cctggagtgc    300
gcagatgcag caacctacta ttgtcaggcc acatacgacc cctacactgg gggcagctat    360
ggagcaggat ttgggggagg aacagccgtc gtcgtgaaaa ggaccgtggc agcaccttcc    420
gtgttcatct tcccccttc tgacgagcag ctgaagtctg gcacagccag cgtggtgtgc    480
ctgctgaaca acttctaccc cagggaggcc aaggtgcagt ggaaggtgga taacgccctg    540
cagagcggca attcccagga gtctgtgacc gagcaggaca gcaaggattc cacatattct    600
ctgagctcca ccctgacact gagcaaggcc gactacgaga agcacaaggt gtatgcctgc    660
gaggtcaccc atcagggct gtcaagtcca gtcacaaagt ccttcaatag gggcgaatgc    720
```

<210> SEQ ID NO 127
<211> LENGTH: 473
<212> TYPE: PRT
<213> ORGANISM: Artificial Sequence
<220> FEATURE:
<223> OTHER INFORMATION: 12N Heavy Chain

<400> SEQUENCE: 127

```
Met Asp Trp Thr Trp Arg Ile Leu Phe Leu Val Ala Ala Ala Thr Gly
1               5                   10                  15

Thr His Ala Asn Ser Gln Leu Val Glu Ser Gly Gly Asp Leu Val Lys
            20                  25                  30

Pro Glu Gly Ser Leu Thr Leu Thr Cys Thr Ala Ser Gly Phe Ser Phe
        35                  40                  45

Ser Ser Gly Tyr Tyr Val Cys Trp Val Arg Gln Ala Pro Gly Lys Gly
    50                  55                  60

Leu Asp Trp Val Ala Cys Ile Tyr Val Gly Ser Ser Gly Ile Thr Asp
65                  70                  75                  80

Tyr Ala Thr Trp Ala Lys Gly Arg Phe Thr Ile Ser Arg Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Gly Gly Val Gly Asp Tyr Gly Val Ile Ser
        115                 120                 125

Asp Phe Arg Leu Trp Gly Pro Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270
```

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 128
<211> LENGTH: 1419
<212> TYPE: DNA
<213> ORGANISM: Artificial Sequence
<220> FEATURE:
<223> OTHER INFORMATION: 12N Heavy Chain

<400> SEQUENCE: 128

```
atggattgga catggaggat tctgtttctg gtcgccgccg ccactggaac tcacgctaac      60
tcacagctgg tggaaagtgg aggcgacctg gtgaaacccg aaggcagtct gaccctgacc     120
tgtaccgcaa gtggattctc attcagctcc ggctactacg tgtgctgggt gcggcaggca     180
ccaggcaagg gcctggactg ggtggcctgt atctacgtgg gctctagcgg catcaccgat     240
tatgccacat gggccaaggg caggttcacc atcagcagaa catcctctac acagtgacc     300 ctgcagatga cctccctgac agcagcagac accgcaacat acttttgcgc cgcggcggc     360 gtgggcgatt atggggtcat ttctgatttt cggctgtggg gcctgggac actggtcacc     420 gtctcatctg ccagcacaaa gggcccatcc gtgtttccac tggcaccctc ctctaagagc     480
acctccggcg gcacagccgc cctgggctgt ctggtgaagg attacttccc agagccagtg     540
accgtgagct ggaactccgg cgccctgacc tccggagtgc acatttcc agccgtgctg     600 cagagctccg gcctgtatag cctgtctagc gtggtgaccg tgccctcctc tagcctgggc     660
acccagacat acatctgcaa cgtgaatcac aagccatcca tacaaaggt ggacaagaag     720 gtggagccca gtcttgtga taagacccac acatgccctc cctgtcctgc accagagctg     780
ctgggcggcc catccgtgtt cctgtttcca cccaagccta aggacaccct gatgatcagc     840
cggaccccag aggtgacatg cgtggtggtg gacgtgtccc acgaggaccc cgaggtgaag     900
```

```
ttcaactggt acgtggatgg cgtggaggtg cacaatgcca agaccaagcc tagggaggag    960
cagtataact ctacctacag agtggtgagc gtgctgacag tgctgcacca ggactggctg   1020
aacggcaagg agtacaagtg caaggtgtct aataaggccc tgcccgcccc tatcgagaag   1080
accatcagca aggcaaaggg acagcctcgg gagccacagg tgtatacact gcctccatct   1140
cgcgacgagc tgaccaagaa ccaggtgagc ctgacatgtc tggtgaaggg cttctaccct   1200
agcgatatcg ccgtggagtg ggagtccaat ggccagccag agaacaatta taagaccaca   1260
ccccctgtgc tggactctga tggcagcttc tttctgtact ccaagctgac cgtggataag   1320
tctcgctggc agcagggcaa cgtgttcagc tgtagcgtga tgcacgaagc cctgcacaac   1380
cactacaccc agaaaagcct gtcactgagc cccggaaaa                          1419
```

<210> SEQ ID NO 129
<211> LENGTH: 241
<212> TYPE: PRT
<213> ORGANISM: Artificial Sequence
<220> FEATURE:
<223> OTHER INFORMATION: 12N Kappa Light Chain

<400> SEQUENCE: 129

```
Met Val Leu Gln Thr Gln Val Phe Ile Ser Leu Leu Trp Ile Ser
1               5                   10                  15

Gly Ala Tyr Gly Asp Ile Val Met Thr Gln Thr Pro Ala Ser Val Glu
            20                  25                  30

Val Pro Val Gly Gly Thr Val Thr Ile Lys Cys Gln Ala Ser Gln Asn
        35                  40                  45

Ile Tyr Ser His Asn Tyr Leu Ser Trp Tyr Gln Leu Lys Leu Gly Gln
    50                  55                  60

Pro Pro Lys Leu Leu Ile Tyr Lys Ala Ser Thr Leu Glu Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Phe
            100                 105                 110

Thr Tyr Gly Ser Ala Ser Thr Gly Thr Tyr Val Ala Phe Gly Gly Gly
        115                 120                 125

Thr Glu Val Val Val Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 130
<211> LENGTH: 723
<212> TYPE: DNA

```
<213> ORGANISM: Artificial Sequence
<220> FEATURE:
<223> OTHER INFORMATION: 12N Kappa Light Chain

<400> SEQUENCE: 130
atggtgctgc agacccaggt gttcatttca ctgctgctgt ggatttcagg agcctacgga      60
gacattgtga tgactcagac accagccagc gtggaagtgc agtgggagg aacagtgacc     120 attaagtgcc aggccagcca gaacatttac tctcacaact atctgagctg gtaccagctg     180
aagctgggcc agcccctaa gctgctgatc tataaggcat ctaccctgga gagcggagtg      240
ccctccaggt tcaagggcag cggctccggc acagagttta ccctgacaat ctccgacctg     300
gagtgcgcag atgcagcaac ctactattgt cagttcacat acggctcagc atcaacagga     360
acctatgtgg cattcggcgg agggacagaa gtggtggtga gcggaccgt ggcagcacct      420 tccgtgttca tctttccccc ttctgacgag cagctgaagt ctggcacagc cagcgtggtg     480
tgcctgctga caacttcta ccccaggga gccaaggtgc agtggaaggt ggataacgcc       540
ctgcagagcg gcaattccca ggagtctgtg accgagcagg acagcaagga ttccacatat     600
tctctgagct ccaccctgac actgagcaag gccgactacg agaagcacaa ggtgtatgcc     660
tgcgaggtca cccatcaggg gctgtcaagt ccagtcacaa agtccttcaa tagggcgaa      720 tgc                                                                    723

<210> SEQ ID NO 131
<211> LENGTH: 476
<212> TYPE: PRT
<213> ORGANISM: Artificial Sequence
<220> FEATURE:
<223> OTHER INFORMATION: 39F Heavy Chain

<400> SEQUENCE: 131

Met Asp Trp Thr Trp Arg Ile Leu Phe Leu Val Ala Ala Thr Gly
1               5                   10                  15

Thr His Ala Glu Val Gln Leu Val Gln Ser Gly Ala Glu Val Lys Lys
            20                  25                  30

Pro Gly Ser Thr Val Lys Ile Ser Cys Lys Ala Ser Gly Tyr Thr Phe
        35                  40                  45

Thr Asp Phe Tyr Ile Gln Trp Leu Arg Gln Ala Pro Val Lys Gly Leu
    50                  55                  60

Glu Trp Met Gly Leu Val Asp Pro Glu Asp Gly Gln Thr Arg Tyr Pro
65                  70                  75                  80

Gln Arg Phe Gln Gly Arg Val Thr Met Thr Ala Asp Pro Ser Thr Asp
                85                  90                  95

Thr Ala Tyr Met Glu Val Ser Gly Leu Asp Phe Glu Asp Thr Ala Asp
            100                 105                 110

Tyr Tyr Cys Ala Thr Thr Leu Leu Gly Gly Pro Tyr Asp Asn Ser
        115                 120                 125

Gly His Asp Ala Phe Asp Ile Trp Gly Gln Gly Thr Lys Val Ile Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
```

```
                195                 200                 205
Tyr Ser Leu Ser Ser Val Val Thr Val Pro Ser Ser Leu Gly Thr
    210                 215                 220
Gln Thr Tyr Ile Cys Asn Val Asn His Lys Pro Ser Asn Thr Lys Val
225                 230                 235                 240
Asp Lys Lys Val Glu Pro Lys Ser Cys Asp Lys Thr His Thr Cys Pro
                245                 250                 255
Pro Cys Pro Ala Pro Glu Leu Leu Gly Gly Pro Ser Val Phe Leu Phe
            260                 265                 270
Pro Pro Lys Pro Lys Asp Thr Leu Met Ile Ser Arg Thr Pro Glu Val
        275                 280                 285
Thr Cys Val Val Val Asp Val Ser His Glu Asp Pro Glu Val Lys Phe
    290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
            340                 345                 350
Ser Asn Lys Ala Leu Pro Ala Pro Ile Glu Lys Thr Ile Ser Lys Ala
        355                 360                 365
Lys Gly Gln Pro Arg Glu Pro Gln Val Tyr Thr Leu Pro Pro Ser Arg
    370                 375                 380
Asp Glu Leu Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
            420                 425                 430
Phe Phe Leu Tyr Ser Lys Leu Thr Val Asp Lys Ser Arg Trp Gln Gln
        435                 440                 445
Gly Asn Val Phe Ser Cys Ser Val Met His Glu Ala Leu His Asn His
    450                 455                 460
Tyr Thr Gln Lys Ser Leu Ser Leu Ser Pro Gly Lys
465                 470                 475

<210> SEQ ID NO 132
<211> LENGTH: 1428
<212> TYPE: DNA
<213> ORGANISM: Artificial Sequence
<220> FEATURE:
<223> OTHER INFORMATION: 39F Heavy Chain

<400> SEQUENCE: 132
atggattgga catggaggat tctgtttctg gtcgccgccg ccactggaac tcacgctgaa      60
gtgcagctgg tccagtcagg ggcagaggtc aaaaaaccog gctccaccgt gaagattagt     120
tgtaaagcaa gcggctatac atttaccgat ttctacatcc agtggctgag gcaggcacca     180
gtgaagggcc tggagtggat gggcctggtg accccgagg atggacagac aaggtaccct     240
cagagattcc agggccgggt gaccatgaca gccgatccaa gcaccgacac agcctatatg     300
gaggtgtccg gcctggactt tgaggatacc gccgactact attgcgccac ctctacactg     360
ctgggcggcc catatgacaa tagcggacac gacgccttcg acatctgggg cagggggact     420
aaagtgattg tgagtagcgc cagcacaaag ggcccatccg tgtttccact ggcaccctcc     480
```

-continued

```
tctaagagca cctccggcgg cacagccgcc ctgggctgtc tggtgaagga ttacttccca   540
gagccagtga ccgtgagctg gaactccggc gccctgacct ccggagtgca cacatttcca   600
gccgtgctgc agagctccgg cctgtatagc ctgtctagcg tggtgaccgt gccctcctct   660
agcctgggca cccagacata catctgcaac gtgaatcaca agccatccaa tacaaaggtg   720
gacaagaagg tggagcccaa gtcttgtgat aagacccaca catgccctcc ctgtcctgca   780
ccagagctgc tgggcggccc atccgtgttc ctgtttccac ccaagcctaa ggacaccctg   840
atgatcagcc ggacccccaga ggtgacatgc gtggtggtgg acgtgtccca cgaggacccc   900
gaggtgaagt tcaactggta cgtggatggc gtggaggtgc acaatgccaa gaccaagcct   960
agggaggagc agtataactc tacctacaga gtggtgagcg tgctgacagt gctgcaccag  1020
gactggctga acggcaagga gtacaagtgc aaggtgtcta ataaggccct gcccgcccct  1080
atcgagaaga ccatcagcaa ggcaaaggga cagcctcggg agccacaggt gtatacactg  1140
cctccatctc gcgacgagct gaccaagaac caggtgagcc tgacatgtct ggtgaagggc  1200
ttctacccta gcgatatcgc cgtggagtgg gagtccaatg ccagccaga gaacaattat  1260 aagaccacac cccctgtgct ggactctgat ggcagcttct ttctgtactc caagctgacc  1320
gtggataagt ctcgctggca gcagggcaac gtgttcagct gtagcgtgat gcacgaagcc  1380
ctgcacaacc actacaccca gaaaagcctg tcactgagcc ccggaaaa             1428
```

<210> SEQ ID NO 133
<211> LENGTH: 236
<212> TYPE: PRT
<213> ORGANISM: Artificial Sequence
<220> FEATURE:
<223> OTHER INFORMATION: 39F Lambda Light Chain

<400> SEQUENCE: 133

```
Met Ala Trp Thr Pro Leu Phe Leu Phe Leu Leu Thr Cys Cys Pro Gly
1               5                   10                  15

Gly Ser Asn Ser Gln Leu Pro Val Leu Thr Gln Pro Pro Ser Ala Ser
            20                  25                  30

Gly Thr Pro Gly Gln Arg Val Thr Ile Ser Cys Ser Gly Ser Gly Ser
        35                  40                  45

Ser Phe Glu Arg Asn Tyr Val Tyr Trp Tyr Gln Gln Leu Pro Gly Met
    50                  55                  60

Ala Pro Lys Leu Leu Ile Tyr Arg Ser Asp Gln Arg Leu Ser Gly Val
65                  70                  75                  80

Pro Asp Arg Phe Ser Gly Ser Lys Ser Asp Thr Ser Ala Ser Leu Ala
                85                  90                  95

Ile Ser Gly Leu Arg Ser Glu Asp Glu Ala Thr Tyr Tyr Cys Ala Ala
            100                 105                 110

Trp Asp Ser Leu Thr Leu Leu Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
```

|   |   |   | 195 |   |   |   | 200 |   |   |   | 205 |   |   |
|---|---|---|---|---|---|---|---|---|---|---|---|---|---|

Trp Lys Ser His Lys Ser Tyr Ser Cys Gln Val Thr His Glu Gly Ser
210 215 220

Thr Val Glu Lys Thr Val Ala Pro Thr Glu Cys Ser
225 230 235

<210> SEQ ID NO 134
<211> LENGTH: 708
<212> TYPE: DNA
<213> ORGANISM: Artificial Sequence
<220> FEATURE:
<223> OTHER INFORMATION: 39F Lambda Light Chain

<400> SEQUENCE: 134

| atggcttgga | cccctctgtt | tctgtttctg | ctgacctgtt | gccccggagg | aagtaattcc | 60 |
| cagctgcccg | tcctgactca | gcctcctagc | gcaagcggca | ctcctggaca | gagggtgacc | 120 |
| attagttgta | gcggaagcgg | aagtagtttc | gagaggaact | acgtgtattg | gtaccagcag | 180 |
| ctgcccggca | tggcccctaa | gctgctgatc | tataggtccg | accagagact | gtctggcgtg | 240 |
| cccgatcggt | ttagcggctc | caagtctgac | accagcgcct | ccctggcaat | ctctggcctg | 300 |
| cgcagcgagg | atgaggccac | atactattgc | gctgcttggg | atgactctct | gacactgctg | 360 |
| ttcggggag | ggacaaaact | gactgtgctg | ggacagccta | aggcagcacc | atccgtgaca | 420 |
| ctgtttcccc | cttcctctga | ggagctgcag | gccaacaagg | ccaccctggt | gtgcctgatc | 480 |
| agcgacttct | acccaggagc | agtgaccgtg | gcatggaagg | cagatagctc | cccagtgaag | 540 |
| gcaggagtgg | agacaacaac | cccttctaag | cagagcaaca | ataagtacgc | cgcctctagc | 600 |
| tatctgtctc | tgacccccga | gcagtggaag | agccacaaga | gctattcctg | ccaggtcacc | 660 |
| catgaaggct | caaccgtgga | gaaaacagtc | gcccctaccg | aatgctca | | 708 |

<210> SEQ ID NO 135
<211> LENGTH: 2142
<212> TYPE: DNA
<213> ORGANISM: Artificial Sequence
<220> FEATURE:
<223> OTHER INFORMATION: Subtype A consensus Envelope DNA sequence
      construct

<400> SEQUENCE: 135

| ggatccatgg | actggacctg | gattctgttc | ctggtggccg | ccgccaccag | agtgcacagc | 60 |
| agagtgatgg | gcatccagcg | gaattgccag | cacctgtgga | gatggggcac | catgatcctg | 120 |
| ggcatgatca | tcatctgctc | tgccgccgag | aacctgtggg | tgaccgtgta | ctacggcgtg | 180 |
| cctgtgtgga | aggacgccga | gaccacccta | ttctgcgcca | gcgacgccaa | ggcctacgat | 240 |
| accgaagtgc | acaatgtgtg | gcccaccac | gcctgcgtgc | ctaccgatcc | caaccccag | 300 |
| gagatcaacc | tggagaacgt | gaccgaggag | ttcaacatgt | ggaagaacaa | catggtggag | 360 |
| cagatgcaca | ccgacatcat | cagcctgtgg | gaccagagcc | tgaagccttg | cgtgaagctg | 420 |
| accccctctgt | gcgtgaccct | gaactgcagc | aacgtgaacg | tgaccaccaa | catcatgaag | 480 |
| ggcgagatca | agaactgcag | cttcaacatg | accaccgagc | tgcgggacaa | gaagcagaaa | 540 |
| gtgtacagcc | tgttctacaa | gctggacgtg | gtgcagatca | caagagcaa | cagcagcagc | 600 |
| cagtaccggc | tgatcaactg | caacaccagc | gccatcaccc | aggcctgccc | caaagtgagc | 660 |
| ttcgagccca | tccccatcca | ctactgcgcc | cctgccggct | tcgccatcct | gaagtgcaag | 720 |
| gacaaggagt | ttaacggcac | cggcccctgc | aagaatgtga | gcaccgtgca | gtgcacccac | 780 |

```
ggcatcaagc ccgtggtgtc cacccagctg ctgctgaacg gcagcctggc cgaggaggaa    840
gtgatgatcc ggagcgagaa catcaccaac aacgccaaga acatcatcgt gcagctgacc    900
aagcccgtga agatcaattg cacccggccc aacaacaaca cccggaagag catcagaatc    960
ggccctggcc aggccttcta cgccaccggc gacatcatcg gcgatatcag gcaggcccac   1020
tgcaatgtga gccggaccga gtggaacgag accctgcaga aagtggccaa gcagctgcgg   1080
aagtacttca acaacaagac catcatcttc accaacagca gcggcggcag actgagaatc   1140
accacccaca gcttcaattg tggcggcgag ttcttctact gcaatacctc cggcctgttc   1200
aacagcacct ggaacggcaa cggcaccaag aagaagaaca gcaccgagag caacgacacc   1260
atcaccctgc cctgccggat caagcagatc atcaatatgt ggcagagggt gggccaggcc   1320
atgtacgccc ctcccatcca gggcgtgatc agatgcgaga gcaacatcac cggcctgctg   1380
ctgaccagag atggcggcga caacaacagc aagaacgaga ccttcagacc tggcggcgga   1440
gacatgaggg acaactggcg gagcgagctg tacaagtaca aagtggtgaa gatcgagccc   1500
ctgggcgtgg cccccaccaa ggccaagaga agagtggtgg agcgggagaa gagagctgtg   1560
ggcatcggcg ccgtgttcct gggcttcctg ggagccgccg gaagcaccat gggagccgcc   1620
agcatcaccc tgaccgtgca ggccagacag ctgctgagcg gcattgtgca gcagcagagc   1680
aacctgctga gagccatcga ggcccagcag cacctgctga agctgacagt gtggggcatc   1740
aaacagctgc aggcccgcgt gctggccgtg gagagatacc tgaaggacca gcagctgctg   1800
ggcatctggg gctgcagcgg caagctgatc tgcaccacca acgtgccctg gaatagcagc   1860
tggagcaaca agagccagag cgagatctgg gacaacatga cctggctgca gtgggacaag   1920
gagatcagca actacaccga tatcatctac aacctgatcg aggagagcca gaaccagcag   1980
gagaagaacg agcaggatct gctggccctg gacaagtggg ccaacctgtg gaactggttc   2040
gacatcagca actggctgtg gtacatcaag atcttcatca tgattgtggg cggcctgatc   2100
ggcctgagaa tcgtgttcgc cgtgctgtct gtgtgactcg ag                      2142
```

<210> SEQ ID NO 136
<211> LENGTH: 709
<212> TYPE: PRT
<213> ORGANISM: Artificial Sequence
<220> FEATURE:
<223> OTHER INFORMATION: Subtype A consensus Envelope protein sequence construct

<400> SEQUENCE: 136

```
Met Asp Trp Thr Trp Ile Leu Phe Leu Val Ala Ala Ala Thr Arg Val
1               5                   10                  15

His Ser Arg Val Met Gly Ile Gln Arg Asn Cys Gln His Leu Trp Arg
            20                  25                  30

Trp Gly Thr Met Ile Leu Gly Met Ile Ile Ile Cys Ser Ala Ala Glu
        35                  40                  45

Asn Leu Trp Val Thr Val Tyr Tyr Gly Val Pro Val Trp Lys Asp Ala
    50                  55                  60

Glu Thr Thr Leu Phe Cys Ala Ser Asp Ala Lys Ala Tyr Asp Thr Glu
65                  70                  75                  80

Val His Asn Val Trp Ala Thr His Ala Cys Val Pro Thr Asp Pro Asn
                85                  90                  95

Pro Gln Glu Ile Asn Leu Glu Asn Val Thr Glu Glu Phe Asn Met Trp
            100                 105                 110

Lys Asn Asn Met Val Glu Gln Met His Thr Asp Ile Ile Ser Leu Trp
```

```
              115                 120                 125
Asp Gln Ser Leu Lys Pro Cys Val Lys Leu Thr Pro Leu Cys Val Thr
              130                 135                 140

Leu Asn Cys Ser Asn Val Asn Val Thr Thr Asn Ile Met Lys Gly Glu
145                 150                 155                 160

Ile Lys Asn Cys Ser Phe Asn Met Thr Thr Glu Leu Arg Asp Lys Lys
                165                 170                 175

Gln Lys Val Tyr Ser Leu Phe Tyr Lys Leu Asp Val Val Gln Ile Asn
            180                 185                 190

Lys Ser Asn Ser Ser Gln Tyr Arg Leu Ile Asn Cys Asn Thr Ser
        195                 200                 205

Ala Ile Thr Gln Ala Cys Pro Lys Val Ser Phe Glu Pro Ile Pro Ile
    210                 215                 220

His Tyr Cys Ala Pro Ala Gly Phe Ala Ile Leu Lys Cys Lys Asp Lys
225                 230                 235                 240

Glu Phe Asn Gly Thr Gly Pro Cys Lys Asn Val Ser Thr Val Gln Cys
                245                 250                 255

Thr His Gly Ile Lys Pro Val Val Ser Thr Gln Leu Leu Leu Asn Gly
                260                 265                 270

Ser Leu Ala Glu Glu Val Met Ile Arg Ser Glu Asn Ile Thr Asn
        275                 280                 285

Asn Ala Lys Asn Ile Ile Val Gln Leu Thr Lys Pro Val Lys Ile Asn
    290                 295                 300

Cys Thr Arg Pro Asn Asn Asn Thr Arg Lys Ser Ile Arg Ile Gly Pro
305                 310                 315                 320

Gly Gln Ala Phe Tyr Ala Thr Gly Asp Ile Ile Gly Asp Ile Arg Gln
                325                 330                 335

Ala His Cys Asn Val Ser Arg Thr Glu Trp Asn Glu Thr Leu Gln Lys
            340                 345                 350

Val Ala Lys Gln Leu Arg Lys Tyr Phe Asn Asn Lys Thr Ile Ile Phe
        355                 360                 365

Thr Asn Ser Ser Gly Gly Arg Leu Arg Ile Thr Thr His Ser Phe Asn
    370                 375                 380

Cys Gly Gly Glu Phe Phe Tyr Cys Asn Thr Ser Gly Leu Phe Asn Ser
385                 390                 395                 400

Thr Trp Asn Gly Asn Gly Thr Lys Lys Lys Asn Ser Thr Glu Ser Asn
                405                 410                 415

Asp Thr Ile Thr Leu Pro Cys Arg Ile Lys Gln Ile Ile Asn Met Trp
            420                 425                 430

Gln Arg Val Gly Gln Ala Met Tyr Ala Pro Pro Ile Gln Gly Val Ile
        435                 440                 445

Arg Cys Glu Ser Asn Ile Thr Gly Leu Leu Leu Thr Arg Asp Gly Gly
    450                 455                 460

Asp Asn Asn Ser Lys Asn Glu Thr Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Glu
            500                 505                 510

Arg Glu Lys Arg Ala Val Gly Ile Gly Ala Val Phe Leu Gly Phe Leu
        515                 520                 525

Gly Ala Ala Gly Ser Thr Met Gly Ala Ala Ser Ile Thr Leu Thr Val
    530                 535                 540
```

```
Gln Ala Arg Gln Leu Leu Ser Gly Ile Val Gln Gln Ser Asn Leu
545                 550                 555                 560

Leu Arg Ala Ile Glu Ala Gln Gln His Leu Leu Lys Leu Thr Val Trp
        565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
        595                 600                 605

Cys Thr Thr Asn Val Pro Trp Asn Ser Ser Trp Ser Asn Lys Ser Gln
610                 615                 620

Ser Glu Ile Trp Asp Asn Met Thr Trp Leu Gln Trp Asp Lys Glu Ile
625                 630                 635                 640

Ser Asn Tyr Thr Asp Ile Ile Tyr Asn Leu Ile Glu Glu Ser Gln Asn
            645                 650                 655

Gln Gln Glu Lys Asn Glu Gln Asp Leu Leu Ala Leu Asp Lys Trp Ala
        660                 665                 670

Asn Leu Trp Asn Trp Phe Asp Ile Ser Asn Trp Leu Trp Tyr Ile Lys
    675                 680                 685

Ile Phe Ile Met Ile Val Gly Gly Leu Ile Gly Leu Arg Ile Val Phe
690                 695                 700

Ala Val Leu Ser Val
705

<210> SEQ ID NO 137
<211> LENGTH: 2734
<212> TYPE: DNA
<213> ORGANISM: Artificial Sequence
<220> FEATURE:
<223> OTHER INFORMATION: Subtype B consensus Envelope DNA sequence
      construct

<400> SEQUENCE: 137
ggatccgcca ccatggactg gacctggatt ctgttcctgg tggccgccgc caccagagtg      60
cacagcagag tgaagggcat ccggaagaac taccagcacc tgtggagatg ggcaccatg     120 ctgctgggca tgctgatgat ctgttctgcc gccgagaagc tgtgggtgac cgtgtactac     180
ggcgtgcctg tgtggaagga ggccaccacc accctgttct gcgccagcga cgccaaggcc     240
tacgataccg aagtgcacaa tgtgtgggcc acccacgcct gcgtgcctac cgatcccaac     300
cctcaggaag tggtgctgga aacgtgacc gagaacttca acatgtggaa gaacaacatg     360
gtggagcaga tgcacgagga catcatcagc ctgtgggacc agagcctgaa gccttgcgtg     420
aagctgaccc ctctgtgcgt gaccctgaac tgcaccgacc tgagcggcga agatggagag     480
aagggcgaga tcaagaactg cagcttcaac atcaccacct ccatccggga caaagtgcag     540
aaggagtacg ccctgttcta caagctggac gtggtgccca tcgacaacga caacaccagc     600
taccggctga tcagctgcaa caccagcgtg atcacccagg cctgccccaa agtgagcttc     660
gagcccatcc ccatccacta ctgcgcccct gccggcttcg ccatcctgaa gtgcaacgac     720
aagaagttca cggcaccgg cccttgcacc aatgtgagca ccgtgcagtg cacccacggc     780
atcagacccg tggtgtccac ccagctgctg ctgaacggca gcctggccga ggaagaagtg     840
gtgatccgga gcgagaattt caccaacaac gccaagacca tcatcgtgca gctgaacgag     900
agcgtggaga tcaactgcac ccggcccaac aacaataccc ggaagagcat ccacatcggc     960
cctggccagg ccttctacac caccggcgag atcatcggcg atatcaggca ggcccactgc    1020
```

```
aatatcagcc gggccaagtg aacaacacc ctgaagcaga tcgtgaagaa gctgcgggag    1080
cagttcggca acaagaccat cgtgttcaac cagagcagcg gcggcagacc tagaatcgtg    1140
atgcacagct tcaactgtgg cggcgagttc ttctactgca acacaaccca gctgttcaac    1200
agcacctgga acgtgaacgg gacctggaac aacaacaccg agggcaacga caccatcacc    1260
ctgccctgcc ggatcaagca gatcatcaat atgtggcagg aggtgggcaa ggccatgtac    1320
gcccctccca tcagaggcca gatccggtgc agcagcaata tcaccggcct gctgctgacc    1380
agagatggcg gcaacaataa caccaacgag accgagatct ttagacctgg cggcggagac    1440
atgagggaca ctggcggagc gagctgtac aagtacaaag tggtgaagat cgagcccctg    1500
ggcgtggccc ccaccaaggc caagagaaga gtggtgcagc gggagaagag agctgtgggc    1560
atcggcgcca tgtttctggg ctttctggga gccgccggaa gcaccatggg agccgccagc    1620
atgaccctga ccgtgcaggc cagacagctg ctgagcggca tcgtgcagca gcagaacaac    1680
ctgctgagag ccatcgaggc ccagcagcac ctgctgcagc tgacagtgtg gggcatcaag    1740
cagctgcagg cccgcgtgct ggccgtggag agatacctga aggaccagca gctgctggga    1800
atctggggct gcagcggcaa gctgatctgc accaccaccg tgccctggaa cgccagctgg    1860
agcaacaaga gcctggacga gatctgggac aacatgacct ggatggagtg ggagcgggag    1920
atcgacaact acaccagcct gatctacacc ctgatcgagg agagccagaa ccagcaggag    1980
aagaacgagc aggagctgct ggagctggac aagtgggcca gcctgtggaa ctggttcgac    2040
atcaccaact ggctgtggta catcaagatc ttcatcatga ttgtgggcgg cctgatcggc    2100
ctgagaatcg tgttcgccgt gctgagcatc taccctacg acgtgcccga ttacgcctga    2160
gaattcgtaa gtaagtgtca tatgggagag ctcgactaga ctggacagcc aatgacgggt    2220
aagagagtga catttctcac taacctaaga caggagggcc gtcaaagcta ctgcctaatc    2280
caatgacggg taatagtgac aagaaatgta tcactccaac ctaagacagg cgcagcctcc    2340
gagggatgtg tcttttgttt tttataatta aaaagggtga catgtccgga gccgtgctgc    2400
ccggatgatg tcttggcctc tgtttgctac cggtatcgat gttaacgtcg accccgggct    2460
cgaggtaagt aagtgtcata tgggagagct cgactagact ggacagccaa tgacgggtaa    2520
gagagtgaca tttctcacta acctaagaca ggagggccgt caaagctact gcctaatcca    2580
atgacgggta atagtgacaa gaaatgtatc actccaacct aagacaggcg cagcctccga    2640
gggatgtgtc ttttgttttt tataattaaa aagggtgaca tgtccggagc cgtgctgccc    2700
ggatgatgtc ttggcctctg tttgctgcgg ccgc                                2734
```

<210> SEQ ID NO 138
<211> LENGTH: 715
<212> TYPE: PRT
<213> ORGANISM: Artificial Sequence
<220> FEATURE:
<223> OTHER INFORMATION: Subtype B consensus Envelope protein sequence
      construct

<400> SEQUENCE: 138

Met Asp Trp Thr Trp Ile Leu Phe Leu Val Ala Ala Ala Thr Arg Val
1               5                   10                  15

His Ser Arg Val Lys Gly Ile Arg Lys Asn Tyr Gln His Leu Trp Arg
            20                  25                  30

Trp Gly Thr Met Leu Leu Gly Met Leu Met Ile Cys Ser Ala Ala Glu
        35                  40                  45

Lys Leu Trp Val Thr Val Tyr Tyr Gly Val Pro Val Trp Lys Glu Ala

-continued

```
            50                  55                  60
Thr Thr Thr Leu Phe Cys Ala Ser Asp Ala Lys Ala Tyr Asp Thr Glu
 65                  70                  75                  80

Val His Asn Val Trp Ala Thr His Ala Cys Val Pro Thr Asp Pro Asn
                     85                  90                  95

Pro Gln Glu Val Val Leu Glu Asn Val Thr Glu Asn Phe Asn Met Trp
                    100                 105                 110

Lys Asn Asn Met Val Glu Gln Met His Glu Asp Ile Ile Ser Leu Trp
                    115                 120                 125

Asp Gln Ser Leu Lys Pro Cys Val Lys Leu Thr Pro Leu Cys Val Thr
                    130                 135                 140

Leu Asn Cys Thr Asp Leu Ser Gly Glu Lys Met Glu Lys Gly Glu Ile
145                 150                 155                 160

Lys Asn Cys Ser Phe Asn Ile Thr Thr Ser Ile Arg Asp Lys Val Gln
                    165                 170                 175

Lys Glu Tyr Ala Leu Phe Tyr Lys Leu Asp Val Val Pro Ile Asp Asn
                    180                 185                 190

Asp Asn Thr Ser Tyr Arg Leu Ile Ser Cys Asn Thr Ser Val Ile Thr
                    195                 200                 205

Gln Ala Cys Pro Lys Val Ser Phe Glu Pro Ile Pro Ile His Tyr Cys
                    210                 215                 220

Ala Pro Ala Gly Phe Ala Ile Leu Lys Cys Asn Asp Lys Lys Phe Asn
225                 230                 235                 240

Gly Thr Gly Pro Cys Thr Asn Val Ser Thr Val Gln Cys Thr His Gly
                    245                 250                 255

Ile Arg Pro Val Val Ser Thr Gln Leu Leu Leu Asn Gly Ser Leu Ala
                    260                 265                 270

Glu Glu Glu Val Val Ile Arg Ser Glu Asn Phe Thr Asn Asn Ala Lys
                    275                 280                 285

Thr Ile Ile Val Gln Leu Asn Glu Ser Val Glu Ile Asn Cys Thr Arg
                    290                 295                 300

Pro Asn Asn Asn Thr Arg Lys Ser Ile His Ile Gly Pro Gly Gln Ala
305                 310                 315                 320

Phe Tyr Thr Thr Gly Glu Ile Ile Gly Asp Ile Arg Gln Ala His Cys
                    325                 330                 335

Asn Ile Ser Arg Ala Lys Trp Asn Asn Thr Leu Lys Gln Ile Val Lys
                    340                 345                 350

Lys Leu Arg Glu Gln Phe Gly Asn Lys Thr Ile Val Phe Asn Gln Ser
                    355                 360                 365

Ser Gly Gly Arg Pro Arg Ile Val Met His Ser Phe Asn Cys Gly Gly
                    370                 375                 380

Glu Phe Phe Tyr Cys Asn Thr Thr Gln Leu Phe Asn Ser Thr Trp Asn
385                 390                 395                 400

Val Asn Gly Thr Trp Asn Asn Thr Glu Gly Asn Asp Thr Ile Thr
                    405                 410                 415

Leu Pro Cys Arg Ile Lys Gln Ile Ile Asn Met Trp Gln Glu Val Gly
                    420                 425                 430

Lys Ala Met Tyr Ala Pro Pro Ile Arg Gly Gln Ile Arg Cys Ser Ser
                    435                 440                 445

Asn Ile Thr Gly Leu Leu Leu Thr Arg Asp Gly Gly Asn Asn Asn Thr
                    450                 455                 460

Asn Glu Thr Glu Ile Phe Arg Pro Gly Gly Gly Asp Met Arg Asp Asn
465                 470                 475                 480
```

```
Trp Arg Ser Glu Leu Tyr Lys Tyr Lys Val Val Lys Ile Glu Pro Leu
                485                 490                 495
Gly Val Ala Pro Thr Lys Ala Lys Arg Arg Val Val Gln Arg Glu Lys
            500                 505                 510
Arg Ala Val Gly Ile Gly Ala Met Phe Leu Gly Phe Leu Gly Ala Ala
        515                 520                 525
Gly Ser Thr Met Gly Ala Ala Ser Met Thr Leu Thr Val Gln Ala Arg
    530                 535                 540
Gln Leu Leu Ser Gly Ile Val Gln Gln Asn Asn Leu Leu Arg Ala
545                 550                 555                 560
Ile Glu Ala Gln Gln His Leu Leu Gln Leu Thr Val Trp Gly Ile Lys
                565                 570                 575
Gln Leu Gln Ala Arg Val Leu Ala Val Glu Arg Tyr Leu Lys Asp Gln
            580                 585                 590
Gln Leu Leu Gly Ile Trp Gly Cys Ser Gly Lys Leu Ile Cys Thr Thr
        595                 600                 605
Thr Val Pro Trp Asn Ala Ser Trp Ser Asn Lys Ser Leu Asp Glu Ile
    610                 615                 620
Trp Asp Asn Met Thr Trp Met Glu Trp Glu Arg Glu Ile Asp Asn Tyr
625                 630                 635                 640
Thr Ser Leu Ile Tyr Thr Leu Ile Glu Glu Ser Gln Asn Gln Gln Glu
                645                 650                 655
Lys Asn Glu Gln Glu Leu Leu Glu Leu Asp Lys Trp Ala Ser Leu Trp
            660                 665                 670
Asn Trp Phe Asp Ile Thr Asn Trp Leu Trp Tyr Ile Lys Ile Phe Ile
        675                 680                 685
Met Ile Val Gly Gly Leu Ile Gly Leu Arg Ile Val Phe Ala Val Leu
    690                 695                 700
Ser Ile Tyr Pro Tyr Asp Val Pro Asp Tyr Ala
705                 710                 715

<210> SEQ ID NO 139
<211> LENGTH: 2140
<212> TYPE: DNA
<213> ORGANISM: Artificial Sequence
<220> FEATURE:
<223> OTHER INFORMATION: Subtype C consensus Envelope DNA sequence
      construct

<400> SEQUENCE: 139
ggatccgcca ccatggattg gacctggatt ctgttcctgg tggccgccgc cacaagagtg      60
cacagcagag tgcggggcat cctgagaaat tgccagcagt ggtggatctg gggcattctg     120
gggttctgga tgctgatgat ctgcaacgtg atgggcaacc tgtgggtgac cgtgtactac     180
ggcgtgcctg tgtggaagga ggccaagacc accctgttct gtgccagcga tgccaaggcc     240
tacgagaccg aggtgcacaa tgtgtgggcc acccacgcct gtgtgcccac cgatcccaac     300
cctcaggaga tggtgctgga aacgtgacc gagaacttca acatgtggaa gaacgacatg     360
gtggaccaga tgcacgagga catcatcagc ctgtgggacc agagcctgaa gccttgcgtg     420
aagctgaccc ctctgtgcgt gaccctgaac tgccggaaca cgtgaacaa caacaacacc     480 atgaaggagg agatcaagaa ctgcagcttc aacatcacca ccgagctgcg ggacaagaag     540
cagaaggtgt acgccctgtt ctaccggctg gacatcgtgc ccctgaacga gaagaacaac     600
agcaacgact accggctgat caactgcaac accagcgcca tcacccaggc ctgtcccaag     660
```

-continued

```
gtgtccttcg accccatccc catccactat tgtgcccctg ccggctacgc catcctgaag      720
tgcaacaaca agaccttcaa cggcaccggc ccctgcaata atgtgagcac cgtgcagtgt      780
acccacggca tcaagcctgt ggtgtccacc cagctgctgc tgaatggcag cctggccgag      840
gaggagatta tcatccggag cgagaacctg accaacaacg ccaagaccat cattgtgcac      900
ctgaatgaga gcgtggagat cgtgtgtacc cggcccaaca caatacccg gaagagcatc       960
agaatcggcc ctggccagac cttttacgcc accggcgaca tcatcggcga tatcaggcag     1020
gcccactgca atatcagcga ggagaagtgg aacaagaccc tgcagcgggt gtccgagaag     1080
ctgaaggagc acttccccaa taagaccatc aagttcgccc tagcagcgg cggcagactg      1140
gagatcacca cccacagctt caactgcagg ggcgagttct tctactgcaa taccagcaag    1200
ctgttcaaca gcacctacat gcccaacagc accaacaata ccaacaccac catcaccctg    1260
ccctgccgga tcaagcagat catcaatatg tggcaggaag tgggcagagc catgtacgcc    1320
cctcccatcg agggcaacat cacctgcaag tccaacatca ccggcctgct gctgacaaga    1380
gatggcggca agaacgacac caatgacacc gagaccttca gcctggcgg cggagacatg     1440
agggacaact ggcggagcga gctgtacaag tacaaggtgg tggagatcaa gcctctgggc    1500
gtggcccta ccaaggccaa gaggagagtg gtggagaggg agaagagagc cgtgggcatc     1560
ggcgccgtgt ttctgggctt tctgggagcc gccggatcta caatgggagc cgccagcatc    1620
acactgaccg tgcaggccag acagctgctg agcggcatcg tgcagcagca gagcaatctg    1680
ctgagagcca tcgaggccca gcagcacatg ctgcagctga cagtgtgggg catcaagcag    1740
ctgcagacca gagtgctggc catcgagcgc tacctgaagg atcagcagct gctgggcatc    1800
tggggctgta gcggcaagct gatctgtacc accgccgtgc cttggaatag cagctggagc    1860
aacaagagcc aggaggacat ctgggacaac atgacctgga tgcagtggga ccggagatc     1920
agcaactaca ccgacaccat ctacaggctg ctggaggaca gccagaacca gcaggagaag    1980
aacgagaagg acctgctggc cctggacagc tggaagaacc tgtggaactg gttcgacatc    2040
accaactggc tgtggtacat caagatcttc atcatgattg tgggcggcct gatcggcctg    2100
agaatcatct tcgccgtgct gagcatctga tagcggccgc                          2140
```

<210> SEQ ID NO 140
<211> LENGTH: 705
<212> TYPE: PRT
<213> ORGANISM: Artificial Sequence
<220> FEATURE:
<223> OTHER INFORMATION: Subtype C consensus Envelope protein sequence construct

<400> SEQUENCE: 140

```
Met Asp Trp Thr Trp Ile Leu Phe Leu Val Ala Ala Thr Arg Val
1               5                   10                  15

His Ser Arg Val Arg Gly Ile Leu Arg Asn Cys Gln Gln Trp Trp Ile
            20                  25                  30

Trp Gly Ile Leu Gly Phe Trp Met Leu Met Ile Cys Asn Val Met Gly
        35                  40                  45

Asn Leu Trp Val Thr Val Tyr Tyr Gly Val Pro Val Trp Lys Glu Ala
    50                  55                  60

Lys Thr Thr Leu Phe Cys Ala Ser Asp Ala Lys Ala Tyr Glu Thr Glu
65                  70                  75                  80

Val His Asn Val Trp Ala Thr His Ala Cys Val Pro Thr Asp Pro Asn
                85                  90                  95
```

-continued

```
Pro Gln Glu Met Val Leu Glu Asn Val Thr Glu Asn Phe Asn Met Trp
            100                 105                 110
Lys Asn Asp Met Val Asp Gln Met His Glu Asp Ile Ile Ser Leu Trp
        115                 120                 125
Asp Gln Ser Leu Lys Pro Cys Val Lys Leu Thr Pro Leu Cys Val Thr
    130                 135                 140
Leu Asn Cys Arg Asn Asn Val Asn Asn Asn Thr Met Lys Glu Glu
145                 150                 155                 160
Ile Lys Asn Cys Ser Phe Asn Ile Thr Thr Glu Leu Arg Asp Lys Lys
                165                 170                 175
Gln Lys Val Tyr Ala Leu Phe Tyr Arg Leu Asp Ile Val Pro Leu Asn
            180                 185                 190
Glu Lys Asn Asn Ser Asn Asp Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Glu Ile Ile Ile Arg Ser Glu Asn Leu Thr Asn
        275                 280                 285
Asn Ala Lys Thr Ile Ile Val His Leu Asn Glu Ser Val Glu Ile Val
    290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Ile Ser Glu Glu Lys Trp Asn Lys Thr Leu Gln Arg
            340                 345                 350
Val Ser Glu Lys Leu Lys Glu His Phe Pro Asn Lys Thr Ile Lys Phe
        355                 360                 365
Ala Pro Ser Ser Gly Gly Arg Leu Glu Ile Thr Thr His Ser Phe Asn
    370                 375                 380
Cys Arg Gly Glu Phe Phe Tyr Cys Asn Thr Ser Lys Leu Phe Asn Ser
385                 390                 395                 400
Thr Tyr Met Pro Asn Ser Thr Asn Asn Thr Asn Thr Thr Ile Thr Leu
                405                 410                 415
Pro Cys Arg Ile Lys Gln Ile Ile Asn Met Trp Gln Glu Val Gly Arg
            420                 425                 430
Ala Met Tyr Ala Pro Pro Ile Glu Gly Asn Ile Thr Cys Lys Ser Asn
        435                 440                 445
Ile Thr Gly Leu Leu Leu Thr Arg Asp Gly Gly Lys Asn Asp Thr Asn
    450                 455                 460
Asp Thr Glu Thr Phe Arg Pro Gly Gly Gly Asp Met Arg Asp Asn Trp
465                 470                 475                 480
Arg Ser Glu Leu Tyr Lys Tyr Lys Val Val Glu Ile Lys Pro Leu Gly
                485                 490                 495
Val Ala Pro Thr Lys Ala Lys Arg Arg Val Val Glu Arg Glu Lys Arg
            500                 505                 510
Ala Val Gly Ile Gly Ala Val Phe Leu Gly Phe Leu Gly Ala Ala Gly
```

|  |  | 515 |  |  | 520 |  |  | 525 |  |
|---|---|---|---|---|---|---|---|---|---|

Ser Thr Met Gly Ala Ala Ser Ile Thr Leu Thr Val Gln Ala Arg Gln
530                535                540

Leu Leu Ser Gly Ile Val Gln Gln Ser Asn Leu Leu Arg Ala Ile
545                550                555                560

Glu Ala Gln Gln His Met Leu Gln Leu Thr Val Trp Gly Ile Lys Gln
                565                570                575

Leu Gln Thr Arg Val Leu Ala Ile Glu Arg Tyr Leu Lys Asp Gln Gln
                580                585                590

Leu Leu Gly Ile Trp Gly Cys Ser Gly Lys Leu Ile Cys Thr Thr Ala
                595                600                605

Val Pro Trp Asn Ser Ser Trp Ser Asn Lys Ser Gln Glu Asp Ile Trp
610                615                620

Asp Asn Met Thr Trp Met Gln Trp Asp Arg Glu Ile Ser Asn Tyr Thr
625                630                635                640

Asp Thr Ile Tyr Arg Leu Leu Glu Asp Ser Gln Asn Gln Gln Glu Lys
                645                650                655

Asn Glu Lys Asp Leu Leu Ala Leu Asp Ser Trp Lys Asn Leu Trp Asn
                660                665                670

Trp Phe Asp Ile Thr Asn Trp Leu Trp Tyr Ile Lys Ile Phe Ile Met
                675                680                685

Ile Val Gly Gly Leu Ile Gly Leu Arg Ile Ile Phe Ala Val Leu Ser
690                695                700

Ile
705

<210> SEQ ID NO 141
<211> LENGTH: 2089
<212> TYPE: DNA
<213> ORGANISM: Artificial Sequence
<220> FEATURE:
<223> OTHER INFORMATION: Subtype D consensus Envelope DNA sequence
      construct

<400> SEQUENCE: 141

| gggcatcaag cggaattacc agcacctgtg gaagtggggc accatgctgc tgggcatgct | 60 |
|---|---|
| gatgacctgc agcgtggccg agaacctgtg ggtgaccgtg tactacggcg tgcctgtgtg | 120 |
| gaaggaagcc accaccaccc tgttctgcgc cagcgatgcc aagagctaca agaccgaggc | 180 |
| ccacaatatc tgggccaccc acgcctgcgt gcctaccgat cccaaccctc aggagatcga | 240 |
| gctggagaac gtgaccgaga acttcaacat gtggaagaac aacatggtgg agcagatgca | 300 |
| cgaggacatc atcagcctgt gggaccagag cctgaagcct tgcgtgaagc tgaccccctct | 360 |
| gtgcgtgacc ctgaactgca ccgacggcat gaggaacgac accaacgata ccaacgtgac | 420 |
| catggaggag ggcgagatga gaactgcag cttcaacatc accaccgaag tgcgggacaa | 480 |
| gaagaagcag gtgcacgccc tgttctacaa gctggacgtg gtgcccatcg acgacaacaa | 540 |
| caccaacaac agcaactacc ggctgatcaa ctgcaacacc agcgccatca cccaggcctg | 600 |
| cccccaaagtg accttcgagc ccatccccat ccactactgc gccccctgccg gcttcgccat | 660 |
| cctgaagtgc aaggataaga agttcaacgg caccggcccc tgcaagaatg tgagcaccgt | 720 |
| gcagtgcacc cacggcatca gacccgtggt gtccacccag ctgctgctga acggcagcct | 780 |
| ggccgaggag gagatcatca tccggagcga gaacctgacc aacaacgcca agatcatcat | 840 |
| tgtgcagctg aacgagagcg tgaccatcaa ttgcacccgg ccctacaaca ataccccggaa | 900 |

```
gcgcatcccc atcggcctgg gccaggcctt ctacaccacc agaggcatca tcggcgacat    960
cagacaggcc cactgcaata tcagcggagc cgagtggaat aagaccctgc agcaggtggc   1020
caagaagctg ggcgacctgc tgaacaagac caccatcatc ttcaagccta gcagcggcgg   1080
cagacctaga atcaccaccc acagcttcaa ttgtggcggc gagttcttct actgcaatac   1140
cagccggctg ttcaacagca cctggagcaa gaacagcacc agcaactcca ccaaggagaa   1200
caacaccatc accctgccct gccggatcaa gcagatcatc aatatgtggc agggagtggg   1260
caaggccatg tacgcccctc ccatcgaggg cctgatcaag tgcagcagca acatcaccgg   1320
cctgctgctg accagagatg gcggagccaa caactcccac aacgagacct cagacctgg    1380 cggcggagac atgagggaca ctggcggag cgagctgtac aagtacaaag tggtgaagat   1440
cgagcccctg ggcgtggccc ccaccagagc caagagaaga gtggtggagc gggagaagag   1500
agccatcgga ctgggcgcca tgttcctggg cttcctggga gccgccggaa gcaccatggg   1560
agccgccagc ctgaccctga ccgtgcaggc cagacagctg ctgagcggca tcgtgcagca   1620
gcagaacaac ctgctgagag ccattgaggc ccagcagcac ctgctgcagc tgacagtgtg   1680
gggcattaag cagctgcagg ccaggattct ggccgtggag cgctacctga aggatcagca   1740
gctgctggga atctggggct gcagcggcaa gcacatctgc accaccaccg tgccttggaa   1800
tagcagctgg agcaacaaga gcctggacga gatctggaac aacatgacct ggatggagtg   1860
ggagagggag atcgacaact acaccggcct gatctacagc ctgatcgagg agagccagac   1920
ccagcaggag aagaacgagc aggagctgct ggagctggac aagtgggcca gcctgtggaa   1980
ctggttcagc atcaccccagt ggctgtggta catcaagatc ttcatcatga ttgtgggcgg   2040
cctgatcggc ctgagaatcg tgttcgccgt gctgagcctg tgactcgag              2089
```

<210> SEQ ID NO 142
<211> LENGTH: 714
<212> TYPE: PRT
<213> ORGANISM: Artificial Sequence
<220> FEATURE:
<223> OTHER INFORMATION: Subtype D consensus Envelope protein sequence construct

<400> SEQUENCE: 142

```
Met Asp Trp Thr Trp Ile Leu Phe Leu Val Ala Ala Thr Arg Val
1               5                   10                  15

His Ser Arg Val Arg Gly Ile Lys Arg Asn Tyr Gln His Leu Trp Lys
            20                  25                  30

Trp Gly Thr Met Leu Leu Gly Met Leu Met Thr Cys Ser Val Ala Glu
        35                  40                  45

Asn Leu Trp Val Thr Val Tyr Tyr Gly Val Pro Val Trp Lys Glu Ala
    50                  55                  60

Thr Thr Thr Leu Phe Cys Ala Ser Asp Ala Lys Ser Tyr Lys Thr Glu
65                  70                  75                  80

Ala His Asn Ile Trp Ala Thr His Ala Cys Val Pro Thr Asp Pro Asn
                85                  90                  95

Pro Gln Glu Ile Glu Leu Glu Asn Val Thr Glu Asn Phe Asn Met Trp
            100                 105                 110

Lys Asn Asn Met Val Glu Gln Met His Glu Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Thr Asp Gly Met Arg Asn Asp Thr Asn Asp Thr Asn Val
```

```
                145                 150                 155                 160
        Thr Met Glu Glu Gly Glu Met Lys Asn Cys Ser Phe Asn Ile Thr Thr
                        165                 170                 175
        Glu Val Arg Asp Lys Lys Gln Val His Ala Leu Phe Tyr Lys Leu
                        180                 185                 190
        Asp Val Pro Ile Asp Asn Asn Thr Asn Asn Ser Asn Tyr Arg
                    195                 200                 205
        Leu Ile Asn Cys Asn Thr Ser Ala Ile Thr Gln Ala Cys Pro Lys Val
                210                 215                 220
        Thr Phe Glu Pro Ile Pro Ile His Tyr Cys Ala Pro Ala Gly Phe Ala
        225                 230                 235                 240
        Ile Leu Lys Cys Lys Asp Lys Lys Phe Asn Gly Thr Gly Pro Cys Lys
                        245                 250                 255
        Asn Val Ser Thr Val Gln Cys Thr His Gly Ile Arg Pro Val Val Ser
                    260                 265                 270
        Thr Gln Leu Leu Leu Asn Gly Ser Leu Ala Glu Glu Ile Ile Ile
                275                 280                 285
        Arg Ser Glu Asn Leu Thr Asn Asn Ala Lys Ile Ile Val Gln Leu
            290                 295                 300
        Asn Glu Ser Val Thr Ile Asn Cys Thr Arg Pro Tyr Asn Asn Thr Arg
        305                 310                 315                 320
        Lys Arg Ile Pro Ile Gly Leu Gly Gln Ala Phe Tyr Thr Thr Arg Gly
                        325                 330                 335
        Ile Ile Gly Asp Ile Arg Gln Ala His Cys Asn Ile Ser Gly Ala Glu
                        340                 345                 350
        Trp Asn Lys Thr Leu Gln Gln Val Ala Lys Lys Leu Gly Asp Leu Leu
                    355                 360                 365
        Asn Lys Thr Thr Ile Ile Phe Lys Pro Ser Ser Gly Arg Pro Arg
            370                 375                 380
        Ile Thr Thr His Ser Phe Asn Cys Gly Gly Glu Phe Phe Tyr Cys Asn
        385                 390                 395                 400
        Thr Ser Arg Leu Phe Asn Ser Thr Trp Ser Lys Asn Ser Thr Ser Asn
                        405                 410                 415
        Ser Thr Lys Glu Asn Asn Thr Ile Thr Leu Pro Cys Arg Ile Lys Gln
                        420                 425                 430
        Ile Ile Asn Met Trp Gln Gly Val Gly Lys Ala Met Tyr Ala Pro Pro
                    435                 440                 445
        Ile Glu Gly Leu Ile Lys Cys Ser Ser Asn Ile Thr Gly Leu Leu Leu
            450                 455                 460
        Thr Arg Asp Gly Gly Ala Asn Asn Ser His Asn Glu Thr Phe Arg Pro
        465                 470                 475                 480
        Gly Gly Gly Asp Met Arg Asp Asn Trp Arg Ser Glu Leu Tyr Lys Tyr
                        485                 490                 495
        Lys Val Val Lys Ile Glu Pro Leu Gly Val Ala Pro Thr Arg Ala Lys
                        500                 505                 510
        Arg Arg Val Val Glu Arg Glu Lys Arg Ala Ile Gly Leu Gly Ala Met
                    515                 520                 525
        Phe Leu Gly Phe Leu Gly Ala Ala Gly Ser Thr Met Gly Ala Ala Ser
            530                 535                 540
        Leu Thr Leu Thr Val Gln Ala Arg Gln Leu Leu Ser Gly Ile Val Gln
        545                 550                 555                 560
        Gln Gln Asn Asn Leu Leu Arg Ala Ile Glu Ala Gln Gln His Leu Leu
                        565                 570                 575
```

Gln Leu Thr Val Trp Gly Ile Lys Gln Leu Gln Ala Arg Ile Leu Ala
            580                 585                 590

Val Glu Arg Tyr Leu Lys Asp Gln Gln Leu Leu Gly Ile Trp Gly Cys
        595                 600                 605

Ser Gly Lys His Ile Cys Thr Thr Thr Val Pro Trp Asn Ser Ser Trp
610                 615                 620

Ser Asn Lys Ser Leu Asp Glu Ile Trp Asn Asn Met Thr Trp Met Glu
625                 630                 635                 640

Trp Glu Arg Glu Ile Asp Asn Tyr Thr Gly Leu Ile Tyr Ser Leu Ile
                645                 650                 655

Glu Glu Ser Gln Thr Gln Gln Glu Lys Asn Glu Gln Glu Leu Leu Glu
            660                 665                 670

Leu Asp Lys Trp Ala Ser Leu Trp Asn Trp Phe Ser Ile Thr Gln Trp
        675                 680                 685

Leu Trp Tyr Ile Lys Ile Phe Ile Met Ile Val Gly Gly Leu Ile Gly
    690                 695                 700

Leu Arg Ile Val Phe Ala Val Leu Ser Leu
705                 710

<210> SEQ ID NO 143
<211> LENGTH: 1049
<212> TYPE: DNA
<213> ORGANISM: Artificial Sequence
<220> FEATURE:
<223> OTHER INFORMATION: Subtype B consensus Nef-Rev DNA sequence
      construct

<400> SEQUENCE: 143
ggatccgcca ccatggactg gacctggatt ctgttcctgg tggccgctgc caccagagtg     60
cacagcagca agagaagcgt ggtgggttgg cctacagtgc gggagaggat gagaagagcc    120
gagcctgccg ccgatggagt gggcgccgtg tctagagatc tggagaagca cggcgccatc    180
accagcagca ataccgccgc caacaatgcc gactgcgcct ggctggaggc ccaggaggag    240
gaggaagtgg gcttccctgt gagagcccag gtggccctga gagccatgac ctacaaggcc    300
gccgtggatc tgagccactt cctgaaggag aagggcggcc tggagggcct gatctacagc    360
cagaagcggc aggacatcct ggatctgtgg gtgtaccaca cccagggcta cttccccgac    420
tggcagaatt acacccctgg ccctggcatc agataccctc tgaccttcgg ctggtgcttc    480
aagctggtgc ctgtggagcc tgagaaagtg gaggaggcca acgagggcga gaacaattct    540
gccgcccacc ctatgagcct gcacggcatg gacgatcccg agagggaagt gctggtgtgg    600
aagttcgaca gcaggctggc cttccaccac atggccagag agctgcaccc cgagtactac    660
aaggactgcc ggggcaggaa gagaagaagc gccggcagaa cggcgacag cgacgaggag    720 ctgctgaaaa cagtgcggct gatcaagttc ctgtaccaga gcaaccctcc tcccagcccc    780
gagggcacca gacaggcccg agaaaccgg aggaggcgt ggagagagag gcagcggcag    840
atcagaagca tcagcgagtg gattctgagc acctacctgg gcagacccgc cgagcccgtg    900
cccctgcagc tgcccccct ggagagactg accctggact gcaacgagga ctgcggcacc    960
agcggcaccc agggagtggg cagccccag atcctggtgg agagccctgc cgtgctggag   1020
agcggcacca aggagtgatg agcggccgc                                    1049

<210> SEQ ID NO 144
<211> LENGTH: 341
<212> TYPE: PRT

<213> ORGANISM: Artificial Sequence
<220> FEATURE:
<223> OTHER INFORMATION: Subtype B consensus Nef-Rev protein sequence construct

<400> SEQUENCE: 144

```
Met Asp Trp Thr Trp Ile Leu Phe Leu Val Ala Ala Thr Arg Val
1               5                   10                  15

His Ser Ser Lys Arg Ser Val Val Gly Trp Pro Thr Val Arg Glu Arg
            20                  25                  30

Met Arg Arg Ala Glu Pro Ala Ala Asp Gly Val Gly Ala Val Ser Arg
        35                  40                  45

Asp Leu Glu Lys His Gly Ala Ile Thr Ser Ser Asn Thr Ala Ala Asn
    50                  55                  60

Asn Ala Asp Cys Ala Trp Leu Glu Ala Gln Glu Glu Glu Val Gly
65                  70                  75                  80

Phe Pro Val Arg Ala Gln Val Ala Leu Arg Ala Met Thr Tyr Lys Ala
                85                  90                  95

Ala Val Asp Leu Ser His Phe Leu Lys Glu Lys Gly Gly Leu Glu Gly
            100                 105                 110

Leu Ile Tyr Ser Gln Lys Arg Gln Asp Ile Leu Asp Leu Trp Val Tyr
        115                 120                 125

His Thr Gln Gly Tyr Phe Pro Asp Trp Gln Asn Tyr Thr Pro Gly Pro
    130                 135                 140

Gly Ile Arg Tyr Pro Leu Thr Phe Gly Trp Cys Phe Lys Leu Val Pro
145                 150                 155                 160

Val Glu Pro Glu Lys Val Glu Glu Ala Asn Gly Glu Asn Asn Ser
                165                 170                 175

Ala Ala His Pro Met Ser Leu His Gly Met Asp Asp Pro Glu Arg Glu
            180                 185                 190

Val Leu Val Trp Lys Phe Asp Ser Arg Leu Ala Phe His His Met Ala
        195                 200                 205

Arg Glu Leu His Pro Glu Tyr Tyr Lys Asp Cys Arg Gly Arg Lys Arg
    210                 215                 220

Arg Ser Ala Gly Arg Ser Gly Asp Ser Asp Glu Glu Leu Leu Lys Thr
225                 230                 235                 240

Val Arg Leu Ile Lys Phe Leu Tyr Gln Ser Asn Pro Pro Ser Pro
                245                 250                 255

Glu Gly Thr Arg Gln Ala Arg Arg Asn Arg Arg Arg Trp Arg Glu
            260                 265                 270

Arg Gln Arg Gln Ile Arg Ser Ile Ser Glu Trp Ile Leu Ser Thr Tyr
        275                 280                 285

Leu Gly Arg Pro Ala Glu Pro Val Pro Leu Gln Leu Pro Pro Leu Glu
    290                 295                 300

Arg Leu Thr Leu Asp Cys Asn Glu Asp Cys Gly Thr Ser Gly Thr Gln
305                 310                 315                 320

Gly Val Gly Ser Pro Gln Ile Leu Val Glu Ser Pro Ala Val Leu Glu
                325                 330                 335

Ser Gly Thr Lys Glu
            340
```

<210> SEQ ID NO 145
<211> LENGTH: 1863
<212> TYPE: DNA
<213> ORGANISM: Artificial Sequence
<220> FEATURE:

<223> OTHER INFORMATION: Gag consensus DNA sequence of subtype A, B, C and D construct

<400> SEQUENCE: 145

```
ggatccgcca ccatggactg gacctggatt ctgtttctgg tcgccgccgc cacaagagtg      60
cacagcggcg ccagagccag cgtgctgtcc ggcggcaagc tggacgcctg ggagaagatc     120
agactgaggc ctggcggcaa gaagaagtac cggctgaagc accttgtgtg gccagcaga     180
gagctggaga gattcgccct gaatcctggc ctgctggaga ccagcgaggg ctgtaagcag     240
atcatcggcc agctgcagcc cgccctgcag accggcagcg aggagctgag aagcctgtac     300
aacaccgtgg ccaccctgta ctgcgtgcac gagaagatcg aggtgaagga caccaaggag     360
gccctggaca gatcgagga ggagcagaac aagagcaagc agaaggccca gcaggccgcc     420
gccgacaccg caacagcag ccaggtgtcc cagaactacc ccatcgtgca gaatctgcag     480
ggccagatgg tgcaccaggc catcagcccc agaaccctga atgcctgggt gaaggtgatc     540
gaggagaagg ccttcagccc tgaggtgatc cctatgttca gcgccctgag cgagggcgcc     600
acacctcagg acctgaacac catgctgaac acagtggggg gccaccaggc cgccatgcag     660
atgctgaagg ataccatcaa cgaggaggcc gccgagtggg acagactgca ccccgtgcac     720
gccggaccta tcgcccctgg ccagatgaga gagcccagag gcagcgacat cgccggcacc     780
acctccaccc tgcaagagca gatcggctgg atgaccagca ccccccccat ccctgtgggc     840
gacatctaca gcggtggat catcctgggc ctgaacaaga ttgtgaggat gtacagcccc     900
gtgtccatcc tggatatcag gcagggcccc aaggagccct cagagacta cgtggaccgg     960
ttcttcaaga ccctgagagc cgagcaggcc agccaggacg tgaagaactg gatgaccgag    1020
accctgctgg tgcagaacgc caaccccgac tgtaagacca tcctgagagc cctgggccct    1080
ggcgccaccc tggaggagat gatgaccgcc tgccagggag tgggcggacc cggccacaag    1140
gccagagtgc tggccgaggc catgagccag gccaccaaca gcaacatcat gatgcagcgg    1200
ggcaacttca gaggccccag gaggatcgtg aagtgcttca ctgtggcaa ggagggccac    1260
atcgccagaa actgtagggc ccccaggaag aagggctgct ggaagtgtgg caaagagggg    1320
caccagatga aggactgtac cgagcggcag gccaatttcc tggggaagat ctggcccagc    1380
cacaagggca gacccggcaa tttcctgcag agcagacctg agcccaccgc ccctcccgcc    1440
gagagcttcg gcttcggcga ggagatcacc cccagcccca gcaggagcc caaggacaga    1500
gagctgtacc ctctggccag cctgaagagc ctgttcggca cgatccct gagccagtac    1560
ccctacgacg tgcccgatta cgcctgagaa ttcgtaagta agtgtcatat gggagagctc    1620
gactagactg gacagccaat gacgggtaag agagtgacat ttctcactaa cctaagacag    1680
gagggccgtc aaagctactg cctaatccaa tgacgggtaa tagtgacaag aaatgtatca    1740
ctccaaccta agacaggcgc agcctccgag ggatgtgtct tttgttttt ataattaaaa    1800
agggtgacat gtccggagcc gtgctgcccg gatgatgtct tggcctctgt ttgctgcggc    1860
cgc                                                                  1863
```

<210> SEQ ID NO 146
<211> LENGTH: 524
<212> TYPE: PRT
<213> ORGANISM: Artificial Sequence
<220> FEATURE:
<223> OTHER INFORMATION: Gag consensus protein sequence of subtype A, B, C and D construct

<400> SEQUENCE: 146

```
Met Asp Trp Thr Trp Ile Leu Phe Leu Val Ala Ala Thr Arg Val
1               5                   10                  15

His Ser Gly Ala Arg Ala Ser Val Leu Ser Gly Gly Lys Leu Asp Ala
                20                  25                  30

Trp Glu Lys Ile Arg Leu Arg Pro Gly Gly Lys Lys Tyr Arg Leu
            35                  40              45

Lys His Leu Val Trp Ala Ser Arg Glu Leu Glu Arg Phe Ala Leu Asn
        50                  55                  60

Pro Gly Leu Leu Glu Thr Ser Glu Gly Cys Lys Gln Ile Ile Gly Gln
65              70                  75                  80

Leu Gln Pro Ala Leu Gln Thr Gly Ser Glu Glu Leu Arg Ser Leu Tyr
                85                  90                  95

Asn Thr Val Ala Thr Leu Tyr Cys Val His Glu Lys Ile Glu Val Lys
            100                 105                 110

Asp Thr Lys Glu Ala Leu Asp Lys Ile Glu Glu Gln Asn Lys Ser
        115                 120                 125

Lys Gln Lys Ala Gln Gln Ala Ala Ala Asp Thr Gly Asn Ser Ser Gln
130             135                 140

Val Ser Gln Asn Tyr Pro Ile Val Gln Asn Leu Gln Gly Gln Met Val
145                 150                 155                 160

His Gln Ala Ile Ser Pro Arg Thr Leu Asn Ala Trp Val Lys Val Ile
                165                 170                 175

Glu Glu Lys Ala Phe Ser Pro Glu Val Ile Pro Met Phe Ser Ala Leu
            180                 185                 190

Ser Glu Gly Ala Thr Pro Gln Asp Leu Asn Thr Met Leu Asn Thr Val
        195                 200                 205

Gly Gly His Gln Ala Ala Met Gln Met Leu Lys Asp Thr Ile Asn Glu
210                 215                 220

Glu Ala Ala Glu Trp Asp Arg Leu His Pro Val His Ala Gly Pro Ile
225                 230                 235                 240

Ala Pro Gly Gln Met Arg Glu Pro Arg Gly Ser Asp Ile Ala Gly Thr
                245                 250                 255

Thr Ser Thr Leu Gln Glu Gln Ile Gly Trp Met Thr Ser Asn Pro Pro
            260                 265                 270

Ile Pro Val Gly Asp Ile Tyr Lys Arg Trp Ile Ile Leu Gly Leu Asn
        275                 280                 285

Lys Ile Val Arg Met Tyr Ser Pro Val Ser Ile Leu Asp Ile Arg Gln
290                 295                 300

Gly Pro Lys Glu Pro Phe Arg Asp Tyr Val Asp Arg Phe Phe Lys Thr
305                 310                 315                 320

Leu Arg Ala Glu Gln Ala Ser Gln Asp Val Lys Asn Trp Met Thr Glu
                325                 330                 335

Thr Leu Leu Val Gln Asn Ala Asn Pro Asp Cys Lys Thr Ile Leu Arg
            340                 345                 350

Ala Leu Gly Pro Gly Ala Thr Leu Glu Glu Met Met Thr Ala Cys Gln
        355                 360                 365

Gly Val Gly Gly Pro Gly His Lys Ala Arg Val Leu Ala Glu Ala Met
370                 375                 380

Ser Gln Ala Thr Asn Ser Asn Ile Met Met Gln Arg Gly Asn Phe Arg
385                 390                 395                 400

Gly Pro Arg Arg Ile Val Lys Cys Phe Asn Cys Gly Lys Glu Gly His
                405                 410                 415
```

```
Ile Ala Arg Asn Cys Arg Ala Pro Arg Lys Lys Gly Cys Trp Lys Cys
                420                 425                 430

Gly Lys Glu Gly His Gln Met Lys Asp Cys Thr Glu Arg Gln Ala Asn
            435                 440                 445

Phe Leu Gly Lys Ile Trp Pro Ser His Lys Gly Arg Pro Gly Asn Phe
        450                 455                 460

Leu Gln Ser Arg Pro Glu Pro Thr Ala Pro Ala Glu Ser Phe Gly
465                 470                 475                 480

Phe Gly Glu Glu Ile Thr Pro Ser Pro Lys Gln Glu Pro Lys Asp Arg
                485                 490                 495

Glu Leu Tyr Pro Leu Ala Ser Leu Lys Ser Leu Phe Gly Asn Asp Pro
            500                 505                 510

Leu Ser Gln Tyr Pro Tyr Asp Val Pro Asp Tyr Ala
        515                 520

<210> SEQ ID NO 147
<211> LENGTH: 692
<212> TYPE: PRT
<213> ORGANISM: Artificial Sequence
<220> FEATURE:
<223> OTHER INFORMATION: Subtype A consensus Envelope protein sequence

<400> SEQUENCE: 147

Ser Arg Val Met Gly Ile Gln Arg Asn Cys Gln His Leu Trp Arg Trp
1               5                   10                  15

Gly Thr Met Ile Leu Gly Met Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Asn Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asn Val Asn Val Thr Thr Asn Ile Met Lys Gly Glu Ile
    130                 135                 140

Lys Asn Cys Ser Phe Asn Met Thr Thr Glu Leu Arg Asp Lys Lys Gln
145                 150                 155                 160

Lys Val Tyr Ser Leu Phe Tyr Lys Leu Asp Val Val Gln Ile Asn Lys
                165                 170                 175

Ser Asn Ser Ser Ser Gln Tyr Arg Leu Ile Asn Cys Asn Thr Ser Ala
            180                 185                 190

Ile Thr Gln Ala Cys Pro Lys Val Ser Phe Glu Pro Ile Pro Ile His
        195                 200                 205

Tyr Cys Ala Pro Ala Gly Phe Ala Ile Leu Lys Cys Lys Asp Lys Glu
    210                 215                 220

Phe Asn Gly Thr Gly Pro Cys Lys Asn Val Ser Thr Val Gln Cys Thr
225                 230                 235                 240

His Gly Ile Lys Pro Val Val Ser Thr Gln Leu Leu Leu Asn Gly Ser
                245                 250                 255
```

```
Leu Ala Glu Glu Val Met Ile Arg Ser Glu Asn Ile Thr Asn Asn
            260                 265                 270

Ala Lys Asn Ile Ile Val Gln Leu Thr Lys Pro Val Lys Ile Asn Cys
        275                 280                 285

Thr Arg Pro Asn Asn Asn Thr Arg Lys Ser Ile Arg Ile Gly Pro Gly
    290                 295                 300

Gln Ala Phe Tyr Ala Thr Gly Asp Ile Ile Gly Asp Ile Arg Gln Ala
305                 310                 315                 320

His Cys Asn Val Ser Arg Thr Glu Trp Asn Glu Thr Leu Gln Lys Val
                325                 330                 335

Ala Lys Gln Leu Arg Lys Tyr Phe Asn Asn Lys Thr Ile Ile Phe Thr
            340                 345                 350

Asn Ser Ser Gly Gly Arg Leu Arg Ile Thr Thr His Ser Phe Asn Cys
        355                 360                 365

Gly Gly Glu Phe Phe Tyr Cys Asn Thr Ser Gly Leu Phe Asn Ser Thr
    370                 375                 380

Trp Asn Gly Asn Gly Thr Lys Lys Asn Ser Thr Glu Ser Asn Asp
385                 390                 395                 400

Thr Ile Thr Leu Pro Cys Arg Ile Lys Gln Ile Ile Asn Met Trp Gln
                405                 410                 415

Arg Val Gly Gln Ala Met Tyr Ala Pro Pro Ile Gln Gly Val Ile Arg
            420                 425                 430

Cys Glu Ser Asn Ile Thr Gly Leu Leu Leu Thr Arg Asp Gly Gly Asp
        435                 440                 445

Asn Asn Ser Lys Asn Glu Thr Phe Arg Pro Gly Gly Gly Asp Met Arg
    450                 455                 460

Asp Asn Trp Arg Ser Glu Leu Tyr Lys Tyr Lys Val Val Lys Ile Glu
465                 470                 475                 480

Pro Leu Gly Val Ala Pro Thr Lys Ala Lys Arg Val Val Glu Arg
                485                 490                 495

Glu Lys Arg Ala Val Gly Ile Gly Ala Val Phe Leu Gly Phe Leu Gly
            500                 505                 510

Ala Ala Gly Ser Thr Met Gly Ala Ala Ser Ile Thr Leu Thr Val Gln
        515                 520                 525

Ala Arg Gln Leu Leu Ser Gly Ile Val Gln Gln Ser Asn Leu Leu
    530                 535                 540

Arg Ala Ile Glu Ala Gln Gln His Leu Leu Lys Leu Thr Val Trp Gly
545                 550                 555                 560

Ile Lys Gln Leu Gln Ala Arg Val Leu Ala Val Glu Arg Tyr Leu Lys
                565                 570                 575

Asp Gln Gln Leu Leu Gly Ile Trp Gly Cys Ser Gly Lys Leu Ile Cys
            580                 585                 590

Thr Thr Asn Val Pro Trp Asn Ser Ser Trp Ser Asn Lys Ser Gln Ser
        595                 600                 605

Glu Ile Trp Asp Asn Met Thr Trp Leu Gln Trp Asp Lys Glu Ile Ser
    610                 615                 620

Asn Tyr Thr Asp Ile Ile Tyr Asn Leu Ile Glu Glu Ser Gln Asn Gln
625                 630                 635                 640

Gln Glu Lys Asn Glu Gln Asp Leu Leu Ala Leu Asp Lys Trp Ala Asn
                645                 650                 655

Leu Trp Asn Trp Phe Asp Ile Ser Asn Trp Leu Trp Tyr Ile Lys Ile
            660                 665                 670

Phe Ile Met Ile Val Gly Gly Leu Ile Gly Leu Arg Ile Val Phe Ala
```

-continued

```
              675                 680                 685
Val Leu Ser Val
        690
```

<210> SEQ ID NO 148
<211> LENGTH: 697
<212> TYPE: PRT
<213> ORGANISM: Artificial Sequence
<220> FEATURE:
<223> OTHER INFORMATION: Subtype B consensus Envelope protein sequence

<400> SEQUENCE: 148

```
Arg Val Lys Gly Ile Arg Lys Asn Tyr Gln His Leu Trp Arg Trp Gly
1               5                  10                  15

Thr Met Leu Leu Gly Met Leu Met Ile Cys Ser Ala Ala Glu Lys Leu
            20                  25                  30

Trp Val Thr Val Tyr Tyr Gly Val Pro Val Trp Lys Glu Ala Thr Thr
        35                  40                  45

Thr Leu Phe Cys Ala Ser Asp Ala Lys Ala Tyr Asp Thr Glu Val His
    50                  55                  60

Asn Val Trp Ala Thr His Ala Cys Val Pro Thr Asp Pro Asn Pro Gln
65                  70                  75                  80

Glu Val Val Leu Glu Asn Val Thr Glu Asn Phe Asn Met Trp Lys Asn
                85                  90                  95

Asn Met Val Glu Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Leu Ser Gly Glu Lys Met Glu Lys Gly Glu Ile Lys Asn
    130                 135                 140

Cys Ser Phe Asn Ile Thr Thr Ser Ile Arg Asp Lys Val Gln Lys Glu
145                 150                 155                 160

Tyr Ala Leu Phe Tyr Lys Leu Asp Val Val Pro Ile Asp Asn Asp Asn
                165                 170                 175

Thr Ser Tyr Arg Leu Ile Ser Cys Asn Thr Ser Val Ile Thr Gln Ala
            180                 185                 190

Cys Pro Lys Val Ser Phe Glu Pro Ile Pro Ile His Tyr Cys Ala Pro
        195                 200                 205

Ala Gly Phe Ala Ile Leu Lys Cys Asn Asp Lys Lys Phe Asn Gly Thr
    210                 215                 220

Gly Pro Cys Thr Asn Val Ser Thr Val Gln Cys Thr His Gly Ile Arg
225                 230                 235                 240

Pro Val Val Ser Thr Gln Leu Leu Leu Asn Gly Ser Leu Ala Glu Glu
                245                 250                 255

Glu Val Val Ile Arg Ser Glu Asn Phe Thr Asn Asn Ala Lys Thr Ile
            260                 265                 270

Ile Val Gln Leu Asn Glu Ser Val Glu Ile Asn Cys Thr Arg Pro Asn
        275                 280                 285

Asn Asn Thr Arg Lys Ser Ile His Ile Gly Pro Gly Gln Ala Phe Tyr
    290                 295                 300

Thr Thr Gly Glu Ile Ile Gly Asp Ile Arg Gln Ala His Cys Asn Ile
305                 310                 315                 320

Ser Arg Ala Lys Trp Asn Asn Thr Leu Lys Gln Ile Val Lys Lys Leu
                325                 330                 335

Arg Glu Gln Phe Gly Asn Lys Thr Ile Val Phe Asn Gln Ser Ser Gly
```

340                 345                 350
Gly Arg Pro Arg Ile Val Met His Ser Phe Asn Cys Gly Gly Glu Phe
            355                 360                 365

Phe Tyr Cys Asn Thr Thr Gln Leu Phe Asn Ser Thr Trp Asn Val Asn
        370                 375                 380

Gly Thr Trp Asn Asn Asn Thr Glu Gly Asn Asp Thr Ile Thr Leu Pro
385                 390                 395                 400

Cys Arg Ile Lys Gln Ile Ile Asn Met Trp Gln Glu Val Gly Lys Ala
                405                 410                 415

Met Tyr Ala Pro Pro Ile Arg Gly Gln Ile Arg Cys Ser Ser Asn Ile
            420                 425                 430

Thr Gly Leu Leu Leu Thr Arg Asp Gly Gly Asn Asn Asn Thr Asn Glu
        435                 440                 445

Thr Glu Ile Phe Arg Pro Gly Gly Gly Asp Met Arg Asp Asn Trp Arg
    450                 455                 460

Ser Glu Leu Tyr Lys Tyr Lys Val Val Lys Ile Glu Pro Leu Gly Val
465                 470                 475                 480

Ala Pro Thr Lys Ala Lys Arg Arg Val Val Gln Arg Glu Lys Arg Ala
                485                 490                 495

Val Gly Ile Gly Ala Met Phe Leu Gly Phe Leu Gly Ala Ala Gly Ser
            500                 505                 510

Thr Met Gly Ala Ala Ser Met Thr Leu Thr Val Gln Ala Arg Gln Leu
        515                 520                 525

Leu Ser Gly Ile Val Gln Gln Gln Asn Asn Leu Leu Arg Ala Ile Glu
    530                 535                 540

Ala Gln Gln His Leu Leu Gln Leu Thr Val Trp Gly Ile Lys Gln Leu
545                 550                 555                 560

Gln Ala Arg Val Leu Ala Val Glu Arg Tyr Leu Lys Asp Gln Gln Leu
                565                 570                 575

Leu Gly Ile Trp Gly Cys Ser Gly Lys Leu Ile Cys Thr Thr Thr Val
            580                 585                 590

Pro Trp Asn Ala Ser Trp Ser Asn Lys Ser Leu Asp Glu Ile Trp Asp
        595                 600                 605

Asn Met Thr Trp Met Glu Trp Glu Arg Glu Ile Asp Asn Tyr Thr Ser
    610                 615                 620

Leu Ile Tyr Thr Leu Ile Glu Glu Ser Gln Asn Gln Gln Glu Lys Asn
625                 630                 635                 640

Glu Gln Glu Leu Leu Glu Leu Asp Lys Trp Ala Ser Leu Trp Asn Trp
                645                 650                 655

Phe Asp Ile Thr Asn Trp Leu Trp Tyr Ile Lys Ile Phe Ile Met Ile
            660                 665                 670

Val Gly Gly Leu Ile Gly Leu Arg Ile Val Phe Ala Val Leu Ser Ile
        675                 680                 685

Tyr Pro Tyr Asp Val Pro Asp Tyr Ala
    690                 695

<210> SEQ ID NO 149
<211> LENGTH: 687
<212> TYPE: PRT
<213> ORGANISM: Artificial Sequence
<220> FEATURE:
<223> OTHER INFORMATION: Subtype C consensus Envelope protein sequence

<400> SEQUENCE: 149

Arg Val Arg Gly Ile Leu Arg Asn Cys Gln Gln Trp Trp Ile Trp Gly

-continued

```
1               5                   10                  15
Ile Leu Gly Phe Trp Met Leu Met Ile Cys Asn Val Met Gly Asn Leu
                20                  25                  30
Trp Val Thr Val Tyr Tyr Gly Val Pro Val Trp Lys Glu Ala Lys Thr
                35                  40                  45
Thr Leu Phe Cys Ala Ser Asp Ala Lys Ala Tyr Glu Thr Glu Val His
                50                  55                  60
Asn Val Trp Ala Thr His Ala Cys Val Pro Thr Asp Pro Asn Pro Gln
65                  70                  75                  80
Glu Met Val Leu Glu Asn Val Thr Glu Asn Phe Asn Met Trp Lys Asn
                85                  90                  95
Asp Met Val Asp Gln Met His Glu Asp Ile Ile Ser Leu Trp Asp Gln
                100                 105                 110
Ser Leu Lys Pro Cys Val Lys Leu Thr Pro Leu Cys Val Thr Leu Asn
                115                 120                 125
Cys Arg Asn Asn Val Asn Asn Asn Thr Met Lys Glu Glu Ile Lys
                130                 135                 140
Asn Cys Ser Phe Asn Ile Thr Thr Glu Leu Arg Asp Lys Lys Gln Lys
145                 150                 155                 160
Val Tyr Ala Leu Phe Tyr Arg Leu Asp Ile Val Pro Leu Asn Glu Lys
                165                 170                 175
Asn Asn Ser Asn Asp Tyr Arg Leu Ile Asn Cys Asn Thr Ser Ala Ile
                180                 185                 190
Thr Gln Ala Cys Pro Lys Val Ser Phe Asp Pro Ile Pro Ile His Tyr
                195                 200                 205
Cys Ala Pro Ala Gly Tyr Ala Ile Leu Lys Cys Asn Asn Lys Thr Phe
210                 215                 220
Asn Gly Thr Gly Pro Cys Asn Asn Val Ser Thr Val Gln Cys Thr His
225                 230                 235                 240
Gly Ile Lys Pro Val Val Ser Thr Gln Leu Leu Leu Asn Gly Ser Leu
                245                 250                 255
Ala Glu Glu Glu Ile Ile Ile Arg Ser Glu Asn Leu Thr Asn Asn Ala
                260                 265                 270
Lys Thr Ile Ile Val His Leu Asn Glu Ser Val Glu Ile Val Cys Thr
                275                 280                 285
Arg Pro Asn Asn Asn Thr Arg Lys Ser Ile Arg Ile Gly Pro Gly Gln
                290                 295                 300
Thr Phe Tyr Ala Thr Gly Asp Ile Ile Gly Asp Ile Arg Gln Ala His
305                 310                 315                 320
Cys Asn Ile Ser Glu Glu Lys Trp Asn Lys Thr Leu Gln Arg Val Ser
                325                 330                 335
Glu Lys Leu Lys Glu His Phe Pro Asn Lys Thr Ile Lys Phe Ala Pro
                340                 345                 350
Ser Ser Gly Gly Arg Leu Glu Ile Thr Thr His Ser Phe Asn Cys Arg
                355                 360                 365
Gly Glu Phe Phe Tyr Cys Asn Thr Ser Lys Leu Phe Asn Ser Thr Tyr
                370                 375                 380
Met Pro Asn Ser Thr Asn Asn Thr Asn Thr Ile Thr Leu Pro Cys
385                 390                 395                 400
Arg Ile Lys Gln Ile Ile Asn Met Trp Gln Glu Val Gly Arg Ala Met
                405                 410                 415
Tyr Ala Pro Pro Ile Glu Gly Asn Ile Thr Cys Lys Ser Asn Ile Thr
                420                 425                 430
```

Gly Leu Leu Leu Thr Arg Asp Gly Gly Lys Asn Asp Thr Asn Asp Thr
            435                 440                 445

Glu Thr Phe Arg Pro Gly Gly Gly Asp Met Arg Asp Asn Trp Arg Ser
    450                 455                 460

Glu Leu Tyr Lys Tyr Lys Val Val Glu Ile Lys Pro Leu Gly Val Ala
465                 470                 475                 480

Pro Thr Lys Ala Lys Arg Arg Val Val Glu Arg Glu Lys Arg Ala Val
                485                 490                 495

Gly Ile Gly Ala Val Phe Leu Gly Phe Leu Gly Ala Ala Gly Ser Thr
            500                 505                 510

Met Gly Ala Ala Ser Ile Thr Leu Thr Val Gln Ala Arg Gln Leu Leu
            515                 520                 525

Ser Gly Ile Val Gln Gln Gln Ser Asn Leu Leu Arg Ala Ile Glu Ala
            530                 535                 540

Gln Gln His Met Leu Gln Leu Thr Val Trp Gly Ile Lys Gln Leu Gln
545                 550                 555                 560

Thr Arg Val Leu Ala Ile Glu Arg Tyr Leu Lys Asp Gln Gln Leu Leu
                565                 570                 575

Gly Ile Trp Gly Cys Ser Gly Lys Leu Ile Cys Thr Thr Ala Val Pro
            580                 585                 590

Trp Asn Ser Ser Trp Ser Asn Lys Ser Gln Glu Asp Ile Trp Asp Asn
            595                 600                 605

Met Thr Trp Met Gln Trp Asp Arg Glu Ile Ser Asn Tyr Thr Asp Thr
            610                 615                 620

Ile Tyr Arg Leu Leu Glu Asp Ser Gln Asn Gln Glu Lys Asn Glu
625                 630                 635                 640

Lys Asp Leu Leu Ala Leu Asp Ser Trp Lys Asn Leu Trp Asn Trp Phe
                645                 650                 655

Asp Ile Thr Asn Trp Leu Trp Tyr Ile Lys Ile Phe Ile Met Ile Val
            660                 665                 670

Gly Gly Leu Ile Gly Leu Arg Ile Ile Phe Ala Val Leu Ser Ile
            675                 680                 685

<210> SEQ ID NO 150
<211> LENGTH: 696
<212> TYPE: PRT
<213> ORGANISM: Artificial Sequence
<220> FEATURE:
<223> OTHER INFORMATION: Subtype D consensus Envelope protein sequence

<400> SEQUENCE: 150

Arg Val Arg Gly Ile Lys Arg Asn Tyr Gln His Leu Trp Lys Trp Gly
1               5                   10                  15

Thr Met Leu Leu Gly Met Leu Met Thr Cys Ser Val Ala Glu Asn Leu
            20                  25                  30

Trp Val Thr Val Tyr Tyr Gly Val Pro Val Trp Lys Glu Ala Thr Thr
        35                  40                  45

Thr Leu Phe Cys Ala Ser Asp Ala Lys Ser Tyr Lys Thr Glu Ala His
    50                  55                  60

Asn Ile Trp Ala Thr His Ala Cys Val Pro Thr Asp Pro Asn Pro Gln
65                  70                  75                  80

Glu Ile Glu Leu Glu Asn Val Thr Glu Asn Phe Asn Met Trp Lys Asn
                85                  90                  95

Asn Met Val Glu Gln Met His Glu Asp Ile Ile Ser Leu Trp Asp Gln
            100                 105                 110

```
Ser Leu Lys Pro Cys Val Lys Leu Thr Pro Leu Cys Val Thr Leu Asn
        115                 120                 125
Cys Thr Asp Gly Met Arg Asn Asp Thr Asn Asp Thr Asn Val Thr Met
130                 135                 140
Glu Glu Gly Glu Met Lys Asn Cys Ser Phe Asn Ile Thr Thr Glu Val
145                 150                 155                 160
Arg Asp Lys Lys Lys Gln Val His Ala Leu Phe Tyr Lys Leu Asp Val
                165                 170                 175
Val Pro Ile Asp Asp Asn Asn Thr Asn Asn Ser Asn Tyr Arg Leu Ile
                180                 185                 190
Asn Cys Asn Thr Ser Ala Ile Thr Gln Ala Cys Pro Lys Val Thr Phe
        195                 200                 205
Glu Pro Ile Pro Ile His Tyr Cys Ala Pro Ala Gly Phe Ala Ile Leu
210                 215                 220
Lys Cys Lys Asp Lys Lys Phe Asn Gly Thr Gly Pro Cys Lys Asn Val
225                 230                 235                 240
Ser Thr Val Gln Cys Thr His Gly Ile Arg Pro Val Val Ser Thr Gln
                245                 250                 255
Leu Leu Leu Asn Gly Ser Leu Ala Glu Glu Ile Ile Ile Arg Ser
        260                 265                 270
Glu Asn Leu Thr Asn Asn Ala Lys Ile Ile Val Gln Leu Asn Glu
        275                 280                 285
Ser Val Thr Ile Asn Cys Thr Arg Pro Tyr Asn Asn Thr Arg Lys Arg
290                 295                 300
Ile Pro Ile Gly Leu Gly Gln Ala Phe Tyr Thr Arg Gly Ile Ile
305                 310                 315                 320
Gly Asp Ile Arg Gln Ala His Cys Asn Ile Ser Gly Ala Glu Trp Asn
                325                 330                 335
Lys Thr Leu Gln Gln Val Ala Lys Lys Leu Gly Asp Leu Leu Asn Lys
        340                 345                 350
Thr Thr Ile Ile Phe Lys Pro Ser Ser Gly Gly Arg Pro Arg Ile Thr
        355                 360                 365
Thr His Ser Phe Asn Cys Gly Gly Glu Phe Phe Tyr Cys Asn Thr Ser
        370                 375                 380
Arg Leu Phe Asn Ser Thr Trp Ser Lys Asn Ser Thr Ser Asn Ser Thr
385                 390                 395                 400
Lys Glu Asn Asn Thr Ile Thr Leu Pro Cys Arg Ile Lys Gln Ile Ile
                405                 410                 415
Asn Met Trp Gln Gly Val Gly Lys Ala Met Tyr Ala Pro Pro Ile Glu
        420                 425                 430
Gly Leu Ile Lys Cys Ser Ser Asn Ile Thr Gly Leu Leu Leu Thr Arg
        435                 440                 445
Asp Gly Gly Ala Asn Asn Ser His Asn Glu Thr Phe Arg Pro Gly Gly
450                 455                 460
Gly Asp Met Arg Asp Asn Trp Arg Ser Glu Leu Tyr Lys Tyr Lys Val
465                 470                 475                 480
Val Lys Ile Glu Pro Leu Gly Val Ala Pro Thr Arg Ala Lys Arg Arg
                485                 490                 495
Val Val Glu Arg Glu Lys Arg Ala Ile Gly Leu Gly Ala Met Phe Leu
                500                 505                 510
Gly Phe Leu Gly Ala Ala Gly Ser Thr Met Gly Ala Ala Ser Leu Thr
        515                 520                 525
```

```
Leu Thr Val Gln Ala Arg Gln Leu Leu Ser Gly Ile Val Gln Gln Gln
    530                 535                 540

Asn Asn Leu Leu Arg Ala Ile Glu Ala Gln Gln His Leu Leu Gln Leu
545                 550                 555                 560

Thr Val Trp Gly Ile Lys Gln Leu Gln Ala Arg Ile Leu Ala Val Glu
                565                 570                 575

Arg Tyr Leu Lys Asp Gln Gln Leu Leu Gly Ile Trp Gly Cys Ser Gly
            580                 585                 590

Lys His Ile Cys Thr Thr Thr Val Pro Trp Asn Ser Ser Trp Ser Asn
            595                 600                 605

Lys Ser Leu Asp Glu Ile Trp Asn Asn Met Thr Trp Met Glu Trp Glu
        610                 615                 620

Arg Glu Ile Asp Asn Tyr Thr Gly Leu Ile Tyr Ser Leu Ile Glu Glu
625                 630                 635                 640

Ser Gln Thr Gln Gln Glu Lys Asn Glu Gln Glu Leu Leu Glu Leu Asp
                645                 650                 655

Lys Trp Ala Ser Leu Trp Asn Trp Phe Ser Ile Thr Gln Trp Leu Trp
            660                 665                 670

Tyr Ile Lys Ile Phe Ile Met Ile Val Gly Gly Leu Ile Gly Leu Arg
        675                 680                 685

Ile Val Phe Ala Val Leu Ser Leu
690                 695

<210> SEQ ID NO 151
<211> LENGTH: 323
<212> TYPE: PRT
<213> ORGANISM: Artificial Sequence
<220> FEATURE:
<223> OTHER INFORMATION: Subtype B consensus Nef-Rev protein sequence

<400> SEQUENCE: 151

Ser Lys Arg Ser Val Val Gly Trp Pro Thr Val Arg Glu Arg Met Arg
1               5                   10                  15

Arg Ala Glu Pro Ala Ala Asp Gly Val Gly Ala Val Ser Arg Asp Leu
                20                  25                  30

Glu Lys His Gly Ala Ile Thr Ser Ser Asn Thr Ala Ala Asn Asn Ala
            35                  40                  45

Asp Cys Ala Trp Leu Glu Ala Gln Glu Glu Glu Val Gly Phe Pro
50                  55                  60

Val Arg Ala Gln Val Ala Leu Arg Ala Met Thr Tyr Lys Ala Ala Val
65                  70                  75                  80

Asp Leu Ser His Phe Leu Lys Glu Lys Gly Gly Leu Glu Gly Leu Ile
            85                  90                  95

Tyr Ser Gln Lys Arg Gln Asp Ile Leu Asp Leu Trp Val Tyr His Thr
        100                 105                 110

Gln Gly Tyr Phe Pro Asp Trp Gln Asn Tyr Thr Pro Gly Pro Gly Ile
    115                 120                 125

Arg Tyr Pro Leu Thr Phe Gly Trp Cys Phe Lys Leu Val Pro Val Glu
    130                 135                 140

Pro Glu Lys Val Glu Glu Ala Asn Glu Gly Glu Asn Asn Ser Ala Ala
145                 150                 155                 160

His Pro Met Ser Leu His Gly Met Asp Asp Pro Glu Arg Glu Val Leu
                165                 170                 175

Val Trp Lys Phe Asp Ser Arg Leu Ala Phe His Met Ala Arg Glu
            180                 185                 190
```

```
Leu His Pro Glu Tyr Tyr Lys Asp Cys Arg Gly Arg Lys Arg Ser
            195                 200                 205

Ala Gly Arg Ser Gly Asp Ser Asp Glu Glu Leu Leu Lys Thr Val Arg
210                 215                 220

Leu Ile Lys Phe Leu Tyr Gln Ser Asn Pro Pro Ser Pro Glu Gly
225                 230                 235                 240

Thr Arg Gln Ala Arg Arg Asn Arg Arg Arg Trp Arg Glu Arg Gln
            245                 250                 255

Arg Gln Ile Arg Ser Ile Ser Glu Trp Ile Leu Ser Thr Tyr Leu Gly
                260                 265                 270

Arg Pro Ala Glu Pro Val Pro Leu Gln Leu Pro Pro Leu Glu Arg Leu
            275                 280                 285

Thr Leu Asp Cys Asn Glu Asp Cys Gly Thr Ser Gly Thr Gln Gly Val
290                 295                 300

Gly Ser Pro Gln Ile Leu Val Glu Ser Pro Ala Val Leu Glu Ser Gly
305                 310                 315                 320

Thr Lys Glu

<210> SEQ ID NO 152
<211> LENGTH: 506
<212> TYPE: PRT
<213> ORGANISM: Artificial Sequence
<220> FEATURE:
<223> OTHER INFORMATION: Gag consensus protein sequence of subtype A, B,
      C and D

<400> SEQUENCE: 152

Gly Ala Arg Ala Ser Val Leu Ser Gly Gly Lys Leu Asp Ala Trp Glu
1               5                   10                  15

Lys Ile Arg Leu Arg Pro Gly Gly Lys Lys Lys Tyr Arg Leu Lys His
                20                  25                  30

Leu Val Trp Ala Ser Arg Glu Leu Glu Arg Phe Ala Leu Asn Pro Gly
            35                  40                  45

Leu Leu Glu Thr Ser Glu Gly Cys Lys Gln Ile Ile Gly Gln Leu Gln
    50                  55                  60

Pro Ala Leu Gln Thr Gly Ser Glu Glu Leu Arg Ser Leu Tyr Asn Thr
65                  70                  75                  80

Val Ala Thr Leu Tyr Cys Val His Glu Lys Ile Glu Val Lys Asp Thr
                85                  90                  95

Lys Glu Ala Leu Asp Lys Ile Glu Glu Glu Gln Asn Lys Ser Lys Gln
            100                 105                 110

Lys Ala Gln Gln Ala Ala Ala Asp Thr Gly Asn Ser Ser Gln Val Ser
        115                 120                 125

Gln Asn Tyr Pro Ile Val Gln Asn Leu Gln Gly Gln Met Val His Gln
    130                 135                 140

Ala Ile Ser Pro Arg Thr Leu Asn Ala Trp Val Lys Val Ile Glu Glu
145                 150                 155                 160

Lys Ala Phe Ser Pro Glu Val Ile Pro Met Phe Ser Ala Leu Ser Glu
                165                 170                 175

Gly Ala Thr Pro Gln Asp Leu Asn Thr Met Leu Asn Thr Val Gly Gly
            180                 185                 190

His Gln Ala Ala Met Gln Met Leu Lys Asp Thr Ile Asn Glu Glu Ala
        195                 200                 205

Ala Glu Trp Asp Arg Leu His Pro Val His Ala Gly Pro Ile Ala Pro
    210                 215                 220
```

```
Gly Gln Met Arg Glu Pro Arg Gly Ser Asp Ile Ala Gly Thr Thr Ser
225                 230                 235                 240

Thr Leu Gln Glu Gln Ile Gly Trp Met Thr Ser Asn Pro Pro Ile Pro
                245                 250                 255

Val Gly Asp Ile Tyr Lys Arg Trp Ile Ile Leu Gly Leu Asn Lys Ile
                260                 265                 270

Val Arg Met Tyr Ser Pro Val Ser Ile Leu Asp Ile Arg Gln Gly Pro
            275                 280                 285

Lys Glu Pro Phe Arg Asp Tyr Val Asp Arg Phe Phe Lys Thr Leu Arg
                290                 295                 300

Ala Glu Gln Ala Ser Gln Asp Val Lys Asn Trp Met Thr Glu Thr Leu
305                 310                 315                 320

Leu Val Gln Asn Ala Asn Pro Asp Cys Lys Thr Ile Leu Arg Ala Leu
                325                 330                 335

Gly Pro Gly Ala Thr Leu Glu Glu Met Met Thr Ala Cys Gln Gly Val
                340                 345                 350

Gly Gly Pro Gly His Lys Ala Arg Val Leu Ala Glu Ala Met Ser Gln
            355                 360                 365

Ala Thr Asn Ser Asn Ile Met Met Gln Arg Gly Asn Phe Arg Gly Pro
370                 375                 380

Arg Arg Ile Val Lys Cys Phe Asn Cys Gly Lys Glu Gly His Ile Ala
385                 390                 395                 400

Arg Asn Cys Arg Ala Pro Arg Lys Lys Gly Cys Trp Lys Cys Gly Lys
            405                 410                 415

Glu Gly His Gln Met Lys Asp Cys Thr Glu Arg Gln Ala Asn Phe Leu
            420                 425                 430

Gly Lys Ile Trp Pro Ser His Lys Gly Arg Pro Gly Asn Phe Leu Gln
            435                 440                 445

Ser Arg Pro Glu Pro Thr Ala Pro Pro Ala Glu Ser Phe Gly Phe Gly
        450                 455                 460

Glu Glu Ile Thr Pro Ser Pro Lys Gln Glu Pro Lys Asp Arg Glu Leu
465                 470                 475                 480

Tyr Pro Leu Ala Ser Leu Lys Ser Leu Phe Gly Asn Asp Pro Leu Ser
            485                 490                 495

Gln Tyr Pro Tyr Asp Val Pro Asp Tyr Ala
            500                 505
```